US012703744B2

(12) United States Patent
McComb et al.

(10) Patent No.: US 12,703,744 B2
(45) Date of Patent: Aug. 11, 2026

(54) ANTI-CD22 SINGLE DOMAIN ANTIBODIES AND THERAPEUTIC CONSTRUCTS

(71) Applicant: National Research Council of Canada, Ottawa (CA)

(72) Inventors: Scott McComb, Ottawa (CA); Risini Weeratna, Ottawa (CA); Mehdi Arbabi-Ghahroudi, Ottawa (CA); Tina Nguyen, Ottawa (CA); Cunle Wu, Montreal (CA)

(73) Assignee: National Research Council of Canada, Ottawa (CA)

( * ) Notice: Subject to any disclaimer, the term of this patent is extended or adjusted under 35 U.S.C. 154(b) by 732 days.

(21) Appl. No.: 18/007,131

(22) PCT Filed: Jul. 27, 2021

(86) PCT No.: PCT/CA2021/051046

§ 371 (c)(1),
(2) Date: Jan. 27, 2023

(87) PCT Pub. No.: WO2022/020945

PCT Pub. Date: Feb. 3, 2022

(65) Prior Publication Data

US 2023/0265185 A1 Aug. 24, 2023

Related U.S. Application Data

(60) Provisional application No. 63/058,203, filed on Jul. 29, 2020.

(51) Int. Cl.

| | |
|---|---|
| ***C07K 16/28*** | (2006.01) |
| ***A61K 40/11*** | (2025.01) |
| ***A61K 40/31*** | (2025.01) |
| ***A61K 40/33*** | (2025.01) |
| ***A61K 40/42*** | (2025.01) |
| ***A61P 35/00*** | (2006.01) |
| ***C07K 14/705*** | (2006.01) |

(52) U.S. Cl.

CPC .......... *C07K 16/2803* (2013.01); *A61K 40/11* (2025.01); *A61K 40/31* (2025.01); *A61K 40/33* (2025.01); *A61K 40/4212* (2025.01); *A61P 35/00* (2018.01); *C07K 14/70517* (2013.01); *A61K 2239/13* (2023.05); *C07K 2317/24* (2013.01); *C07K 2317/31* (2013.01); *C07K 2317/35* (2013.01); *C07K 2317/565* (2013.01); *C07K 2317/569* (2013.01); *C07K 2317/92* (2013.01); *C07K 2319/33* (2013.01)

(58) Field of Classification Search

CPC .......... C07K 16/2803; C07K 14/70517; C07K 2317/24; C07K 2317/31; C07K 2317/35; C07K 2317/565; C07K 2317/569; C07K 2317/92; C07K 2319/33; A61K 40/11; A61K 40/31; A61K 40/33; A61K 40/4212; A61K 2239/13; A61P 35/00

See application file for complete search history.

(56) References Cited

U.S. PATENT DOCUMENTS

2015/0299317 A1 10/2015 Orentas et al.

FOREIGN PATENT DOCUMENTS

| | | | | |
|---|---|---|---|---|
| CA | 2994579 A1 | 2/2017 | | |
| CN | 109970858 A | 7/2019 | | |
| CN | 111217908 A | 6/2020 | | |
| WO | 2017025038 A1 | 2/2017 | | |
| WO | 2019126464 A2 | 6/2019 | | |
| WO | WO-2020053634 A1 * | 3/2020 | ......... | C07K 16/2803 |

OTHER PUBLICATIONS

Stancovski et al. (PNAS, 88: 8691-8695, 1991).*
Jiang et al. (J. Biol. Chem., 280: 4656-4662, 2005).*
Xiang et al. (CNS Neurosci Ther., 30: 1-11, 2024).*
Arbabi-Ghahroudi, et al., "Aggregation-resistant VHs Selected by in Vitro Evolution Tend to Have Disulfide-bonded Loops and Acidic Isoelectric Points," Protein Engineering, Design & Selection : PEDS, 2009, vol. 22 (2), pp. 59-66.
Baral, et al., "Expression of Single-domain Antibodies in Bacterial Systems," Methods in Molecular Biology (Clifton, N.J.), 2012, vol. 911, pp. 257-275.

(Continued)

*Primary Examiner* — Nelson B Moseley, II
(74) *Attorney, Agent, or Firm* — Jessica Smith

(57) ABSTRACT

Herein are provided anti-CD22 single domain antibodies (sdAb) prepared by immunizing a llama with the extracellular domain of the predominant human CD22 isoform. By constructing a library of the heavy chain repertoire generated, VHH antibodies specific to the immunogen were isolated. The 27 example antibodies initially produced comprise CDR1, CDR2, and CDR3 sequences corresponding, respectively to SEQNOs: 1-3, 4-6, 7-9, 10-12, 13-15, 16-18, 19-21, 22-24, 25-27, 28-30, 31-33, 34-36, 37-39, 40-42, 43-45, 46-48, 49-51, 52-54, 55-57, 58-60, 61-63, 64-66, 67-69, 70-72, 73-75, 75-78, and 79-81; and related sequences. Also provided are multivalent antibodies comprising any one of the sdAbs, including bispecific T-cell engagers, bispecific killer cell engagers (BiKEs), and trispecific killer cell engagers (TrikEs). Also described are chimeric antigen receptors (CARs) for CAR-T therapy comprising any one of the aforementioned sdAbs. Uses of these molecules in the treatment of cancer are also described.

20 Claims, 31 Drawing Sheets

Specification includes a Sequence Listing.

(56) References Cited

OTHER PUBLICATIONS

Bariosone et al., "Bispecific Anti-CD22 T-cell Engager Efficiently Promotes Cell-Mediated Cytotoxicity of Lymphoma, Leukemia and Sarcoma Targets," Journal of Immunology, May 2020, vol. 204 (1), pp. 1-5.
Bloemberg, et al., "A High-throughput Method for Characterizing Novel Chimeric Antigen Receptors in Jurkat Cells," Molecular Therapy. Methods & Clinical Development, 2020, vol. 16, pp. 238-254.
Feldhaus, et al., "Flow-cytometric Isolation of Human Antibodies From a Nonimmune *Saccharomyces cerevisiae* Surface Display Library," Nature Biotechnology, 2003, vol. 21 (2), pp. 163-170.
Fry, et al., "CD22-targeted Car T Cells Induce Remission in B-all That is Naive or Resistant to Cd19-targeted Car Immunotherapy," Nature Medicine, 2015, vol. 24 (1), pp. 20-28.
Gauthier, et al., "Multifunctional Natural Killer Cell Engagers Targeting Nkp46 Trigger Protective Tumor Immunity," Cell, 2019, vol. 177 (7), pp. 1701-1713.
Gleason, et al., "Bispecific and Trispecific Killer Cell Engagers Directly Activate Human NK Cells Through Cd16 Signaling and Induce Cytotoxicity and Cytokine Production," Molecular Cancer Therapeutics, 2012, vol. 11 (12), pp. 2674-2684.
Henry, et al., "Llama Peripheral B-cell Populations Producing Conventional and Heavy Chain-only Igg Subtypes are Phenotypically Indistinguishable but Immunogenetically Distinct," Immunogenetics, 2019, vol. 71 (4), pp. 14 pages.
Hussack, et al., "Protease-resistant Single-domain Antibodies Inhibit Campylobacter Jejuni Motility," Protein Engineering, Design Selection : PEDS, 2014, vol. 27 (6), pp. 191-198.
Intemational Patent Application No. PCT/CA2021/051046, International Preliminary Report on Patentability, dated Jan. 31, 2023.
International Patent Application No. PCT /CA2021/051046, International Search Report and Written Opinion dated Nov. 9, 2021.
Munter et al., "Nanobody Based Dual Specific CARs," International Journal of Molecular Sciences, Jan. 2018, vol. 19 (2), 11 Pages.
Pan, et al., "CD22 Car T-cell Therapy in Refractory or Relapsed B Acute Lymphoblastic Leukemia," Leukemia, 2019, vol. 33 (12), pp. 1-13.
Rangaswamy et al., "A Novel T-Cell Bispecific Antibody Platform for Efficient T-Cell Mediated Killing of Tumor Cells With Minimal Cytokine Release," Journal of Clinical Oncology, Feb. 2018, vol. 36 (5), pp. 1-4.
Stoiber, et al., "Limitations in the Design of Chimeric Antigen Receptors for Cancer Therapy," Cells, 2019, vol. 8 (5), 26 pages.
Vallera, et al., "IL 15 Trispecific Killer Engagers (Trike) Make Natural Killer Cells Specific to CD33+ Targets While Also Inducing Persistence, in Vivo Expansion, and Enhanced Function," Clinical Cancer Research : an Official Journal of the American Association for Cancer Research, 2016, vol. 22 (14), pp. 40 pages.
Van Der Stegen, et al., "The Pharmacology of Second-generation Chimeric Antigen Receptors," Nature Reviews. Drug Discovery, 2015, vol. 14 (7), pp. 499-509.
Faraji et al., "Functional Study of a Camelid Single Domain Anti-CD22 Antibody." International Journal of Peptide Research and Therapeutics, 2020, vol. 26, pp. 633-639.
Bannas et al., "Nanobodies and Nanobody-Based Human Heavy Chain Antibodies as Antitumor Therapeutics," Frontiers in Immunology, Nov. 2017, vol. 8, pp. 1-13.
European Patent Application No. 21850799.4, Partial Supplementary European Search Report dated Nov. 25, 2024.
Munter et al., "Rapid and Effective Generation of Nanobody Based CARs using PCR and Gibson Assembly", International Journal of Molecular Sciences, Jan. 2020, vol. 21(3), pp. 1-18.
Dai et al., "Bispecific Car-t Cells Targeting Both Cd19 and Cd22 for Therapy of Adults With Relapsed or Refractory B Cell Acute Lymphoblastic Leukemia," Journal of Hematology Oncology, Apr. 2020, vol. 13(1), pp. 1-11.
Faraji et al., "Development and Characterization of a Camelid Single-domain Antibody Directed to Human Cd22 Biomarker," Biotechnology and applied biochemistry, Sep. 2018, vol. 65(5), pp. 718-725.

* cited by examiner

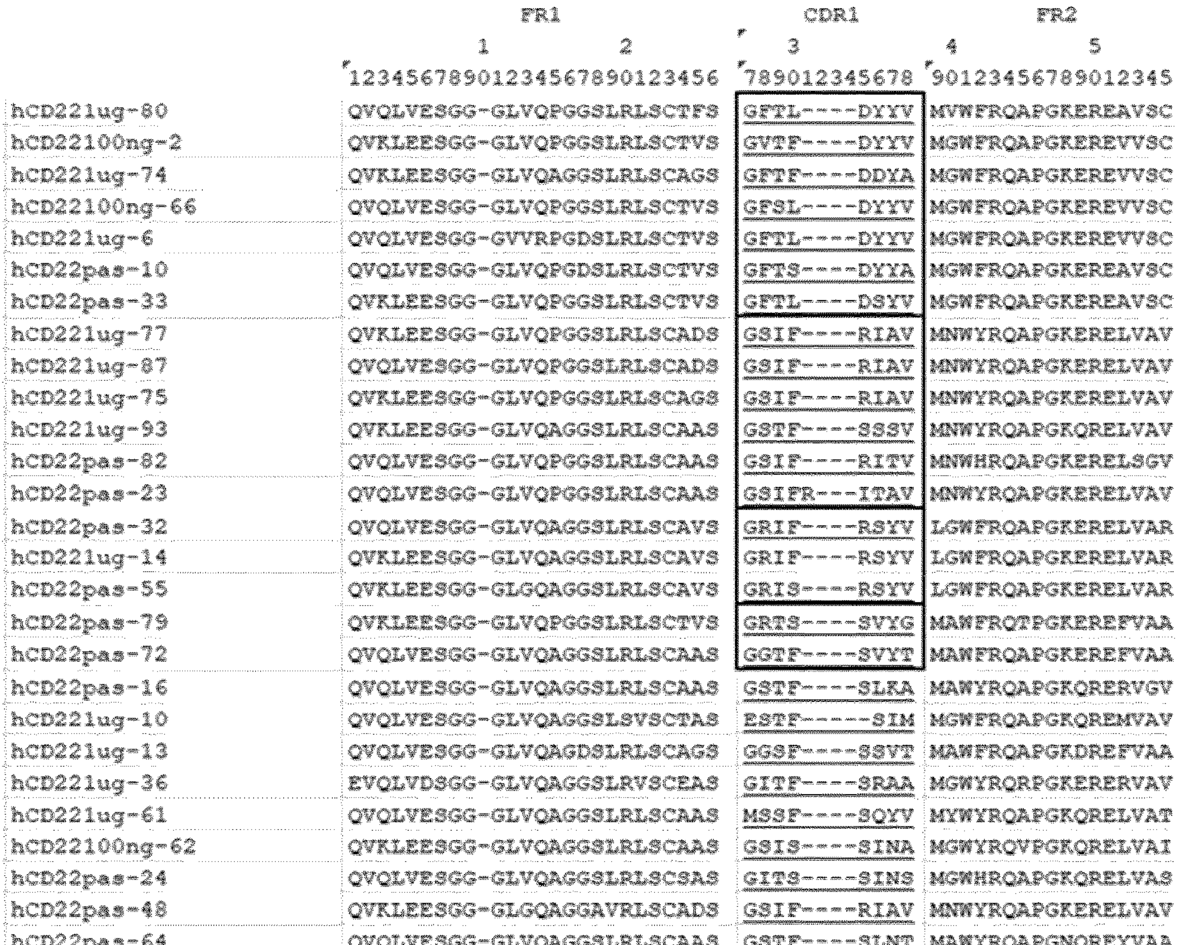

| | FR1 | CDR1 | FR2 |
|---|---|---|---|
| | 1 2 | 3 | 4 5 |
| | 12345678901234567890123456 | 789012345678 | 90123456789012345 |
| hCD221ug-80 | QVQLVESGG-GLVQPGGSLRLSCTFS | GFTL----DYYV | MVWFRQAPGKEREAVSC |
| hCD22100ng-2 | QVKLEESGG-GLVQPGGSLRLSCTVS | GVTF----DYYV | MGWFRQAPGKEREVVSC |
| hCD221ug-74 | QVKLEESGG-GLVQAGGSLRLSCAGS | GFTF----DDYA | MGWFRQAPGKEREVVSC |
| hCD22100ng-66 | QVQLVESGG-GLVQPGGSLRLSCTVS | GFSL----DYYV | MGWFRQAPGKEREVVSC |
| hCD221ug-6 | QVQLVESGG-GVVRPGDSLRLSCTVS | GFTL----DYYV | MGWFRQAPGKEREVVSC |
| hCD22pas-10 | QVQLVESGG-GLVQPGDSLRLSCTVS | GFTS----DYYA | MGWFRQAPGKEREAVSC |
| hCD22pas-33 | QVKLEESGG-GLVQPGGSLRLSCTVS | GFTL----DSYV | MGWFRQAPGKEREAVSC |
| hCD221ug-77 | QVKLEESGG-GLVQPGGSLRLSCADS | GSIF----RIAV | MNWYRQAPGKERELVAV |
| hCD221ug-87 | QVQLVESGG-GLVQPGGSLRLSCADS | GSIF----RIAV | MNWYRQAPGKERELVAV |
| hCD221ug-75 | QVKLEESGG-GLVQPGGSLRLSCAGS | GSIF----RIAV | MNWYRQAPGKERELVAV |
| hCD221ug-93 | QVKLEESGG-GLVQAGGSLRLSCAAS | GSTF----SSSV | MNWYRQAPGKQRELVAV |
| hCD22pas-82 | QVQLVESGG-GLVQPGGSLRLSCAAS | GSIF----RITV | MNWHRQAPGKERELSGV |
| hCD22pas-23 | QVQLVESGG-GLVQPGGSLRLSCAAS | GSIFR---ITAV | MNWYRQAPGKERELVAV |
| hCD22pas-32 | QVQLVESGG-GLVQAGGSLRLSCAVS | GRIF----RSYV | LGWFRQAPGKERELVAR |
| hCD221ug-14 | QVKLEESGG-GLVQAGGSLRLSCAVS | GRIF----RSYV | LGWFRQAPGKERELVAR |
| hCD22pas-55 | QVKLEESGG-GLGQAGGSLRLSCAVS | GRIS----RSYV | LGWFRQAPGKERELVAR |
| hCD22pas-79 | QVKLEESGG-GLVQPGGSLRLSCTVS | GRTS----SVYG | MAWFRQTPGKEREFVAA |
| hCD22pas-72 | QVQLVESGG-GLVQAGGSLRLSCAAS | GGTF----SVYT | MAWFRQAPGKEREFVAA |
| hCD22pas-16 | QVQLVESGG-GLVQAGGSLRLSCAAS | GSTF----SLKA | MAWYRQAPGKQRERVGV |
| hCD221ug-10 | QVQLVESGG-GLVQAGGSLSVSCTAS | ESTF-----SIM | MGWFRQAPGKQREMVAV |
| hCD221ug-13 | QVQLVESGG-GLVQAGDSLRLSCAGS | GGSF----SSVT | MAWFRQAPGKDREFVAA |
| hCD221ug-36 | EVQLVDSGG-GLVQAGGSLRVSCEAS | GITF----SRAA | MGWYRQRPGKERERVAV |
| hCD221ug-61 | QVQLVESGG-GLVQAGGSLRLSCAAS | MSSF----SQYV | MYWYRQAPGKQRELVAT |
| hCD22100ng-62 | QVKLEESGG-GLVQAGGSLRLSCAAS | GSIS----SINA | MGWYRQVPGKQRELVAI |
| hCD22pas-24 | QVQLVESGG-GLVQAGGSLRLSCSAS | GITS----SINS | MGWHRQAPGKQRELVAS |
| hCD22pas-48 | QVKLEESGG-GLGQAGGAVRLSCADS | GSIF----RIAV | MNWYRQAPGKERELVAV |
| hCD22pas-64 | QVQLVESGG-GLVQAGGSLRLSCAAS | GSTF----SLNT | MAWYRQAPGNQREYVAA |

Figure 4A

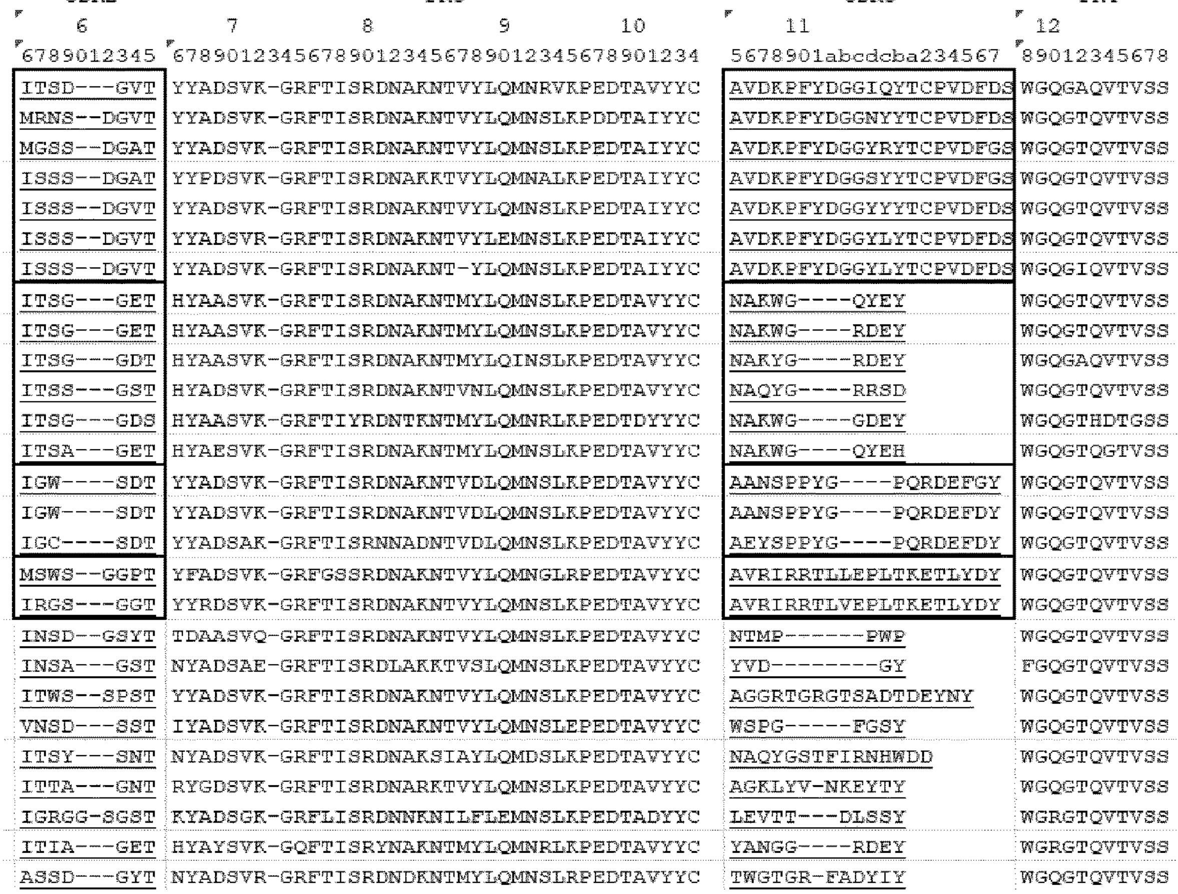

| CDR2 | FR3 | CDR3 | FR4 |
| --- | --- | --- | --- |
| 6 | 7 8 9 10 | 11 | 12 |
| 6789012345 | 67890123456789012345678901234567890123 4 | 5678901abcdcba234567 | 89012345678 |
| ITSD---GVT | YYADSVK-GRFTISRDNAKNTVYLQMNRVKPEDTAVYYC | AVDKPFYDGGIQYTCPVDFDS | WGQGAQVTVSS |
| MRNS--DGVT | YYADSVK-GRFTISRDNAKNTVYLQMNSLKPDDTAIYYC | AVDKPFYDGGNYYTCPVDFDS | WGQGTQVTVSS |
| MGSS--DGAT | YYADSVK-GRFTISRDNAKNTVYLQMNSLKPEDTAIYYC | AVDKPFYDGGYRYTCPVDFGS | WGQGTQVTVSS |
| ISSS--DGAT | YYPDSVK-GRFTISRDNAKKTVYLQMNALKPEDTAIYYC | AVDKPFYDGGSYYTCPVDFGS | WGQGTQVTVSS |
| ISSS--DGVT | YYADSVK-GRFTISRDNAKNTVYLQMNSLKPEDTAIYYC | AVDKPFYDGGYYYTCPVDFDS | WGQGTQVTVSS |
| ISSS--DGVT | YYADSVR-GRFTISRDNAKNTVYLEMNSLKPEDTAIYYC | AVDKPFYDGGYLYTCPVDFDS | WGQGTQVTVSS |
| ISSS--DGVT | YYADSVK-GRFTISRDNAKNT-YLQMNSLKPEDTAIYYC | AVDKPFYDGGYLYTCPVDFDS | WGQGIQVTVSS |
| ITSG---GET | HYAASVK-GRFTISRDNAKNTMYLQMNSLKPEDTAVYYC | NAKWG----QYEY | WGQGTQVTVSS |
| ITSG---GET | HYAASVK-GRFTISRDNAKNTMYLQMNSLKPEDTAVYYC | NAKWG----RDEY | WGQGTQVTVSS |
| ITSG---GDT | HYAASVK-GRFTISRDNAKNTMYLQINSLKPEDTAVYYC | NAKYG----RDEY | WGQGAQVTVSS |
| ITSS---GST | HYADSVK-GRFTISRDNAKNTVNLQMNSLKPEDTAVYYC | NAQYG----RRSD | WGQGTQVTVSS |
| ITSG---GDS | HYAASVK-GRFTIYRDNTKNTMYLQMNRLKPEDTDYYYC | NAKWG----GDEY | WGQGTHDTGSS |
| ITSA---GET | HYAESVK-GRFTISRDNAKNTMYLQMNSLKPEDTAVYYC | NAKWG----QYEH | WGQGTQGTVSS |
| IGW----SDT | YYADSVK-GRFTISRDNAKNTVDLQMNSLKPEDTAVYYC | AANSPPYG----PQRDEFGY | WGQGTQVTVSS |
| IGW----SDT | YYADSVK-GRFTISRDNAKNTVDLQMNSLKPEDTAVYYC | AANSPPYG----PQRDEFDY | WGQGTQVTVSS |
| IGC----SDT | YYADSAK-GRFTISRNNADNTVDLQMNSLKPEDTAVYYC | AEYSPPYG----PQRDEFDY | WGQGTQVTVSS |
| MSWS--GGPT | YFADSVK-GRFGSSRDNAKNTVYLQMNGLRPEDTAVYYC | AVRIRRTLLEPLTKETLYDY | WGQGTQVTVSS |
| IRGS---GGT | YYRDSVK-GRFTISRDNAKNTVYLQMNSLKPEDTAVYYC | AVRIRRTLVEPLTKETLYDY | WGQGTQVTVSS |
| INSD--GSYT | TDAASVQ-GRFTISRDNAKNTVYLQMNSLKPEDTAVYYC | NTMP------PWP | WGQGTQVTVSS |
| INSA---GST | NYADSAE-GRFTISRDLAKKTVSLQMNSLKPEDTAVYYC | YVD--------GY | FGQGTQVTVSS |
| ITWS--SPST | YYADSVK-GRFTISRDNAKNTVYLQMNSLKPEDTAVYYC | AGGRTGRGTSADTDEYNY | WGQGTQVTVSS |
| VNSD---SST | IYADSVK-GRFTISRDNAKNTVYLQMNSLEPEDTAVYYC | WSPG-----FGSY | WGQGTQVTVSS |
| ITSY---SNT | NYADSVK-GRFTISRDNAKSIAYLQMDSLKPEDTAVYYC | NAQYGSTFIRNHWDD | WGQGTQVTVSS |
| ITTA---GNT | RYGDSVK-GRFTISRDNARKTVYLQMNSLKPEDTAVYYC | AGKLYV-NKEYTY | WGQGTQVTVSS |
| IGRGG-SGST | KYADSGK-GRFLISRDNNKNILFLEMNSLKPEDTADYYC | LEVTT---DLSSY | WGRGTQVTVSS |
| ITIA---GET | HYAYSVK-GQFTISRYNAKNTMYLQMNRLKPEDTAVYYC | YANGG----RDEY | WGRGTQVTVSS |
| ASSD---GYT | NYADSVR-GRFTISRDNDKNTMYLQMNSLRPEDTAVYYC | TWGTGR-FADYIY | WGQGTQVTVSS |

Figure 4B

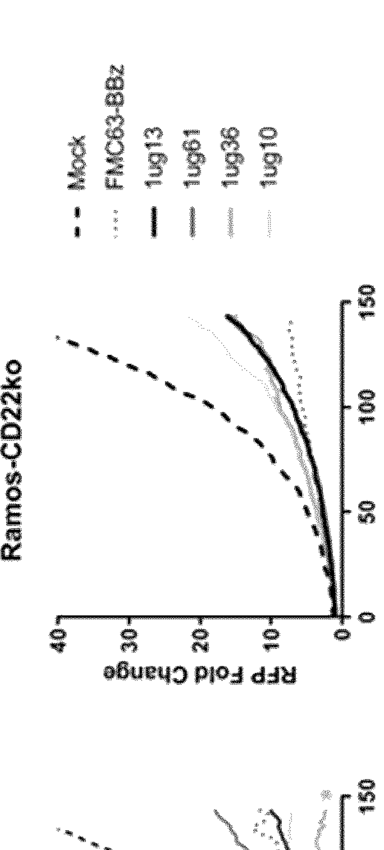
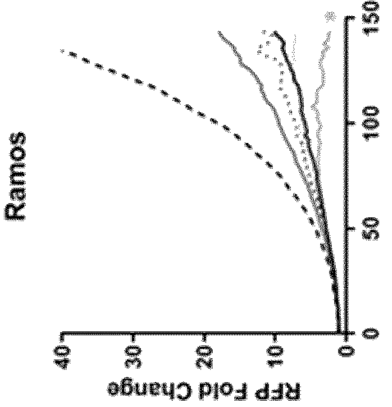
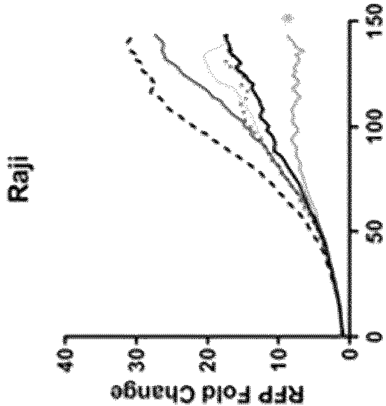
Figure 11

ANTI-CD22 SINGLE DOMAIN ANTIBODIES AND THERAPEUTIC CONSTRUCTS

CROSS REFERENCE TO RELATED APPLICATIONS

This application claims the benefit of priority of U.S. Provisional Application No. 63/058,203 entitled "ANTI-CD22 SINGLE DOMAIN ANTIBODIES AND THERAPEUTIC CONSTRUCTS" and filed Jul. 29, 2020, the contents of which are hereby incorporated by reference.

SEQUENCE LISTING

This application incorporates by reference the Sequence Listing submitted in Computer Readable Form as file "PAT 108623W-1 Updated Sequence Listing.txt", created on Sep. 5, 2024 and containing 73,398 bytes.

FIELD

The present disclosure relates generally to anti-CD22 antibodies. More particularly, the present disclosure relates to anti-CD22 single domain antibodies.

BACKGROUND

Cancer is a major public health problem and the second leading cause of death worldwide. Traditional therapy for cancer has included surgery, radiation and chemotherapy. These have been moderately successful for treatment of some cancers, particularly those diagnosed at early stages. However effective therapy is lacking for many aggressive cancers. Recent technological innovations suggest that immunotherapy (stimulating or restoring a patient's own immune system to fight cancer) can potentially provide potent and long term responses against many cancers including aggressive hard to treat cancers.

Immunotherapy has had phenomenal success in treating hematologic cancers leading to the regulatory approval of numerous forms of these therapies; therapeutic antibodies (i.e. multiple approved monoclonal antibodies targeting CD20, CD30, CD33 and CD52), antibody-drug conjugates targeting CD22 and CD33, and multivalent antibodies such bi-specific T cell engagers (Blinatumomab targeting CD19 on B cells).

Such antibodies have also found use in therapeutic constructs.

For example, bi-specific T cell engagers, and bi- and tri-specific killer cell engagres (BiKEs and TriKEs) incorporating single-chain variable fragments (scFvs) have been developed to direct a host's immune system to target cancer cell.

Chimeric Antigen Receptor (CAR) constructs have been produced to combined facets of T cell activation into a single protein. These molecules link an extracellular antigen recognition domain to an intracellular signaling domain, which activates the T cell when an antigen is bound.

Chimeric Antigen Receptor (CAR) modified immune cell therapies are an emergent form of cancer immunotherapy whereby single or multiple antigen binding domains from antibodies that specifically target cell surface protein(s) on cancer cells are combined with immune cell activating domains to generate "armored" Immune cells that seek and kill specific cells that harbor the targeting antigen(s). CAR modified T cell therapies (CAR-T) have provided unprecedented responses for patients suffering from incurable, aggressive forms of B cell leukemia and lymphoma leading to the FDA and Health Canada approval of CD19-targeted CAR-T cell products, such as Tisangenlecleucel (Kymriah®) and axicabtagene ciloleucel (Yescarta®) for the treatment of relapsed or refractory pediatric and young adult patients with B-cell ALL, adult patients with relapsed or refractory large B-cell lymphoma including diffuse large B-cell lymphoma (DLBCL) not otherwise specified, primary mediastinal large B-cell lymphoma, high grade B-cell lymphoma, and DLBCL arising from follicular lymphoma. While these CD19-targeted CAR therapies have significant clinical value, responses are not always long-lasting and post CAR-T relapse remains a problem, with overt loss of CD19-antigen on the leukemia cells occurring in approximately one third of cases of post CAR-T relapse. Development of new CAR receptors targeting leukemia antigens other than CD19 is an area of active investigation, with similar B-cell restricted antigens such as CD22 or CD20 showing strong promise as alternative targets for CAR-T therapy. Additionally, molecular optimization of the signaling properties of CD22-targeted CAR-T receptors has strong potential to lead to better therapeutic response rates, and the use of multiple CAR therapeutics targeting different B-cell restricted antigens has been shown to be an effective strategy to improve treatment outcomes.

For example, currently, patients with relapsed and chemotherapy refractory B-cell malignancy (a cluster of diseases that includes various forms of leukemia and lymphoma) are candidates for CD19-targeted CAR-T therapy. While the response statistics vary depending on the specific clinical application of CAR-T therapy, on average more than half of adult patients will relapse after CD19-targeted therapy.

It is, therefore, desirable to provide immunogenic molecules with affinity for therapeutic targets relevant to cancer.

SUMMARY

It is an object of the present disclosure to obviate or mitigate at least one disadvantage of previous approaches.

In one aspect, there is provided an isolated single domain antibody (sdAb), which binds specifically to human CD22, the sdAb comprising:

a) a CDR1 amino acid sequence $GX_1X_2X_3DX_4YX_5$ (SEQ ID NO: 126), wherein:
   - $X_1$ is F or V,
   - $X_2$ is T or S,
   - $X_3$ is L, F, or S,
   - $X_4$ is Y, D, or S, and
   - $X_5$ is V or A, a CDR2 amino acid sequence $X_6X_7X_8X_9X_{10}GX_{11}T$ (SEQ ID NO: 127), wherein:
   - $X_6$ is I or M,
   - $X_7$ is T, R, G, or S,
   - $X_8$ is S or N,
   - $X_9$ is D or S,
   - $X_{10}$ is D or is absent,
   - $X_{11}$ is V or A, and a CDR3 amino acid sequence $AVDKPFYDGGX_{12}X_{13}YTCPVDFX_{14}S$ (SEQ ID NO: 128), wherein:
   - $X_{12}$ is I, N, Y, or S,
   - $X_{13}$ is Q, Y, R, or L, and
   - $X_{14}$ is D or G;

b) a CDR1 amino acid sequence $GSX_1F X_2X_3X_4 X_5V$ (SEQ ID NO: 129), wherein:
$X_1$ is I or T,
$X_2$ is R or is absent,
$X_3$ is R, S, or I,
$X_4$ is I, S, or T, and
$X_5$ is A, S, or T.
a CDR2 amino acid sequence $ITSX_6GX_7X_8$ (SEQ ID NO: 130), wherein:
$X_6$ is G, S, or A,
$X_7$ is E, D, or S,
$X_8$ is T or S, and
a CDR3 amino acid sequence $NAX_9X_{10}GX_{11}X_{12}X_{13}X_{14}$ (SEQ ID NO: 131), wherein:
$X_9$ is K or Q,
$X_{10}$ is W or Y.
$X_{11}$ is Q, R, or G,
$X_{12}$ is Y, D, or R,
$X_{13}$ is E or S, and
$X_{14}$ is Y, D, or H;
c) a CDR1 amino acid sequence $GRIX_1RSYV$ (SEQ ID NO: 132), wherein:
$X_1$ is F or S,
a CDR2 amino acid sequence $IGX_2SDT$ (SEQ ID NO: 133), wherein:
$X_2$ is W or C, and
a CDR3 amino acid sequence $AX_3X_4SPPYGPQRDEFX_5Y$ (SEQ ID NO: 134), wherein:
$X_3$ is A or E,
$X_4$ is N or Y, and
$X_5$ is G or D;
d) a CDR1 amino acid sequence G $X_1TX_2SVYX_3$ (SEQ ID NO: 135), wherein:
$X_1$ is R or G,
$X_2$ is S or F, and
$X_3$ is G or T,
a CDR2 amino acid sequence $X_4X_5X_6SX_7GX_8T$ (SEQ ID NO: 136), wherein:
$X_4$ is M or I,
$X_5$ is S or R,
$X_6$ is W or G,
$X_7$ is G or is absent, and
$X_8$ is P or G,
a CDR3 amino acid sequence $AVRIRRTLX_9EPLTKETLYDY$ (SEQ ID NO: 137), wherein:
$X_9$ is L or V;
e) a CDR1 amino acid sequence as set forth in SEQ ID NO: 49,
a CDR2 amino acid sequence as set forth in SEQ ID NO: 50, and
a CDR3 amino acid sequence as set forth in SEQ ID NO: 51;
f) a CDR1 amino acid sequence as set forth in SEQ ID NO: 4,
a CDR2 amino acid sequence as set forth in SEQ ID NO: 5, and
a CDR3 amino acid sequence as set forth in SEQ ID NO: 6;
g) a CDR1 amino acid sequence as set forth in SEQ ID NO: 7,
a CDR2 amino acid sequence as set forth in SEQ ID NO: 8, and
a CDR3 amino acid sequence as set forth in SEQ ID NO: 9;
h) a CDR1 amino acid sequence as set forth in SEQ ID NO: 13,
a CDR2 amino acid sequence as set forth in SEQ ID NO: 14, and
a CDR3 amino acid sequence as set forth in SEQ ID NO: 15;
i) a CDR1 amino acid sequence as set forth in SEQ ID NO: 16,
a CDR2 amino acid sequence as set forth in SEQ ID NO: 17, and
a CDR3 amino acid sequence as set forth in SEQ ID NO: 18;
j) a CDR1 amino acid sequence as set forth in SEQ ID NO: 40,
a CDR2 amino acid sequence as set forth in SEQ ID NO: 41, and
a CDR3 amino acid sequence as set forth in SEQ ID NO: 42;
k) a CDR1 amino acid sequence as set forth in SEQ ID NO: 55,
a CDR2 amino acid sequence as set forth in SEQ ID NO: 56, and
a CDR3 amino acid sequence as set forth in SEQ ID NO: 57;
l) a CDR1 amino acid sequence as set forth in SEQ ID NO: 64,
a CDR2 amino acid sequence as set forth in SEQ ID NO: 65, and
a CDR3 amino acid sequence as set forth in SEQ ID NO: 66; or
m) a CDR1 amino acid sequence as set forth in SEQ ID NO: 70,
a CDR2 amino acid sequence as set forth in SEQ ID NO: 71, and
a CDR3 amino acid sequence as set forth in SEQ ID NO: 72.

In the above:
group a) provides consensus sequences defined by antibodies herein termed hCD221ug-80, hCD22100 ng-2, hCD221ug-74, hCD22100 ng-66, hCD221ug-6, hCD22pas-10, hCD22pass-33,
group b) provides consensus sequences defined by antibodies herein termed hCD221ug-77, hCD221ug-87, hCD221ug-75, hCD221ug-93, hCD22pas-82, and hCD22pas-23,
group c) provides consensus sequences defined by antibodies herein termed hCD22pas-32, hCD221ug-14, and hCD22pas-55,
group d) provides consensus sequences defined by antibodies herein termed hCD22pas-79 and hCD22pas-72,
group f) is defined by CDRs from the antibody termed hCD22pas-16,
group f) is defined by CDRs from the antibody termed hCD221ug-10,
group g) is defined by CDRs from the antibody termed hCD221ug-13,
group h) is defined by CDRs from the antibody termed hCD221ug-36,
group i) is defined by CDRs from the antibody termed hCD221ug-61,
group j) is defined by CDRs from the antibody termed hCD22100ug-62,
group k) is defined by CDRs from the antibody termed hCD22pas-24,
group l) is defined by CDRs from the antibody termed hCD22pas-48, and group m) is defined by CDRs from the antibody termed hCD22pas-64.

In another aspect, there is provide an isolated VHH single domain antibody (sdAb), which binds specifically to human CD22, the sdAb comprising:

A)

a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6), a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10), a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13), a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14), a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36), a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61), a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74), a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75), a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77), a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80), a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87), a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93), a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2), a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62), a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66), a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10), a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16), a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23), a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24), a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32), a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33), a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48), a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55), a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64), a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72), a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79), or a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82).

In another aspect, there is provided an isolated VHH single domain antibody (sdAb), which binds specifically to human CD22, the sdAb comprising

A)

a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6), a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10), a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13), a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14), a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36), a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61), a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74), a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75), a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77), a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80), a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87), a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93), a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2), a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62), a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66), a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10), a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16), a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23), a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24), a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32), a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33), a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48), a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55), a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64), a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72), a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79), or a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82); or

B)

CDR1, CDR2, and CDR3 amino acid sequences that are at least 80% identical to the CDR1, CDR2, and CDR3 sequences defined in any one of part A) i) to xxviii).

In another aspect, there is provided an isolated VHH single domain antibody (sdAb), which binds specifically to human CD22, the sdAb comprising:

A)

a CDR3 amino acid sequence as set forth in SEQ ID NO: 3, a CDR3 amino acid sequence as set forth in SEQ ID NO: 6, a CDR3 amino acid sequence as set forth in SEQ ID NO: 9, a CDR3 amino acid sequence as set forth in SEQ ID NO: 12, a CDR3 amino acid sequence as set forth in SEQ ID NO: 15, a CDR3 amino acid sequence as set forth in SEQ ID NO: 18, a CDR3 amino acid sequence as set forth in SEQ ID NO: 21, a CDR3 amino acid sequence as set forth in SEQ ID NO: 24, a CDR3 amino acid sequence as set forth in SEQ ID NO: 27, a CDR3 amino acid sequence as set forth in SEQ ID NO: 30, a CDR3 amino acid sequence as set forth in SEQ ID NO: 33, a CDR3 amino acid sequence as set forth in SEQ ID NO: 36, a CDR3 amino acid sequence as set forth in SEQ ID NO: 39, a CDR3 amino acid sequence as set forth in SEQ ID NO: 42, a CDR3 amino acid sequence as set forth in SEQ ID NO: 45, a CDR3 amino acid sequence as set forth in SEQ ID NO: 48, a CDR3 amino acid sequence as set forth in SEQ ID NO: 51, a CDR3 amino acid sequence as set forth in SEQ ID NO: 54, a CDR3 amino acid sequence as set forth in SEQ ID NO: 57, a CDR3 amino acid sequence as set forth in SEQ ID NO: 60, a CDR3 amino acid sequence as set forth in SEQ ID NO: 63, a CDR3 amino acid sequence as set forth in SEQ ID NO: 66, a CDR3 amino acid sequence as set forth in SEQ ID NO: 69, a CDR3 amino acid sequence as set forth in SEQ ID NO: 72, a CDR3 amino acid sequence as set forth in SEQ ID NO: 75, a CDR3 amino acid sequence as set forth in SEQ ID NO: 79, or a CDR3 amino acid sequence as set forth in SEQ ID NO: 81.

In one embodiment, the isolated sdAb comprises:

a CDR1 amino acid sequence as set forth in SEQ ID NO: 1, and a CDR3 amino acid sequence as set forth in SEQ ID NO: 3, a CDR1 amino acid sequence as set forth in SEQ ID NO: 4, and a CDR3 amino acid sequence as set forth in SEQ ID NO: 6, a CDR1 amino acid sequence as set forth in SEQ ID NO: 7, and a CDR3 amino acid sequence as set forth in SEQ ID NO: 9, a CDR1 amino acid sequence as set forth in SEQ ID NO: 10, and a CDR3 amino acid sequence as set forth in SEQ ID NO: 12, a CDR1 amino acid sequence as set forth in SEQ ID NO: 13, and a CDR3 amino acid sequence as set forth in SEQ ID NO: 15, a CDR1 amino acid sequence as set forth in SEQ ID NO: 16, and a CDR3 amino acid sequence as set forth in SEQ ID NO: 18, a CDR1 amino acid sequence as set forth in SEQ ID NO: 19, and a CDR3 amino acid sequence as set forth in SEQ ID NO: 21, a CDR1 amino acid sequence as set forth in SEQ ID NO: 22, and a CDR3 amino acid sequence as set forth in SEQ ID NO: 24, a CDR1 amino acid sequence as set forth in SEQ ID NO: 25, and a CDR3 amino acid sequence as set forth in SEQ ID NO: 27, a CDR1 amino acid sequence as set forth in SEQ ID NO: 28, and a CDR3 amino acid sequence as set forth in SEQ ID NO: 30, a CDR1 amino acid sequence as set forth in SEQ ID NO: 31, and a CDR3 amino acid sequence as set forth in SEQ ID NO: 33, a CDR1 amino acid sequence as set forth in SEQ ID NO: 34, and a CDR3 amino acid sequence as set forth in SEQ ID NO: 36, a CDR1 amino acid sequence as set forth in SEQ ID NO: 37, and a CDR3 amino acid sequence as set forth in SEQ ID NO: 39, a CDR1 amino acid sequence as set forth in SEQ ID NO: 40, and a CDR3 amino acid sequence as set forth in SEQ ID NO: 42, a CDR1 amino acid sequence as set forth in SEQ ID NO: 43, and a CDR3 amino acid sequence as set forth in SEQ ID NO: 45, a CDR1 amino acid sequence as set forth in SEQ ID NO: 46, and a CDR3 amino acid sequence as set forth in SEQ ID NO: 48, a CDR1 amino acid sequence as set forth in SEQ ID NO: 49, and a CDR3 amino acid sequence as set forth in SEQ ID NO: 51, a CDR1 amino acid sequence as set forth in SEQ ID NO: 52, and a CDR3 amino acid sequence as set forth in SEQ ID NO: 54, a CDR1 amino acid sequence as set forth in SEQ ID NO: 55, and a CDR3 amino acid sequence as set forth in SEQ ID NO: 57.

a CDR1 amino acid sequence as set forth in SEQ ID NO: 58, and a CDR3 amino acid sequence as set forth in SEQ ID NO: 60, a CDR1 amino acid sequence as set forth in SEQ ID NO: 61, and a CDR3 amino acid sequence as set forth in SEQ ID NO: 63, a CDR1 amino acid sequence as set forth in SEQ ID NO: 64, and a CDR3 amino acid sequence as set forth in SEQ ID. NO: 66, a CDR1 amino acid sequence as set forth in SEQ ID NO: 67, and a CDR3 amino acid sequence as set forth in SEQ ID NO: 69, a CDR1 amino acid sequence as set forth in SEQ ID NO: 70, and a CDR3 amino acid sequence as set forth in SEQ ID NO: 72, a CDR1 amino acid sequence as set forth in SEQ ID NO: 73, and a CDR3 amino acid sequence as set forth in SEQ ID NO: 75, a CDR1 amino acid sequence as set forth in SEQ ID NO: 76, and a CDR3 amino acid sequence as set forth in SEQ ID NO: 78, or a CDR1 amino acid sequence as set forth in SEQ ID NO: 79, and a CDR3 amino acid sequence as set forth in SEQ ID NO: 81.

In one aspect, there is provided a VHH single domain antibody (sdAb) that competes for specific binding to CD22 with the isolated sdAb described herein.

In one aspect, there is provided a recombinant polypeptide comprising an sdAb as defined herein.

In a further aspect, the present disclosure provides anti-CD22 sdAb as defined herein linked to a cargo molecule.

In aspect, there is provided a recombinant nucleic acid molecule encoding an sdAb, the recombinant polypeptide, or the $V_H H:F_c$ fusion as defined herein.

In one aspect, there is provided a composition comprising an sdAb as defined herein, or a polypeptide comprising such an sdAb; together with an acceptable excipient, diluent or carrier.

In one aspect, there is provided a use of the sdAb as defined herein or of an antibody comprising one or more $V_H H:F_c$ fusion as defined herein for treatment of a cancer or an auto-immune disease.

In one aspect, there is provided a use of the sdAb as defined herein or of an antibody comprising one or more $V_H H:F_c$ fusion as defined herein for preparation of a medicament for treatment of a cancer or an auto-immune disease.

In one aspect, there is provided the sdAb as defined herein or of an antibody comprising one or more $V_H H:F_c$ fusion as defined herein for use in treatment of a cancer or an auto-immune disease.

In one aspect, there is provided a method of treating a cancer or an auto-immune disease in subject comprising administering to the subject the sdAb as defined herein or of an antibody comprising one or more $V_HH:F_c$ fusion as defined herein.

In one aspect, there is provided a multivalent antibody comprising an sdAb as defined herein.

In one aspect, there is provided a multivalent antibody comprising: a first antigen-binding portion, an amino acid linker comprising a polypeptide hinge from human CD8, and a second antigen-binding portion.

In aspect, there is provided a recombinant nucleic acid molecule encoding the multivalent antibody as defined herein.

In one aspect, there is provided a composition comprising a multivalent antibody as defined herein; together with an acceptable excipient, diluent or carrier.

In one aspect, there is provided a use of the multivalent antibody as defined herein for treatment of a cancer or auto-immune disease. In one embodiment, the cancer is a hematological malignancy.

In one aspect, there is provided a use of the multivalent antibody as defined herein for preparation of a medicament for treatment of a cancer or auto-immune disease.

In one aspect, there is provided the multivalent antibody as defined herein for use in treatment of a cancer or auto-immune disease. In one embodiment, the cancer is a hematological malignancy.

In one aspect, there is provided a method of treating a cancer or auto-immune disease in subject comprising administering to the subject the multivalent antibody as defined herein.

In one aspect, there is provided a chimeric antibody receptor (CAR), which binds to human CD22, comprising the VHH sdAb as defined herein.

In one aspect, there is provided a recombinant nucleic acid molecule encoding the CAR as defined herein.

In one aspect, there is provided a vector comprising the recombinant nucleic acid molecule as defined herein.

In one aspect, there is provided a recombinant viral particle comprising the recombinant nucleic acid as defined herein.

In one aspect, there is provided a cell comprising the recombinant nucleic acid molecule as defined herein.

In one aspect, there is providing a use of the nucleic acid, vector, or viral particle as described herein for preparation of cells for CAR-T.

In one aspect, there is providing a method of preparing cells for CAR-T comprising contacting a T-cell with the viral particle as described herein.

In one aspect, there is providing a method of preparing cells for CAR-T comprising introducing into a T-cell the nucleic acid or vector as described herein.

In one aspect, there is provided a use of the CAR or of the engineered cell as described herein for treatment of a cancer or an auto-immune disease.

In one aspect, there is provided a use of the CAR or of the engineered cell as described herein for preparation of a medicament treatment of a cancer or an auto-immune disease.

In one aspect, there is provided the CAR or the engineered cell as described herein for use in treatment of a cancer or an auto-immune disease.

In one aspect there is provided a method of treating a cancer or an auto-immune disease in a subject, comprising administering to the subject the engineered cell as defined herein.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 4A depicts the first part of an alignment of amino acid sequences of 27 VHHs. The CDR sequences VHHs with discernable sequence similarity across the CDRs are boxed.

FIG. 4B depicts the second part of the alignment of sequences of the 27 VHHs, continuing on from FIG. 4A.

FIG. 11 depicts the results of CAR-T antigen-specific target cell growth repression assay performed using donor blood derived T cells transduced with varying CD22-single domain antibody or control (FMC63) CAR constructs as described herein. Mock refers to unmodified donor derived T cells without CAR expression exposed to similar treatment conditions. CAR-T cells were placed in co-culture with CD22+ target cells (left graph—Raji, middle graph—Ramos targets), or with CD22-negative target cells (right graph—Ramos-CD22ko targets) and examined via live fluorescent microscopy.

DETAILED DESCRIPTION

Figure 1:
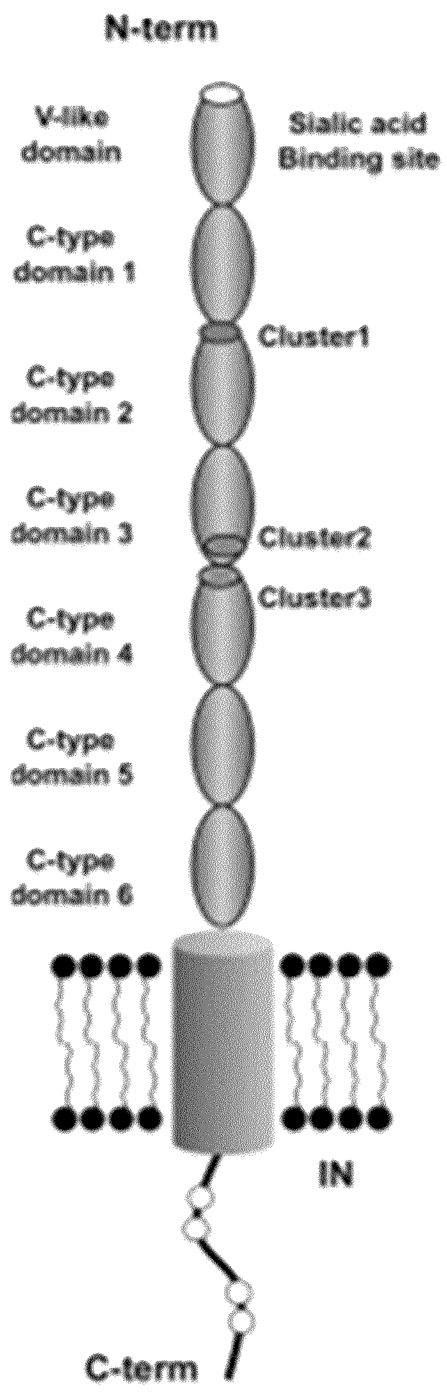
FIG. 1 depicts the structure of human CD22 molecule which is encoded by the CD22 gene located on chromosome 19q13.12.

Generally, the present disclosure provides anti-CD22 single domain antibodies (sdAb) prepared by immunizing a llama with the extracellular domain of the predominant human CD22 isoform. By constructing a library of the heavy chain repertoire, VHH antibody domains specific to the immunogen were isolated by phage panning. The 27 example antibodies initially produced comprise CDR1, CDR2, and CDR3 sequences corresponding, respectively to SEQ NOs: 1-3, 4-6, 7-9, 10-12, 13-15, 16-18, 19-21, 22-24, 25-27, 28-30, 31-33, 34-36, 37-39, 40-42, 43-45, 46-48, 49-51, 52-54, 55-57, 58-60, 61-63, 64-66, 67-69, 70-72, 73-75, 75-78, and 79-81, though antibodies having related sequences are described and encompassed. Also provided are multivalent antibodies comprising any one of the sdAbs, including bispecific T-cell engagers, bispecific killer cell engagers (BIKEs), and trispecific killer cell engagers (TrikEs). Also described are chimeric antigen receptors (CARs) for CAR-T therapy comprising any one of the aforementioned sdAbs.

Single Domain Antibodies & Polypeptides Comprising them

A Single domain antibody (sdAb), also known as a nanobody, is an antibody fragment consisting of a single monomeric variable antibody domain. sdAbs have been derived from heavy-chain antibodies found in Camelidae species (such as camel, llama, dromedary, alpaca and guanaco) using molecular biology techniques, which are also known as $V_HH$ fragments (herein also termed "$V_HH$" or "VHH"). Other examples include $V_{NAR}$ fragments derived from heavy chain antibodies found in cartilaginous fish, such as sharks. sdAbs have also been generated from a heavy chain/light chain of conventional immunoglobulin G (IgGs) by engineering techniques.

$V_HH$ molecules are about 10 times smaller than IgG molecules. These single polypeptides are generally quite stable, often resisting extreme pH and temperature conditions that can be problematic for conventional antibodies and antibody fragments. Moreover, $V_HHs$ tend to be more resistant to the action of proteases. Furthermore, in vitro expression of VHHs tends to produce high yield of properly folded/functional VHHs. In addition, heavy chain antibodies and their engineered fragments (i.e., VHHs) generated in Camelidae species may recognize cryptic or hidden epitopes which otherwise inaccessible to larger conventional antibodies and antibody fragments generated in vitro through the use of antibody libraries or by immunization of other mammals.

In one aspect, there is provided an isolated single domain antibody (sdAb), which binds specifically to human CD22, the sdAb comprising:

a) a CDR1 amino acid sequence $GX_1X_2X_3DX_4YX_5$ (SEQ ID NO: 126), wherein:
   - $X_1$ is F or V,
   - $X_2$ is T or S,
   - $X_3$ is L, F, or S,
   - $X_4$ is Y, D, or S, and
   - $X_5$ is V or A, a CDR2 amino acid sequence $X_6X_7X_8X_9X_{10}GX_{11}T$ (SEQ ID NO: 127), wherein:
   - $X_6$ is I or M,
   - $X_7$ is T, R, G, or S,
   - $X_8$ is S or N,
   - $X_9$ is D or S, $X_{10}$ is D or is absent, $X_{11}$ is V or A, and a CDR3 amino acid sequence AVDKPFYDGG$X_{12}X_{13}$YTCPVDF$X_{14}$S (SEQ ID NO: 128), wherein:

$X_{12}$ is I, N, Y, or S, $X_{13}$ is Q, Y, R, or L, and $X_{14}$ is D or G;

b) a CDR1 amino acid sequence GS$X_1$F $X_2X_3X_4$ $X_3$V (SEQ ID NO: 129), wherein:

$X_1$ is I or T, $X_2$ is R or is absent, $X_3$ is R, S, or I, $X_4$ is I, S, or T, and $X_5$ is A, S, or T;

a CDR2 amino acid sequence ITS$X_6$G$X_7X_8$ (SEQ ID NO: 130), wherein:

$X_6$ is G, S, or A, $X_7$ is E, D, or S, $X_8$ is T or S, and a CDR3 amino acid sequence NA$X_9X_{10}$G$X_{11}X_{12}X_{13}X_{14}$ (SEQ ID NO: 131), wherein:

$X_9$ is Kor Q, $X_{10}$ is W or Y, $X_{11}$ is Q, R, or G, $X_{12}$ is Y, D, or R, $X_{13}$ is E or S, and $X_{14}$ is Y, D, or H;

c) a CDR1 amino acid sequence GRI$X_1$RSYV (SEQ ID NO: 132), wherein:

$X_1$ is F or S, a CDR2 amino acid sequence IG$X_2$SDT (SEQ ID NO: 133), wherein:

$X_2$ is W or C, and a CDR3 amino acid sequence A$X_3X_4$SPPYGPQRDEF$X_5$Y (SEQ ID NO: 134), wherein:

$X_3$ is A or E, $X_4$ is N or Y, and $X_5$ is G or D;

d) a CDR1 amino acid sequence G $X_1$T$X_2$SVY$X_3$ (SEQ ID NO: 135), wherein:

$X_1$ is R or G, $X_2$ is S or F, and $X_3$ is G or T, a CDR2 amino acid sequence $X_4X_5X_6$S$X_7$G$X_8$T (SEQ ID NO: 136), wherein:

$X_4$ is M or I, $X_5$ is S or R, $X_6$ is W or G, $X_7$ is G or is absent, and $X_8$ is P or G, a CDR3 amino acid sequence AVRIRRTL$X_9$EPLTKETLYDY (SEQ ID NO: 137), wherein:

$X_9$ is L or V;

e) a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51;

f) a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6;

g) a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9;

h) a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15;

i) a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18;

j) a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42;

k) a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57;

l) a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66; or m) a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72.

In the above:

group a) provides consensus sequences defined by antibodies herein termed hCD221ug-80, hCD22100 ng-2, hCD221ug-74, hCD22100 ng-66, hCD221ug-6, hCD22pas-10, hCD22pass-33, group b) provides consensus sequences defined by antibodies herein termed hCD221ug-77, hCD221ug-87, hCD221ug-75, hCD221ug-93, hCD22pas-82, and hCD22pas-23.

group c) provides consensus sequences defined by antibodies herein termed hCD22pas-32, hCD221ug-14, and hCD22pas-55, group d) provides consensus sequences defined by antibodies herein termed hCD22pas-79 and hCD22pas-72, group f) is defined by CDRs from the antibody termed hCD22pas-16, group f) is defined by CDRs from the antibody termed hCD221ug-10, group g) is defined by CDRs from the antibody termed hCD221ug-13, group h) is defined by CDRs from the antibody termed hCD221ug-36, group i) is defined by CDRs from the antibody termed hCD221ug-61, group j) is defined by CDRs from the antibody termed hCD22100ug-62, group k) is defined by CDRs from the antibody termed hCD22pas-24, group l) is defined by CDRs from the antibody termed hCD22pas-48, and group m) is defined by CDRs from the antibody termed hCD22pas-64.

"CDRs" or "complementarity-determining regions" are the portion of the variable chains in immunoglobulins that collectively constitute the paratope, and thereby impart binding specificity and affinity to the antibody. As used here, the term refers to CDRs mapped in sdAbs according to the standards or conventions set by IMGT™ (international ImMunoGeneTics information system).

The antibodies described herein have been raised to the recombinant extracellular domain (ECD) of the predominant human CD22-beta isoform. An example mRNA sequence for this isoform may be found in GenBank entry NM_001771.4, wherein amino acids 1-19 of the encoded protein correspond to a leader sequence, and amino acids 20-687 correspond to the ECD (see also UniProt entry P20273).

In another aspect, there is provide an isolated VHH single domain antibody (sdAb), which binds specifically to human CD22, the sdAb comprising:

A)

a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6), a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10), a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13), a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14), a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36), a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61), a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74), a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75), a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77), a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80), a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87), a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93), a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2), a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62), a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66), a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10), a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16), a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23), a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24), a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32), a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33), a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48), a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55), a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64), a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72), a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79), or a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82).

In one embodiment, the antibody comprises a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6).

In one embodiment, the antibody comprises a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10).

In one embodiment, the antibody comprises a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13).

In one embodiment, the antibody comprises a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14).

In one embodiment, the antibody comprises a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36).

In one embodiment, the antibody comprises a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61).

In one embodiment, the antibody comprises a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74)

In one embodiment, the antibody comprises a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75).

In one embodiment, the antibody comprises a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77).

In one embodiment, the antibody comprises a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80).

In one embodiment, the antibody comprises a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87).

In one embodiment, the antibody comprises a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93).

In one embodiment, the antibody comprises a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2).

In one embodiment, the antibody comprises a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62).

In one embodiment, the antibody comprises a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66).

In one embodiment, the antibody comprises a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10).

In one embodiment, the antibody comprises a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16).

In one embodiment, the antibody comprises a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23).

In one embodiment, the antibody comprises a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24).

In one embodiment, the antibody comprises a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32).

In one embodiment, the antibody comprises a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33).

In one embodiment, the antibody comprises a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48).

In one embodiment, the antibody comprises a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55).

In one embodiment, the antibody comprises a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64).

In one embodiment, the antibody comprises a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72).

In one embodiment, the antibody comprises a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79).

In one embodiment, the antibody comprises a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82).

In another aspect, there is provided an isolated VHH single domain antibody (sdAb), which binds specifically to human CD22, the sdAb comprising:

A)

a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6), a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10), a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13), a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14), a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36), a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61), a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74), a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75), a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77), a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80), a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87), a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93), a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2), a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62), a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66), a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10), a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16), a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23), a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24), a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32), a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33), a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48), a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55), a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64), a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72), a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79), or a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82); or

B)

CDR1, CDR2, and CDR3 amino acid sequences that are at least 80% identical to the CDR1, CDR2, and CDR3 sequences defined in any one of part A) i) to xxviii).

In one embodiment, in B) the CDR 1 CDR2, and CDR3 amino acid sequences are at least 90% identical to the CDR1, CDR2, and CDR3 sequences defined in any one of part A) i) to xxviii). In one embodiment, in B) the CDR 1 CDR2, and CDR3 amino acid sequences are at least 95% identical to the CDR1, CDR2, and CDR3 sequences defined in any one of part A) i) to xxviii). In one embodiment, in B) the CDR 1 CDR2, and CDR3 amino acid sequences have at most three substitutions compared to the CDR1, CDR2, and CDR3 sequences defined in any one of part A) i) to xxviii). In one embodiment, in B) the CDR 1 CDR2, and CDR3 amino acid sequences have at most two substitutions compared to the CDR1, CDR2, and CDR3 sequences defined in any one of part A) i) to xxviii). In one embodiment, in B) the CDR 1 CDR2, and CDR3 amino acid sequences have at most one substitution compared to the CDR1, CDR2, and CDR3 sequences defined in any one of part A) i) to xxviii). In some embodiment, sequence differences vs. the sequences set forth in A) are conservative sequence substitutions.

The term "conservative amino acid substitutions" which is known in the art is defined herein as follows, with conservative substitutable candidate amino acids showing in parentheses: Ala (Gly, Ser); Arg (Gly, Gin); Asn (Gin; His); Asp (Glu); Cys (Ser); Gin (Asn, Lys); Glu (Asp); Gly (Ala, Pro); His (Asn; Gln); Ile (Leu; Val); Leu (Ile; Val); Lys (Arg; Gln); Met (Leu, Ile); Phe (Met, Leu, Tyr); Ser (Thr; Gly); Thr (Ser; Val); Trp (Tyr); Tyr (Trp; Phe); Val (Ile; Leu).

Sequence variants according to certain embodiments are intended to encompass molecules in which binding affinity and/or specificity is substantially unaltered vs. the parent molecule from which it is derived. Such parameters can be readily tested, e.g., using techniques described herein and techniques known in the art. Such embodiments may encompass sequence substitutions, insertions, or deletions.

In another aspect, there is provided an isolated VHH single domain antibody (sdAb), which binds specifically to human CD22, the sdAb comprising:

A)

a CDR3 amino acid sequence as set forth in SEQ ID NO: 3, a CDR3 amino acid sequence as set forth in SEQ ID NO: 6, a CDR3 amino acid sequence as set forth in SEQ ID NO: 9, a CDR3 amino acid sequence as set forth in SEQ ID NO: 12, a CDR3 amino acid sequence as set forth in SEQ ID NO: 15, a CDR3 amino acid sequence as set forth in SEQ ID NO: 18, a CDR3 amino acid sequence as set forth in SEQ ID NO: 21, a CDR3 amino acid sequence as set forth in SEQ ID NO: 24, a CDR3 amino acid sequence as set forth in SEQ ID NO: 27, a CDR3 amino acid sequence as set forth in SEQ ID NO: 30, a CDR3 amino acid sequence as set forth in SEQ ID NO: 33, a CDR3 amino acid sequence as set forth in SEQ ID NO: 36, a CDR3 amino acid sequence as set forth in SEQ ID NO: 39, a CDR3 amino acid sequence as set forth in SEQ ID NO: 42, a CDR3 amino acid sequence as set forth in SEQ ID NO: 45, a CDR3 amino acid sequence as set forth in SEQ ID NO: 48, a CDR3 amino acid sequence as set forth in SEQ ID NO: 51, a CDR3 amino acid sequence as set forth in SEQ ID NO: 54, a CDR3 amino acid sequence as set forth in SEQ ID NO: 57, a CDR3 amino acid sequence as set forth in SEQ ID NO: 60, a CDR3 amino acid sequence as set forth in SEQ ID NO: 63, a CDR3 amino acid sequence as set forth in SEQ ID NO: 66, a CDR3 amino acid sequence as set forth in SEQ ID NO: 69, a CDR3 amino acid sequence as set forth in SEQ ID NO: 72, a CDR3 amino acid sequence as set forth in SEQ ID NO: 75, a CDR3 amino acid sequence as set forth in SEQ ID NO: 79, or a CDR3 amino acid sequence as set forth in SEQ ID NO: 81.

Recognizing that CDR3 is often the major determinant of binding for $V_H$H sdAbs, it would be understood that other CDRs could be mutagenized or otherwise diversified and a resulting library (or candidate molecule) screened for antibodies that bind to CD22 and/or cross-compete for binding to CD22 with the parent molecule. These embodiments are intended to cover, inter alia, molecules identified in this manner.

In one embodiment, the isolated sdAb comprises:

a CDR1 amino acid sequence as set forth in SEQ ID NO: 1, and a CDR3 amino acid sequence as set forth in SEQ ID NO: 3, a CDR1 amino acid sequence as set forth in SEQ ID NO: 4, and a CDR3 amino acid sequence as set forth in SEQ ID NO: 6, a CDR1 amino acid sequence as set forth in SEQ ID NO: 7, and a CDR3 amino acid sequence as set forth in SEQ ID NO: 9, a CDR1 amino acid sequence as set forth in SEQ ID NO: 10, and a CDR3 amino acid sequence as set forth in SEQ ID NO: 12, a CDR1 amino acid sequence as set forth in SEQ ID NO: 13, and a CDR3 amino acid sequence as set forth in SEQ ID NO: 15, a CDR1 amino acid sequence as set forth in SEQ ID NO: 16, and a CDR3 amino acid sequence as set forth in SEQ ID NO: 18, a CDR1 amino acid sequence as set forth in SEQ ID NO: 19, and a CDR3 amino acid sequence as set forth in SEQ ID NO: 21, a CDR1 amino acid sequence as set forth in SEQ ID NO: 22, and a CDR3 amino acid sequence as set forth in SEQ ID NO: 24, a CDR1 amino acid sequence as set forth in SEQ ID NO: 25, and a CDR3 amino acid sequence as set forth in SEQ ID NO: 27, a CDR1 amino acid sequence as set forth in SEQ ID NO: 28, and a CDR3 amino acid sequence as set forth in SEQ ID NO: 30, a CDR1 amino acid sequence as set forth in SEQ ID NO: 31, and a CDR3 amino acid sequence as set forth in SEQ ID NO: 33, a CDR1 amino acid sequence as set forth in SEQ ID NO: 34, and a CDR3 amino acid sequence as set forth in SEQ ID NO: 36, a CDR1 amino acid sequence as set forth in SEQ ID NO: 37, and a CDR3 amino acid sequence as set forth in SEQ ID NO: 39, a CDR1 amino acid sequence as set forth in SEQ ID NO: 40, and a CDR3 amino acid sequence as set forth in SEQ ID NO: 42, a CDR1 amino acid sequence as set forth in SEQ ID NO: 43, and a CDR3 amino acid sequence as set forth in SEQ ID NO: 45, a CDR1 amino acid sequence as set forth in SEQ ID NO: 46, and a CDR3 amino acid sequence as set forth in SEQ ID NO: 48, a CDR1 amino acid sequence as set forth in SEQ ID NO: 49, and a CDR3 amino acid sequence as set forth in SEQ ID NO: 51, a CDR1 amino acid sequence as set forth in SEQ ID NO: 52, and a CDR3 amino acid sequence as set forth in SEQ ID NO: 54, a CDR1 amino acid sequence as set forth in SEQ ID NO: 55, and a CDR3 amino acid sequence as set forth in SEQ ID NO: 57, a CDR1 amino acid sequence as set forth in SEQ ID NO: 58, and a CDR3 amino acid sequence as set forth in SEQ ID NO: 60, a CDR1 amino acid sequence as set forth in SEQ ID NO: 61, and a CDR3 amino acid sequence as set forth in SEQ ID NO: 63, a CDR1 amino acid sequence as set forth in SEQ ID NO: 64, and a CDR3 amino acid sequence as set forth in SEQ ID NO: 66, a CDR1 amino acid sequence as set forth in SEQ ID NO: 67, and a CDR3 amino acid sequence as set forth in SEQ ID NO: 69, a CDR1 amino acid sequence as set forth in SEQ ID NO: 70, and a CDR3 amino acid sequence as set forth in SEQ ID NO: 72, a CDR1 amino acid sequence as set forth in SEQ ID NO: 73, and a CDR3 amino acid sequence as set forth in SEQ ID NO: 75, a CDR1 amino acid sequence as set forth in SEQ ID NO: 76, and a CDR3 amino acid sequence as set forth in SEQ ID NO: 78, or a CDR1 amino acid sequence as set forth in SEQ ID NO: 79, and a CDR3 amino acid sequence as set forth in SEQ ID NO: 81.

These embodiments are intended to encompass, inter alia, embodiments in which molecules recovered following mutagenization/diversification of CDR2, and screening for variant molecules that bind to CD22 and/or cross-compete for binding to CD22 with the parent molecule from which they are defined. As above, a library could be screened or individual candidate molecules could be tested.

In one embodiment, sdAb comprises A) the amino acid sequence of any one of SEQ ID NO: 85 to 112 and 120 to 125, or B) an amino acid sequence that is at least 80% identical to any one of SEQ ID NO: 82 to 108 and 120 to 125 across the full length thereof. In one embodiment, the amino acid sequence of B) is at least 85% identical across the full length therefore to one of the amino acid sequences of A). In one embodiment, the amino acid sequence of B) is at least 90% identical across the full length therefore to one of the amino acid sequences of A). In one embodiment, the amino acid sequence of B) is at least 95% identical across the full length therefore to one of the amino acid sequences of A). In one embodiment, the amino acid sequence of B) is at least 98% identical across the full length therefore to one of the amino acid sequences of A). In one embodiment, the amino acid sequence of B) is at least 98% identical across the full length therefore to one of the amino acid sequences of A). In some of these embodiments, sequences differences vs. sequences of A) are outside the CDR sequences.

In one embodiment, the sdAb comprises A) the amino acid sequence of any one of SEQ ID NO: 82 to 108 and 120 to 125.

In one embodiment, the sdAb comprises a CDR1, CDR2, and CDR2 of the sdAb sequence set forth in SEQ ID NO: 82.

In one embodiment, the sdAb comprises a CDR1, CDR2, and CDR2 of the sdAb sequence set forth in SEQ ID NO: 83.

In one embodiment, the sdAb comprises a CDR1, CDR2, and CDR2 of the sdAb sequence set forth in SEQ ID NO: 84.

In one embodiment, the sdAb comprises a CDR1, CDR2, and CDR2 of the sdAb sequence set forth in SEQ ID NO: 85.

In one embodiment, the sdAb comprises a CDR1, CDR2, and CDR2 of the sdAb sequence set forth in SEQ ID NO: 86.

In one embodiment, the sdAb comprises a CDR1, CDR2, and CDR2 of the sdAb sequence set forth in SEQ ID NO: 87.

In one embodiment, the sdAb comprises a CDR1, CDR2, and CDR2 of the sdAb sequence set forth in SEQ ID NO: 88.

In one embodiment, the sdAb comprises a CDR1, CDR2, and CDR2 of the sdAb sequence set forth in SEQ ID NO: 89.

In one embodiment, the sdAb comprises a CDR1, CDR2, and CDR2 of the sdAb sequence set forth in SEQ ID NO: 90.

In one embodiment, the sdAb comprises a CDR1, CDR2, and CDR2 of the sdAb sequence set forth in SEQ ID NO: 91.

In one embodiment, the sdAb comprises a CDR1, CDR2, and CDR2 of the sdAb sequence set forth in SEQ ID NO: 92.

In one embodiment, the sdAb comprises a CDR1, CDR2, and CDR2 of the sdAb sequence set forth in SEQ ID NO: 93.

In one embodiment, the sdAb comprises a CDR1, CDR2, and CDR2 of the sdAb sequence set forth in SEQ ID NO: 94.

In one embodiment, the sdAb comprises a CDR1, CDR2, and CDR2 of the sdAb sequence set forth in SEQ ID NO: 95.

In one embodiment, the sdAb comprises a CDR1, CDR2, and CDR2 of the sdAb sequence set forth in SEQ ID NO: 96.

In one embodiment, the sdAb comprises a CDR1, CDR2, and CDR2 of the sdAb sequence set forth in SEQ ID NO: 97.

In one embodiment, the sdAb comprises a CDR1, CDR2, and CDR2 of the sdAb sequence set forth in SEQ ID NO: 98.

In one embodiment, the sdAb comprises a CDR1, CDR2, and CDR2 of the sdAb sequence set forth in SEQ ID NO: 99.

In one embodiment, the sdAb comprises a CDR1, CDR2, and CDR2 of the sdAb sequence set forth in SEQ ID NO: 100.

In one embodiment, the sdAb comprises a CDR1, CDR2, and CDR2 of the sdAb sequence set forth in SEQ ID NO: 101.

In one embodiment, the sdAb comprises a CDR1, CDR2, and CDR2 of the sdAb sequence set forth in SEQ ID NO: 102.

In one embodiment, the sdAb comprises a CDR1, CDR2, and CDR2 of the sdAb sequence set forth in SEQ ID NO: 103.

In one embodiment, the sdAb comprises a CDR1, CDR2, and CDR2 of the sdAb sequence set forth in SEQ ID NO: 104.

In one embodiment, the sdAb comprises a CDR1, CDR2, and CDR2 of the sdAb sequence set forth in SEQ ID NO: 105.

In one embodiment, the sdAb comprises a CDR1, CDR2, and CDR2 of the sdAb sequence set forth in SEQ ID NO: 106.

In one embodiment, the sdAb comprises a CDR1, CDR2, and CDR2 of the sdAb sequence set forth in SEQ ID NO: 107.

In one embodiment, the sdAb comprises a CDR1, CDR2, and CDR2 of the sdAb sequence set forth in SEQ ID NO: 108.

In one embodiment, the sdAb comprises a CDR1, CDR2, and CDR2 of the sdAb sequence set forth in SEQ ID NO: 120.

In one embodiment, the sdAb comprises a CDR1, CDR2, and CDR2 of the sdAb sequence set forth in SEQ ID NO: 121.

In one embodiment, the sdAb comprises a CDR1, CDR2, and CDR2 of the sdAb sequence set forth in SEQ ID NO: 122.

In one embodiment, the sdAb comprises a CDR1, CDR2, and CDR2 of the sdAb sequence set forth in SEQ ID NO: 123.

In one embodiment, the sdAb comprises a CDR1, CDR2, and CDR2 of the sdAb sequence set forth in SEQ ID NO: 124.

In one embodiment, the sdAb comprises a CDR1, CDR2, and CDR2 of the sdAb sequence set forth in SEQ ID NO: 125.

In one embodiment, the sdAb comprises SEQ ID NO: 82.

In one embodiment, the sdAb comprises SEQ ID NO: 83.

In one embodiment, the sdAb comprises SEQ ID NO: 84.

In one embodiment, the sdAb comprises SEQ ID NO: 85.

In one embodiment, the sdAb comprises SEQ ID NO: 86.

In one embodiment, the sdAb comprises SEQ ID NO: 87.

In one embodiment, the sdAb comprises SEQ ID NO: 88.

In one embodiment, the sdAb comprises SEQ ID NO: 89.

In one embodiment, the sdAb comprises SEQ ID NO: 90.

In one embodiment, the sdAb comprises SEQ ID NO: 91.

In one embodiment, the sdAb comprises SEQ ID NO: 92.

In one embodiment, the sdAb comprises SEQ ID NO: 93.

In one embodiment, the sdAb comprises SEQ ID NO: 94.

In one embodiment, the sdAb comprises SEQ ID NO: 95.

In one embodiment, the sdAb comprises SEQ ID NO: 96.

In one embodiment, the sdAb comprises SEQ ID NO: 97.

In one embodiment, the sdAb comprises SEQ ID NO: 98.

In one embodiment, the sdAb comprises SEQ ID NO: 99.

In one embodiment, the sdAb comprises SEQ ID NO: 100.

In one embodiment, the sdAb comprises SEQ ID NO: 101.

In one embodiment, the sdAb comprises SEQ ID NO: 102.

In one embodiment, the sdAb comprises SEQ ID NO: 103.

In one embodiment, the sdAb comprises SEQ ID NO: 104.

In one embodiment, the sdAb comprises SEQ ID NO: 105.

In one embodiment, the sdAb comprises SEQ ID NO: 106.

In one embodiment, the sdAb comprises SEQ ID NO: 107.

In one embodiment, the sdAb comprises SEQ ID NO: 108.

In one embodiment, the sdAb comprises SEQ ID NO: 120.

In one embodiment, the sdAb comprises SEQ ID NO: 121.

In one embodiment, the sdAb comprises SEQ ID NO: 122.

In one embodiment, the sdAb comprises SEQ ID NO: 123.

In one embodiment, the sdAb comprises SEQ ID NO: 124.

In one embodiment, the sdAb comprises SEQ ID NO: 125.

In one embodiment, the sdAb is a Camelidae $V_H$HsdAb.

In one embodiment, the sdAb is a llama $V_H$HsdAb

In one embodiment, the sdAb is humanized camelidae $V_H$H.

By the term "humanized" as used herein is meant mutated so that immunogenicity upon administration in human patients is minor or nonexistent. Humanizing a polypeptide, according to the present invention, comprises a step of replacing one or more of the Camelidae amino acids by their human counterpart as found in the human consensus sequence, without that polypeptide losing its typical character, i.e. the humanization does not significantly affect the antigen binding capacity of the resulting polypeptide. A humanized antibody can be produced using a variety of techniques known in the art, including but not limited to, CDR-grafting, veneering or resurfacing, chain shuffling, etc.

In one embodiment, the sdAb has an affinity for human CD22 of $2.5\times10^{-7}$ nm or less. In one embodiment, the sdAb has an affinity for human CD22 of $3\times10^{-8}$ nm or less. In one embodiment, the sdAb has an affinity for human CD22 of $9.6\times10^{-9}$ nm or less. In one embodiment, the sdAb has an affinity for human CD22 of $9.3\times10^{-10}$ nm or less. In one embodiment, the sdAb has an affinity for human CD22 of $7\times10^{-12}$ nm or less. Binding affinity can be determined, e.g., according to assays described herein It will be appreciated that CD22 comprises seven Ig-like domains, numbered herein as 1 to 7 from membrane-distal to membrane-proximal (see FIG. 7 for reference). In some embodiments, the sdAb exhibits selective or preferential binding to one or more of these Ig-like domains. The mature human CD22 ECD extends from amino acids 20 to 687 of UniProt entry P20273. Within this subsequence, the seven Ig-like domains generally correspond to regions of amino acids 1-119 (1), 124-216 (2), 223-302 (3), 312-397 (4), 400-481 (5), 486-563 (6), and 574-657 (7). Elsewhere it is common to refer to the domains named herein as 1 to 7 as IgL-V and IgL-1 to IgL-6, respectively. For simplicity, the domains are herein numbered by order from 1 ("the first") to 7 ("the seventh"). For epitope mapping, seven fragments contain the respective Ig-like domains as bins 1 to 7 and correspond to regions of amino acids 1-135 (bin1), 111-230 (bin2), (211-317) (bin3), 303-405 (bin4), 391-490 (bin5), 476-575 (bin6), and 561-668 (bin7).

In one embodiment, the sdAb binds to the first Ig-like domain of human CD22. In one such particular embodiment, the sdAb that binds to the first Ig-like domain comprises SEQ ID NO: 91 (hCD221ug-80). In one embodiment, the sdAb binds to the fourth Ig-like domain of human CD22. In one such particular embodiment, the sdAb that binds to the fourth Ig-like domain comprises SEQ ID NO: 84 (hCD221ug-13). In one embodiment, the sdAb binds to the sixth Ig-like domain of human CD22. In one such particular embodiment, the sdAb that binds to the sixth Ig-like domain comprises SEQ ID NO: 84 (hCD221ug-13), SEQ ID NO: 91 (hCD221ug-80), SEQ ID NO: 86 (hCD221ug-36), or SEQ ID NO: 105 (hCD221pas-64). In one embodiment, the sdAb binds to the seventh Ig-like domain of human CD22. In one such particular embodiment, the sdAb that binds to the seventh Ig-like domain comprises SEQ ID NO: 87 (hCD221ug-61), SEQ ID NO: 83 (hCD221ug-10), or SEQ ID NO: 100 (hCD22pas-24).

In one aspect, there is provided a VHH single domain antibody (sdAb) that competes for specific binding to CD22 with the isolated sdAb described above. An sdAb of the invention may be identified by a method that comprises a binding assay which assesses whether or not a test antibody is able to cross-compete with a known antibody of the invention for a binding site on the target molecule. For example, the antibodies described hereinabove may be used as reference antibodies. Methods for carrying out competitive binding assays are well known in the art. For example they may involve contacting together a known antibody of the invention and a target molecule under conditions under which the antibody can bind to the target molecule. The antibody/target complex may then be contacted with a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes. Such antibodies may be identified by generating new sdAbs to CD22 and screening the resulting library for cross-competition. Alternatively, one of the antibodies described herein may serve as a starting point for diversification, library generation, and screening, A further alternative could involve testing individual variants of an antibody described herein.

In one embodiment, the sdAb defined herein is a camelid sdAb.

In one embodiment, the sdAb defined herein is a llama sdAb.

In one embodiment, the sdAb defined herein is humanized form of camelidae sdAb.

Table 1 lists the full length sequences for various sdAb disclosed herein. CDR1, CDR2, and CDR3 sequences are underlined. CDR identification and numbering used herein is according to the IMGT™ convention.

TABLE 1

| VHH Sequences | | |
|---|---|---|
| VHH # | Name | Amino Acid sequence (CDR1, CDR2, and CDR3 according to the IMGT convention are underlined and appear sequentially) |
| VHH # 1 | hCD221ug-80 | QVQLVESGGGLVQPGGSLRLSCTFSGFTLDYYVMVWFRQAPGKEREAVSCITSDGVTYYADSVKGRFTISRDNAKNTVYLQMNRVKPEDTAVYYCAVDKPFYDGGIQYTCPVDFDSWGQGAQVTVSS |
| VHH # 2 | hCD22100ng-2 | QVKLEESGGGLVQPGGSLRLSCTVSGVTFDYYVMGWFRQAPGKEREVVSCMRNSDGVTYYADSVKGRFTISRDNAKNTVYLQMNSLKPDDTAIYYCAVDKPFYDGGNYYTCPVDFDSWGQGTQVTVSS |
| VHH # 3 | hCD221ug-74 | QVKLEESGGGLVQAGGSLRLSCAGSGFTFDDYAMGWFRQAPGKEREVVSCMGSSDGATYYADSVKGRFTISRDNAKNTVYLQMNSLKPEDTAIYYCAVDKPFYDGGYRYTCPVDFGSWGQGTQVTVSS |
| VHH # 4 | hCD22100ng-66 | QVQLVESGGGLVQPGGSLRLSCTVSGFSLDYYVMGWFRQAPGKEREVVSCISSSDGATYYPDSVKGRFTISRDNAKKTVYLQMNALKPEDTAIYYCAVDKPFYDGGSYYTCPVDFGSWGQGTQVTVSS |
| VHH # 5 | hCD221ug-6 | QVQLVESGGGVVRPGDSLRLSCTVSGFTLDYYVMGWFRQAPGKEREVVSCISSSDGVTYYADSVKGRFTISRDNAKNTVYLQMNSLKPEDTAIYYCAVDKPFYDGGYYYTCPVDFDSWGQGTQVTVSS |
| VHH # 6 | hCD22pas-10 | QVQLVESGGGLVQPGDSLRLSCTVSGFTSDYYAMGWFRQAPGKEREAVSCISSSDGVTYYADSVRGRFTISRDNAKNTVYLEMNSLKPEDTAIYYCAVDKPFYDGGYLYTCPVDFDSWGQGTQVTVSS |
| VHH # 7 | hCD22pas-33 | QVKLEESGGGLVQPGGSLRLSCTVSGFTLDSYVMGWFRQAPGKEREAVSCISSSDGVTYYADSVKGRFTISRDNAKNTYLQMNSLKPEDTAIYYCAVDKPFYDGGYLYTCPVDFDSWGQGIQVTVSS |
| VHH # 8 | hCD221ug-77 | QVKLEESGGGLVQPGGSLRLSCADSGSIFRIAVMNWYRQAPGKERELVAVITSGGETHYAASVKGRFTISRDNAKNTMYLQMNSLKPEDTAVYYCNAKWGQYEYWGQGTQVTVSS |
| VHH # 9 | hCD221ug-87 | QVQLVESGGGLVQPGGSLRLSCADSGSIFRIAVMNWYRQAPGKERELVAVITSGGETHYAASVKGRFTISRDNAKNTMYLQMNSLKPEDTAVYYCNAKWGRDEYWGQGTQVTVSS |
| VHH # 10 | hCD221ug-75 | QVKLEESGGGLVQPGGSLRLSCAGSGSIFRIAVMNWYRQAPGKERELVAVITSGGDTHYAASVKGRFTISRDNAKNTMYLQINSLKPEDTAVYYCNAKYGRDEYWGQGAQVTVSS |

TABLE 1-continued

VHH Sequences

| VHH # | Name | Amino Acid sequence (CDR1, CDR2, and CDR3 according to the IMGT convention are underlined and appear sequentially) |
|---|---|---|
| VHH # 11 | hCD221ug-93 | QVKLEESGGGLVQAGGSLRLSCAASGSTFSSSVMNWYRQAPGKQRELVAVITSSGSTHYADSVKGRFTISRDNAKNTVNLQMNSLKPEDTAVYYCNAQYGRRSDWGQGTQVTVSS |
| VHH # 12 | hCD22pas-82 | QVQLVESGGGLVQPGGSLRLSCAASGSIFRITVMNWHRQAPGKERELSGVITSGGDSHYAASVKGRFTIYRDNTKNTMYLQMNRLKPEDTDYYYCNAKWGGDEYWGQGTHDTGSS |
| VHH # 13 | hCD22pas-23 | QVQLVESGGGLVQPGGSLRLSCAASGSIFRITAVMNWYRQAPGKERELVAVITSAGETHYAESVKGRFTISRDNAKNTMYLQMNSLKPEDTAVYYCNAKWGQYEHWGQGTQGTVSS |
| VHH # 14 | hCD221ug-61 | QVQLVESGGGLVQAGGSLRLSCAASMSSFSQYVMYWYRQAPGKQRELVATITSYSNTNYADSVKGRFTISRDNAKSIAYLQMDSLKPEDTAVYYCNAQYGSTFIRNHWDDWGQGTQVTVSS |
| VHH # 15 | hCD22pas-32 | QVQLVESGGGLVQAGGSLRLSCAVSGRIFRSYVLGWFRQAPGKERELVARIGWSDTYYADSVKGRFTISRDNAKNTVDLQMNSLKPEDTAVYYCAANSPPYGPQRDEFGYWGQGTQVTVSS |
| VHH # 16 | hCD221ug-14 | QVKLEESGGGLVQAGGSLRLSCAVSGRIFRSYVLGWFRQAPGKERELVARIGWSDTYYADSVKGRFTISRDNAKNTVDLQMNSLKPEDTAVYYCAANSPPYGPQRDEFDYWGQGTQVTVSS |
| VHH # 17 | hCD22pas-55 | QVKLEESGGGLGQAGGSLRLSCAVSGRISRSYVLGWFRQAPGKERELVARIGCSDTYYADSAKGRFTISRNNADNTVDLQMNSLKPEDTAVYYCAEYSPPYGPQRDEFDYWGQGTQVTVSS |
| VHH # 18 | hCD22pas-79 | QVKLEESGGGLVQPGGSLRLSCTVSGRTSSVYGMAWFRQTPGKEREFVAAMSWSGGPTYFADSVKGRFGSSRDNAKNTVYLQMNGLRPEDTAVYYCAVRIRRTLLEPLTKETLYDYWGQGTQVTVSS |
| VHH # 19 | hCD22pas-72 | QVQLVESGGGLVQAGGSLRLSCAASGGTFSVYTMAWFRQAPGKEREFVAAIRGSGGTYYRDSVKGRFTISRDNAKNTVYLQMNSLKPEDTAVYYCAVRIRRTLVEPLTKETLYDYWGQGTQVTVSS |
| VHH # 20 | hCD22pas-16 | QVQLVESGGGLVQAGGSLRLSCAASGSTFSLKAMAWYRQAPGKQRERVGVINSDGSYTTDAASVQGRFTISRDNAKNTVYLQMNSLKPEDTAVYYCNTMPPWPWGQGTQVTVSS |
| VHH # 21 | hCD221ug-13 | QVQLVESGGGLVQAGDSLRLSCAGSGGSFSSVTMAWFRQAPGKDREFVAAITWSSPSTYYADSVKGRFTISRDNAKNTVYLQMNSLKPEDTAVYYCAGGRTGRGTSADTDEYNYWGQGTQVTVSS |
| VHH # 22 | hCD221ug-36 | EVQLVDSGGGLVQAGGSLRVSCEASGITFSRAAMGWYRQRPGKERERVAVVNSDSSTIYADSVKGRFTISRDNAKNTVYLQMNSLEPEDTAVYYCWSPGFGSYWGQGTQVTVSS |
| VHH #23 | hCD221ug-10 | QVQLVESGGGLVQAGGSLSVSCTASESTFSIMMGWFRQAPGKQREMVAVINSAGSTNYADSAEGRFTISRDLAKKTVSLQMNSLKPEDTAVYYCYVDGYFGQGTQVTVSS |
| VHH # 24 | hCD22100ng-62 | QVKLEESGGGLVQAGGSLRLSCAASGSISSINAMGWYRQVPGKQRELVAIITTAGNTRYGDSVKGRFTISRDNARKTVYLQMNSLKPEDTAVYYCAGKLYVNKEYTYWGQGTQVTVSS |
| VHH # 25 | hCD22pas-64 | QVQLVESGGGLVQAGGSLRLSCAASGSTFSLNTMAWYRQAPGNQREYVAAASSDGYTNYADSVRGRFTISRDNDKNTMYLQMNSLRPEDTAVYYCTWGTGRFADYIYWGQGTQVTVSS |

TABLE 1-continued

VHH Sequences

| VHH # | Name | Amino Acid sequence (CDR1, CDR2, and CDR3 according to the IMGT convention are underlined and appear sequentially) |
|---|---|---|
| VHH #26 | hCD22pas-24 | QVQLVESGGGLVQAGGSLRLSCSASGITSSINSMGWHR QAPGKQRELVASIGRGGSGSTKYADSGKGRFLISRDNNK NILFLEMNSLKPEDTADYYCLEVTTDLSSYWGRGTQVTV SS |
| VHH # 27 | hCD22pas-48 | QVKLEESGGGLGQAGGAVRLSCADSGSIFRIAVMNWYR QAPGKERELVAVITIAGETHYAYSVKGQFTISRYNAKNTM YLQMNRLKPEDTAVYYCYANGGRDEYWGRGTQVTVSS |

Table 2 provides correspondence between antibody names used herein with VHH #, and SEQ ID NOs for CDR1, CDR2, CDR3, and full-length sequences for each sdAb.

TABLE 2

VHH Sequence ID Numbers

| Name | VHH # | Sequence ID Nos. CDR1 | CDR2 | CDR3 | Full Length |
|---|---|---|---|---|---|
| hCD221ug-6 | VHH #5 | 1 | 2 | 3 | 82 |
| hCD221ug-10 | VHH #23 | 4 | 5 | 6 | 83 |
| hCD221ug-13 | VHH #21 | 7 | 8 | 9 | 84 |
| hCD221ug-14 | VHH #16 | 10 | 11 | 12 | 85 |
| hCD221ug-36 | VHH #22 | 13 | 14 | 15 | 86 |
| hCD221ug-61 | VHH #14 | 16 | 17 | 18 | 87 |
| hCD221ug-74 | VHH #3 | 19 | 20 | 21 | 88 |
| hCD221ug-75 | VHH #10 | 22 | 23 | 24 | 89 |
| hCD221ug-77 | VHH #8 | 25 | 26 | 27 | 90 |
| hCD221ug-80 | VHH #1 | 28 | 29 | 30 | 91 |
| hCD221ug-87 | VHH #9 | 31 | 32 | 33 | 92 |
| hCD221ug-93 | VHH #11 | 34 | 35 | 36 | 93 |
| hCD22100ng-2 | VHH #2 | 37 | 38 | 39 | 94 |
| hCD22100ng-62 | VHH #24 | 40 | 41 | 42 | 95 |
| hCD22100ng-66 | VHH #4 | 43 | 44 | 45 | 96 |
| hCD22pas-10 | VHH #6 | 46 | 47 | 48 | 97 |
| hCD22pas-16 | VHH #20 | 49 | 50 | 51 | 98 |
| hCD22pas-23 | VHH #13 | 52 | 53 | 54 | 99 |
| hCD22pas-24 | VHH #26 | 55 | 56 | 57 | 100 |
| hCD22pas-32 | VHH #15 | 58 | 59 | 60 | 101 |
| hCD22pas-33 | VHH #7 | 61 | 62 | 63 | 102 |
| hCD22pas-48 | VHH #27 | 64 | 65 | 66 | 103 |
| hCD22pas-55 | VHH #17 | 67 | 68 | 69 | 104 |
| hCD22pas-64 | VHH #25 | 70 | 71 | 72 | 105 |
| hCD22pas-72 | VHH #19 | 73 | 74 | 75 | 106 |
| hCD22pas-79 | VHH #18 | 76 | 77 | 78 | 107 |
| hCD22pas-82 | VHH #12 | 79 | 80 | 81 | 108 |

Recombinant Polypeptides

In one aspect, there is provided a recombinant polypeptide comprising an sdAb as defined herein. In one embodiment, there is provided a recombinant polypeptide comprising one or more sdAb as defined herein. In one embodiment, there is provided a recombinant polypeptide comprising two or more sdAb as defined herein. In one embodiment, there is provided a recombinant polypeptide comprising two or more sdAb as defined herein.

$V_H$H:$F_c$ Fusions

In one embodiment, there is provided the sdAb defined herein fused to a human $F_c$ (termed a "$V_H$H:$F_c$ fusion"). For example, the $V_H$H:$F_c$ fusion may comprise at least a CH2 and a CH3 of the IgG, IgA, or IgD isotype. The $V_H$H:$F_c$ fusion may comprise at least a CH2, a CH3, and a CH4 of the IgM or IgE isotype. Such embodiments may be useful in activating the immune system in higher order recombinant molecules. For example, according to some embodiments, two such $F_c$-containing $V_H$H:$F_c$ fusions may assemble to form a recombinant monomeric antibody. In some embodiment, such a monomeric antibody is capable of activating the immune system. Such monomeric antibodies may be of IgG, IgA, IgD, IgE, or IgM isotype. In one embodiment, IgA $F_c$-containing $V_H$H:$F_c$ fusions may also assemble into a recombinant dimeric (secretory) form. Multimeric forms are also envisaged in some embodiments. For example, five IgM monomers may assemble to form a recombinant pentameric antibody.

In some embodiments, the multivalent antibody described herein may be an assembly of the same VHH:Fc fusions.

In some embodiments, the multivalent antibody described herein may be an assembly of the different VHH:Fc fusions having the same binding target. For example, these may bind to different epitopes on the same target molecule. Examples may include assemblies of different VHH:Fc fusions, each comprising a different anti-CD22 sdAb as defined herein.

In some embodiments, the multivalent antibody described herein may be an assembly of an VHH:Fc fusion defined herein (comprising an anti-CD22 sdAb as defined herein) and another VHH:Fc fusion comprising a paratope directed to a different target.

Fusions to Cargo Molecules

In a further aspect, the present disclosure provides anti-CD22 sdAb as defined herein linked to a cargo molecule. The cargo molecule may comprise, for example, a therapeutic moiety, such as for example, a cytotoxic agent, a cytostatic agent, an anti-cancer agent or a radiotherapeutic. In particular embodiments of the disclosure, the antibody drug conjugates may comprise a cytotoxic agent. Another particular embodiment of the disclosure relates to antibody drug conjugates comprising a radiotherapeutic.

Recombinant Nucleic Acid Molecules

In aspect, there is provided a recombinant nucleic acid molecule encoding an sdAb, the recombinant polypeptide, or the $V_H$H:$F_c$ fusion as defined herein.

Compositions

In one aspect, there is provided a composition comprising an sdAb as defined herein, or a polypeptide comprising such an sdAb; together with an acceptable excipient, diluent or carrier. In one embodiment the composition is a pharmaceutical composition, and the excipient, diluent or carrier is a pharmaceutically acceptable excipient, diluent or carrier.

Uses & Methods

In one aspect, there is provided a use of the sdAb as defined herein or of an antibody comprising one or more $V_H$H:$F_c$ fusion as defined herein for treatment of a cancer or an auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect, there is provided a use of the sdAb as defined herein or of an antibody comprising one or more $V_H$H:$F_c$ fusion as defined herein for preparation of a medicament for treatment of a cancer or an auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL), In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect, there is provided the sdAb as defined herein or of an antibody comprising one or more $V_H$H:$F_c$ fusion as defined herein for use in treatment of a cancer or an auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect, there is provided a method of treating a cancer or an auto-immune disease in subject comprising administering to the subject the sdAb as defined herein or of an antibody comprising one or more $V_H$H:$F_c$ fusion as defined herein. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

Multivalent Antibodies & Related Embodiments

In one aspect, there is provided a multivalent antibody comprising an sdAb as defined above.

By "multivalent antibody" is use herein to mean a molecule comprising more than one variable region or paratope for binding to one or more antigen(s) within the same or different target molecule(s).

In some embodiments, the paratopes may bind to different epitopes on the same target molecule. In some embodiments, the paratopes may bind to different target molecules. In these embodiments, the multivalent antibody may be termed bispecific, trispecific, or multispecific, depending on the number of paratopes of different specificity that are present. As the multivalent antibody comprises one of the anti-CD22 sdAbs as herein defined, the multivalent antibody comprises CD22 binding affinity.

For example, as explained above, in some embodiments a multivalent antibody may be an assembly of a $V_H$H:$F_c$ fusion defined herein (comprising an sdAb as defined herein) and another $V_H$H:$F_c$ fusion comprising a different paratope conferring a different specificity.

In one embodiment, there is provided a bispecific antibody comprising an sdAb as defined above, and a second antigen-binding portion. In some embodiments, the second antigen binding portion may comprise a monoclonal antibody, an Fab, and F(ab')$_2$, an Fab', an scFv, or an sdAb, such as a $V_H$H or a $V_{NAR}$.

An "antigen-binding portion" is meant a polypeptide that comprises an antibody or antigen-binding fragment thereof having antigen-binding activity, including engineered antibodies fragments thereof.

In some embodiments, the second antigen-binding portion may bind to human serum albumin, e.g., for the purposes of stabilization/half-life extension.

In one embodiment, there is provided a trispecific antibody comprising an sdAb as defined above, and a second-binding portion, and a third antigen-binding portion. In some embodiments, the second antigen binding portion comprises a monoclonal antibody, an Fab, and F(ab')$_2$, and Fab', an sdFv, or an sdAb, such as a $V_H$H or a $V_{NAR}$. In some embodiments, the third antigen binding portion comprises, independently, a monoclonal antibody, an Fab, and F(ab'), and Fab', an sdFv, or an sdAb, such as a $V_H$H or a $V_{NAR}$.

The second and/or third antigen-binding portion may bind to human serum albumin, e.g., for the purposes of stabilization/half-life extension.

In some embodiments, the trispecific antibody may be multispecific and the antibody may comprise one or more additional antigen-binding portion(s). In such embodiments, the additional antigen-binding portion(s) may be, independently, an Fab, and F(ab')$_2$, and Fab', an sdFv, or an sdAb, such as a $V_H$H or a $V_{NAR}$.

In one embodiment, the multispecific antibody comprises a first antigen-binding portion comprising an sdAb as defined herein, and a second antigen-binding portion. In one embodiment, the second antigen-binding moiety binds specifically to a cell-surface marker of an immune cell.

A "cell surface marker" is a molecule expressed at the surface of the cell that is particular to (or enriched in) a cell type, and that is capable of being bound or recognized by an antigen-binding portion.

Bispecific T-Cell Engager

In one embodiment, the multivalent antibody is a bispecific T-cell engager comprising an sdAb as defined herein and second antigen-binding moiety that binds specifically to a cell-surface marker of a T-cell. In one embodiment, the T-cell marker comprises human CD3.

Human CD3, we will be recognized, is a multi-subunit antigen, of which various subunits may participate in CD3 activation. One such subunit is CD3 epsilon (see, e.g., GenBank NP_000724.1). Other non-limiting examples include CD3 gamma (see, e.g., GenBank NP_000064.1) and delta (see, e.g., GenBank NP_000723.1 for delta isoform A, and, e.g., GenBank NP_001035741.1 for delta isoform B).

In some embodiments, T-cell marker comprises CD3 epsilon, CD3 gamma, or CD3 delta. In one specific embodiment, the T-cell marker comprises CD3 epsilon.

The term "bispecific T-cell engager", as used herein, refers to a recombinant bispecific protein that has two linked variable regions from two different antibodies, one targeting a cell-surface molecule on T cells (for example, CD3E), and the other targeting antigens on the surface of disease cells, typically malignant cells. For example a bispecific T-cell engager may comprises an sdAb as defined herein and an scFvs. A bispecific T-cell engager may comprise an sdAb as defined herein and a second VHH/sdAb. The two variable regions are typically linked together by a short flexible linker such as GlySer linker. By binding to tumor antigens and T cells simultaneously, bispecific T-cell engagers mediate T-cell responses and killing of tumor cells. The T-cell/target cell adherence facilitated by a bispecific T-cell engager is independent of MHC haplotype.

In one embodiment, the bispecific T-cell engager comprises in N-terminal to C-terminal direction:

the first antigen-binding portion, an amino acid linker, and the second antigen-binding portion.

In one embodiment, the signal peptide further comprises a signal peptide N-terminal to the first antigen-binding portion.

A "signal peptide", as referred to herein allows the nascent protein to be directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. The signal peptide may be at the amino terminus of the molecule.

In one embodiment, the signal peptide is a signal peptide from human CD28. In one embodiment, the signal peptide from human CD28 comprises SEQ ID NO: 110. In one embodiment, the signal peptide is at least 80% identical to SEQ ID NO: 110. In one embodiment, the signal peptide is at least 90% identical to SEQ ID NO: 110. In one embodiment, the signal peptide is at least 95% identical to SEQ ID NO: 110. In one embodiment, the signal peptide is at least 98% identical to SEQ ID NO: 110.

By "amino acid linker", in this context, will be understood a sequence of sufficient length, flexibility, and composition to permit the bispecific T-cell engager to be properly functional an engage with both targets.

The amino acid linker may comprise a hinge. The hinge may be from human CD8, e.g. as set forth in SEQ ID NO: 12.

In one embodiment, the amino acid linker comprises (in N- to C-terminal direction) SEQ ID NO: 111-SEQ ID NO: 112-SEQ ID NO: 118; or sequences at least 80% identical to SEQ ID NO: 111-SEQ ID NO: 112-SEQ ID NO: 118. In one embodiment, the amino acid linker comprises a sequence that is at least 80% identical to SEQ ID NO: 111. In one embodiment, the amino acid linker comprises a sequence that is at least 90% identical to SEQ ID NO: 111. In one embodiment, the amino acid linker comprises a sequence that is at least 95% identical to SEQ ID NO: 111. In one embodiment, the amino acid linker comprises a sequence that is at least 98% identical to SEQ ID NO: 111. In one embodiment, amino acid linker comprises a sequence that is at least 80% identical to SEQ ID NO: 112. In one embodiment, amino acid linker comprises a sequence that is at least 90% identical to SEQ ID NO: 112. In one embodiment, the amino acid linker comprises a sequence that is at least 95% identical to SEQ ID NO: 112. In one embodiment, the amino acid linker comprises a sequence that is at least 98% identical to SEQ ID NO: 112. In one embodiment, the amino acid linker comprises a sequence that is at least 80% identical to SEQ ID NO: 118. In one embodiment, the amino acid linker comprises a sequence that is at least 90% identical to SEQ ID NO: 118. In one embodiment, the amino acid linker comprises a sequence that is at least 95% identical to SEQ ID NO: 118. In one embodiment, the amino acid linker comprises a sequence that is at least 98% identical to SEQ ID NO: 118.

In one embodiment, the multivalent antibody is encoded by SEQ ID NO: 119.

In one embodiment, the sdAb comprises a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6).

In one embodiment, the sdAb comprises a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10).

In one embodiment, the sdAb comprises a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13).

In one embodiment, the sdAb comprises a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14).

In one embodiment, the sdAb comprises a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36).

In one embodiment, the sdAb comprises a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61).

In one embodiment, the sdAb comprises a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74)

In one embodiment, the sdAb comprises a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75).

In one embodiment, the sdAb comprises a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77).

In one embodiment, the sdAb comprises a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80).

In one embodiment, the sdAb comprises a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87).

In one embodiment, the sdAb comprises a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93).

In one embodiment, the sdAb comprises a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2).

In one embodiment, the sdAb comprises a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62).

In one embodiment, the sdAb comprises a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66).

In one embodiment, the sdAb comprises a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10).

In one embodiment, the sdAb comprises a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16).

In one embodiment, the sdAb comprises a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23).

In one embodiment, the sdAb comprises a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24).

In one embodiment, the sdAb comprises a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32).

In one embodiment, the sdAb comprises a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33).

In one embodiment, the sdAb comprises a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48).

In one embodiment, the sdAb comprises a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55).

In one embodiment, the sdAb comprises a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64).

In one embodiment, the sdAb comprises a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72).

In one embodiment, the sdAb comprises a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79).

In one embodiment, the sdAb comprises a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82).

In one embodiment, the sdAb comprises a CDR1, CDR2, and CDR2 of the sdAb sequence set forth in SEQ ID NO: 82.

In one embodiment, the sdAb comprises a CDR1, CDR2, and CDR2 of the sdAb sequence set forth in SEQ ID NO: 83.

In one embodiment, the sdAb comprises a CDR1, CDR2, and CDR2 of the sdAb sequence set forth in SEQ ID NO: 84.

In one embodiment, the sdAb comprises a CDR1, CDR2, and CDR2 of the sdAb sequence set forth in SEQ ID NO: 85.

In one embodiment, the sdAb comprises a CDR1, CDR2, and CDR2 of the sdAb sequence set forth in SEQ ID NO: 86.

In one embodiment, the sdAb comprises a CDR1, CDR2, and CDR2 of the sdAb sequence set forth in SEQ ID NO: 87.

In one embodiment, the sdAb comprises a CDR1, CDR2, and CDR2 of the sdAb sequence set forth in SEQ ID NO: 88.

In one embodiment, the sdAb comprises a CDR1, CDR2, and CDR2 of the sdAb sequence set forth in SEQ ID NO: 89.

In one embodiment, the sdAb comprises a CDR1, CDR2, and CDR2 of the sdAb sequence set forth in SEQ ID NO: 90.

In one embodiment, the sdAb comprises a CDR1, CDR2, and CDR2 of the sdAb sequence set forth in SEQ ID NO: 91.

In one embodiment, the sdAb comprises a CDR1, CDR2, and CDR2 of the sdAb sequence set forth in SEQ ID NO: 92.

In one embodiment, the sdAb comprises a CDR1, CDR2, and CDR2 of the sdAb sequence set forth in SEQ ID NO: 93.

In one embodiment, the sdAb comprises a CDR1, CDR2, and CDR2 of the sdAb sequence set forth in SEQ ID NO: 94.

In one embodiment, the sdAb comprises a CDR1, CDR2, and CDR2 of the sdAb sequence set forth in SEQ ID NO: 95.

In one embodiment, the sdAb comprises a CDR1, CDR2, and CDR2 of the sdAb sequence set forth in SEQ ID NO: 96.

In one embodiment, the sdAb comprises a CDR1, CDR2, and CDR2 of the sdAb sequence set forth in SEQ ID NO: 97.

In one embodiment, the sdAb comprises a CDR1, CDR2, and CDR2 of the sdAb sequence set forth in SEQ ID NO: 98.

In one embodiment, the sdAb comprises a CDR1, CDR2, and CDR2 of the sdAb sequence set forth in SEQ ID NO: 99.

In one embodiment, the sdAb comprises a CDR1, CDR2, and CDR2 of the sdAb sequence set forth in SEQ ID NO: 100.

In one embodiment, the sdAb comprises a CDR1, CDR2, and CDR2 of the sdAb sequence set forth in SEQ ID NO: 101.

In one embodiment, the sdAb comprises a CDR1, CDR2, and CDR2 of the sdAb sequence set forth in SEQ ID NO: 102.

In one embodiment, the sdAb comprises a CDR1, CDR2, and CDR2 of the sdAb sequence set forth in SEQ ID NO: 103.

In one embodiment, the sdAb comprises a CDR1, CDR2, and CDR2 of the sdAb sequence set forth in SEQ ID NO: 104.

In one embodiment, the sdAb comprises a CDR1, CDR2, and CDR2 of the sdAb sequence set forth in SEQ ID NO: 105.

In one embodiment, the sdAb comprises a CDR1, CDR2, and CDR2 of the sdAb sequence set forth in SEQ ID NO: 106.

In one embodiment, the sdAb comprises a CDR1, CDR2, and CDR2 of the sdAb sequence set forth in SEQ ID NO: 107.

In one embodiment, the sdAb comprises a CDR1, CDR2, and CDR2 of the sdAb sequence set forth in SEQ ID NO: 108.

In one embodiment, the sdAb comprises a CDR1, CDR2, and CDR2 of the sdAb sequence set forth in SEQ ID NO: 120.

In one embodiment, the sdAb comprises a CDR1, CDR2, and CDR2 of the sdAb sequence set forth in SEQ ID NO: 121.

In one embodiment, the sdAb comprises a CDR1, CDR2, and CDR2 of the sdAb sequence set forth in SEQ ID NO: 122.

In one embodiment, the sdAb comprises a CDR1, CDR2, and CDR2 of the sdAb sequence set forth in SEQ ID NO: 123.

In one embodiment, the sdAb comprises a CDR1, CDR2, and CDR2 of the sdAb sequence set forth in SEQ ID NO: 124.

In one embodiment, the sdAb comprises a CDR1, CDR2, and CDR2 of the sdAb sequence set forth in SEQ ID NO: 125.

In one embodiment, the sdAb comprises SEQ ID NO: 82.

In one embodiment, the sdAb comprises SEQ ID NO: 83.

In one embodiment, the sdAb comprises SEQ ID NO: 84.

In one embodiment, the sdAb comprises SEQ ID NO: 85.

In one embodiment, the sdAb comprises SEQ ID NO: 86.

In one embodiment, the sdAb comprises SEQ ID NO: 87.

In one embodiment, the sdAb comprises SEQ ID NO: 88.

In one embodiment, the sdAb comprises SEQ ID NO: 89.

In one embodiment, the sdAb comprises SEQ ID NO: 90.

In one embodiment, the sdAb comprises SEQ ID NO: 91.

In one embodiment, the sdAb comprises SEQ ID NO: 92.

In one embodiment, the sdAb comprises SEQ ID NO: 93.

In one embodiment, the sdAb comprises SEQ ID NO: 94.

In one embodiment, the sdAb comprises SEQ ID NO: 95.

In one embodiment, the sdAb comprises SEQ ID NO: 96.

In one embodiment, the sdAb comprises SEQ ID NO: 97.

In one embodiment, the sdAb comprises SEQ ID NO: 98.

In one embodiment, the sdAb comprises SEQ ID NO: 99.

In one embodiment, the sdAb comprises SEQ ID NO: 100.

In one embodiment, the sdAb comprises SEQ ID NO: 101.

In one embodiment, the sdAb comprises SEQ ID NO: 102.

In one embodiment, the sdAb comprises SEQ ID NO: 103.

In one embodiment, the sdAb comprises SEQ ID NO: 104.

In one embodiment, the sdAb comprises SEQ ID NO: 105.

In one embodiment, the sdAb comprises SEQ ID NO: 106.

In one embodiment, the sdAb comprises SEQ ID NO: 107.

In one embodiment, the sdAb comprises SEQ ID NO: 108.

In one embodiment, the sdAb comprises SEQ ID NO: 120.

In one embodiment, the sdAb comprises SEQ ID NO: 121.

In one embodiment, the sdAb comprises SEQ ID NO: 122.

In one embodiment, the sdAb comprises SEQ ID NO: 123.

In one embodiment, the sdAb comprises SEQ ID NO: 124.

In one embodiment, the sdAb comprises SEQ ID NO: 125.

In some embodiments, the BIKE is a sequence variant of the above BIKE having 80%, 90%, 95%, 98%, or 99% identity to one of the above-described BiKEs. In some embodiments, the variant retains substantially the same binding specificity as the parent molecule from which it is derived. In some embodiments the variant retains substantially the same binding affinity as the parent molecule from which it is derived.

BiKEs & TriKEs

In one embodiment, the multivalent antibody is a bispecific killer cell engager.

The term "BIKE" refers to a recombinant bispecific protein that has two linked variable regions from two different antibodies, one targeting a cell-surface molecule on natural killer (NK) cells (for example, CD16), and the other targeting antigens on the surface of disease cells, typically malignant cells. For example the BIKE may comprises two scFvs, two VHHs, or a combination thereof. The two are typically linked together by a short flexible linker. By binding to tumor antigens and NK cells simultaneously, BiKEs mediate NK-cell responses and killing of tumor cells.

In one embodiment, the cell-surface marker of the immune cell comprises a natural killer (NK) cell marker. In one embodiment, the NK cell marker comprises human CD16.

In one embodiment, the multivalent antibody is a trispecific killer cell engager (BiKE).

The term "TriKE" indicates at a BIKE that has been further modified to include another functionality. This term has been used to encompass various approaches. One approach involves inserting an intervening immunomodulatory molecule (a modified human IL-15 crosslinker) to promote NK cell activation, expansion, and/or survival (Vallera et al. IL-15 Trispecific Killer Engagers (TrikEs) Make Natural Killer Cells Specific to CD33+ Targets While Also Inducing In Vivo Expansion, and Enhanced Function. *Clinical Cancer Research.* 2012; 22(14):3440-50). Other TriKE approaches are trispecific molecules that include three antibody variable regions: one targeting an NK cell receptor and two that target tumour-associated antigens (Gleason et al. Bispecific and Trispecific Killer Cell Engagers Directly Activate Human NK Cells Through CD16 Signaling and Induce Cytotoxicity and Cytokine Production.

*Mol Cancer Ther.* 2012; 11(12):2674-84). Yet other TriKE approaches target two NK cell receptors (e.g., CD16 and NKp46) and one tumour-associated antigen (Gauthier et al. Multifunctional Natural Killer Cell Engagers Targeting NKp46 Trigger Protective Tumor Immunity. Cell. 2019; 177(7):1701-13).

In one embodiment, the multivalent antibody further comprises a cytokine for stimulating activation, expansion, and/or survival of NK cells. In one embodiment, the cytokine for stimulating expansion of NK cells is interleukin-15 (IL15), a variant thereof, or a functional fragment thereof.

In one embodiment, the multivalent antibody further comprises at least a third antigen-binding portion that binds to a second NK cell marker. In one embodiment, the second NK cell marker is human NKp46.

In one embodiment, the multivalent antibody further comprises at least a third antigen-binding portion that binds to a tumour-associated antigen. In some embodiment, the tumour-associated antigen is distinct from human CD22.

In one embodiment, the third antigen-binding portion comprises a $V_H$H, a $V_{NAR}$, or an scVF.

In one embodiment, the second antigen-binding portion comprises a $V_H$H.

In one embodiment, the third antigen-binding portion binds to human serum albumin. In such embodiment, the affinity for human serum albumin may contribute to stabilization/increased half-life.

In one embodiment, the sdAb comprises a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6).

In one embodiment, the sdAb comprises a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10).

In one embodiment, the sdAb comprises a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13).

In one embodiment, the sdAb comprises a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14).

In one embodiment, the sdAb comprises a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36).

In one embodiment, the sdAb comprises a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61).

In one embodiment, the sdAb comprises a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74)

In one embodiment, the sdAb comprises a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75).

In one embodiment, the sdAb comprises a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77).

In one embodiment, the sdAb comprises a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80).

In one embodiment, the sdAb comprises a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87).

In one embodiment, the sdAb comprises a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93).

In one embodiment, the sdAb comprises a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2).

In one embodiment, the sdAb comprises a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62).

In one embodiment, the sdAb comprises a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66).

In one embodiment, the sdAb comprises a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10).

In one embodiment, the sdAb comprises a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16).

In one embodiment, the sdAb comprises a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23).

In one embodiment, the sdAb comprises a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24).

In one embodiment, the sdAb comprises a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32).

In one embodiment, the sdAb comprises a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33).

In one embodiment, the sdAb comprises a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48).

In one embodiment, the sdAb comprises a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55).

In one embodiment, the sdAb comprises a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64).

In one embodiment, the sdAb comprises a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72).

In one embodiment, the sdAb comprises a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79).

In one embodiment, the sdAb comprises a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82).

In one embodiment, the sdAb comprises a CDR1, CDR2, and CDR2 of the sdAb sequence set forth in SEQ ID NO: 82.

In one embodiment, the sdAb comprises a CDR1, CDR2, and CDR2 of the sdAb sequence set forth in SEQ ID NO: 83.

In one embodiment, the sdAb comprises a CDR1, CDR2, and CDR2 of the sdAb sequence set forth in SEQ ID NO: 84.

In one embodiment, the sdAb comprises a CDR1, CDR2, and CDR2 of the sdAb sequence set forth in SEQ ID NO: 85.

In one embodiment, the sdAb comprises a CDR1, CDR2, and CDR2 of the sdAb sequence set forth in SEQ ID NO: 86.

In one embodiment, the sdAb comprises a CDR1, CDR2, and CDR2 of the sdAb sequence set forth in SEQ ID NO: 87.

In one embodiment, the sdAb comprises a CDR1, CDR2, and CDR2 of the sdAb sequence set forth in SEQ ID NO: 88.

In one embodiment, the sdAb comprises a CDR1, CDR2, and CDR2 of the sdAb sequence set forth in SEQ ID NO: 89.

In one embodiment, the sdAb comprises a CDR1, CDR2, and CDR2 of the sdAb sequence set forth in SEQ ID NO: 90.

In one embodiment, the sdAb comprises a CDR1, CDR2, and CDR2 of the sdAb sequence set forth in SEQ ID NO: 91.

In one embodiment, the sdAb comprises a CDR1, CDR2, and CDR2 of the sdAb sequence set forth in SEQ ID NO: 92.

In one embodiment, the sdAb comprises a CDR1, CDR2, and CDR2 of the sdAb sequence set forth in SEQ ID NO: 93.

In one embodiment, the sdAb comprises a CDR1, CDR2, and CDR2 of the sdAb sequence set forth in SEQ ID NO: 94.

In one embodiment, the sdAb comprises a CDR1, CDR2, and CDR2 of the sdAb sequence set forth in SEQ ID NO: 95.

In one embodiment, the sdAb comprises a CDR1, CDR2, and CDR2 of the sdAb sequence set forth in SEQ ID NO: 96.

In one embodiment, the sdAb comprises a CDR1, CDR2, and CDR2 of the sdAb sequence set forth in SEQ ID NO: 97.

In one embodiment, the sdAb comprises a CDR1, CDR2, and CDR2 of the sdAb sequence set forth in SEQ ID NO: 98.

In one embodiment, the sdAb comprises a CDR1, CDR2, and CDR2 of the sdAb sequence set forth in SEQ ID NO: 99.

In one embodiment, the sdAb comprises a CDR1, CDR2, and CDR2 of the sdAb sequence set forth in SEQ ID NO: 100.

In one embodiment, the sdAb comprises a CDR1, CDR2, and CDR2 of the sdAb sequence set forth in SEQ ID NO: 101.

In one embodiment, the sdAb comprises a CDR1, CDR2, and CDR2 of the sdAb sequence set forth in SEQ ID NO: 102.

In one embodiment, the sdAb comprises a CDR1, CDR2, and CDR2 of the sdAb sequence set forth in SEQ ID NO: 103.

In one embodiment, the sdAb comprises a CDR1, CDR2, and CDR2 of the sdAb sequence set forth in SEQ ID NO: 104.

In one embodiment, the sdAb comprises a CDR1, CDR2, and CDR2 of the sdAb sequence set forth in SEQ ID NO: 105.

In one embodiment, the sdAb comprises a CDR1, CDR2, and CDR2 of the sdAb sequence set forth in SEQ ID NO: 106.

In one embodiment, the sdAb comprises a CDR1, CDR2, and CDR2 of the sdAb sequence set forth in SEQ ID NO: 107.

In one embodiment, the sdAb comprises a CDR1, CDR2, and CDR2 of the sdAb sequence set forth in SEQ ID NO: 108.

In one embodiment, the sdAb comprises a CDR1, CDR2, and CDR2 of the sdAb sequence set forth in SEQ ID NO: 120.

In one embodiment, the sdAb comprises a CDR1, CDR2, and CDR2 of the sdAb sequence set forth in SEQ ID NO: 121.

In one embodiment, the sdAb comprises a CDR1, CDR2, and CDR2 of the sdAb sequence set forth in SEQ ID NO: 122.

In one embodiment, the sdAb comprises a CDR1, CDR2, and CDR2 of the sdAb sequence set forth in SEQ ID NO: 123.

In one embodiment, the sdAb comprises a CDR1, CDR2, and CDR2 of the sdAb sequence set forth in SEQ ID NO: 124.

In one embodiment, the sdAb comprises a CDR1, CDR2, and CDR2 of the sdAb sequence set forth in SEQ ID NO: 125.

In one embodiment, the sdAb comprises SEQ ID NO: 82.

In one embodiment, the sdAb comprises SEQ ID NO: 83.

In one embodiment, the sdAb comprises SEQ ID NO: 84.

In one embodiment, the sdAb comprises SEQ ID NO: 85.

In one embodiment, the sdAb comprises SEQ ID NO: 86.

In one embodiment, the sdAb comprises SEQ ID NO: 87.

In one embodiment, the sdAb comprises SEQ ID NO: 88.

In one embodiment, the sdAb comprises SEQ ID NO: 89.

In one embodiment, the sdAb comprises SEQ ID NO: 90.

In one embodiment, the sdAb comprises SEQ ID NO: 91.

In one embodiment, the sdAb comprises SEQ ID NO: 92.

In one embodiment, the sdAb comprises SEQ ID NO: 93.

In one embodiment, the sdAb comprises SEQ ID NO: 94.

In one embodiment, the sdAb comprises SEQ ID NO: 95.

In one embodiment, the sdAb comprises SEQ ID NO: 96.

In one embodiment, the sdAb comprises SEQ ID NO: 97.

In one embodiment, the sdAb comprises SEQ ID NO: 98.

In one embodiment, the sdAb comprises SEQ ID NO: 99.

In one embodiment, the sdAb comprises SEQ ID NO: 100.

In one embodiment, the sdAb comprises SEQ ID NO: 101.

In one embodiment, the sdAb comprises SEQ ID NO: 102.

In one embodiment, the sdAb comprises SEQ ID NO: 103.

In one embodiment, the sdAb comprises SEQ ID NO: 104.

In one embodiment, the sdAb comprises SEQ ID NO: 105.

In one embodiment, the sdAb comprises SEQ ID NO: 106.

In one embodiment, the sdAb comprises SEQ ID NO: 107.

In one embodiment, the sdAb comprises SEQ ID NO: 108.

In one embodiment, the sdAb comprises SEQ ID NO: 120.

In one embodiment, the sdAb comprises SEQ ID NO: 121.

In one embodiment, the sdAb comprises SEQ ID NO: 122.

In one embodiment, the sdAb comprises SEQ ID NO: 123.

In one embodiment, the sdAb comprises SEQ ID NO: 124.

In one embodiment, the sdAb comprises SEQ ID NO: 125.

In some embodiments, the BIKE or TriKE is a sequence variant of one of the above BiKEs and TriKEs having 80%, 90%, 95%, 98%, or 99% identity thereto. In some embodiments, the variant retains substantially the same binding specificity as the parent molecule from which it is derived. In some embodiments the variant retains substantially the same binding affinity as the parent molecule from which it is derived.

In one aspect, there is provided a multivalent antibody comprising: a first antigen-binding portion, an amino acid linker comprising a polypeptide hinge from human CD8, and a second antigen-binding portion. In one embodiment, the polypeptide hinge from human CD8 comprises SEQ ID NO: 112. In one embodiment, the amino acid linker further comprises at least one G4S N-terminal to the polypeptide hinge from human CD8, and at least one G4S C-terminal to the polypeptide hinge from human CD8. In one embodiment, the amino acid linker is at least 47aa in length, preferably is at least 52 residues in length, preferably at least 57 residues in length, more preferably at least 62 residues in length, even more preferably at least 67 residues in length. In one embodiment, the amino acid linker comprises, in N-terminal to C-terminal, direction SEQ ID NOs: 111, 112, and 118. In one embodiment, the first antigen-binding portion binds specifically to human CD22. In one embodiment, the first antigen-binding portion is a $V_H$H, $V_{NAR}$, or an scVF. In one embodiment, the first antigen-binding portion is one the anti-CD22 sdAbs as described herein. In one embodiment, the second antigen-binding moiety binds specifically to a cell-surface marker of an immune cell. In one embodiment, the cell-surface marker of the immune cell comprises a T-cell marker. In one embodiment, the T-cell marker comprises human CD3. In one embodiment, the second antigen binding portion is a $V_H$H, $V_{NAR}$, or an scVF.

Recombinant Nucleic Acid Molecules

In aspect, there is provided a recombinant nucleic acid molecule encoding the multivalent antibody as defined herein. In one embodiment, nucleic acid is a vector.

Compositions

In one aspect, there is provided a composition comprising a multivalent antibody as defined herein; together with an acceptable excipient, diluent or carrier. In one embodiment, the composition comprises a bispecific T-cell engager as herein defined. In one embodiment, the composition comprises a BIKE as herein defined. In one embodiment, the composition comprises a TriKE as herein defined. In one embodiment the composition is a pharmaceutical composition, and the excipient, diluent or carrier is a pharmaceutically acceptable excipient, diluent or carrier.

Uses & Methods

In one aspect, there is provided a use of the multivalent antibody as defined herein for treatment of a cancer or auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect, there is provided a use of the multivalent antibody as defined herein for preparation of a medicament for treatment of a cancer or auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect, there is provided the multivalent antibody as defined herein for use in treatment of a cancer or auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect, there is provided a method of treating a cancer or auto-immune disease in subject comprising administering to the subject the multivalent antibody as defined herein. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

Table 3 lists example sequences for and modules of multivalent antibodies and CARs described herein, according to certain aspects and embodiments.

TABLE 3

Construct Sequences and Components

| Seq. ID | Description | Sequence |
|---|---|---|
| 109 | CAR modular construct DNA sequence Restriction sites in bold | ATGCTCAGGCTGCTCTTGGCTCTCAACTTATTCCCTTCAATTCAA<br>GTAACAGGA**GGGTCTTC[sdAb_sequence]GAAGACTT**CCTTTG<br>**CGAGACGAC**GGTGGCGGGGATCAGGTGGTGGAGGTAGCGG<br>GGGAGGGGGCTCAGGCGGTACAACTACGCCTGCACCTCGCCC<br>ACCGACCCCAGCACCAACCATCGCTTCACAGCCTTTGAGCCTG<br>CGACCAGAGGCATGTCGCCCTGCTGCGGGCGGTGCCGTTCAT<br>ACTCGCGGACTTGATTTTGCGTGTGACGTCGTCTCGCCTTCTAA<br>GCCCTTTTGGGTGCTGGTGGTGGTTGGTGGAGTCCTGGCTTGC<br>TATAGCTTGCTAGTAACAGTGGCCTTTATTATTTTCTGGGTGAG<br>GAAACGGGGCAGAAAGAAACTCCTGTATATATTCAAACAACCAT<br>TTATGCGACCAGTACAAACTACTCAAGAGGAAGATGGCTGTAGC<br>TGCCGATTTCCAGAAGAAGAAGAAGGAGGATGTGAACTGCTGA<br>GAGTGAAGTTCAGCAGGAGCGCAGACGCCCCCGCGTACCAGC<br>AGGGCCAGAACCAGCTCTATAACGAGCTCAATCTAGGACGAAG<br>AGAGGAGTACGATGTTTTGGACAAGCGACGTGGCCGGGACCCT<br>GAGATGGGGGGAAAGCCGCAGAGAAGGAAGAACCCTCAGGAA<br>GGCCTGTACAATGAACTGCAGAAAGATAAGATGGCGGAGGCCT<br>ACAGTGAGATTGGGATGAAAGGCGAGCGCCGGAGGGGCAAGG<br>GGCACGATGGCCTTTACCAGGGACTCAGTACAGCCACCAAGGA<br>CACCTACGACGCCCTTCACATGCAGGCOCTGCCCCCTCGCGCT<br>AGCGCCACGAACTTCTCTCTGTTAAAGCAAGCAGGCGACGTGG<br>AAGAAAACCCCGGTCCCATGGTGAGCAAGGGCGAGGAGGACA<br>ACATGGCCAGCCTGCCCGCCACCCACGAGCTGCACATCTTCGG<br>CAGCATCAACGGCGTGGACTTCGACATGGTGGGCCAGGGCAC<br>CGGCAACCCCAACGACGGCTACGAGGAGCTGAACCTGAAGAG<br>CACCAAGGGCGACCTGCAGTTCAGCCCCTGGATTCTGGTGCCC<br>CACATCGGCTACGGCTTCCACCAGTACCTGCCCTACCCCGACG<br>GCATGAGCCCCTTCCAGGCCGCCATGGTGGACGGCAGCGGCT<br>ACCAGGTGCACAGGACCATGCAGTTCGAGGACGGCGCCAGCC<br>TGACCGTGAACTACAGGTACACCTACGAGGGCAGCCACATCAA<br>GGGCGAGGCCCAGGTGAAGGGCACCGGCTTCCCCGCCGACG<br>GCCCCGTGATGACCAACAGCCTGACCGCCGCCGACTGGTGCA<br>GGAGCAAAAAGACCTACCCCAACGACAAGACCATCATCAGCAC<br>CTTCAAGTGGAGCTACACCACCGGCAACGGCAAGAGGTACAGG<br>AGCACCGCCAGGACCACCTACACCTTCGCCAAGCCCATGGCCG<br>CCAACTACCTGAAGAACCAGCCCATGTACGTGTTCAGAAAGAC<br>CGAGCTGAAGCACAGCAAGACCGAGCTGAACTTCAAGGAGTGG<br>CAGAAGGCCTTCACCGACGTGATGGGCATGGACGAGCTGTACA<br>AGCCCAAGAAGAAGAGGAAGGTGGAGGACCCCCCCGCCGCCA<br>AGAGGGTGAAGCTGGACTAA |
| 110 | Human CD28 Signal Peptide | MLRLLLALNLFPSIQVTG |
| 111 | Synthetic Flexible Linker Domain | GGGGSGGGGSGGGGSGG |
| 112 | Human CD8 Hinge Domain | TTTPAPRPPTPAPTIASQPLSLRPEACRPAAGGAVHTRGLDFACD |
| 113 | Human CD28 Transmembrane Domain | PSKPFWVLVVVGGVLACYSLLVTVAFIIFWVR |
| 114 | Human 4-1BB Co-stimulatory Domain | KRGRKKLLYIFKQPFMRPVQTTQEEDGCSCRFPEEEEGGCEL |
| 115 | Human CD3zeta Signaling Domain | LRVKFSRSADAPAYQQGQNQLYNELNLGRREEYDVLDKRRGRDP<br>EMGGKPQRRKNPQEGLYNELQKDKMAEAYSEIGMKGERRRGKG<br>HDGLYQGLSTATKDTYDALHMQALPPR |
| 116 | M971 scFV | QVQLQQSGPGLVKPSQTLSLTCAISGDSVSSNSAAWNWIRQSPSR<br>GLEWLGRTYYRSKWYNDYAVSVKSRITINPDTSKNQFSLQLNSVT<br>PEDTAVYYCAREVTGDLEDAFDIWGQGTMVTVSSGGGGSDIQMT<br>QSPSSLSASVGDRVTITCRASQTIWSYLNWYQQRPGKAPNLLIYAA |

TABLE 3-continued

| Seq. ID | Description | Sequence |
|---|---|---|
| Construct Sequences and Components | | |
| | | SSLQSGVPSRFSGRGSGTDFTLTISSLQAEDFATYYCQQSYSIPQT FGQGTKLEIK |
| 117 | FMC63 scFV | DYKDHDGDYKDHDIDYKDDDDKDIQMTQTTSSLSASLGDRVTISC RASQDISKYLNWYQQKPDGTVKLLIYHTSRLHSGVPSRFSGSGSG TDYSLTISNLEQEDIATYFCQQGNTLPYTFGGGTKLEITGSTSGSGK PGSGEGSTKGEVKLQESGPGLVAPSQSLSVTCTVSGVSLPDYGV SWIRQPPRKGLEWLGVIWGSETTYYNSALKSRLTIIKDNSKSQVFL KMNSLQTDDTAIYYCAKHYYYGGSYAMDYWGQGTSVTVSS |
| 118 | Short flexible linker amino acid sequence | GGGGS |
| 119 | Bi-specific T cell engager modular construct DNA sequence Restriction sites in bold | ATGGAGTTTGGGCTGAGCTGGGTTTTCCTCGTTGCTCTTTTAG AGGTGTCCAGTGTACAGGAGG**GTCTTCG**[**sdAb_sequence**]**GAA GAC**TTCCTTGGAGGAGGCGGAAGT[**anti_CD3_Mab_heavy_chain**] GGCGGTGGTGGGTCAGGCGGCGGTGGGAGCGGAGGAGGTG GAAGC[**anti_CD3_Mab_Light_chain**]CACCACCACCACCACCACT AG |
| 120 | hCD221ug-36 Cloned Segment | QVQLVESGGGLVQAGGSLRVSCEASGITFSRAAMGWYRQRPGKE RERVAVVNSDSSTIYADSVKGRFTISRDNAKNTVYLQMNSLEPEDT AVYYCWSPGFGSYWGQGTQVTVSS |
| 121 | hCD221ug-93 Cloned Segment | QVQLVESGGGLVQAGGSLRLSCAASMSSFSQYVMYWYRQAPGR QRELVATITSASSTSYADSVKGRFTISRDNAKSIVYLQMNSLKPEDT AVYYCNAQYGSTFIRKPYDTWGQGTQVTVSS |
| 122 | hCD221ug-10 Cloned Segment | QVQLVESGGGLVQAGGSLSVSCTASESTFSIMMGWFRQAPGKQR EMVAVINSAGSTNYADSAEGRFTISRDLAKKTVSLQMNSLKPEDTA VYYCYVDGYFGQGTQVTVSS |
| 123 | hCD221ug-61 Cloned Segment | QVQLVESGGGLVQAGGSLRLSCAASMSSFSQYVMYWYRQAPGK QRELVATITSYSNTNYADSVKGRFTISRDNAKSIAYLQMDSLKPEDT AVYYCNAQYGSTFIRNHWDDWGQGTQVTVSS |
| 124 | hCD22pas-16 Cloned Segment | QVQLVESGGGLVQAGGSLRLSCAASGSTFSLKAMAWYRQAPGK QRERVGVINSDGSYTTDAASVQGRFTISRDNAKNTVYLQMNSLKP EDTAVYYCNTMPPWPWGQGTQVTVSS |
| 125 | hCD221ug-80 Cloned Segment | QVQLVESGGGLVQPGGSLRLSCTFSGFTLDYYVMGWFRQAPGKE REAVSCITSDGVTYYADSVKGRFTISRDNAKNTVYLQMNRVKPED TAVYYCAVDKPFYDGGIQYTCPVDFDSWGQGTQVTVSS |
| 138 | hCD221ug36 Example CAR | ATGCTCAGGCTGCTCTTGGCTCTCAACTTATTCCCTTCAATTCAA GTAACAGGACAGGTACAGCTGGTGGAGTCTGGGGGAGGCTTG GTGCAGGCTGGGGGGTCTCTGAGAGTCTCCTGTGAAGCCTCTG GAATCACGTTCAGTCGCGCGGCCATGGGCTGGTACCGCCAGC GTCCAGGCAAGGAGCGCGAACGAGTCGCAGTTGTTAATAGTGA TAGCAGTACAATATATGCAGACTCCGTGAAGGGCCGGTTCACC ATCTCCAGAGACAATGCCAAGAACACAGTGTATCTGCAAATGAA CAGCCTGGAACCTGAGGACACGGCCGTCTATTACTGTTGGTCC CCAGGGTTCGGGTCCTACTGGGGCCAGGGGACCCAGGTCACC GTTTCCTCACCTTTGCGAGACGACGGTGGCGGGGGATCAGGTG GTGGAGGTAGCGGGGGAGGGGGCTCAGGCGGTACAACTACGC CTGCACCTCGCCCACCGACCCCAGCACCAACCATCGCTTCACA GCCTTTGAGCCTGCGACCAGAGGCATGTCGCCCTGCTGCGGG CGGTGCCGTTCATACTCGCGGACTTGATTTTGCGTGTGACGTC GTCTCGCCTTCTAAGCCCTTTTGGGTGCTGGTGGTGGTTGGTG GAGTCCTGGCTTGCTATAGCTTGCTAGTAACAGTGGCCTTTATT ATTTTCTGGGTGAGGAAACGGGGCAGAAAGAAACTCCTGTATAT ATTCAAACAACCATTTATGCGACCAGTACAAACTACTCAAGAGG AAGATGGCTGTAGCTGCCGATTTCCAGAAGAAGAAGAAGGAGG ATGTGAACTGCTGAGAGTGAAGTTCAGCAGGAGCGCAGACGCC CCCGCGTACCAGCAGGGCCAGAACCAGCTCTATAACGAGCTCA ATCTAGGACGAAGAGAGGAGTACGATGTTTTGGACAAGCGACG TGGCCGGGACCCTGAGATGGGGGGAAAGCCGCAGAGAAGGAA GAACCCTCAGGAAGGCCTGTACAATGAACTGCAGAAAGATAAG ATGGCGGAGGCCTACAGTGAGATTGGGATGAAAGGCGAGCGC CGGAGGGGCAAGGGGCACGATGGCCTTTACCAGGGACTCAGT ACAGCCACCAAGGACACCTACGACGCCCTTCACATGCAGGCCC TGCCCCCTCGC[**optional_P2A-GFP_marker**] |

TABLE 3-continued

Construct Sequences and Components

| Seq. ID | Description | Sequence |
|---|---|---|
| 139 | hCD221ug36 Example Bispecific T-cell Engager | ATGGAGTTTGGGCTGAGCTGGGTTTTCCTCGTTGCTCTTTTTAG AGGTGTCCAGTGTACAGGACAGGTACAGCTGGTGGAGTCTGGG GGAGGCTTGGTGCAGGCTGGGGGGTCTCTGAGAGTCTCCTGT GAAGCCTCTGGAATCACGTTCAGTCGCGCGGCCATGGGCTGGT ACCGCCAGCGTCCAGGCAAGGAGCGCGAACGAGTCGCAGTTG TTAATAGTGATAGCAGTACAATATATGCAGACTCCGTGAAGGGC CGGTTCACCATCTCCAGAGACAATGCCAAGAACACAGTGTATCT GCAAATGAACAGCCTGGAACCTGAGGACACGGCCGTCTATTAC TGTTGGTCCCCAGGGTTCGGGTCCTACTGGGGCCAGGGGACC CAGGTCACCGTTTCCTCACCTTTGCGAGACGACGGTGGCGGGG GATCAGGTGGTGGAGGTAGCGGGGGAGGGGGCTCAGGCGGT ACAACTACGCCTGCACCTCGCCCACCGACCCCAGCACCAACCA TCGCTTCACAGCCTTTGAGCCTGCGACCAGAGGCATGTCGCCC TGCTGCGGGCGGTGCCGTTCATACTCGCGGACTTGATTTTGCG TGTGACGTCGTCTCGCTTGGAGGAGGCGGAAGT[**CD3_specific_ scFV_heavy_chain**]GGCGGTGGTGGGTCAGGCGGCGGTGGGA GCGGAGGAGGTGGAAGC[**CD3_specific_scFV_light_chain**]CAC CACCACCACCACCACTAG |

For the example CAR construct comprising antibody hCD221ug36 (SEQ ID NO: 138):

- positions 1-54 correspond to the signal peptide,
- positions 55-396 correspond to antibody 1ug36 ABD (but could, alternatively, be any other anti-CD22 sdAb described herein),
- positions 397-606 correspond to the (G4S) 3-human CD8a hinge and restriction scars,
- positions 607-702 correspond to the human CD28 transmembrane domain, and
- positions 703-828 correspond to the human 41BB co-stimulatory domain, and
- positions 829-1170 correspond to human CD3-zeta signaling domain.

For the purposes of experimentation and testing, the construct thereafter comprises an optional in-frame P2A-GFP marker.

For the example bispecific T-cell engager construct comprising antibody hCD221ug36 (SEQ ID NO: 139):

- positions 1-72 correspond to the signal peptide and restriction scar
- positions 64-405 correspond to antibody hCD221ug36 (but could, alternatively, be any other anti-CD22 sdAb described herein)
- positions 406-633 correspond to the (G4S) 3-hCD8a-(G4S) linker domain (also contains restriction sites for modular hinge)
- positions 633 and 634 are separated by the heavy chain for an CD3-specific murine scFv
- positions 634-678 correspond to the (G4S) 3 linker, and
- positions 678-679 are separated by correspond to the light chain for the CD3-specific murine scFv.

For the purposes of experimentation and testing, the construct thereafter comprises positions 679 to 699, which correspond to a 6× His tag and stop codon.

For the example antibody sequences corresponding to SEQ ID NOs: 120-125 depicted in Table 3, it will be noted that there are sequences differences, particularly towards the amino terminus. Specifically, positions 1, 3, and 5 are Q, Q, V, respectively (compare SEQ ID NOS; 120 and 121 in Table 3 vs. VHH #22 (SEQ ID NO: 86) and VHH #11 (SEQ ID NO: 93) in Tables 1 and 3). Without being bound by theory, these sequences differences may contribute to stability and/or protease resistance (see Hussack G et al. Protein Engineering Design & Selection. 2014; 27(6); 191-198). Accordingly, embodiments multivalent antibodies and CARs embodiments disclosed herein encompass variants comprising any one of the sdAbs disclosed herein modified to comprise Q, Q, and V at positions 1, 3, and 5, respectively.

Chimeric Antibody Receptors & Related Embodiments

In one aspect, there is provided a chimeric antibody receptor (CAR), which binds to human CD22, comprising the VHH sdAb as defined herein.

"Chimeric antigen receptors" are receptor proteins engineered to give T cells the new ability to target a specific protein. The receptors are chimeric because they combine both antigen-binding and T-cell activating functions into a single receptor (see Stoiber et al. Limitations in the Design of Chimeric Antigen Receptors for Cancer Therapy. Cells. 2012; 8(5):472 and van der Stegen et al. The pharmacology of second-generation chimeric antigen receptors. Nat Rev Drug Discov. 2019; 14(7):499-509).

In one embodiment, the CAR comprises, in N-terminal to C-terminal direction:

- a CD22 binding domain comprising an sdAb as described herein,
- a polypeptide hinge,
- a transmembrane domain, and
- a cytoplasmic domain comprising a co-stimulatory domain and a signaling domain.

The term "polypeptide hinge" used herein generally means any oligo- or polypeptide that functions to link the extracellular ligand-binding domain to the transmembrane domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence.

In one embodiment, the polypeptide hinge is a CD8 hinge domain. In one embodiment, the CD8 hinge domain comprises SEQ ID NO: 112. In one embodiment, the CD8 hinge domain is at least 80% identical to SEQ ID NO: 112. In one embodiment, hinge domain is at least 90% identical to SEQ ID NO: 112. In one embodiment, the hinge domain is at least 95% identical to SEQ ID NO: 112. In one embodiment, the hinge domain is at least 98% identical to SEQ ID NO: 112.

The term "transmembrane domain" indicates a polypeptide having the ability to span a cell membrane and thereby link the extracellular portion of the CAR (which comprises the CD22-binding portion) to the intracellular portion responsible for signaling. Commonly used transmembrane domains for CARs have been derived from CD4, CD8α, CD28 and CD3ζ.

In one embodiment, the transmembrane domain is a CD28 transmembrane domain. In one embodiment, the CD28 transmembrane domain comprises SEQ ID NO: 113. In one embodiment, the transmembrane domain is at least 80% identical to SEQ ID NO: 113. In one embodiment, the transmembrane domain is at least 90% identical to SEQ ID NO: 113. In one embodiment, the transmembrane domain is at least 95% identical to SEQ ID NO: 113. In one embodiment, the transmembrane domain is at least 98% identical to SEQ ID NO: 113.

The term "cytoplasmic domain" (also termed a "signal transduction domain") refers to the intracellular portion of the CAR that is responsible for intracellular signaling following the binding of extracellular ligand binding domain to the target resulting in the activation of the immune cell and immune response. In other words, cytoplasmic domain is responsible for the activation of at least one of the normal effector functions of the immune cell in which the CAR is expressed. For example, the effector function of a T cell can be a cytolytic activity or helper activity including the secretion of cytokines. Thus, the term "cytoplasmic domain" refers to the portion of a protein which transduces the effector signal and directs the cell to perform a specialized function. It is common for such cytoplasmic domains to comprise a co-stimulatory domain in addition to a signaling domain.

The term "signaling domain" refers to the portion of a protein which transduces the effector signal and directs the cell to perform a specialized function. Examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transducing domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs or ITAMs. ITAMs are well defined signaling motifs found in the intracytoplasmic tail of a variety of receptors that serve as binding sites for syk/zap70 class tyrosine kinases. Non-limiting examples of signaling domains used in the invention can include those derived from TCRzeta, common FcR gamma (FCERIG), Fcgamma RIIa, FcRbeta (Fc Epsilon Rib), FcRepsilon, CD3 zeta, CD3gamma, CD3delta, CD3epsilon, CD5, CD22, CD79a, CD79b, CD66d, DAP10, or DAP12. In a preferred embodiment, the signaling transducing domain of the CAR can comprise the CD3zeta signaling domain.

In one embodiment, the signaling domain is a CD3-zeta signaling domain. In one embodiment, the CD3-zeta signaling domain comprises SEQ ID NO: 115. In one embodiment, the signaling domain is at least 80% identical to SEQ ID NO: 115. In one embodiment, the signaling domain is at least 90% identical to SEQ ID NO: 115. In one embodiment, the signaling domain is at least 95% identical to SEQ ID NO: 115. In one embodiment, the signaling domain is at least 98% identical to SEQ ID NO: 115.

The term "co-stimulatory domain" refers to the cognate binding partner on a T-cell that specifically binds with a co-stimulatory ligand, thereby mediating a co-stimulatory response by the cell, such as, but not limited to proliferation. Co-stimulatory molecules include, but are not limited to, an MHC class I molecule, BTLA and Toll ligand receptor. Examples of costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CDI Id, ITGAE, CD103, ITGAL, CDIIa, LFA-1, ITGAM, CDIIb, ITGAX, CDIIc, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D or a combination thereof.

In one embodiment, the co-stimulatory domain is a 4-1BB co-stimulatory domain. In one embodiment, the 4-1BB signal transduction domain comprises SEQ ID NO: 114. In one embodiment, the co-stimulatory domain is at least 80% identical to SEQ ID NO: 114. In one embodiment, the co-stimulatory domain is at least 90% identical to SEQ ID NO: 114. In one embodiment, the co-stimulatory domain is at least 95% identical to SEQ ID NO: 114. In one embodiment, the co-stimulatory domain is at least 98% identical to SEQ ID NO: 114.

In one embodiment, CAR further comprises a flexible amino acid linker between the sdAb and the polypeptide hinge. In one embodiment, the amino acid linker comprises SEQ ID NO: 111. In one embodiment, the amino acid linker is at least 80% identical to SEQ ID NO: 111. In one embodiment, the amino acid linker is at least 90% identical to SEQ ID NO: 111. In one embodiment, the amino acid linker is at least 95% identical to SEQ ID NO: 111. In one embodiment, the amino acid linker is at least 98% identical to SEQ ID NO: 111.

In one embodiment, the CAR further comprises a signal peptide.

In one embodiment, the signal peptide is a signal peptide from human CD28.

In one embodiment, the signal peptide from human CD28 comprises SEQ ID NO: 110. In one embodiment, the signal peptide is at least 80% identical to SEQ ID NO: 110. In one embodiment, the signal peptide is at least 90% identical to SEQ ID NO: 110. In one embodiment, the signal peptide is at least 95% identical to SEQ ID NO: 110. In one embodiment, the signal peptide is at least 98% identical to SEQ ID NO: 110.

In one embodiment, the CAR is encoded by SEQ ID NO: 119.

In one embodiment, the sdAb comprises SEQ ID NO: 86 (hCD221ug-36), SEQ ID NO: 83 (hCD221ug-10), SEQ ID NO: 87 (hCD221ug-61), SEQ ID NO: 82 (hCD221ug-6), SEQ ID NO: 88 (hCD221ug-74), SEQ ID NO: 85 (hCD221ug-14), SEQ ID NO: 102 (hCD22pas-33), or SEQ ID NO: 84 (hCD221ug-13).

In one embodiment, the sdAb comprises a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3 (hCD221ug-6).

In one embodiment, the sdAb comprises a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6 (hCD221ug-10).

In one embodiment, the sdAb comprises a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9 (hCD221ug-13).

In one embodiment, the sdAb comprises a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12 (hCD221ug-14).

In one embodiment, the sdAb comprises a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15 (hCD221ug-36).

In one embodiment, the sdAb comprises a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18 (hCD221ug-61).

In one embodiment, the sdAb comprises a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21 (hCD221ug-74)

In one embodiment, the sdAb comprises a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24 (hCD221ug-75).

In one embodiment, the sdAb comprises a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27 (hCD221ug-77).

In one embodiment, the sdAb comprises a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30 (hCD221ug-80).

In one embodiment, the sdAb comprises a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33 (hCD221ug-87).

In one embodiment, the sdAb comprises a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36 (hCD221ug-93).

In one embodiment, the sdAb comprises a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39 (hCD22100ug-2).

In one embodiment, the sdAb comprises a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42 (hCD22100ug-62).

In one embodiment, the sdAb comprises a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45 (hCD22100ug-66).

In one embodiment, the sdAb comprises a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48 (hCD22pas-10).

In one embodiment, the sdAb comprises a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51 (hCD22pas-16).

In one embodiment, the sdAb comprises a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54 (hCD22pas-23).

In one embodiment, the sdAb comprises a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57 (hCD22pas-24).

In one embodiment, the sdAb comprises a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60 (hCD22pas-32).

In one embodiment, the sdAb comprises a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63 (hCD22pas-33).

In one embodiment, the sdAb comprises a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66 (hCD22pas-48).

In one embodiment, the sdAb comprises a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69 (hCD22pas-55).

In one embodiment, the sdAb comprises a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72 (hCD22pas-64).

In one embodiment, the sdAb comprises a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75 (hCD22pas-72).

In one embodiment, the sdAb comprises a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78 (hCD22pas-79).

In one embodiment, the sdAb comprises a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81 (hCD22pas-82).

In one embodiment, the sdAb comprises a CDR1, CDR2, and CDR2 of the sdAb sequence set forth in SEQ ID NO: 82.

In one embodiment, the sdAb comprises a CDR1, CDR2, and CDR2 of the sdAb sequence set forth in SEQ ID NO: 83.

In one embodiment, the sdAb comprises a CDR1, CDR2, and CDR2 of the sdAb sequence set forth in SEQ ID NO: 84.

In one embodiment, the sdAb comprises a CDR1, CDR2, and CDR2 of the sdAb sequence set forth in SEQ ID NO: 85.

In one embodiment, the sdAb comprises a CDR1, CDR2, and CDR2 of the sdAb sequence set forth in SEQ ID NO: 86.

In one embodiment, the sdAb comprises a CDR1, CDR2, and CDR2 of the sdAb sequence set forth in SEQ ID NO: 87.

In one embodiment, the sdAb comprises a CDR1, CDR2, and CDR2 of the sdAb sequence set forth in SEQ ID NO: 88.

In one embodiment, the sdAb comprises a CDR1, CDR2, and CDR2 of the sdAb sequence set forth in SEQ ID NO: 89.

In one embodiment, the sdAb comprises a CDR1, CDR2, and CDR2 of the sdAb sequence set forth in SEQ ID NO: 90.

In one embodiment, the sdAb comprises a CDR1, CDR2, and CDR2 of the sdAb sequence set forth in SEQ ID NO: 91.

In one embodiment, the sdAb comprises a CDR1, CDR2, and CDR2 of the sdAb sequence set forth in SEQ ID NO: 92.

In one embodiment, the sdAb comprises a CDR1, CDR2, and CDR2 of the sdAb sequence set forth in SEQ ID NO: 93.

In one embodiment, the sdAb comprises a CDR1, CDR2, and CDR2 of the sdAb sequence set forth in SEQ ID NO: 94.

In one embodiment, the sdAb comprises a CDR1, CDR2, and CDR2 of the sdAb sequence set forth in SEQ ID NO: 95.

In one embodiment, the sdAb comprises a CDR1, CDR2, and CDR2 of the sdAb sequence set forth in SEQ ID NO: 96.

In one embodiment, the sdAb comprises a CDR1, CDR2, and CDR2 of the sdAb sequence set forth in SEQ ID NO: 97.

In one embodiment, the sdAb comprises a CDR1, CDR2, and CDR2 of the sdAb sequence set forth in SEQ ID NO: 98.

In one embodiment, the sdAb comprises a CDR1, CDR2, and CDR2 of the sdAb sequence set forth in SEQ ID NO: 99.

In one embodiment, the sdAb comprises a CDR1, CDR2, and CDR2 of the sdAb sequence set forth in SEQ ID NO: 100.

In one embodiment, the sdAb comprises a CDR1, CDR2, and CDR2 of the sdAb sequence set forth in SEQ ID NO: 101.

In one embodiment, the sdAb comprises a CDR1, CDR2, and CDR2 of the sdAb sequence set forth in SEQ ID NO: 102.

In one embodiment, the sdAb comprises a CDR1, CDR2, and CDR2 of the sdAb sequence set forth in SEQ ID NO: 103.

In one embodiment, the sdAb comprises a CDR1, CDR2, and CDR2 of the sdAb sequence set forth in SEQ ID NO: 104.

In one embodiment, the sdAb comprises a CDR1, CDR2, and CDR2 of the sdAb sequence set forth in SEQ ID NO: 105.

In one embodiment, the sdAb comprises a CDR1, CDR2, and CDR2 of the sdAb sequence set forth in SEQ ID NO: 106.

In one embodiment, the sdAb comprises a CDR1, CDR2, and CDR2 of the sdAb sequence set forth in SEQ ID NO: 107.

In one embodiment, the sdAb comprises a CDR1, CDR2, and CDR2 of the sdAb sequence set forth in SEQ ID NO: 108.

In one embodiment, the sdAb comprises a CDR1, CDR2, and CDR2 of the sdAb sequence set forth in SEQ ID NO: 120.

In one embodiment, the sdAb comprises a CDR1, CDR2, and CDR2 of the sdAb sequence set forth in SEQ ID NO: 121.

In one embodiment, the sdAb comprises a CDR1, CDR2, and CDR2 of the sdAb sequence set forth in SEQ ID NO: 122.

In one embodiment, the sdAb comprises a CDR1, CDR2, and CDR2 of the sdAb sequence set forth in SEQ ID NO: 123.

In one embodiment, the sdAb comprises a CDR1, CDR2, and CDR2 of the sdAb sequence set forth in SEQ ID NO: 124.

In one embodiment, the sdAb comprises a CDR1, CDR2, and CDR2 of the sdAb sequence set forth in SEQ ID NO: 125.

In one embodiment, the sdAb comprises SEQ ID NO: 82.

In one embodiment, the sdAb comprises SEQ ID NO: 83.

In one embodiment, the sdAb comprises SEQ ID NO: 84.

In one embodiment, the sdAb comprises SEQ ID NO: 85.

In one embodiment, the sdAb comprises SEQ ID NO: 86.

In one embodiment, the sdAb comprises SEQ ID NO: 87.

In one embodiment, the sdAb comprises SEQ ID NO: 88.

In one embodiment, the sdAb comprises SEQ ID NO: 89.

In one embodiment, the sdAb comprises SEQ ID NO: 90.

In one embodiment, the sdAb comprises SEQ ID NO: 91.

In one embodiment, the sdAb comprises SEQ ID NO: 92.

In one embodiment, the sdAb comprises SEQ ID NO: 93.

In one embodiment, the sdAb comprises SEQ ID NO: 94.

In one embodiment, the sdAb comprises SEQ ID NO: 95.

In one embodiment, the sdAb comprises SEQ ID NO: 96.

In one embodiment, the sdAb comprises SEQ ID NO: 97.

In one embodiment, the sdAb comprises SEQ ID NO: 98.

In one embodiment, the sdAb comprises SEQ ID NO: 99.

In one embodiment, the sdAb comprises SEQ ID NO: 100.

In one embodiment, the sdAb comprises SEQ ID NO: 101.

In one embodiment, the sdAb comprises SEQ ID NO: 102.

In one embodiment, the sdAb comprises SEQ ID NO: 103.

In one embodiment, the sdAb comprises SEQ ID NO: 104.

In one embodiment, the sdAb comprises SEQ ID NO: 105.

In one embodiment, the sdAb comprises SEQ ID NO: 106.

In one embodiment, the sdAb comprises SEQ ID NO: 107.

In one embodiment, the sdAb comprises SEQ ID NO: 108.

In one embodiment, the sdAb comprises SEQ ID NO: 120.

In one embodiment, the sdAb comprises SEQ ID NO: 121.

In one embodiment, the sdAb comprises SEQ ID NO: 122.

In one embodiment, the sdAb comprises SEQ ID NO: 123.

In one embodiment, the sdAb comprises SEQ ID NO: 124.

In one embodiment, the sdAb comprises SEQ ID NO: 125.

In one embodiment, the CAR further comprises a second CD22 binding domain positioned N-terminally or C-terminally with respect to the first CD22 binding domain, and may be spaced apart from the first CD22 binding domain by an amino acid linker.

In one embodiment, the second CD22 binding domain comprises and sdAb that is the same as the sdAb of the first CD22 binding domain. These embodiments are referred to herein as "double binders". For example, the first and second CD22 binding domains may both comprise antibody 1ug36.

In another embodiment, the second CD22 binding domain comprises an sdAb that is different to the sdAb of the first CD22 binding domain. These embodiments are referred to herein as "bi-paratopic". In this embodiment, the sdAb of the second CD22 binding domain may bind to a different epitope of CD22 to that bound by the sdAb of the first CD22 binding domain. For example, the CAR may comprise a first CD22 binding domain that comprises sdAb 1ug36 and a second CD22 binding domain that comprises sdAb 1ug74. For example, 1ug36 may be positioned N-terminally to 1ug74 (see, e.g., the schematic in FIG. 30). A "different epitope" may alternatively be an epitope that overlaps that bound by the sdAb of the first CD22 binding domain. Alternatively, the sdAb may bind to the same epitope to that bound by the sdAb of the first CD22 binding domain.

In one embodiment, the CAR further comprises an additional binding domain that binds to a target molecule other than CD22. These embodiments are referred to herein as "tandem constructs". The additional binding domain may comprise an additional sdAb. The additional binding domain may be positioned N-terminally or C-terminally with respect to the CD22 binding domain. The additional binding domain may be separated from the CD22 binding domain by an amino acid linker. In one embodiment, the target molecule bound by the additional binding domain is expressed by a target cell that also expresses CD22, thereby providing a CAR having dual affinity for the same target cell. For example, the target molecule other than CD22 may be B-cell maturation antigen (BCMA). The CD22 binding domain may comprise, for example, sdAb 1ug36 and the additional binding domain may comprise an anti-BCMA sdAb (see, e.g., the schematic depicted in FIG. 33).

In some embodiments, the tandem constructs may comprise a third binding domain that targets yet another target molecule distinct from CD22 and distinct from that bound by additional binding domain. Such constructs are referred to herein as "multi-binders".

In some embodiments, the CAR is a sequence variant of one of the above CARs having 80%, 90%, 95%, 98%, or 99% identity thereto. In some embodiments, the variant retains substantially the same binding specificity as the parent molecule from which it is derived. In some embodiments the variant retains substantially the same binding affinity as the parent molecule from which it is derived.

Nucleic Acids & Vectors

In one aspect, there is provided a recombinant nucleic acid molecule encoding the CAR as defined herein.

In one aspect, there is provided a vector comprising the recombinant nucleic acid molecule as defined herein. In one embodiment, the vector is a viral vector. In one embodiment, the viral vector is a lentivirus vector.

Viral Particles

In one aspect, there is provided a recombinant viral particle comprising the recombinant nucleic acid as defined herein. In one embodiment, the recombinant viral particle is a recombinant lentiviral particle.

Cells

In one aspect, there is provided a cell comprising the recombinant nucleic acid molecule as defined herein.

In one aspect, there is provided an engineered cell expressing at the cell surface membrane the CAR as defined herein. In one embodiment, the engineered cell is an immune cell. In one embodiment, the immune cell is a T-lymphocyte or is derived from T-lymphocytes.

Use & Methods

"CAR-T" cell therapy uses T cells engineered with CARs for cancer therapy. The premise of CAR-T immunotherapy is to modify T cells to recognize disease cells, typically cancer cells, in order to more effectively target and destroy them. Generally, T are genetically altered to express a CAR, and these cells are infused into a patient to attack their tumors. CAR-T cells can be either derived from T cells in a patient's own blood (autologous) or derived from the T cells of another healthy donor (allogeneic).

In one aspect, there is providing a use of the nucleic acid, vector, or viral particle as described herein for preparation of cells for CAR-T.

In one aspect, there is providing a method of preparing cells for CAR-T comprising contacting a T-cell with the viral particle as described herein. In one embodiment, the T-cell is from a donor. In one embodiment, the T-cell is from a patient.

In one aspect, there is providing a method of preparing cells for CAR-T comprising introducing into a T-cell the nucleic acid or vector as described herein. In one embodiment, the T-cell is from a donor. In one embodiment, the T-cell is from a patient.

In one aspect, there is provided a use of the CAR or of the engineered cell as described herein for treatment of a cancer or an auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one embodiment, the method further comprises an initial step of obtaining cells from a patient or donor and introducing the recombinant nucleic acid molecule or vector encoding the CAR, as described herein.

In one embodiment, the method further comprises an initial step of obtaining cells from a patient or donor and contacting the cells with the viral particle, as described herein.

In one aspect, there is provided a use of the CAR or of the engineered cell as described herein for preparation of a medicament treatment of a cancer or an auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect, there is provided the CAR or the engineered cell as described herein for use in treatment of a cancer or an auto-immune disease. In one embodiment, the cancer is a hematological malignancy. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL), In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

In one aspect there is provided a method of treating a cancer or an auto-immune disease in a subject, comprising administering to the subject the engineered cell as defined herein. In one embodiment, the hematological malignancy is a leukemia, a lymphoma, or a myelodysplastic syndrome. In one embodiment, the leukemia is acute lymphoid leukemia (ALL) or chronic lymphoid leukemia (CLL). In one embodiment, the lymphoma is selected from the group consisting of multiple myeloma, non-Hodgkin's lymphoma, Burkitt's lymphoma, small cell follicular lymphoma, and large cell follicular lymphoma. In one embodiment, the auto-immune disease is an inflammatory disease. In one embodiment, the auto-immune disease is lupus. In one embodiment, the auto-immune disease is multiple sclerosis. In one embodiment, the auto-immune disease is autoimmune diabetes.

EXAMPLES

The following Examples outline embodiments of the invention and/or studies conducted pertaining to the invention. While the Examples are illustrative, the invention is in no way limited the following exemplified embodiments.

Introduction to the Examples

Previous trials using CD22-targeted CAR-T have all used single-chain variable fragment (scFv) based on mouse monoclonal antibodies, which poses many complexities of domain pairing (VH:VL pairing) such as expression level, stability, etc. This may eventually limit the productivity and effectiveness of the final CAR-T constructs. The approach described herein utilizes camelid single domain antibodies (nanobodies) for CAR targeting as alternative to scFv antibody domains. The applicability of camelid single domain antibodies as soluble, stable and modular domains for a number of therapeutic applications has well-been established with the first FDA-approved bivalent nanobody in 2018. Therefore, nanobodies present an excellent building block in CAR-T molecules, allowing to build a pool of functional CAR-T constructs, therefore, increasing the chance of screening much more effective CAR-T cells for the treatment of non-solid tumor cells.

In addition these nanobodies could also be utilized to develop additional safe and efficacious immunotherapy regimens including but not limited to naked or drug conjugated antibody therapies and bi-specific immune cell engagers.

The approach described herein uses single domain antibodies (sdAb) derived from an immunized llama. These sdAb sequences specifically bind to CD22 antigen which is specifically expressed on human B cells and B-cell leukemia. Using the sdAb sequences, a novel chimeric receptor sequence that combines CD22 specific sdAb with T cell signaling molecules has been generated (in the form of 41BB, CD28 or other co-stimulation domain and CD3zeta signaling domains). In addition to chimeric antigen receptor applications, these CD22 targeting antibodies may be useful for developing other forms of immunotherapies including but not limited to bi-specific/tri-specific T or NK cell engager applications, antibody-drug conjugates, or as naked antibodies.

Example 1: sdAb Antibody Production

Introduction

Single domain antibodies (sdAbs) (also known as VHHs or nanobodies) derived from the variable domains of the camelid heavy chain, are characteristically stable with functional N-terminal domain fully capable of antigen binding. In addition to their small size, sdAbs possess high affinity, solubility, low immunogenicity in humans due to their high homology to human VH3 family, high expression levels in microorganisms such as *E. coli*, and remarkable stability at high temperature, extreme pH and high salt concentrations. Due to their superb antibody engineering potential, sdAbs are considered as ideal building blocks for bi- and multi-specific therapeutic reagents. Notable examples include the first FDA-approved bivalent anti-vWF nanobodies (Caplacizumab, 2019) and ten other therapeutic nanobodies, in bi-/multi-valent or bi-/multi-specific formats, which have been advanced into pre-clinical and clinical development by Ablynx/Sanofi and other biopharmaceutical companies thus far.

sdAbs are also ideal building blocks for the generation of Chimeric Antigen Receptor (CAR), whereby cancer-specific antigen binding domains (scFv, Fab) of conventional IgGs are genetically fused with immune cell activating domains to generated "armored" Immune T lymphocytes (CAR-T) that seek and kill specific cells that harbor the targeting antigen (s). Applying sdAbs in CAR-T constructs reduces domain complexity of scFv/Fab fragments and significantly increases the productivity and effectiveness of the final CAR-T constructs. It also allows additional specificity (against a second cancer biomarker) to be added to the CAR-T construct (i.e., to generate bi-specific CAR-T cell), therefore, increasing the chance of screening much more effective CAR-T cells for the treatment of haematological tumors. Similarly, these sdAbs are ideal candidates for the development of other forms of immunotherapies such as bi-, tri- and multi-specific immune cell engagers.

This study aimed to generate functional camelid sdAbs against the ectodomain of CD22 which is a B-cell restricted leukemia antigen for development of immunotherapies including but not limited to CAR-T therapies, bi-, tri- and multi-specific immune engager therapies, naked therapeutic antibodies with appropriate human IgG fusions. These therapies are intended for use as treatment modalities for cancer, auto-immune and inflammatory diseases. Examples are presented of the use of these sdAb sequences for developing CAR-T and bi-specific immune engagers with effective anti-tumor activity.

Materials and Methods

Cloning and Expression of CD22-ECD

The gene encoding the extracellular domain of human predominant CD22-beta isoform was cloned into pTT5: NRC proprietary mammalian expression vector. Upon transfection of NRC CHO-3E7 cells, the cells were grown in a 1 L flask and the expressed protein containing a C-terminal 6×His tag was purified by Immunoaffinity chromatography (IMAC) followed by Size Exclusion Chromatography and analyzed on SDS-PAGE.

Llama Immunizations.

A llama was immunized with the recombinant ECD domain of CD22 antigen. For each injection, 100 μg of recombinant human CD22 protein in a total volume of 0.5 mL was mixed with an equal volume of complete (first injection) and incomplete Freund's adjuvant (subsequent injection) and was injected, subcutaneously. Five injections were performed at approximately two week intervals and blood was collected after the third injection and 7 days after the last injection.

RNA Isolation and PCR Amplification

Total RNA was isolated from approximately $1\times10^7$ lymphocytes collected from day 49 of the immunization protocol with a QIAamp RNA blood mini kit (QIAGEN Sciences, Mississauga, ON) and according to the kit instructions. About 5 μg of total RNA was used as template for first strand cDNA synthesis with an oligo dT primer using a first-strand cDNA synthesis kit (Amersham Biosciences, USA). Based on the Camelidae and llama immunoglobulin databases, three variable domain sense primers (MJ1-3) and two CH2 domain antisense primers (CH2 and CH2b3) were designed (Baral T N et al 2013). The first PCR was performed with the cDNA as template and the variable regions of both conventional (IgG1) and heavy chain antibodies (IgG2 and IgG3) were amplified with combinations of MJ1-3/CH2 and MJ1-3/CH2b primers in two separate reactions. The PCR reaction mixtures contained the following components: 2 μL cDNA, 5 μmol of MJ1-3 primer mixture, 5 μmol of either CH2 or CH2b primer, 5 μL of 10× reaction buffer, 3 μL of 2.5 mM dNTP, 2.5 units of Taq DNA polymerase (Roche Applied Science, Indianapolis, IN) and water to a final volume of 50 μL. The PCR protocol consisted of an initial step at 94° C. for 3 minutes followed by 30 cycles of 94° C. for 30 seconds, 55° C. for 30 seconds, 72° C. for 1 minute and a final extension step at 72° C. for 7 minutes. The amplified PCR products were run onto a 2% agarose gel and consisted of two major bands of about 850 bp corresponding to conventional IgG1 and about 600 bp (550-650 bp) corresponding to heavy chain antibodies. The smaller bands were cut out of the gel, purified with a QIAquick gel extraction kit (QIAGEN Inc.) and re-amplified in a second PCR reaction containing 1 μL of the purified DNA template, 5 μmol each of MJ7, a VH sense primer with a SfiI restriction site, underlined, (5'-CAT GTG TAG ACT CGC GGC CCA GCC GGC CAT GGC C-3') and MJ8, an antisense primer with a SfiI restriction enzyme site, underlined, (5'-CAT GTG TAG ATT CCT GGC CGG CCT GGC CTG AGG AGA CGG TGA CCT GG), 5 μL of 10× reaction buffer, 3 μL of 2.5 mM dNTP, 2.5 unit of Taq DNA polymerase (Roche Applied Science, Indianapolis, IN) and water to a final volume of 50 μL. The PCR protocol consisted of an initial step at 94° C. for 3 minutes followed by 30 cycles of 94° C. for 30 seconds, 57° C. for 30 seconds, 72° C. for 1 minute and a final extension step at 72° C. for 7 minutes. The amplified PCR products (about 400-450 bp) that correspond to VHH fragments of heavy chain antibodies were purified with a QIAquick PCR purification kit (QIAGEN Inc.), digested with SfiI (New England BioLabs) and re-purified with the same kit.

Library Construction

Thirty ug of pMED1 (Arbabi-Ghahroudi et al. 2009) DNA was digested with SfiI overnight at 50° C. To minimize the chance of self-ligation, the digestion was continued for additional 2 hours at 37° C. by adding 20 units of both XhoI and PstI restriction enzymes. For library construction, 10 μg of phagemid DNA was ligated with 1.75 μg of VHH fragments and incubated for 2 hours at room temperature using the LigaFast DNA ligation system (Promega, Corp., Madison, WI) and according to the recommended protocol. The ligated product was electroporated into competent *E. coli* TG1cells (Stratagene, Cedar Creek, TX). Transformed bacterial cells were diluted in SOC medium and incubated for 1 hour at 37° C. with slow shaking. The size of library was calculated by plating aliquots on LB-Amp. The VHH fragments from 96 colonies were PCR-amplified and sequenced for diversity analysis. The library was aliquoted and stored at −80° C.

Library Panning and Screening

Two strategies of biotinylated and passive absorption were used for the panning of the CD22-immune library:

a) Biotinylated CD22 ECD Panning:

The constructed LPAR1 Library 2 with a size of $3.3\times10^7$ was phage-recued and the phage titer of $1.4\times10^9$ cfu/uL was used to pan against the CD22 ECD antigen previously biotinylated by using EZ-link sulfo-NHS-LC-LC-Biotin (Thermoscientific cat #21338). Four rounds of panning was performed with alternating blocking buffers [e.g. Starter Block (Thermo Fisher Cat #37559) for rounds1, 3 and biotin-free casein for rounds 2, 4. Panning was alternated between both Pierce™ streptavidin coated wells (Round 1, 3) (Thermoscientific cat #15501; lot #TF252884) and Pierce™ neutravidin coated wells (Round 2, 4) (Thermoscientific cat #15508; lot #SK253835). Two wells and either one or two microfuge tubes were first incubated in appropriate blocking buffer overnight at 4° C.

The next day, library input phage ($-3\times10^{11}$) was added to one of the blocked streptavidin wells in appropriate blocking buffer for 1 hour at room temperature then transferred to the blocked microfuge tube and mixed with biotinylated CD22 antigen. In subsequent rounds, $\sim3\times10^{11}$ of input phage from each round of amplified phage was used. In the first round 1 ug of biotinylated CD22 antigen was used. In subsequent rounds both 1 ug and 100 ng of antigen were used. After an hour Incubation at room temperature the input phage/biotinylated CD22 mixture was transferred to the other blocked streptavidin well and incubated for 30 minutes at room temperature. This was followed with wash steps {3×300 μL PBS-T (PBS+0.05% Tween 20) (quick); 2×300 μL PBS-T+ (PBS+0.05% Tween 20) (incubate 5 minutes each wash); 3×300 μL PBS (quick); 2×300 μL PBS (incubate 5 minutes each wash)} and elution with 100 μL of 100 mM TEA. Phage were then removed from wells and neutralized with 50 μL of 1M Tris-HCl PH 7.4 in a new tube. 3 mL of exponentially growing TG1 *E. coli* culture previously grown at 37° C., 250 rpm, until $OD_{600}$=0.5 in 2YT+2% glucose in a 15 mL Falcon tube, was infected with the eluted phage. A 100 μL aliquot of uninfected TG1 *E. coli* cells was set aside as a control. Eluted phage were Incubated at 37° C. for 30 minutes with no shaking and then an aliquot was used for titer (dilutions of $10^2$ to $10^8$) and plating on 2YT plates overnight at 32° C. The remaining 3 mL of infected TG1 culture, proceeded with overnight phage amplification using M13KO7 helper phage (~$1\times10^{10}$ cfu).

The next day the eluted titers were calculated to determine the amount of input phage for the subsequent round. The cell culture containing the amplified phage was centrifuged at 5000 rpm, 30 minutes and the supernatant was filtered through 0.22 μM filter unit (Millipore) and precipitated in 20% PEG/2.5M sodium chloride (NaCl) followed by centrifugation and re-solubilization in PBS (pH7.5). Amplified phage titer was determined (dilutions of $10^4$ to $10^{12}$) in TG1 *E. coli* cells as grown previously. After 4 rounds of panning, the sequences of positive colonies from phage ELISA were analyzed, b) Passive Panning of CD22-ECD The same recued phages was used to pan against the CD22 ECD antigen. Four rounds of panning was implemented with alternating blocking buffers [e.g. Starter Block (Thermo Fisher Cat #37559) for rounds 1, 3 and 4% milk PBS for rounds 2, 4. The amount of CD22 ECD passively adsorbed onto Nunc wells decreased from 40 ug to 10 ug over the four rounds of panning (Round1: 40 μg, Round 2:30 μg; Round 3:20 μg; and Round 4:10 μg). A well was first blocked with appropriate buffer for 2 hours at room temperature followed by addition of input phage (~$3\times10^{11}$). In subsequent rounds, ~$3\times10^{11}$ of input phage from each round of amplified phage was used. The incubation was followed by wash steps {R1: 5×PBS-T; 2×PBS: R2: 5×PBS-T; 5×PBS; R3: 7×PBS-T; 5×PBS; and R4: 10×PBS-T; 10×PBS}.)} and elution with 100 μL of 100 mM TEA. Phage were then removed from wells and neutralized with 50 μL of 1M Tris-HCl pH 7.4 in a new tube. 2 mL of exponentially growing TG1 *E. coli* culture previously grown at 37° C., 250 rpm, until $OD_{600}$=0.5 in 2YT+2% glucose in a 15 mL Falcon tube, were infected with the eluted phage. A 100 μL aliquot of uninfected TG1 *E. coli* cells was set aside as a control. Eluted phage were Incubated at 37° C. for 30 minutes with no shaking and then an aliquot was used for titer (dilutions of 102 to 108) and plating on 2YT plates overnight at 32° C. Proceeded with overnight phage amplification using M13KO7 helper phage (~$1\times10^{10}$ cfu). The next day the eluted titers were calculated to determine the amount of input phage for the subsequent round. The cell culture containing the amplified phage was centrifuged at 5000 rpm, 30 minutes and the supernatant was filtered through 0.22 μM filter unit (Millipore) and precipitated in 20% PEG/2.5M NaCl followed by centrifugation and re-solubilization in PBS (pH7.5). Amplified phage titer was determined (dilutions of 104 to 1012) in TG1 *E. coli* cells as grown previously. After 4 rounds of panning, the sequences of positive colonies from phage ELISA were analyze.

Results

Figure 3:
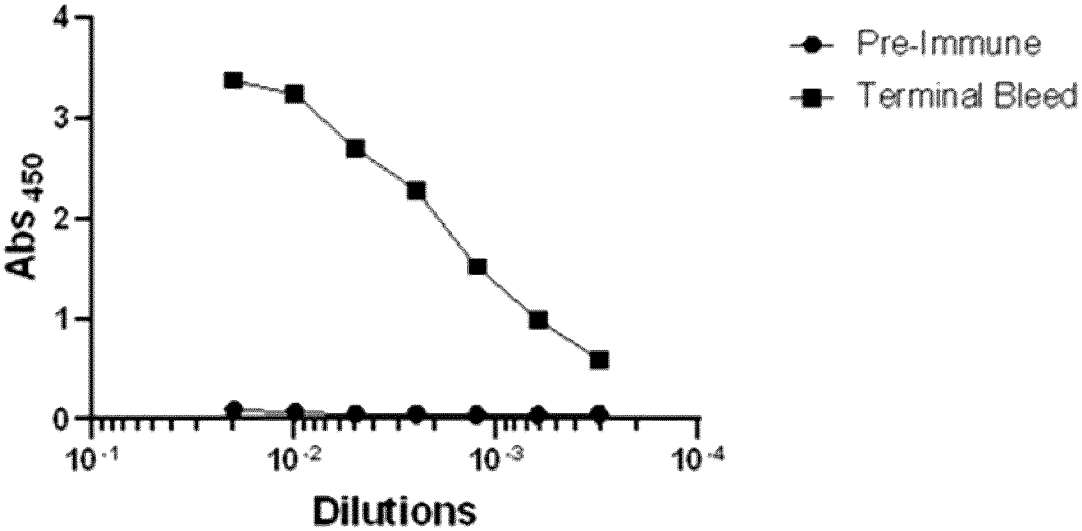
FIG. 3 depicts the llama heavy chain immune response from the final bleed against CD22-ECD along with pre-immune serum as negative control

The recombinant CD22-ECD was used to immunize a llama and the serum titer was monitored and analyzed by ELISA. As shown in FIG. 3, CD22 elicited a strong heavy chain immune response in llama. The heavy chain immune response in the serum was measured by the use two monoclonal antibodies, which specifically bind to the hinge-CH2 boundary of llama IgG2b and the Fc of llama IgG2c respectively (Henry K A et al. Llama Peripheral B-cell Populations Producing Conventional and Heavy Chain-Only IgG Subtypes Are Phenotypically Indistinguishable but Immunogenetically Distinct. *Immunogenetics* 2019 April; 71(4):307-320).

The heavy chain repertoire of llama immunoglobulins was amplified by gene-specific primers and cloned into a phagemid vector (pMED1). A medium size library ($3.3\times10^7$) was constructed and its complexity was analyzed by sending 96 colonies for sequencing. The sequencing data showed that the library has high complexity as all the VHH sequences were full-length with no repeating sequences. The library was phage-rescued using M13 helper phage as described elsewhere (Baral T N, Mackenzie R, Arbabi Ghahroudi M. Single-domain antibodies and their utility. Curr Protoc Immunol. 2013 Nov. 18; 103:2.17.1-2.17.57) and the phage antibodies were used in two separate panning experiments. After four rounds of pannings, 96 colonies from each panning strategy were grown and superinfected by M13 helper phage as described elsewhere (Baral T N et al 2013) and the phages were used in ELISA. Positive colonies were sent for sequencing and the sequencing data were analyzed. Alignment of the sequences using OPIG software (http://opig.stats.ox.ac.uk/webapps/newsabdab/sabpred/anarci/) and IMGT numbering (see FIGS. 4A and 4B). 27 unique VHH sequences were selected for gene synthesis and cloning into an expression vector (pMRO).

FIG. 1 depicts the structure of human CD22 molecule which is encoded by the CD22 gene located on chromosome 19q13.12. CD22 β is the predominant isoform (with 7 domains; 847 aa). The cytoplasmic tail (140 aa) with four immune receptor motifs is connected by the transmembrane region (18 aa) to the extra cellular domains (669 aa).

Figure 2:
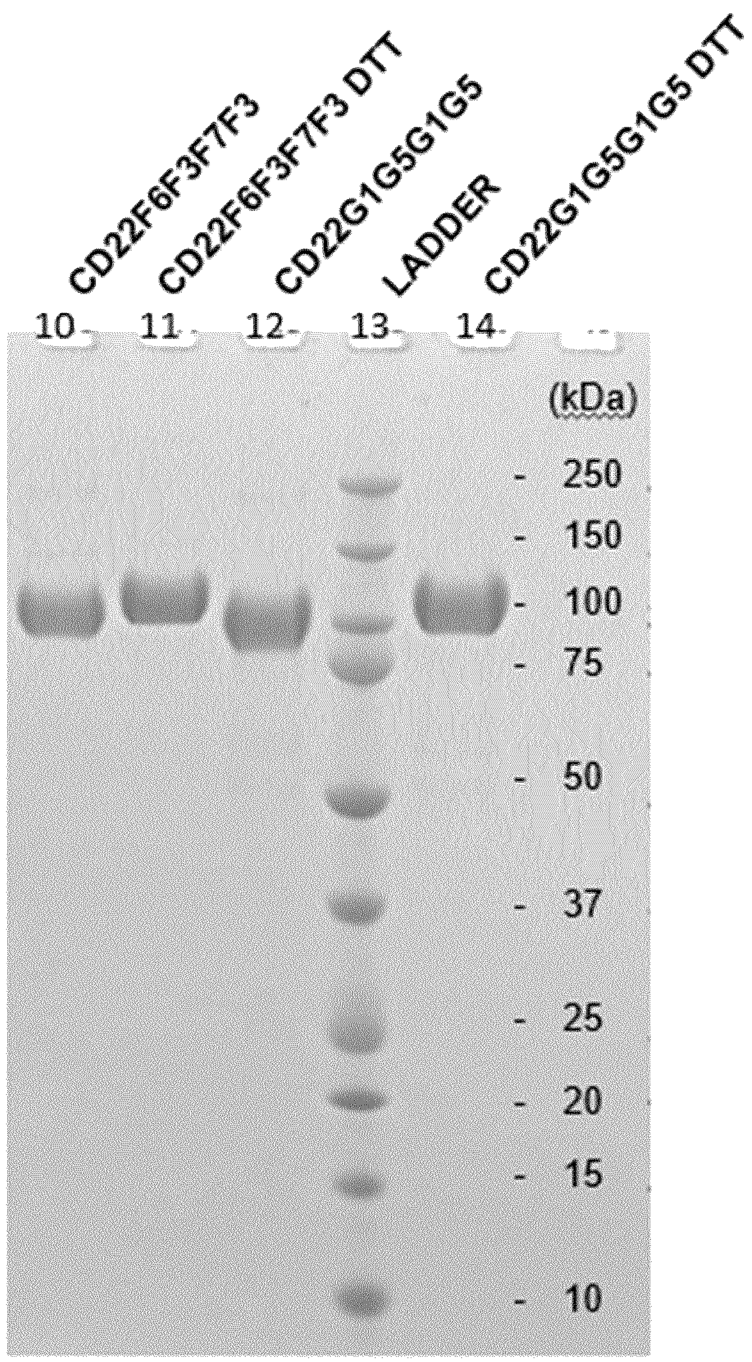
FIG. 2 depicts a SDS-PAGE of IMAC-purified CD22 extracellular domain (CD22-ECD) from two different expression batches under non-reduced and reduced conditions.

FIG. 2 depicts a SDS-PAGE of IMAC-purified CD22 extracellular domain (CD22-ECD) form two different expression batches under non-reduced and reduced conditions. The purified protein has the expected molecular weight of approximately 75 kDa.

FIG. 3 depicts the llama heavy chain immune response form the final bleed ($3^{rd}$ August) against CD22-ECD. As control, llama pre-immune serum was used. The binding of heavy chain antibodies was detected by anti-llama mAbs (in-house NRC) followed by donkey-anti-mouse-HRP. As shown, there is a strong and specific anti-CD22-ECD heavy chain immune response.

Discussion

The extracellular domain of the predominant human CD22 isoform was successfully expressed in mammalian CHO system and the recombinant CD22-ECD performed well in all downstream analytical assays (data not shown). After immunizing a llama with the recombinant CD22-ECD, a strong heavy chain immune response was generated as determined by ELISA using heavy chain-specific mAbs. By constructing a library on the heavy chain repertoire, VHH domain antibodies specific to the immunogen (CD22-ECD) were isolated.

Example 2: sdAb Antibody Characterization

Introduction

Library construction on the heavy chain repertoire of immunized llama was performed following obtaining a positive immune response against the human CD22-ECD. More than two hundred individual colonies were subsequently screened by phage-ELISA after performing two distinct panning strategies where biotinylated and non-biotinylated human CD22-ECD proteins were used. The individual VHH clones were sequenced and grouped based on their CDR1-3 sequences, resulting in 27 unique VHH sequences. The gene-encoding these VHHs were cloned into an NRC bacterial expression vector and purified proteins were characterized.

Materials and Methods

Expression of Soluble $V_HH$.

The DNA sequences of the most repeated clones with phage ELISA $OD_{450}$>0.8 were sent for Gene synthesis to TWIST Bioscience and subsequently cloned into pMRO (a pET28a derivative, Novagen) expression vector. *E. coli* TG1 cells were transformed with the VHH constructs and the respective clones were grown in 0.25-liter cultures of 2×YT medium+ampicillin (100 mg·mL-1) with 0.1% glucose to an OD600 of 0.8. Cultures were induced with 1 mM IPTG and grown overnight on a rotary shaker at 37° C. After confirming of expression by SDS-PAGE and Western blotting, recombinant VHH proteins were extracted from the bacterial cells by standard lysis methods and purified by immobilized metal affinity chromatography (IMAC) and quantified as described elsewhere (Baral T N, Arbabi-Ghahroudi M. Expression of single-domain antibodies in bacterial systems. Methods Mol Biol. 2012; 911:257-75). The VHH proteins were run on a Supdex 75 Size exclusion chromatography and the monomeric fractions were collected.

SPR Analysis

For surface Plasmon resonance, 21 selected VHHs were passed though size exclusion columns, superdex 75 (GE Healthcare), respectively, in 10 mM HEPES, PH 7.4, containing 150 mM NaCl, 3 mM EDTA, monomeric sdAb fractions were collected and protein concentrations were determined by measuring absorbance at 280 nm (A280). Analysis were performed with Biacore T200 instrument (GE Healthcare). All measurements were carried out at 25° C. in 10 mM HEPES, pH 7.4, containing 150 mM NaCl, 3 mM EDTA and 0.005% surfactant P20 (GE Healthcare). Approximately 1919 RUs of the recombinant monomeric CD22-ECD (obtained after SEC purification of the CD22-ECD) were captured on SA sensor chip (GE Healthcare) at a flow rate of 5 μL/min. Various concentration of the monomeric VHHs were injected over CD22-ECD surface, respectively using an SA surface as a reference at a flow rate of 40 L/min. Surfaces were generated by washing with running buffer. Data were analysed with BIAevaluation 4.1 software.

Epitope Binning by SPR

In addition to obtaining binding kinetic data, Biacore co-injection experiments were also performed on 11 selected VHHs to determine whether these anti-CD22 VHHs could bind unique or overlapping epitopes on CD22-ECD protein surface. Briefly, 80 μL of the first VHH diluted in HBS-EP buffer to a concentration of 5 times its KD value and was injected over 1919 RUs of immobilized CD22-ECD at 40 μL/min. Following injection of the first VHH, buffer or a second VHH (80 μL total volume, at 5×KD) was injected at 40 μL/min over the CD22-ECD surface already saturated with the first VHH. Data were collected on all possible paired combinations of 11 VHHs, in both orientations (i.e. each VHH acted as the first and second VHH) and evaluated as described above.

Epitope Mapping Using Yeast Surface Display

The hCD22 ecto-domain (ECD) and its derived fragments were expressed and covalently displayed on the surface of yeast cell using the yeast surface display (Feldhaus et al., 2003, Nat. Biotechnol. Vol. 21, 163-170). The YSD vector (pPNL6) was from The Pacific Northwest National Laboratory, USA. Seven hCD22 fragments, designated as Bin1 to 7, with over lapping ends (15-25aa) covering the entire hCD22-ECD (668aa), along with the full-length hCD22-ECD were cloned and expressed as fusion proteins (Aga2-HA-(hAXL)-MYC on the yeast cell surface. The displayed hCD22 fragments were used to map the domains of hCD22 to which the anti-hCD22 sdAbs of Example 1 bind. The binding of the sdAbs (biotinylated) to CD22 fragments on yeast cells was performed using a whole yeast cell ELISA probed with HRP-conjugated streptavidin. The relative amount of the displayed fusion protein was measured by probing with an anti-MYC antibody, followed by an HRP-conjugated secondary antibody, and used to normalize the binding signal for the sdAbs. The HRP activity was assayed with substrate TMB (tetramethyl benzidine) according to the manufacture's conditions and read at OD450. For determination the nature of epitopes, linear versus conformational, yeast cells with displayed CD22 fragments were heated at 80° C. for 30 minutes, then chilled on ice for 20 minutes prior to labeling with antibodies.

Evaluating Target Specificity of sdCD22 VHH

Biotinylated VHH were used to assess the target specificity of the sdCD22 Ab by flow cytometry. CD22 expressing human Burkitt's lymphoma cell lines Raji and Ramos and Ramos cells deleted for CD22 expression using CRISPR gene knockout were incubated with 5 fold dilution of biotin labelled sdCD22 VHH from 7.5-0.06 μg/mL. The binding of the CD22-targeted VHH to cell surface CD22 was detected by flow cytometry using fluorophore conjugated streptavidin.

Results

Figure 5:
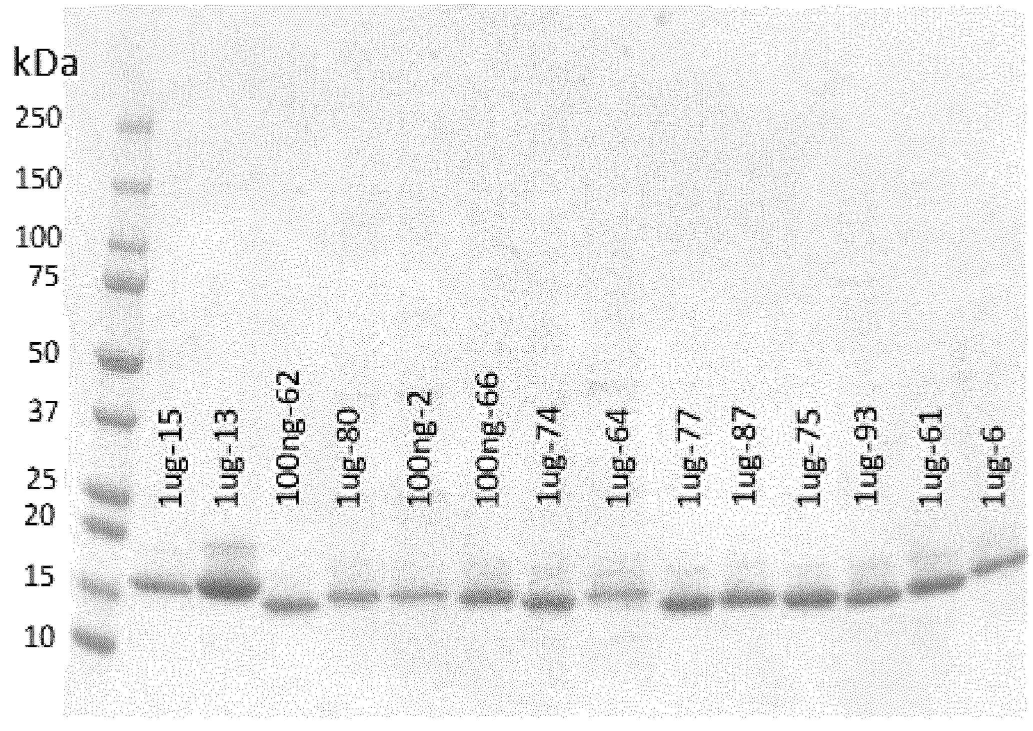
FIG. 5 depicts the SDS-PAGE of 14 anti-CD22 VHH antibodies expressed in TG1 *E. coli* and purified by IMAC.

The gene synthesis and sub-cloning was performed by TWIST Bioscience (USA) and the plasmid DNA were transformed into TG1 *E. coli* for protein expression. The presence of a Histidine tag and biotinylation signal sequence in the pMRO vector allows facile purification by IMAC column as well as specific addition of a biotin moiety at the VHH C-terminal. The single biotin addition facilitates VHH detection in future epitope mapping assays. The IMAC-purified VHH proteins were ran on a SDS-PAGE (FIG. 5; only 14 VHHs are shown). As shown, the VHH antibodies show an expected molecular weight of around 15-17 kDa.

The state of aggregation of the purified protein was checked by size exclusion chromatography and as expected all were non-aggregating monomers (data not shown). The reactivity of the individual VHH protein was also confirmed by ELISA in which rabbit anti-$His_6$ antibody conjugated to HRP was used for the detection of VHH binding to the immobilized CD22-ECD (data not shown).

The monomeric fraction of all 21 VHHs were used for SPR experiment where the human CD22-ECD was immobilized onto the CM5 dextran chip and various VHH concentration (0.6-400 nM) were passed over the sensor chip. SPR analysis revealed all 21 VHHs specifically bound CD22-ECD with equilibrium constants ranging from 250 nM for hCD22pas-64 to 6 pM for hCD221ug-14. All of the data collected fit a 1:1 binding model.

For epitope binning of anti-CD22 VHHs, co-injection SPR experiments were performed with pairs of VHHs in both orientations to determine if antibodies could bind CD22-ECD simultaneously. If there is an increase in response upon co-injection of any two VHHs, this will indicate that binding of the first VHH (at saturation concentration) does not hinder the binding of the second one and, therefore, these antibodies recognize independent epitopes. However, if there is a minor change in response upon co-injection of two VHHs, this will indicate that the two VHHs could not bind simultaneously to the same region and, therefore, they recognize overlapping/identical epitopes. The co-injection SPR experiments were performed for 11 anti-CD22 VHHs and identified seven bind as shown in Table 5. The remaining 10 VHHs had high sequence similarities at their CDR regions with the 11 VHHs, which were binned by SPR. Therefore, the 10 VHHs were placed into the bin which had the closest amino acid similarities as shown in Table 5.

FIGS. 4A and 4B depicts the alignment of amino acid sequences of 27 VHHs.

Table 1 (above) depicts the amino acid sequences of the 27 VHHs. The CDR (underlined) and Framework regions are numbered according to IMGT numbering system (www.IMGT.com).

Table 2 (above) provides correspondence between VHH names, numbers, and SEQ ID NOS.

FIG. 5 depicts the SDS-PAGE of 14 anti-CD22 VHH antibodies expressed in TG1 *E. coli* and purified by IMAC. The purified proteins showed expected molecular weight of 15-17 kDa and there was no sign of degradation in all protein samples Table 4 depicts the measured affinities of all 27 VHHs as described in the text. The affinities data range from pM (6 pM for hCD221ug-14)) to high nM (250 nM0; for hCD22pass-64).

TABLE 4

Affinity of sdCD22 VHH by Surface Plasmon Resonance (SPR)

| VHH # | Name | Target | ka (1/Ms) | kd (1/s) | KD (M) |
|---|---|---|---|---|---|
| VHH # 1 | hCD221ug-80 | CD22-ECD | 2.09E+04 | 6.33E−04 | 3.028E−08 |
| VHH # 2 | hCD22100ng-2 | CD22-ECD | 4.68E+04 | 1.30E−04 | 2.779E−09 |
| VHH # 3 | hCD221ug-74 | CD22-ECD | 9.25E+04 | 6.55E−04 | 7.081E−09 |
| VHH # 4 | hCD22100ng-66 | CD22-ECD | 1.45E+05 | 1.34E−04 | 9.24E−10 |
| VHH # 5 | hCD221ug-6 | CD22-ECD | 5.36E+04 | 1.29E−04 | 2.408E−09 |
| VHH # 6 | hCD22pas-10 | CD22-ECD | 1.52E+05 | 2.89E−03 | 1.901E−08 |
| VHH # 7 | hCD22pas-33 | CD22-ECD | 5.40E+04 | 1.40E−04 | 2.6E−09 |
| VHH # 8 | hCD221ug-77 | CD22-ECD | 5.50E+05 | 2.62E−03 | 4.771E−09 |
| VHH # 9 | hCD221ug-87 | CD22-ECD | 1.23E+06 | 7.97E−04 | 6.475E−10 |
| VHH # 10 | hCD221ug-75 | CD22-ECD | 1.40E+06 | 1.21E−03 | 8.647E−10 |
| VHH # 11 | hCD221ug-93 | CD22-ECD | 1.36E+06 | 1.05E−02 | 7.7E−09 |
| VHH # 12 | hCD22pas-82 | | | | ND |
| VHH # 13 | hCD22pas-23 | | | | ND |
| VHH # 14 | hCD221ug-61 | CD22-ECD | 1.25E+06 | 6.81E−04 | 5.465E−10 |
| VHH # 15 | hCD22pas-32 | CD22-ECD | 1.58E+05 | 3.69E−03 | 2.335E−08 |
| VHH # 16 | hCD221ug-14 | CD22-ECD | 3.07E+06 | 2.10E−05 | 6.844E−12 |
| VHH # 17 | hCD22pas-55 | | | | ND |
| VHH # 18 | hCD22pas-79 | CD22-ECD | 5.14E+05 | 3.97E−03 | 7.723E−09 |
| VHH # 19 | hCD22pas-72 | | | | ND |
| VHH # 20 | hCD22pas-16 | CD22-ECD | 3.65E+05 | 1.00E−03 | 2.75E−09 |
| VHH # 21 | hCD221ug-13 | CD22-ECD | 2.32E+05 | 6.75E−04 | 2.914E−09 |
| VHH # 22 | hCD221ug-36 | CD22-ECD | 1.19E+05 | 1.14E−03 | 9.593E−09 |
| VHH # 23 | hCD221ug-10 | CD22-ECD | 4.77E+05 | 1.76E−03 | 3.682E−09 |
| VHH # 24 | hCD22100ng-62 | | | | ND |
| VHH # 25 | hCD22pas-64 | CD22-ECD | 1.08E+05 | 2.71E−02 | 2.504E−07 |
| VHH # 26 | hCD22pas-24 | CD22-ECD | 1.48E+05 | 3.86E−03 | 2.602E−08 |
| VHH # 27 | hCD22pas-48 | | | | ND |

Table 5 depicts epitope binning by co-injection SPR experiments. Pairs of VHHs in both orientations were co-injected and the increase in response unit was measured for 11 anti-CD22 VHHs. As shown, 7 bins were identified with 1 to 4 members. The remaining 10 VHHs had high amino acid sequence similarities with the 11 VHH binned by the SPR and, therefore, were placed into the respective bin.

TABLE 5

Binning by SPR Competitive Binding

| VHH # | Name | Selected for binning | Bin |
|---|---|---|---|
| VHH # 6 | hCD22pas-10 | | bin 6 |
| VHH # 7 | hCD22pas-33 | | bin 6 |
| VHH # 3 | hCD221ug-74 | | bin 6 |
| VHH # 1 | hCD221ug-80 | | bin 6 |
| VHH # 5 | hCD22100ng-64 | | bin 6 |
| VHH # 4 | hCD22100ng-66 | hCD22100ng-66 | bin 6 |
| VHH # 2 | hCD22100ng-2 | | bin 6 |
| VHH # 15 | hCD22pas-32 | | bin 5 |
| VHH # 16 | hCD221ug-14 | hCD221ug-14 | bin 5 |
| VHH # 3 | hCD221ug-77 | | bin 3 |
| VHH # 9 | hCD221ug-87 | | bin 3 |
| VHH # 10 | hCD221ug-75 | hCD221ug-75 | bin 3 |
| VHH # 11 | hCD221ug-93 | | bin 3 |
| VHH # 18 | hCD22pas-79 | hCD22pas-79 | bin 3 |
| VHH # 20 | hCD22pas-16 | hCD22pas-16 | bin 2 |
| VHH # 25 | hCD22pas-64 | hCD22pas-64 | bin 7 |
| VHH # 26 | hCD22pas-24 | hCD22pas-24 | bin 4 |
| VHH # 21 | hCD221ug-13 | hCD221ug-13 | bin 1 |
| VHH # 14 | hCD221ug-61 | hCD221ug-61 | bin 3 |
| VHH # 22 | hCD221ug-36 | hCD221ug-36 | bin 2 |
| VHH # 23 | hCD221ug-10 | hCD221ug-10 | bin 3 |

Figure 6:
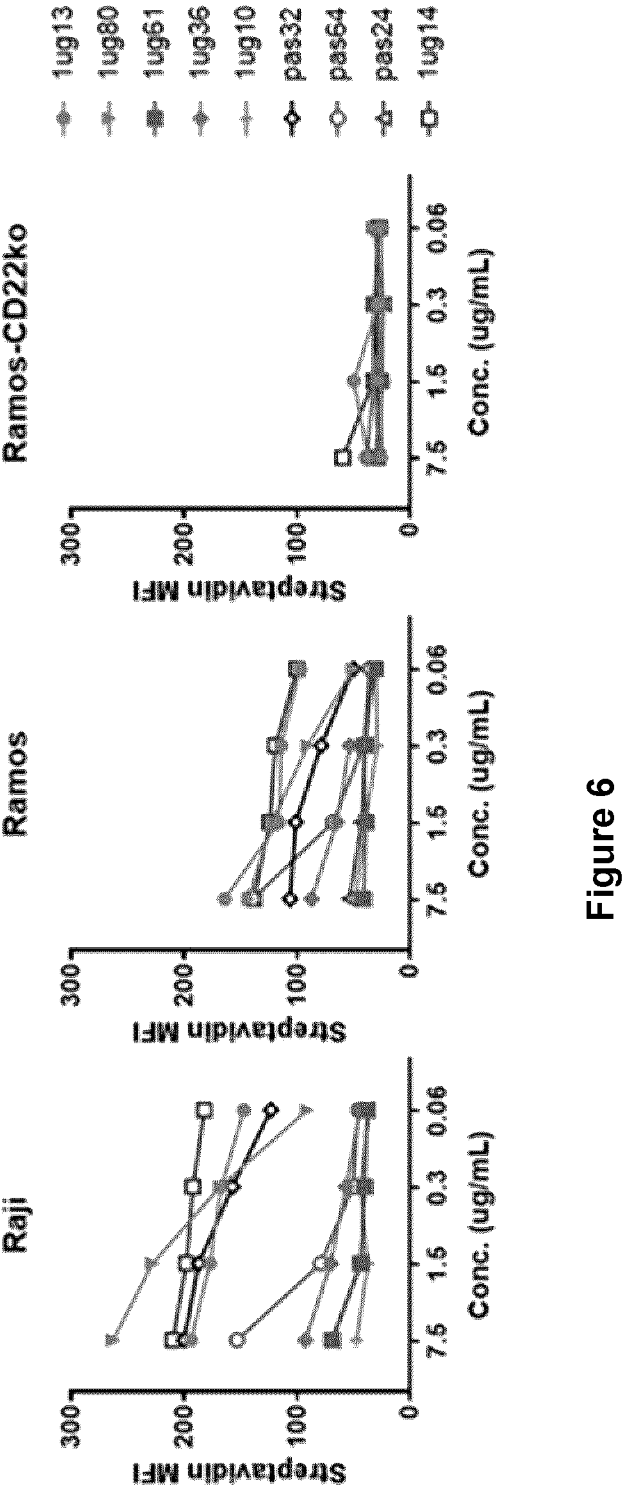
FIG. 6 depicts binding of biotin conjugated anti-CD22 VHH to CD22 expressing tumor cells Raji (left panel), Ramos (middle panel) or Ramos cells engineered to be devoid of CD22 expression by CRISPR gene knockout (right panel).

FIG. 6 depicts binding of biotin conjugated anti-CD22 VHH to CD22 expressing tumor cells Raji (left panel), Ramos (middle panel) or Ramos cells engineered to be devoid of CD22 expression by CRISPR gene knockout (right panel). A representative panel of 9 VHH sequences were included in the cell binding analysis which shows varying degrees of dose depended binding to CD22 positive Raji and Ramos cells. In all cases, the intensity of binding was significantly diminished or eliminated when tested on CD22 negative Ramos cells.

Table 6 depicts the physical binning of the CD22 sdAbs presented in Example 1 against yeast surface displayed hCD22 ecto-domain fragments using cell ELISA. The CD22 fragments displayed define as physical Bins with indicated covering range (in amino acid residues according to the numbering) of the mature CD22. The binding of each sdAb (biotinylated) at 250 nM to particular CD22 fragment(s) on yeast cell surface was revealed by streptavidin conjugated HRP enzymatic activity. The wells that gave rise to OD450 above 0.25 were highlighted, indicating significant antibody-antigen interactions. All the sdAbs tested except hCd22_1ug-14 were assigned to specific Bin(s). Both hCD221ug-13 and hCD221 ug-80 could be assigned to two Bins, suggesting that these sdAbs recognize epitopes that are shared by more than one location on CD22.

Figure 7:
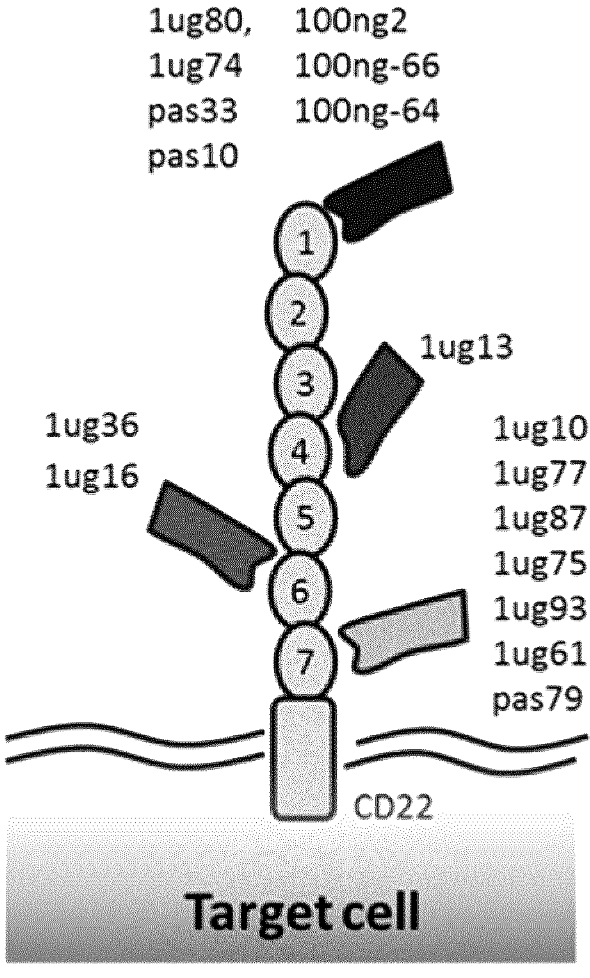
FIG. 7 depicts schematic presentation of the perceptive binding of the sdAbs in Example 1 to the subdomains of CD22 Ecto-domain relative to its cell surface location according to the epitope mapping/binning result in Table 5 & 6.

FIG. 7 depicts schematic presentation of the perceptive binding of the sdAbs in Example 1 to the subdomains of CD22 Ecto-domain relative to its cell surface location according to the epitope mapping/Binning result in Table 5 & 6. Each subdomain/Bin was defined and numbered same as in Table 6, and represented as ellipse with Bin-1 being on the distal and Bin-7 proximal relative to plasma membrane. The binding of sdAb (indicated by specific shape and name) to a subdomain/Bin is indicated by its vicinity to the subdomain/Bin it bins.

Discussion

Anti-CD22-ECD VHHs were expressed in *E. coli* and the proteins were purified and biotinylated. The antibodies showed non-aggregating and monomeric behaviors as determined by size exclusion chromatography. The binding kinetics of 21 VHHs were determined by SPR and the antibodies showed specific binding to human CD22-ECD with affinities ranging from low to high nanomolar except one VHH which had affinity of 6 picomolar. This diverse set of affinities allows us to study the effect of affinity in productivity of CAR-T construct. Epitope binning of 11 VHHs by SPR indicates that some VHHs bind to the overlapping epitopes while others bind to the unique epitopes. This was confirmed through epitope binning of the antibodies using yeast surface display library of the humanCD22 ecto-domain fragments and by using cell ELISA. All the sdCD22 Abs tested except 1ug-14 were assigned to specific Bin(s). Both 1ug-13 and 1ug-80 could be assigned to two bins, suggesting that these sdAbs recognize epitopes that are shared by more than one location on CD22. These epitope binning information will

TABLE 6

Binning CD22 sdAbs Using Yeast Surface Display Library

| sample name | Bin | Bin 1 IVR1 (aa1-135) | Bin 2 IVR2 (aa111-230) | Bin 3 IVR3 (aa211-317) | Bin 4 IVR4 (aa303-405) | Bin 5 IVR5 (aa391-490) | Bin 6 IVR6 (aa476-575) | Bin 7 IVR7 (aa561-668) | Bin 8 (CD22-ECD Full lenght) | Bin 9 Negative Ctl |
|---|---|---|---|---|---|---|---|---|---|---|
| 1-hCD22 1 ug-13 | 4, 6 | 0.036 | 0.043 | 0.000 | 0.752 | 0.000 | 0.433 | 0.090 | 1.189 | 0.011 |
| 2-hCD22 1 ug-80 | 1, 6 | 2.030 | 0.025 | 0.000 | 0.017 | 0.068 | 2.254 | 0.196 | 1.814 | 0.038 |
| 3-hCD22 1 ug-61 | 7 | 0.000 | 0.000 | 0.000 | 0.000 | 0.000 | 0.006 | 2.842 | 1.477 | 0.000 |
| 4-hCD22 1 ug-36 | 6 | 0.000 | 0.000 | 0.038 | 0.000 | 0.000 | 2.974 | 0.001 | 1.422 | 0.000 |
| 5-hCD22 1 ug-10 | 7 | 0.128 | 0.118 | 0.122 | 0.103 | 0.124 | 0.151 | 0.750 | 0.332 | 0.112 |
| 6-hCD22 pas-32 | 8 | 0.000 | 0.000 | 0.000 | 0.000 | 0.000 | 0.060 | 0.008 | 0.289 | 0.000 |
| 7-hCD22 pas-64 | 6 | 0.000 | 0.014 | 0.012 | 0.019 | 0.009 | 1.381 | 0.005 | 0.079 | 0.046 |
| 8-hCD22 pas-24 | 7 | 0.008 | 0.013 | 0.062 | 0.046 | 0.064 | 0.115 | 2.893 | 1.178 | 0.030 |
| 9-hCD22 1 ug-14 | None | 0.000 | 0.000 | 0.000 | 0.000 | 0.000 | 0.000 | 0.000 | 0.000 | 0.000 |

Table 7 depicts the assessment of the nature of the epitopes of CD22 sdAbs to determine if the epitopes for the sdAbs are continuous (linear) or non-continuous (conformational). Various fragments of CD22 domains were expressed and displayed on yeast cells and assayed for binding to the sdAbs using cell ELISA as described in Table 6 with either native (ND) or heat denatured (D) YSD cells as described. The binding of each sdAb to native and denatured CD22 fragments was measured as OD450, and the ratio of the binding to denatured CD22 to non-denatured CD22 was calculated, with the ratio ≥0.5 indicative linear (L), and the ratio <0.5 indicative of conformational (C) epitopes.

TABLE 7

Assessment of the nature of the epitopes for the sdAbs from Example 1

| Sample name | CD22 Sub-Domain | Non denatured CD22 OD | Non denatured Myc OD | Heat Inactivated CD22 OD | Heat denatured Myc OD | Myc Ratio (D/ND) | CD22 Ratio (D/ND) | Epitope Nature |
|---|---|---|---|---|---|---|---|---|
| 1-hCD22 1 ug-13 | 4 | 1.232 | 1.291 | 0.686 | 1.226 | 0.949 | 0.557 | L |
| | 6 | 0.453 | 1.978 | 0.272 | 1.536 | 0.776 | 0.600 | L |
| 2-hCD22 1 ug-80 | 1 | 2.323 | 0.487 | 1.771 | 0.815 | 1.674 | 0.762 | L |
| | 6 | 2.570 | 1.978 | 2.623 | 1.536 | 0.776 | 1.021 | L |
| 3-hCD22 1 ug-61 | 7 | 3.500 | 1.082 | 2.327 | 0.783 | 0.723 | 0.665 | L |
| 4-hCD22 1 ug-36 | 6 | 3.500 | 1.978 | 3.500 | 1.536 | 0.776 | 1.000 | L |
| 5-hCD22 1 ug-10 | 7 | 3.500 | 1.082 | 0.320 | 0.783 | 0.723 | 0.091 | C |
| 6-hCD22 pas-32 | 8 (ECD) | 0.789 | 0.165 | 0.000 | 0.100 | 0.603 | 0.000 | C |
| 7-hCD22 pas-64 | 6 | 2.982 | 1.978 | 2.040 | 1.536 | 0.776 | 0.684 | L |
| 8-hCD22 pas-24 | 7 | 3.500 | 1.082 | 2.110 | 0.783 | 0.723 | 0.603 | L |
| 9-hCD22 1 ug-14 | None | ND | ND | ND | ND | | | |

be utilized in designing bi-paratopic therapeutic agents containing multiple sdCD22 VHH sequences.

Example 3: CAR-T In Vitro Testing

Introduction

After identifying novel CD22-binding single domain antibody (sdAb) sequences described above, it was desired to test their activity within the context of chimeric antigen receptor (CAR) molecules which can be used to redirect human T cell responses towards cells bearing specific surface antigens. Thus, using high throughput techniques previously described (Bloemberg, et. al. 2020) novel CD22-sdAb targeted CAR constructs were generated and tested their relative T cell activating activity via various assays described below.

Materials and Methods

Single domain antibody antigen binding sequences were transferred to a modular CAR plasmid backbone [SEQ ID No: 119] containing restriction sites to allow efficient recombination wherein the antigen binding domain could be removed and replaced with the novel CD22-antigen binding domain (ABD) sequences. Specific CAR design used was as follows: Human CD28 signal peptide [SEQ ID No: 110], any one of VHH antibody (ABD) [SEQ ID NOs: 82 to 108], flexible linker domain [SEQ ID No: 111], human CD8 hinge domain [SEQ ID No: 112], human CD28 transmembrane domain [SEQ ID No: 113], human 4-1BB co-stimulatory domain [SEQ ID No: 114], and human CD3-zeta signaling domain [SEQ ID No: 115]. Control constructs were also generated using sequences derived from previously demonstrated CD19-specific CAR sequence, wherein the ABD is FMC63-scFv sequence [SEQ ID No: 117], or CD22-specific CAR sequence, wherein ABD is M971-scFv sequence [SEQ ID No: 116].

Figure 8:
FIG. 8 depicts the results of CAR-Jurkat assay wherein Jurkat cells were transiently electroporated with varying CD22-single domain antibody CAR plasmids and cultured alone or in co-culture with CD22-positive (Ramos) or CD22-negative (Ramos-CD22ko) cell lines.

Novel CD22-targeting CAR constructs were then tested for activity in an immortalized human T cell line (Jurkat) similarly as described in Bloemberg et al 2020. In brief, plasmids were electroporated into Jurkat T cells and allowed to recover for several hours. Jurkat-CAR cells were then mixed at varying doses with target cell lines exhibiting varying expression levels of human CD22. Target cell lines with high expression of CD22 (Ramos) were utilized for this study to confirm CAR activation activity in Jurkat cells. Cells wherein CRISPR-genome editing was used to remove CD22 expression were also used to confirm specificity of novel CAR constructs for human CD22 antigen. CAR-expressing Jurkat cell and target cell co-cultures were then incubated overnight in standard mammalian cell culture condition to allow CAR activation to occur. In order to quantitate CAR-mediated Jurkat cell activation, expression of CD69 was measured using specific antibody staining and flow cytometry. Using expression of GFP-marker to gate CAR-expressing cells, the level of T cell activation as determined using the CD69-surface marker. CD69 marker was clearly elevated in various Jurkat cells expressing various CD22-sdAb targeted CAR constructs when cells were placed in co-culture with CD22 expressing Ramos cells but not with CD22-knockout cells (FIG. 8).

Following this CAR-J testing, several CD22-CAR constructs were selected for testing in primary human T cells. To accomplish this, lentivirus was prepared through co-transfection of CAR plasmids with lentiviral packaging cell lines. Lentiviral particles in the cell supernatant were collected and concentrated using ultracentrifugation. Primary human T cells were then isolated from a donor blood samples using magnetic bead separation and polyclonally activated using anti-CD3 and anti-CD28 beads. Activated human T cells were then transduced with concentrated lentivirus containing various CD22-targeted CAR constructs at a multiplicity of infection in excess of 10. Following viral transduction, cells were confirmed to express CAR using flow cytometric analysis for GFP-marker. Virally transduced T cells (CAR-T cells) were then expanded for 9 days before examination for CAR activity.

Figure 9:
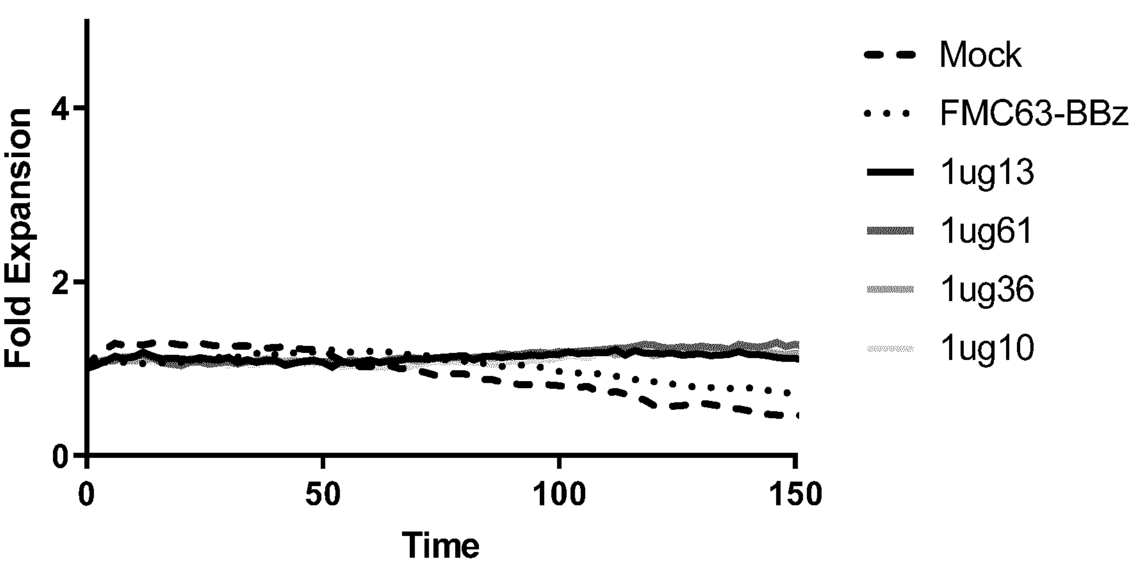
FIG. 9 depicts the results of CAR-T tonic activation assay wherein primary donor blood derived T cells were transduced with varying CAR constructs and examined for target-independent expansion.

To examine CAR activity in virally transduced CAR-T cells a number of assays were utilized. Firstly cells were placed without additional stimulation in controlled cell culture conditions and examined for non-specific cellular expansion over an additional 6 days via live microscopy using an IncuCyte® S3 device (Sartorius, USA). Total cell count was determined using automated cell counting. Primary human T cells stably transduced with various CD22-sdAb targeted CAR constructs did not show significant cell expansion when left in unstimulated conditions between day 9 and 15 post-polyclonal activation (FIG. 9). These results indicate that CD22-sdAb targeted CAR constructs tested do not confer target-independent tonic T cell activation to primary human T cells.

Figure 10:
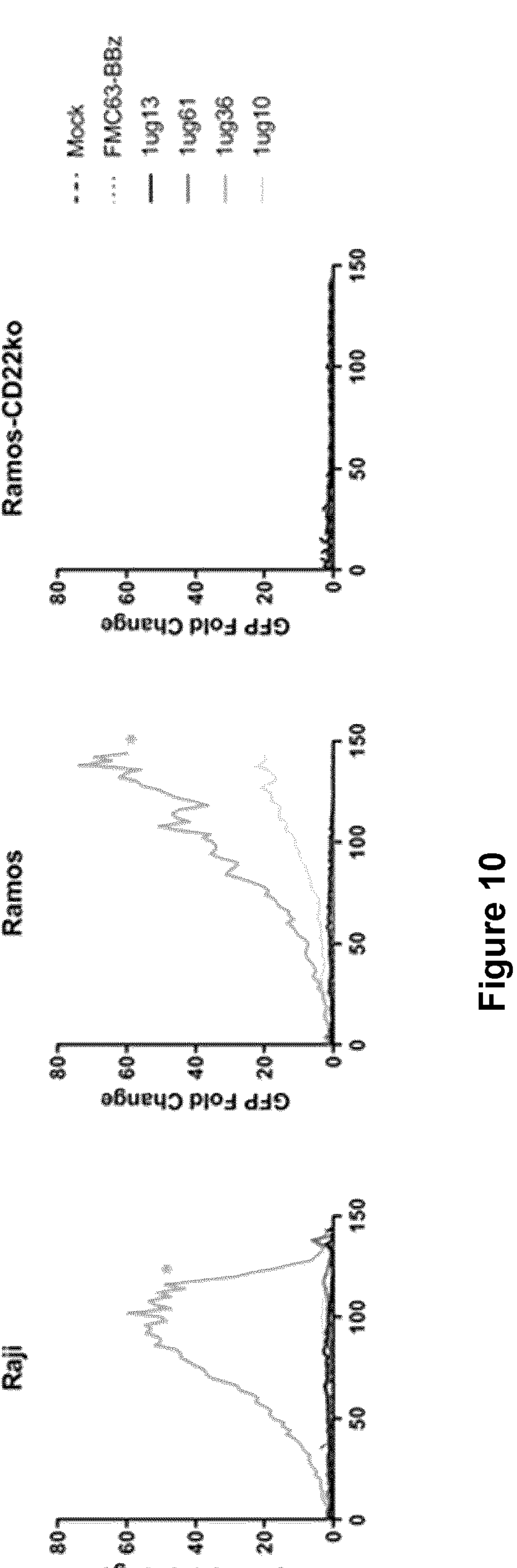
FIG. 10 depicts the results of CAR-T target-specific activation assay performed using donor blood derived T cells transduced with varying CD22-single domain antibody or control (FMC63) CAR constructs.

Following this, primary CAR-T cells were tested for antigen specific activation and target cell killing in response to cells with and without CD22 expression. CAR-T cells were placed in co-culture with various target cells expressing a red-fluorescent protein tag, Nuclight-*Lenti* (Sartorius, USA), and monitored for 6 days using the IncuCyte S3 live microscopy device. Examining the number of GFP-labelled CAR-T cells, two CAR constructs (1ug36 and 1ug10) showed clear expansion of GFP+ cells in response to CD22+ cell lines (Raji, Ramos) but not in response to CD22-knockout cells (Ramos-CD22ko) demonstrating antigen-specific activation and expansion (FIG. 10). Examining the number of Nuclight labelled target cells in co-culture with the most active CD22-CAR construct (1ug36), clear repression of CD22+ target cell growth was identified in CD22+ target cells with none to low effect on CD22-knockout cells (FIG. 11). Based on these results a lead molecule (1ug36) was selected for further testing.

Figure 12:
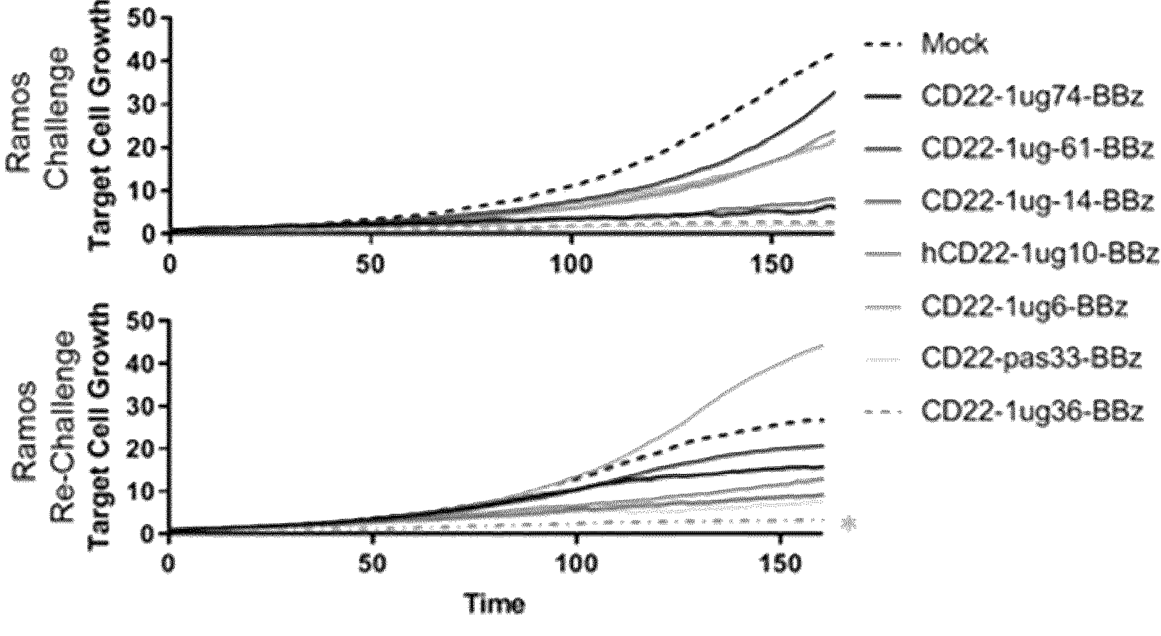
FIG. 12 depicts the results of CAR-T target-specific serial killing assay performed using donor blood derived T cells transduced with varying CD22-single domain antibody CAR constructs generated as described herein. Mock refers to unmodified donor derived T cells without CAR expression exposed to similar treatment conditions.

Next, experiments were undertaken to demonstrate serial killing capacity in novel CD22-sdAb targeted primary CAR-T cells. As described above, CAR-T cells were generated from donor blood derived T cells using lentiviral transduction and expanded for 9 days in cell culture. CAR-T cells were then placed in co-culture with fluorescently labelled Ramos cells and examined for target cell growth. Similarly as described above, the lead construct showed the most effective target cell repression of those constructs tested (FIG. 12 top). Following 1 week in co-culture, CAR-T cells were re-challenged with fresh Ramos target cells and examined for their ability to continue to kill target cells (FIG. 12 bottom). Again, 1ug36-CAR construct showed the clearest repression of target cell growth out of those constructs tested and was thus was selected for further analysis.

Figure 13:
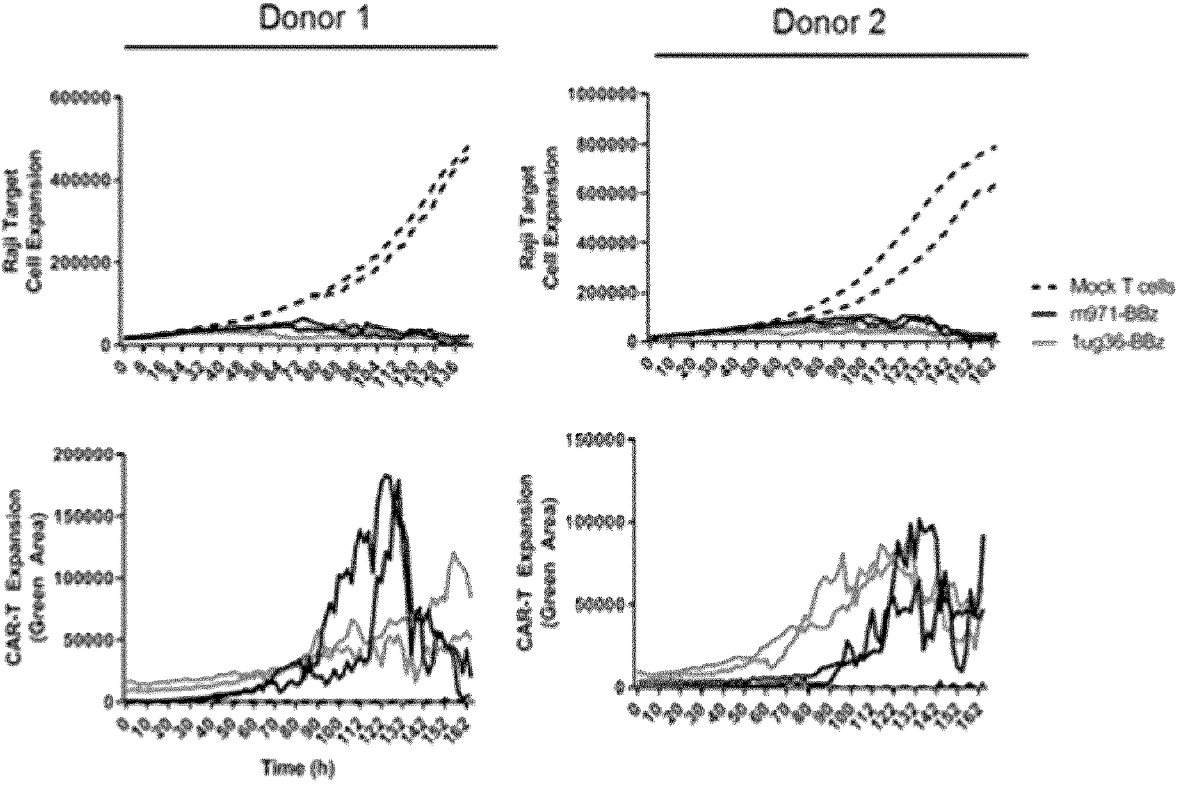
FIG. 13 depicts results of consistency analysis and comparison with benchmark CD22-targeted scFv CAR for single-domain antibody targeted CAR-T cells generated from 2 separate donors as described herein.

To investigate intra- and inter-donor variability with the novel CD22-sdAb targeted CAR constructs additional CAR-T cells were generated as described above from two different donor blood samples. In this experiment, the novel CAR-T constructs were also compared to a benchmark CD22-targeted CAR, wherein a previously demonstrated CAR construct consisting of a human CD22-specific single chain variable fragment [SEQ ID NO. 116] within a CAR construct similar to that being used for testing novel sdAb constructs described here. CAR-T cells were then placed in co-culture with CD22-expressing target cells (Raji) and examined for tumour cell growth repression (FIG. 13 top)

and CAR-T cell expansion (FIG. 13 bottom). Results demonstrate that lead CAR construct shows consistent and similar response to benchmark CAR response among varying donors.

Next CD22-sdAb targeted CAR-T cells from 2 donors were examined for specific lysis of CD22-expressing (Raji) and CD22-negative (MCF7) target cells. Various CAR-T cells generated as described above were co-cultured with radioactive chromium loaded target cells for 4.5 hours in standard cell culture conditions. Following co-culture, cell supernatants were removed and enumerated for chromium content using a scintillation counter. Experiments were either performed with various CAR constructs using CAR-T cells derived from 2 donors at a single effector to target ratio (FIG. 14), or performed with the lead CD22-sdAb CAR construct identified above at varying effector to target ratios (FIG. 15). Results demonstrate specific target cell lysis induced by CAR-T cells transduced with novel CD22-sdAb CAR constructs.

Figure 16:
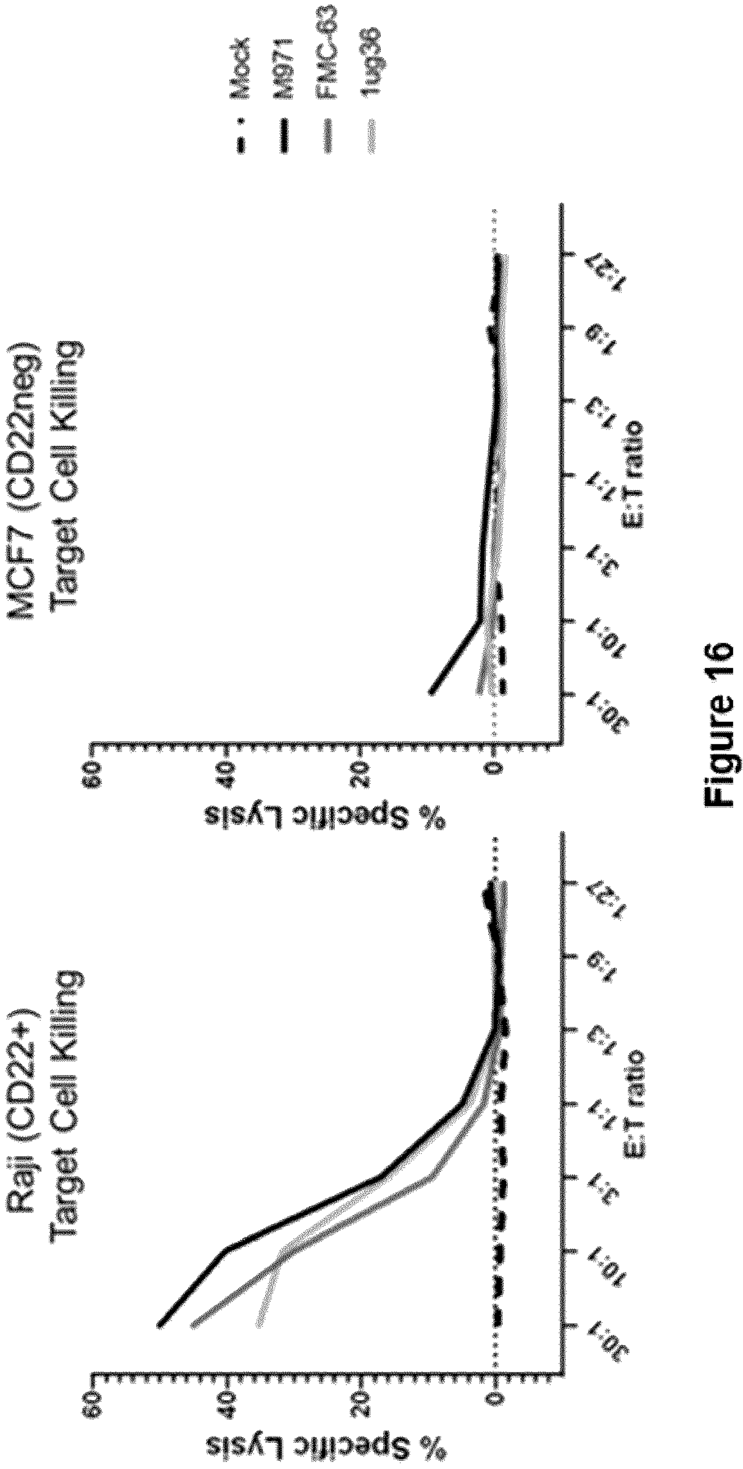
FIG. 16 depicts results of direct tumour lysis measurements using chromium release assay from CAR-T cells following re-stimulation with CD22 bearing tumor cells.

Lastly, CD22-sdAb targeted CAR-T cells were evaluated for their ability to be re-stimulated with CD22-expressing tumor cells (Ramos). Various CAR-T cells including the lead 1ug36-CAR construct were generated as described above and cultured through the day 9 expansion phase to day 17 proliferative quiescence. The CAR-T cells were then stimulated with irradiated CD22 expressing Ramos cells for an additional 5 days whereupon they were evaluated for their cytotoxicity potential against chromium loaded CD22-expressing (Raji) and CD22-negative (MCF7) target cells. Following a 4.5 hours co-culture at various effector to target ratios, released chromium was quantified using a scintillation counter (FIG. 16). Results indicate that re-stimulation of quiescent CD22 targeted CAR-T cells, including the lead 1ug36-CAR construct, with CD22 bearing Ramos cells resulted in the retention of specific lysis activity against CD22-expressing Raji target cells at levels similar to scFv CAR benchmarks.

Results

FIG. 8 depicts the results of CAR-Jurkat assay wherein Jurkat cells were transiently electroporated with varying CAR plasmids and cultured alone or in co-culture with CD22-positive (Ramos) or CD22-negative (Ramos-CD22ko) cell lines. The level of T cell activation was measured using human CD69-specific antibody staining and flow cytometry. Graphs depict the mean fluorescent intensity for CD69-staining for each 28 single domain antibody targeted CAR constructs performed in a single experiment in duplicate, either in culture with no target cells (open bars), Ramos target cells (closed bars), or Ramos-CD22ko cells (grey bars). Error bars show the standard error of the mean for duplicate wells. Results demonstrate antigen-specific response with approximately half (15/28) of novel CAR constructs tested.

FIG. 9 depicts the results of CAR-T tonic activation assay wherein primary donor blood derived T cells were transduced with varying CAR constructs and examined for target-independent expansion. Mock refers to donor derived T cells exposed to similar treatment conditions in the absence of any CAR-expressing lentivirus. As described in methods, CAR-T cells were examined between day 9 and 15 post-polyclonal activation for proliferation in cell culture via live microscopy. Graphs depict the fold change in cell number relative to number of cells the start of this assay as determined using automated cell counting. Results demonstrate a lack of antigen-independent T cell expansion in those CAR constructs tested.

FIG. 10 depicts the results of CAR-T target-specific activation assay performed using donor blood derived T cells transduced with varying CD22-single domain antibody or control (FMC63) CAR constructs. Mock refers to unmodified donor derived T cells without CAR expression exposed to similar treatment conditions. As described above, CAR-T cells were examined via live fluorescent microscopy between day 9 and 15 post-polyclonal activation for proliferation in co-culture with CD22+ target cells (left graph—Raji, middle graph—Ramos targets), or with CD22-negative target cells (right graph—Ramos-CD22ko targets). Graphs depict the fold expansion of green fluorescent protein marked CAR-expressing cells as determined using automated counting. Results demonstrate specific expansion of CAR-T cells in response to CD22-expressing target cells, wherein 1ug36-BBz CAR construct shows greatest activity relative to other constructs tested.

FIG. 11 depicts the results of CAR-T antigen-specific target cell growth repression assay performed using donor blood derived T cells transduced with varying CD22-single domain antibody or control (FMC63) CAR constructs as described above. Mock refers to unmodified donor derived T cells without CAR expression exposed to similar treatment conditions. CAR-T cells were placed in co-culture with CD22+ target cells (left graph—Raji, middle graph—Ramos targets), or with CD22-negative target cells (right graph—Ramos-CD22ko targets) and examined via live fluorescent microscopy. Graphs depict the fold expansion of red fluorescent protein (Nuclight) marked target cells as determined using automated counting. Results demonstrate CAR-T specific repression of growth of CD22-expressing target cells, wherein 1ug36-BBz CAR construct shows greatest activity relative to other constructs tested.

FIG. 12 depicts the results of CAR-T target-specific serial killing assay performed using donor blood derived T cells transduced with varying CD22-single domain antibody CAR constructs generated as described above. Mock refers to unmodified donor derived T cells without CAR expression exposed to similar treatment conditions. CAR-T or Mock-T cells were placed in co-culture with CD22+ target cells (top graph—Ramos targets). Six days post initial challenge, cells were split 1 in 5 in fresh media and challenged with additional CD22+ target cells (bottom graph—Ramos targets). Graphs depict the fold expansion of red fluorescent protein (Nuclight) marked target cells as determined using automated counting. Results demonstrate CAR-T specific serial repression of growth of CD22-expressing target cells, wherein 1ug36-BBz CAR construct shows greatest activity relative to other constructs tested.

FIG. 13 depicts results of consistency analysis and comparison with benchmark CD22-targeted scFv CAR for single-domain antibody targeted CAR-T cells generated from 2 separate donors as described above. Mock refers to donor derived T cells exposed to similar treatment conditions in the absence of any CAR-expressing lentivirus. CAR-T cells were placed in duplicate wells in co-culture with CD22+ target cells (Raji) and examined via live fluorescent microscopy. Graphs depict the fold expansion of red fluorescent protein (Nuclight) marked target cells (top graphs) or fold expansion of green fluorescent protein marked CAR cells (bottom graphs) as determined using automated counting. Results demonstrate intra- and inter-donor consistency for CAR-T specific repression of growth of CD22+ target cells and target-induced expansion of CAR-T cells similar to a benchmark CD22-scFv CAR.

Figure 14:
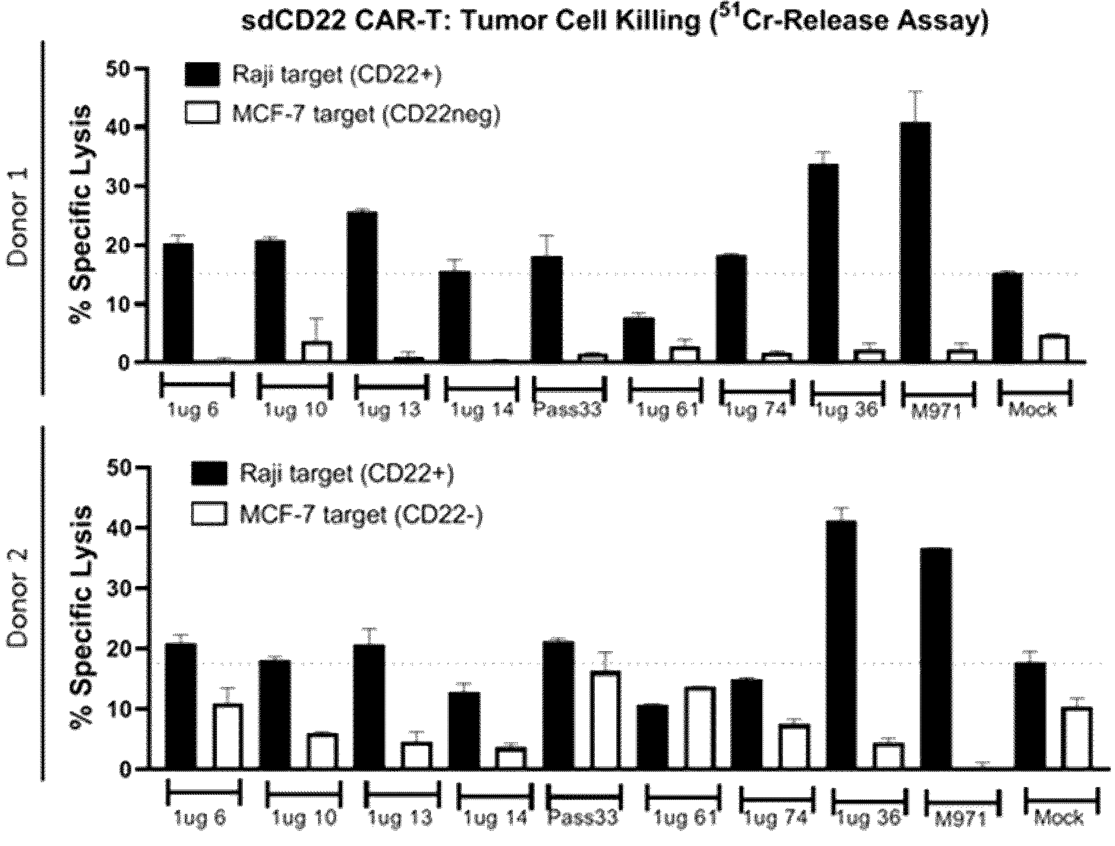
FIG. 14 depicts results of direct tumour lysis measurements using radioactive chromium ($^{51}$Cr) release assay.
Figure 15:
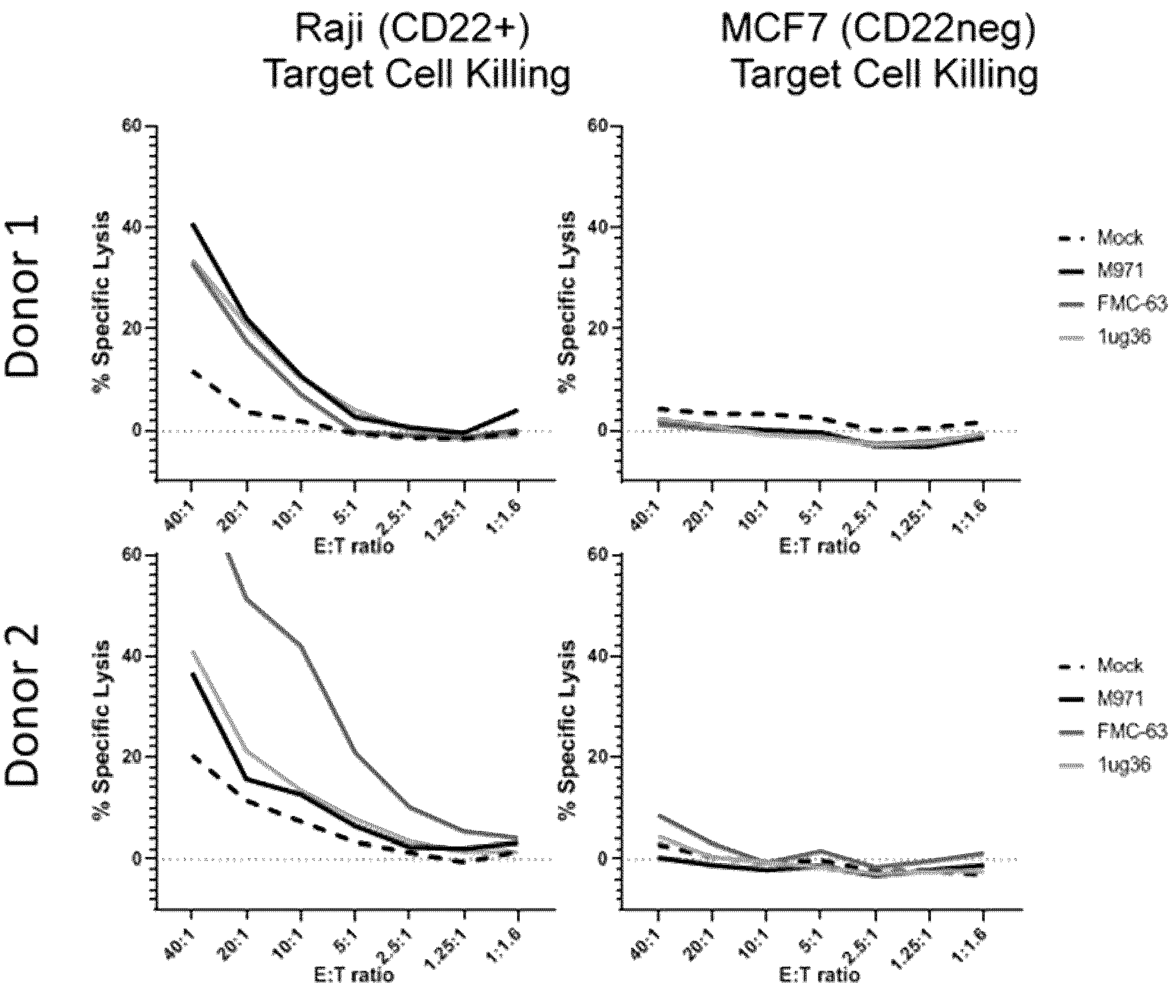
FIG. 15 depicts the results of direct CAR-T cell induced tumour lysis at different effector to target ratios using a chromium release assay.

FIG. 14 depicts results of direct tumour lysis measurements using radioactive chromium ($^{51}$Cr) release assay. As described above, various CD22-single domain antibody and control CAR-T cells were generated. Mock refers to donor derived T cells exposed to similar treatment conditions in the absence of any CAR-expressing lentivirus. At day 9 following lentiviral transduction, CAR-T cells were placed in co-culture with CD22-positive (Raji) or CD22-negative (MCF7) target cells loaded with radioactive chromium. Graphs depict the relative lysis of target cells at a single effector to target ratio based on quantification of chromium release into the supernatant. Error bars depict the standard deviation of measurements from duplicate wells. Results demonstrate comparable direct lysis of lead CD22-sdAb CAR molecule in comparison to a benchmark CD22-scFv CAR.

FIG. 15 depicts the results of direct CAR-T cell induced tumour lysis at different effector to target ratios using a chromium release assay. The CD22-CAR constructs 1ug36 along with scFv benchmarks, M971 and CD19 CAR construct FMC-63 CAR-T cells were generated as described above. Mock refers to donor derived T cells exposed to similar treatment conditions in the absence of any CAR-expressing lentivirus. Following a 9 day expansion of CAR-T cells, cells were co-cultured at decreasing effector to target ratios with chromium loaded CD22-positive Raji or CD22-negative MCF7 target cells for 4.5 h. Specific lysis was calculated based on released chromium measured using a scintillation counter. Results demonstrate that 1ug36-CAR-T cells specifically lyse CD22-expressing Raji targets in a dose dependent manner at levels similar to scFV benchmarks. No target cell killing over background (Mock control) was seen when these CAR constructs were co-cultured with CD22 or CD19 negative MCF-7 tumor cells.

FIG. 16 depicts results of direct tumour lysis measurements using chromium release assay from CAR-T cells following re-stimulation with CD22 bearing tumor cells. As described above, various CD22-single domain antibody and control CAR-T cells were generated. Mock refers to donor derived T cells exposed to similar treatment conditions in the absence of any CAR-expressing lentivirus. CAR-T cells were cultured until proliferation arrest (day 17) and then stimulated with irradiated CD22-expressing Ramos cells to induce target-specific activation. Following 5 days of co-culture, activated CAR-T cells were mixed at decreasing effector to target ratios with CD22-positive (Raji) or CD22-negative (MCF7) target cells loaded with radioactive chromium. Graphs depict the relative lysis of target cells based on quantification of chromium release into the supernatant. Results demonstrate efficient re-activation of quiescent CAR-T cells with specific CD22 antigen and comparable dose dependent Raji tumour lysis (CD22 positive) of the lead CD22-sdAb CAR molecule relative to a benchmark CD22-scFv CAR.

Discussion

Overall these results exemplify that CD22-specific single domain binders can generate strong antigen-driven T cell activation signaling which can drive target cell killing and serial killing, long-term tumour cell growth repression, CAR-T expansion, and direct target cell lysis. While a lead molecule was identified in the exemplary data provided here, molecular optimization may be performed with additional CD22-specific single domain antibody sequences in order to generate highly functional CAR molecules. In addition, combining multiple CD22-specific single domain antibody sequences in a single molecule may be an effective strategy to increase target-specific CAR activating activity.

Example 4: CAR-T In Vivo Testing

Introduction

To further confirm the anti-tumor effect of CD22-binding single domain CAR-T cells in vitro, a xenograft model was established by intravenously inoculating Ramos tumor cells expressing firefly luciferase as a reporter into NOD/SCID/IL2r-gamma-chain$^{null}$ (NSG) mice prior to infusion of CD22-binding single domain CAR-T cells.

Materials and Methods

For in vivo studies, luciferase-expressing cell lines were generated by stably transducing wild-type tumor lines with lentiviral vector encoding firefly luciferase (FLUC) followed by selection of luciferase-positive cells using puromycin resistance as a selection marker. Ramos-FLUC was maintained in RPMI 1640 supplemented with 10% heat inactivated fetal bovine serum and 2 mM L-glutamine and 1 mM sodium pyruvate. All cell culture reagent were purchased from Gibco. The cell line were confirmed for the absence of *mycoplasma* contamination PCR.

Female NOD/SCID/IL2Ry$^{-/-}$ (NSG) mice, 6-8 weeks of age, were obtained from Jackson Laboratories and maintained at the Animal Resource Group at the National Research Council of Canada. The mice were housed in pathogen-free individually ventilated cages in a barrier system under conditions. Animals had access to certified rodent diet and sterilized water was given via water bottles. NSG mice lack mature T cells, B cells and natural killer cells; thus, they are better than nu/nu mice for the study. Eight-week-old NSG mice were injected with $5\times10^4$ Ramos-FLUC cells in 100 μL HBSS intravenously via the tail vein. On day 4 post tumor cells injection, mice were injected intravenously via the retro orbital plexus with CD22-targeted single domain CAR-T cells, CD19 targeted CAR-T cells where the targeting domain is similar to clinically validated CD19 CAR constructs Kymriah and Yescarta or Mock CAR-T cells without CAR expression. Tumor growth in mice was monitored through bioluminescent (IVIS imager; PerkinElmer) and blood was collected once a week for monitoring of circulating CAR-T cells and tumor cells. Mice were monitored daily for signs of illness and sacrificed immediately if they met pre-specified humane endpoints including but not limited to hind-limb paralysis, respiratory distress, or 20% body weight loss as approved by the Animal Care Committee of the Research Center.

Blood samples from mice were washed in PBS/0.1% BSA and re-suspended in 50 μl Brilliant Buffer (BD Biosciences, USA). Cells were stained using the following antibody fluorophore conjugates (all from BD Biosciences, USA, unless otherwise noted) directed to: hCD45-APC-H7, hCD45RA-BV650, hCD45RO-PE-CF594, hCD27-BUV737, hCCR7-PE, hCD4-BUV395, and hCD8-PerCP-Cy5.5.

CD45 is a protein tyrosine phosphatase regulating src-family kinases, is expressed on all hematopoietic cells. Thus anti-human CD45 antibody was used to detect human hematopoietic cells in mice. CD45 can be expressed as one of several isoforms by alternative splicing of exons that comprise the extracellular domain; the expression of various isoforms is indicative of T cell differentiation status. CD45RA is expressed on naïve T cells, as well as the effector cells in both CD4 and CD8. After antigen experience, central and effector memory T cells gain expression of CD45RO and lose expression of CD45RA. Thus antibodies against human CD45RA and CD45RO were used to differentiate the naïve and memory T cell populations. Differentiation between central and effector memory populations and between naïve and effector populations can be achieved by adding a second marker. There are several markers that have been used for this purpose and these tend to mark these populations at slightly different stages of the differentiation pathway that is thought to occur in T cells as they change from central to effector memory cells. The chemokine receptor CCR7 discriminates between these two populations and thus antibodies against human CCR7 was used in this study for this purpose. CAR expression was detected with GFP incorporated in the plasmid. To evaluate exhaustion, antibody directed against hPD-1-BV421 (BioLegend, USA) was applied. T cell activation was detected with fluorescent-labeled antibodies against hCD25-PE-Cy7 and hCD69-BV786. For in vivo studies, mouse CD45-BV711 was used to gate the murine cells and leukemia cells were identified using human CD19 expression via anti-human CD19-BUV496 antibody. Samples were incubated for 30 minutes at 4° C. in the dark. Blood was then lysed by adding RBC lysis buffer (Sigma-Aldrich, USA). Samples were mixed briefly to re-suspend cells and incubated for 10 minutes at room temperature. Cells were then washed in PBS/0.1% BSA and were re-suspended in PBS/0.1% BSA. Data was acquired on BD Fortessa cytometer (BD Biosciences). UltraComp™ eBeads (eBiosciences, USA) were used for compensation. Analyses were performed using FlowJo software (FloJo, USA).

In vivo bioluminescence imaging to monitor tumor growth in mice was performed using the IVIS Lumina III imaging system (PerkinElmer, Waltham, MA, USA). On a repeated basis, mice were anesthetized using isofluorane (3.0% induction and reduced to 2.0% for maintenance) and hair was removed. At time 0, mice were given a subcutaneous injection of 150 mg/kg Redi-Ject D-Luciferin (Perkin Elmer, Waltham, MA, USA). The animal was then transferred to the imaging system under maintenance anesthesia and imaged using an open filter at 20 mins post D-Luciferin to allow the D-Luciferin to distribute evenly and reach a plateau in signal. To calculate the relative amounts of luciferase gene expression from the images, the Living Image Software (Perkin Elmer, Waltham, MA, USA) was utilized to calculate the total radiance expressed as photons per second per square centimeter per steradian (p/s/cm2/sr) in a whole body region of interest (ROI).

Results

Figure 17:
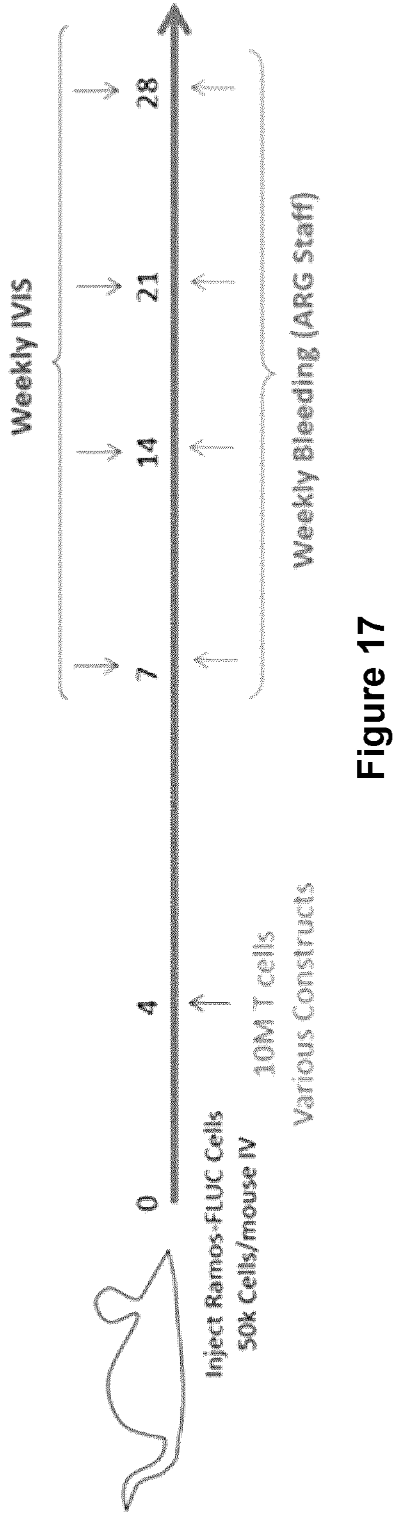
FIG. 17 depicts a schema of an experimental protocol for an in vivo model.

FIG. 17 depicts a schema of the experimental protocol for this in vivo model. To assess the activity of CD22-binding single domain-CAR-T in a xenogeneic model, 8 week old NOD/SCID mice were inoculated intravenously with 50,000 Ramos-FLUC cells on day 0, and subsequently treated by retro-orbital injection with $1\times10^7$ CD22-targeted single domain-CAR-T (1ug13 or 1ug36), FMC63-CAR-T (CD19 targeted CAR-T using same antigen binding domain as used in clinically validated CAR constructs), or Mock T cells without CAR expression on day 4. Mice were imaged by bioluminescence in vivo imaging and blood were collected from mice weekly.

Figure 18:
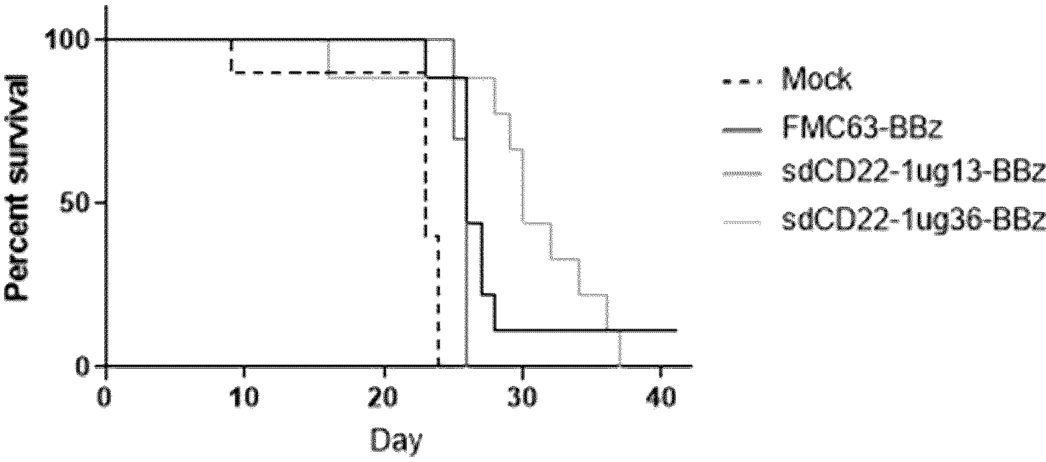
FIG. 18 depicts results of the survival analysis of NSG mice that were inoculated with Ramos-Luc followed by treatment of various CAR-T cells.

FIG. 18 depicts results of the survival analysis of NSG mice that were inoculated with Ramos-Luc followed by treatment of various CAR-T cells. Mock refers to donor derived T cells exposed to similar treatment conditions in the absence of any CAR-expressing lentivirus. Animal experimental set up was described above. Graph depicts the survival in days of the mice in the study. Results demonstrate extended survival observed in the mice treated with CD22-targeting single domain antibody 1ug13 and 1ug36 CAR-T cells compared to those treated with FMC63 and mock T cells.

Figure 19:
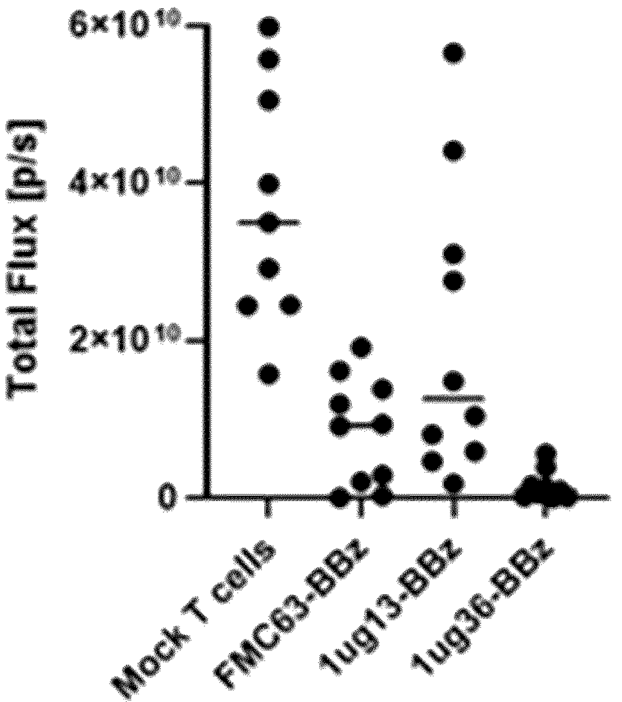
FIG. 19 depicts result of tumor burden in mice that were inoculated with Ramos-FLUC and treated with various CAR-T cells.

FIG. 19 depicts result of tumor burden in mice that were inoculated with Ramos-FLUC and treated with various CAR-T cells. Mice were monitored for tumor burden by quantifying bioluminescence using IVIS Lumina III. Graph depicts the total flux (photons/second) in individual animals within each treatment group (dark circles) and the mean total flux per group (horizontal bar) on day 18 post injection of tumour cells; the final experimental time point where mice from all groups were alive. Mice treated with 1ug36 CAR-T cells or FMC63 CAR-T cells showed significant reduction in tumor burden ($p<0.001$ and $p=0.0004$ respectively) compared to mice receiving mock T cells.

Figure 20:
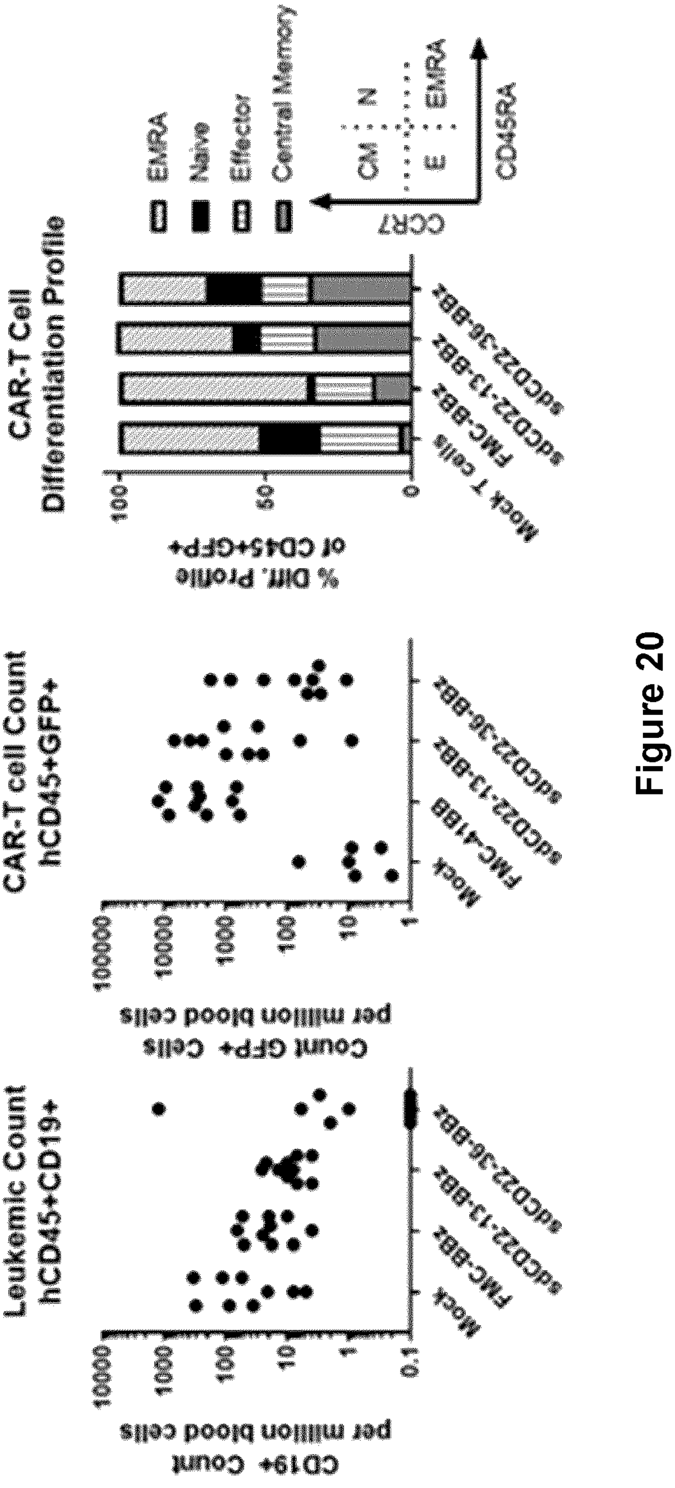
FIG. 20 depicts result of tumor burden, total CAR-T cell population and differential phenotype of circulating CAR-T cell population in peripheral blood of mice inoculated with Ramos-FLUC and treated with various CAR-T cells.

FIG. 20 depicts result of tumor burden, total CAR-T cell population and differential phenotype of circulating CAR-T cell population in peripheral blood of mice inoculated with Ramos-FLUC and treated with various CAR-T cells. Blood was collected at day 23 post tumour cell challenge, red blood cells lysed and remaining cells stained with various fluorescent conjugated antibodies as described above. Left graph depicts the number of human CD19+ leukemia cells per 1 million total blood cell events analyzed via flow cytometry. Middle graph depicts the number of CD45+/GFP+ CAR-T cells detected per 1 million blood cells analyzed by flow cytometry. Right hand graph depicts the differentiation status of gated CAR-T cells or ungated CD45+ cells in mock T cell group based on expression of T cell surface markers CD45RA and CCR7. Collectively, results demonstrate an overall reduction in leukemic burden in mice treated with 1ug36-sdAb targeted CAR-T cells, an expansion of CAR-T cells in all groups treated with CAR-T and a showed clear expansion in treated mice, and a balanced differentiation profile which favors more central memory T cells in groups treated with sdCD22 CAR-T cells.

Discussion

NSG mice are widely used to study the interactions between the human immune system and cancer, a practical platform for evaluating immunotherapeutics in the context of human immune cells and human tumors. Overall, these results clearly demonstrate anti-leukemic activity of CD22-targeting single domain CAR modified T cells in vivo, similar to in vitro, and demonstrate that the efficacy of CD22-targeting single domain CAR-T cells is similar or better than that of the CD19 (FMC63)-CAR-T cells, which has already demonstrated clinical responses in the clinic.

Example 5: Bispecific T-Cell Engager Constructs

Introduction

Similar to chimeric antigen receptor technology, novel antigen binding elements can also be linked to CD3-engaging antibody elements in order generate a soluble molecule that can simultaneously bind T cells and cellular target molecules, resulting in an antigen-specific T cell activation signal. This type of molecule, referred to as a bi-specific T cell engagers, is exemplified by Blinatumomab, wherein a single molecule simultaneously engages human CD19 and human CD3; used as a therapy for CD19 expressing B-cell family malignancies. In order to assess whether the human CD22-specific single domain antibodies generated herein could be used in such a bi-specific T cell engager molecule, molecules wherein one end of the molecule was comprised of a CD22-specific single domain antibody sequence and the other end was comprised of a CD3-engager molecule were generated. These novel bi-specific T cell engagers were then screened for non-specific and antigen-specific induction of T cell activation and T cell killing of target cells.

Materials and Methods

Figure 21:
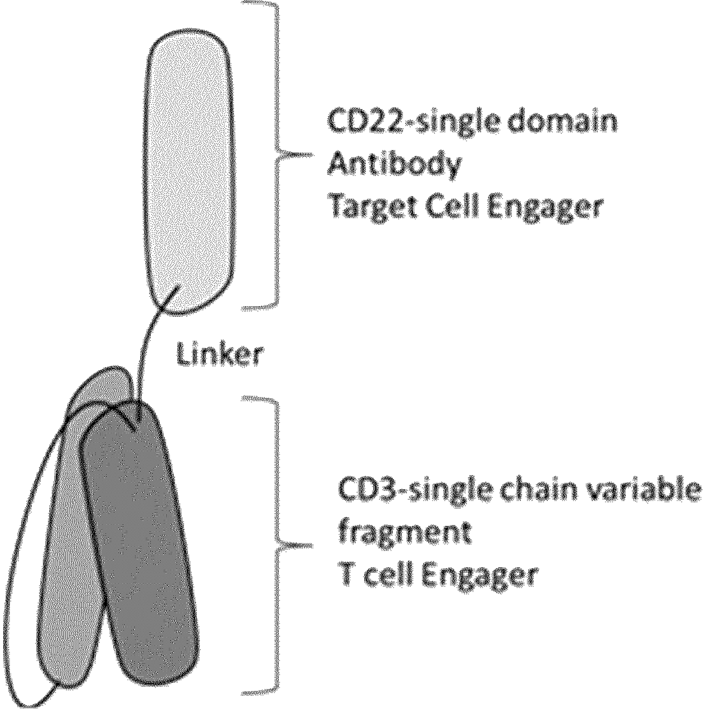
FIG. 21 depicts the molecular structure of CD22-specific single domain antibody bi-specific T cell engager proteins; with a CD22-sdAb sequence at the 5' end of a DNA construct, followed by a linker sequence which can be of varying composition, followed by a CD3-specific single chain variable fragment.

Single domain antibody antigen binding sequences were transferred to a modular bi-specific T cell engager DNA sequence [SEQ ID NO: 119] within a plasmid backbone; the DNA sequence used contains restriction sites to allow efficient recombination wherein the antigen binding domain could be replaced with the novel CD22-antigen binding domain (ABD) sequences. Specific bi-specific T cell engager design used was as follows: Human CD28 signal peptide [SEQ ID NO:110], VHH antibody (ABD) (any one of SEQ ID NOs. 82 to 108), flexible linker domain [SEQ ID NO: 111], human CD8 hinge domain [SEQ ID NO: 112], short flexible linker domain [SEQ ID NO: 118], and a CD3-specific single chain variable fragment sequence. A model of CD22-CD3 bi-specific T cell engager molecules is provided (FIG. 21). Constructs were generated using golden gate assembly and confirmed using Sanger sequencing before proceeding to downstream testing.

Figure 24:
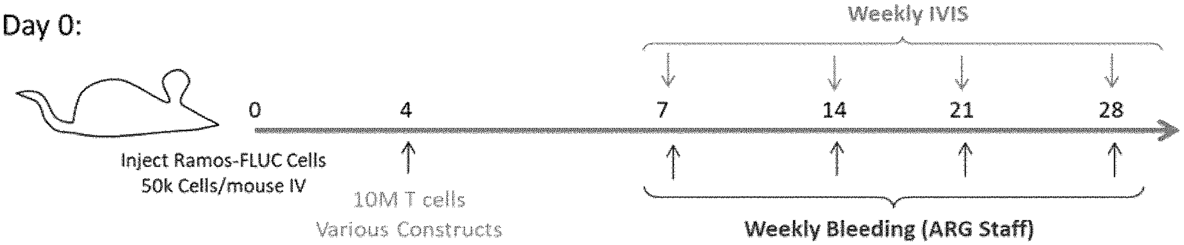
FIG. 24 depicts a diagram timing for treatment and testing for in vivo studies of CAR-T constructs.

To generate purified protein forms of bi-specific T cell engager molecules, plasmid DNA containing various constructs were transfected into HEK293T cells using polyethylenimine via standard process. Transfected cells were placed in cell culture and supernatant was collected over several days. Supernatant was then tested for bi-specific T cell engager activity by placing supernatant directly on Jurkat cells alone or in co-culture with CD22-positive (Ramos) or CD22-negative (U87vIII) target cells and incubated under standard conditions overnight. Jurkat cells were then examined for T cell activation using antibody staining for the human CD69 marker and flow cytometric analysis (FIG. 24). Results demonstrate that when delivered in solution, a CD22-sdAb targeted bi-specific T cell engager can induce target dependent T cell activation, with varying activity between different constructs.

Figure 25:
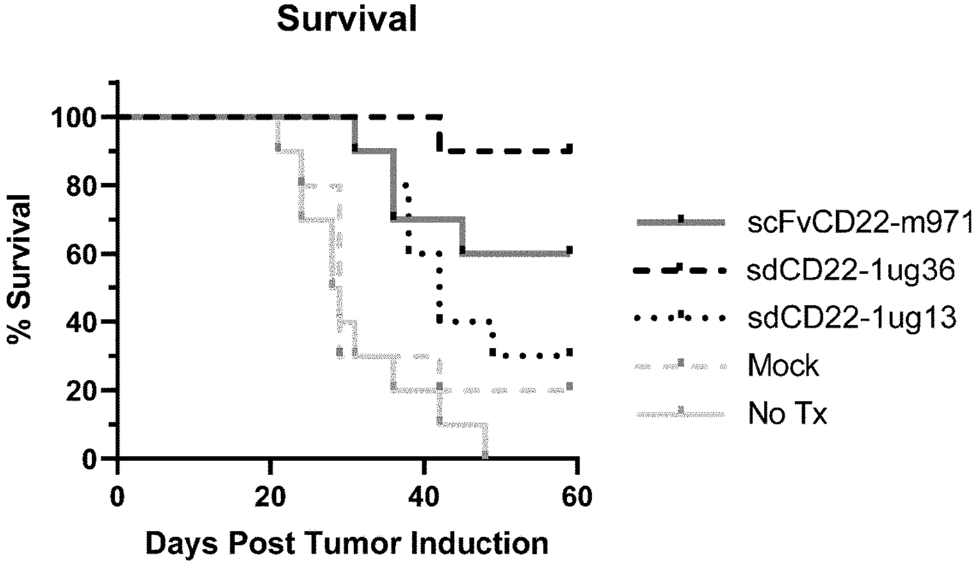
FIG. 25 depicts survival of mice for the treatment and testing depicted in FIG. 24.

To test whether these results extend to induction of specific anti-tumour responses in primary human T cells, the novel bi-specific T cell engager containing supernatants generated above was used in an assay with primary T cells. Specifically, T cells were isolated from human donor blood and polyclonally expanded for 10 days. Following polyclonal expansion, T cells were placed in co-culture with stable fluorescent protein (Nuclight; Sartorius, USA) expressing CD22-expressing target cells (Ramos) in the presence of supernatant containing various bi-specific T cell engagers or control supernatant (Mock). Co-cultures were then monitored for target cell growth using IncuCyte (Sartorius, USA) live microscopy device. Using automated cell counting of fluorescently labelled target cells, the relative growth of target cells was quantified over 3 days (FIG. 25). Results demonstrate that CD22-sdAb containing bi-specific T cell engager molecules can re-target cytolytic human T cell responses against CD22-expressing target cells.

Results

FIG. 21 depicts the molecular structure of CD22-specific single domain antibody bi-specific T cell engager proteins; with a CD22-sdAb sequence at the 5' end of a DNA construct, followed by a linker sequence which can be of varying composition, followed by a CD3-specific single chain variable fragment.

Figure 22:
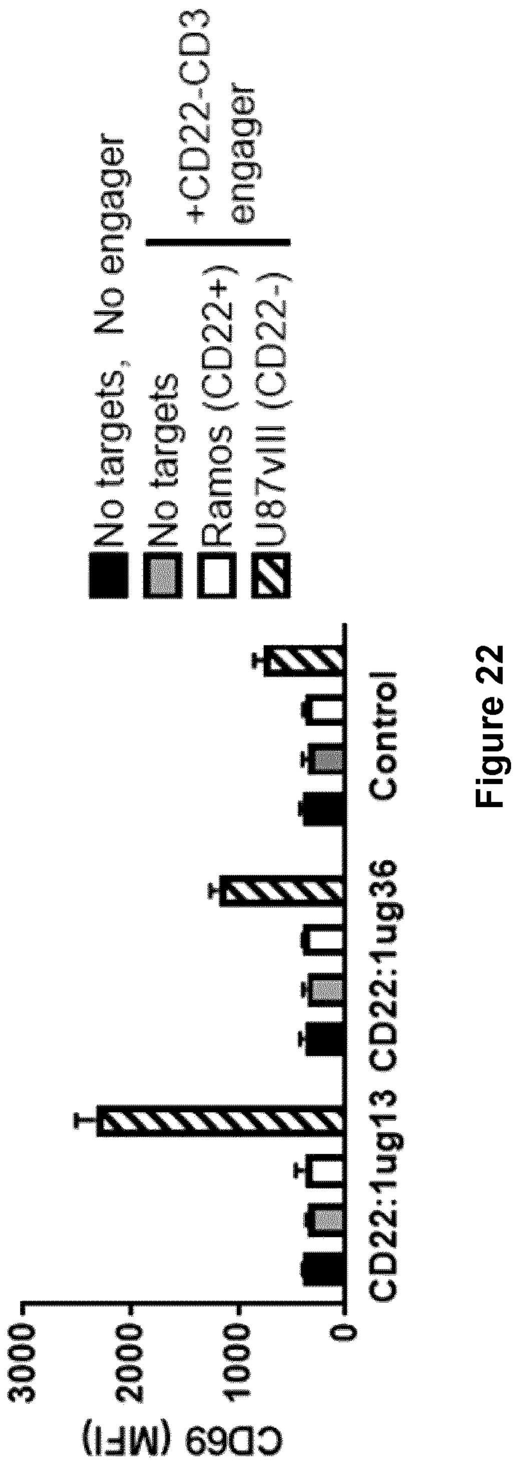
FIG. 22 depicts the results of Jurkat cell bi-specific T cell engager activation activity assay wherein HEK293T supernatants containing various bi-specific T cell engager molecules was placed on top of co-cultures containing Jurkat cells and CD22-positive (Ramos) or CD22-negative (U87vIII) target cells.

FIG. 22 depicts the results of Jurkat cell bi-specific T cell engager activation activity assay wherein HEK293T supernatants containing various bi-specific T cell engager molecules was placed on top of co-cultures containing Jurkat cells and CD22-positive (Ramos) or CD22-negative (U87vIII) target cells. Graphs depict the average CD69-specific antibody staining of Jurkat cells as measured by flow cytometry. Error bars present the standard error of the mean over 2 duplicate co-culture wells. Results demonstrate CD22-antigen specific activation of T cells in the presence of novel CD22-sdAb bi-specific T cell engager molecules.

Figure 23:
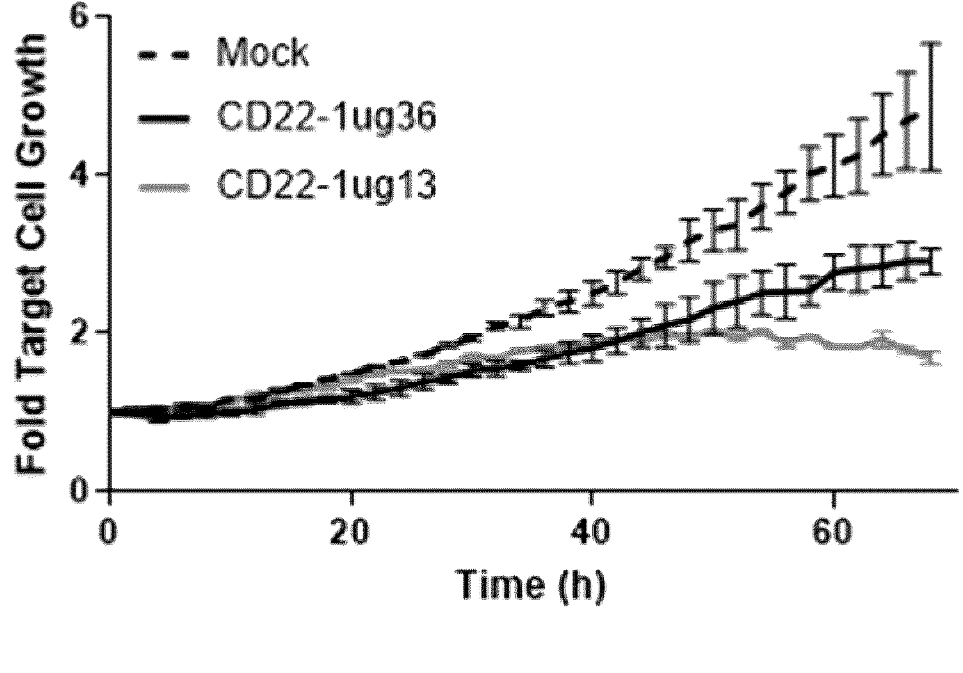
FIG. 23 depicts the results of a bi-specific T cell engager activity assay using primary human T cells in co-culture with CD22-positive target cells (Ramos).

FIG. 23 depicts the results of a bi-specific T cell engager activity assay using primary human T cells in co-culture with CD22-positive target cells (Ramos). As described above donor blood derived T cells were placed in co-culture with fluorescently labelled target cells in the presence of control (mock) or CD22-specific bi-specific T cell engager containing supernatants and examined hourly over 3 days via live fluorescence microscopy. Graphs depict the fold growth of fluorescently labelled target cells as determined using automated cell counting. Error bars present the standard error of the mean over 2 duplicate co-culture wells. Results demonstrate T-cell mediated tumour growth suppression in the presence of CD22-sdAb targeted bi-specific T cell engager molecules.

Notably, this construct with the extended linker comprising SEQ ID NO: 111, SEQ ID NO: 112 (human CD8 hinge domain), and SEQ ID NO: 118 exhibited a higher activity than a similar construct comprising only a shorter, G4S linker (data not shown).

Discussion

Overall these results exemplify that CD22-specific single domain binders can generate strong antigen-driven T cell activation signaling when combined in a bi-specific T cell engager molecule. CD22-sdAb targeted bi-specific T cell engager molecules are demonstrated to drive target specific T cell activation and direct target cell killing by primary human T cells. While exemplary data is provided for 2 CD22-specific single domain antibodies, this data indicates that additional high affinity CD22-binders are likely to have similar activity. Furthermore, molecular optimization may be performed in order to further increase functionality of bi-specific T cell engager molecules. In addition, combining multiple CD22-specific single domain antibody sequences in a single molecule may be an effective strategy to increase target-specific activating activity.

Example 6: In Vivo Studies of CAR-T Constructs

Survival analysis and measurement of circulating CAR-T cells was studied for NSG mice that were inoculated with $1\times10^5$ Ramos-Luc tumor cells followed by treatment with $2.5\times10^6$ sdCD22 (1ug13 or 1ug36) or benchmark scFvCD22 CAR-T cells. Mock refers to donor derived T cells exposed to similar treatment conditions in the absence of any CAR-expressing lentivirus. No Tx mice received vehicle (Hank's Balanced Salt Solution).

FIG. 24 is a diagram of treatment and testing.

FIG. 25 depicts the survival if mice.

Figure 26:
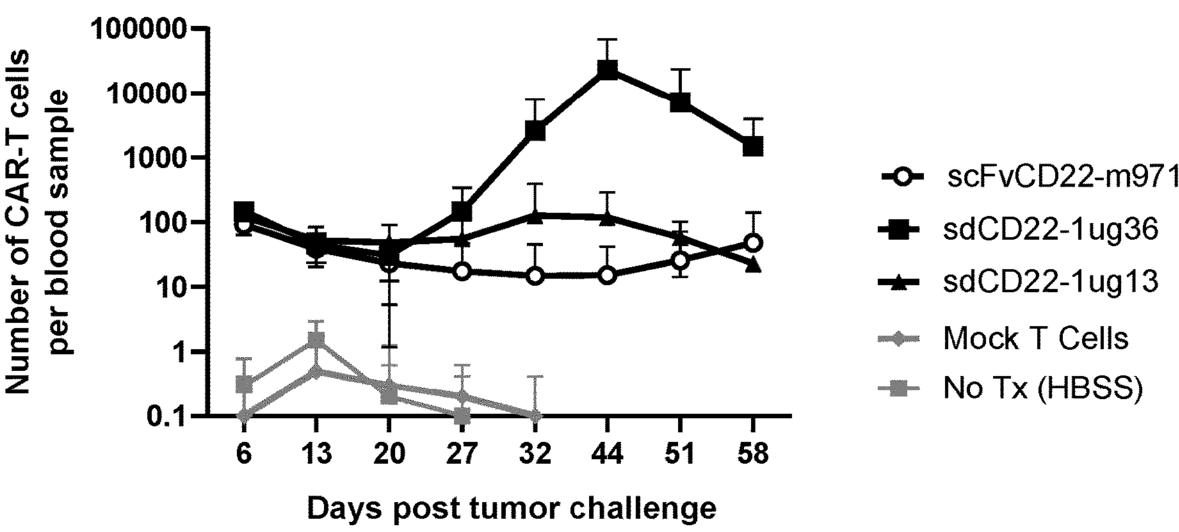
FIG. 26 depicts CAR-T cells enumerated in peripheral blood in mice for the treatment and testing of FIG. 24.

FIG. 26 depicts the CAR-T cells enumerated in peripheral blood in mice.

Results demonstrate extended survival and persistence of CAR-T cells observed in the mice treated with CD22-CAR-T cells compared to those treated mock T cells or left untreated. Mice treated with sdCD22-1ug36 CAR-T cells showed enhanced survival and proliferation/persistence of circulating CAR-T cells compared to the benchmark scFv CAR-T or the sdCD22-1ug13 CAR-T.

Survival analysis and tumor growth kinetics was also studied for NSG mice that were inoculated with $0.5\times10^5$ Ramos-Luc tumor cells followed by treatment with varying doses of sdCD22-1ug36 CAR-T or the benchmark scFvCD22-m971 CAR-T cells. Mock refers to donor derived T cells exposed to similar treatment conditions in the absence of any CAR-expressing lentivirus. No Tx mice received vehicle (Hank's Balanced Salt Solution).

Figure 27:
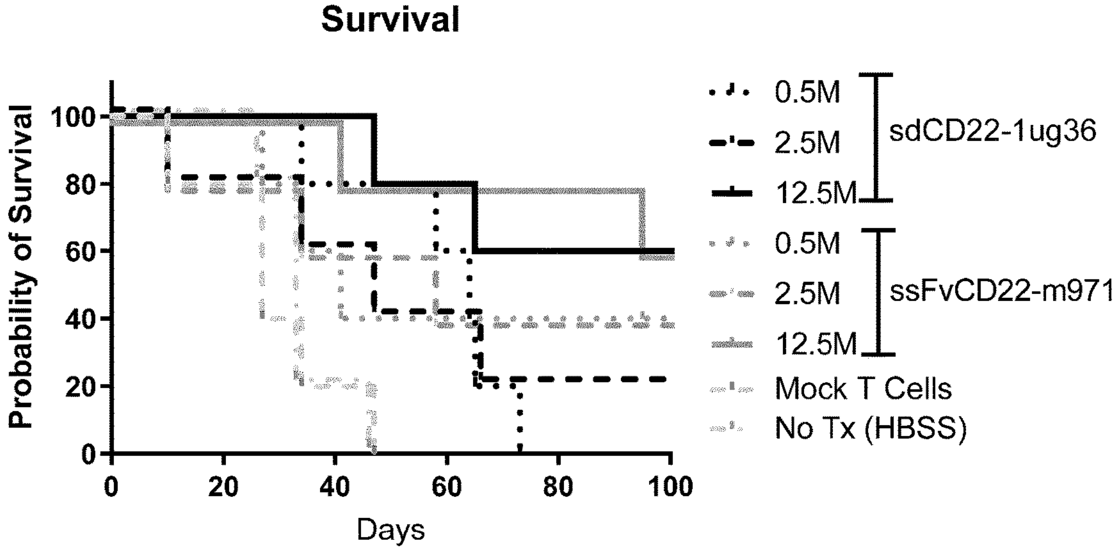
FIG. 27 depicts survival of mice following first tumor challenge and CAR-T treatment.

FIG. 27 depicts the survival of mice following first tumor challenge and CAR-T treatment. There was dose dependent increase in survival time of mice treated with CAR-T over mice receiving mock T cells or vehicle control. Greater than 50% of the mice treated with the highest dose of CAR-T cells survived long term and were re-challenged on day 88 post first tumor challenge with $0.5\times10^5$ Ramos-Luc tumor cells and monitored for survival and tumor growth.

Figure 28:
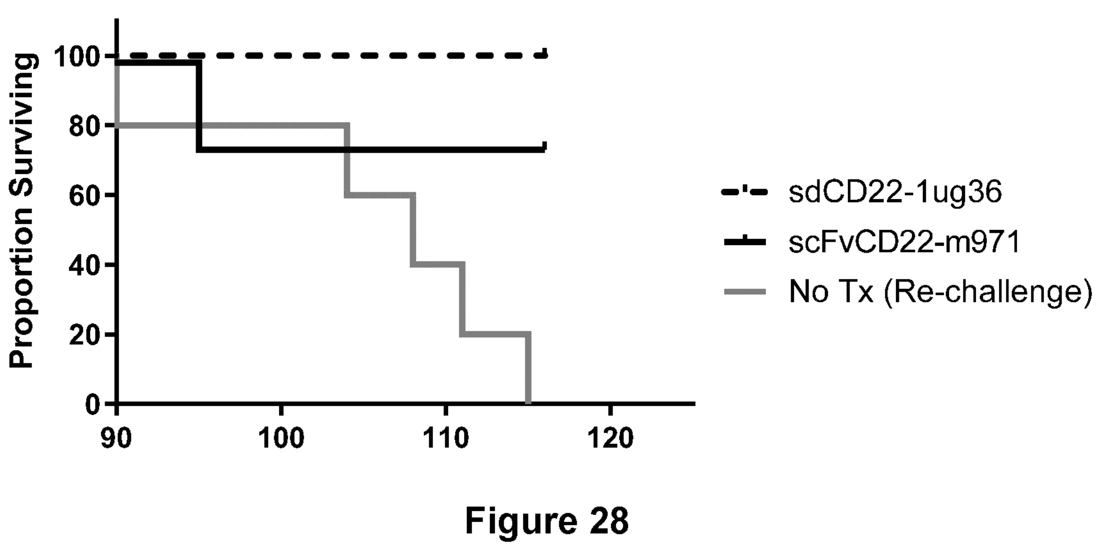
FIG. 28 depicts survival of mice upon re-challenge.

FIG. 28 depicts the survival of mice upon re-challenge. Untreated (vehicle control) animals all succumbed to disease while all (sdCD22-1ug36) or majority (benchmark scFvCD22-m971) of the CAR-T treated mice survived the second tumor challenge.

Figure 29:
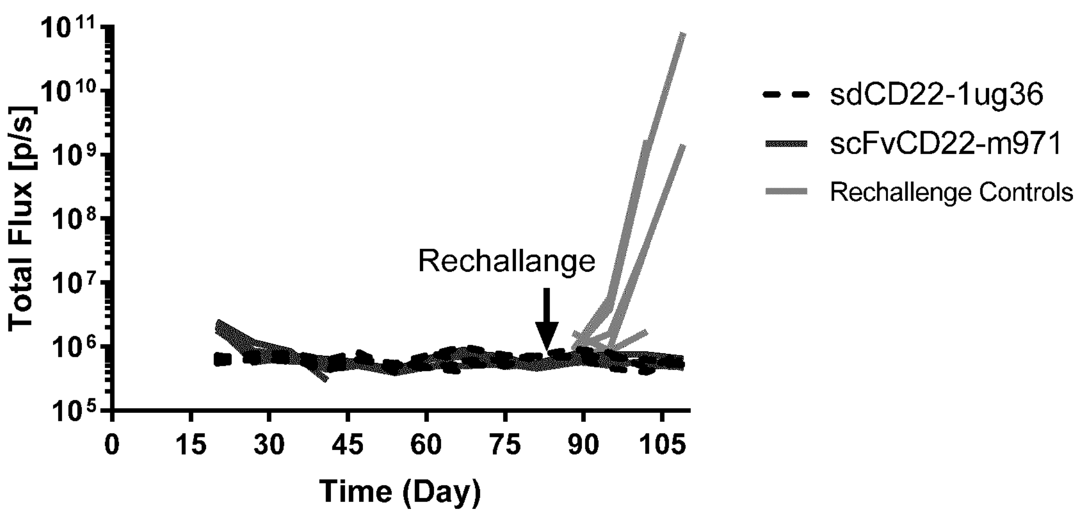
FIG. 29 depicts a graph of the tumor growth post challenge.

FIG. 29 depicts a graph of the tumor growth post challenge. Untreated control mice all developed tumors whereas mice treated with CAR-T were able to reject re-challenge demonstrating the long term persistence of CAR-T cells and hence the durability of the anti-tumor response.

Example 7: Bi-Paratopic and Multi-Paratopic CAR Constructs

Figure 30:
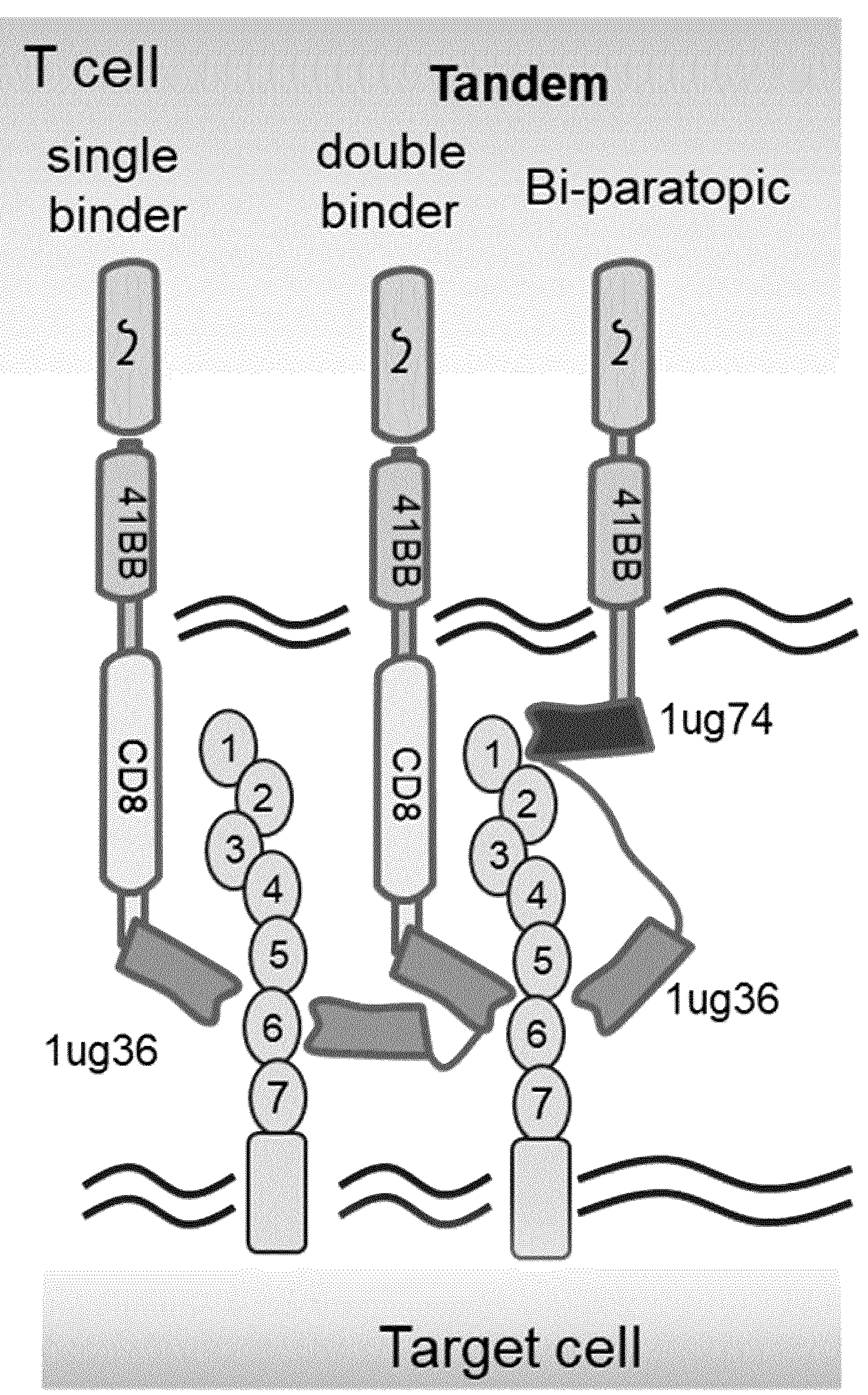
FIG. 30 depicts molecular structures of multi-binder domain containing CD22-specific CAR molecules.

FIG. 30 depicts molecular structures of multi-binder domain containing CD22-specific CAR molecules, containing (left) an N-terminal CD22-sdAb sequence followed by a linker sequence which can be the followed by (centre) another copy of the same sdAb binder sequence or (right) a different sdAb binder. This may result in a higher affinity and/or higher activity CAR molecule.

Figure 31:
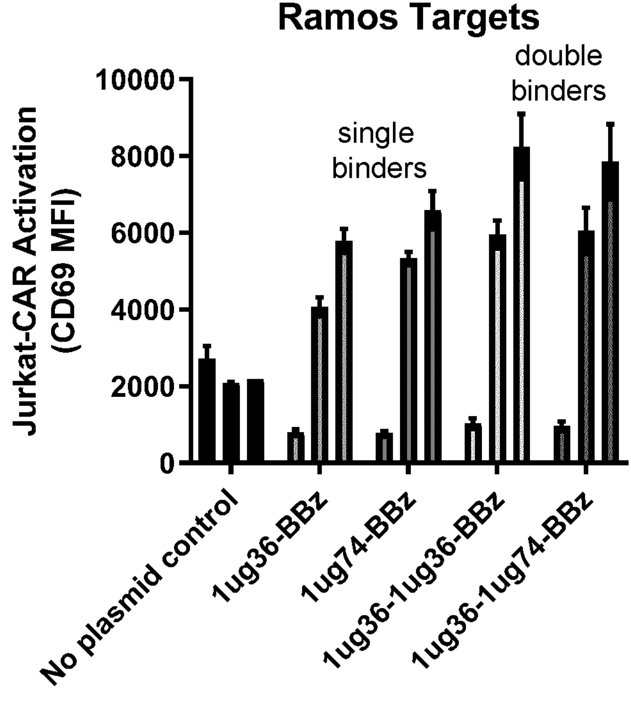
FIG. 31 depicts the results of CAR-Jurkat assay wherein Jurkat cells were transiently electroporated with varying CAR plasmids, including single and multi-binders.

FIG. 31 depicts the results of CAR-Jurkat assay wherein Jurkat cells were transiently electroporated with varying CAR plasmids (encoding single binds and multi-binders) and cultured alone or in co-culture with CD22-positive (Ramos) target cell lines.

Figure 32:
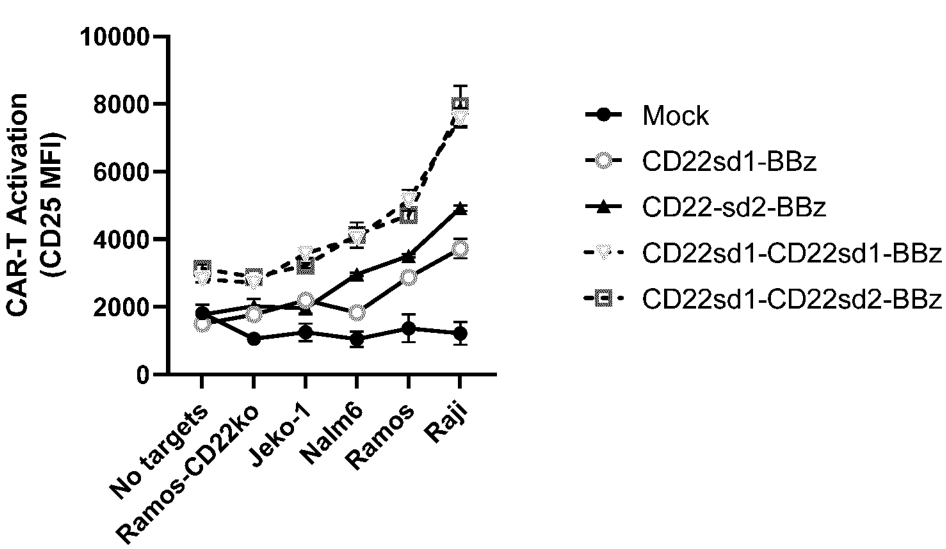
FIG. 32 depicts the results of similar CAR-activation studies using primary human blood derived T cells which have been transduced with lentiviral vectors encoding multi-sdAb containing CAR constructs.

FIG. 32 depicts the results of similar CAR-activation studies using primary human blood derived T cells which have been transduced with lentiviral vectors encoding multi-sdAb containing CAR constructs. These data demonstrate that multi-CD22 sdAb containing CAR molecules can show higher molecular responsiveness to CD22-expressing target cells.

Figure 33:
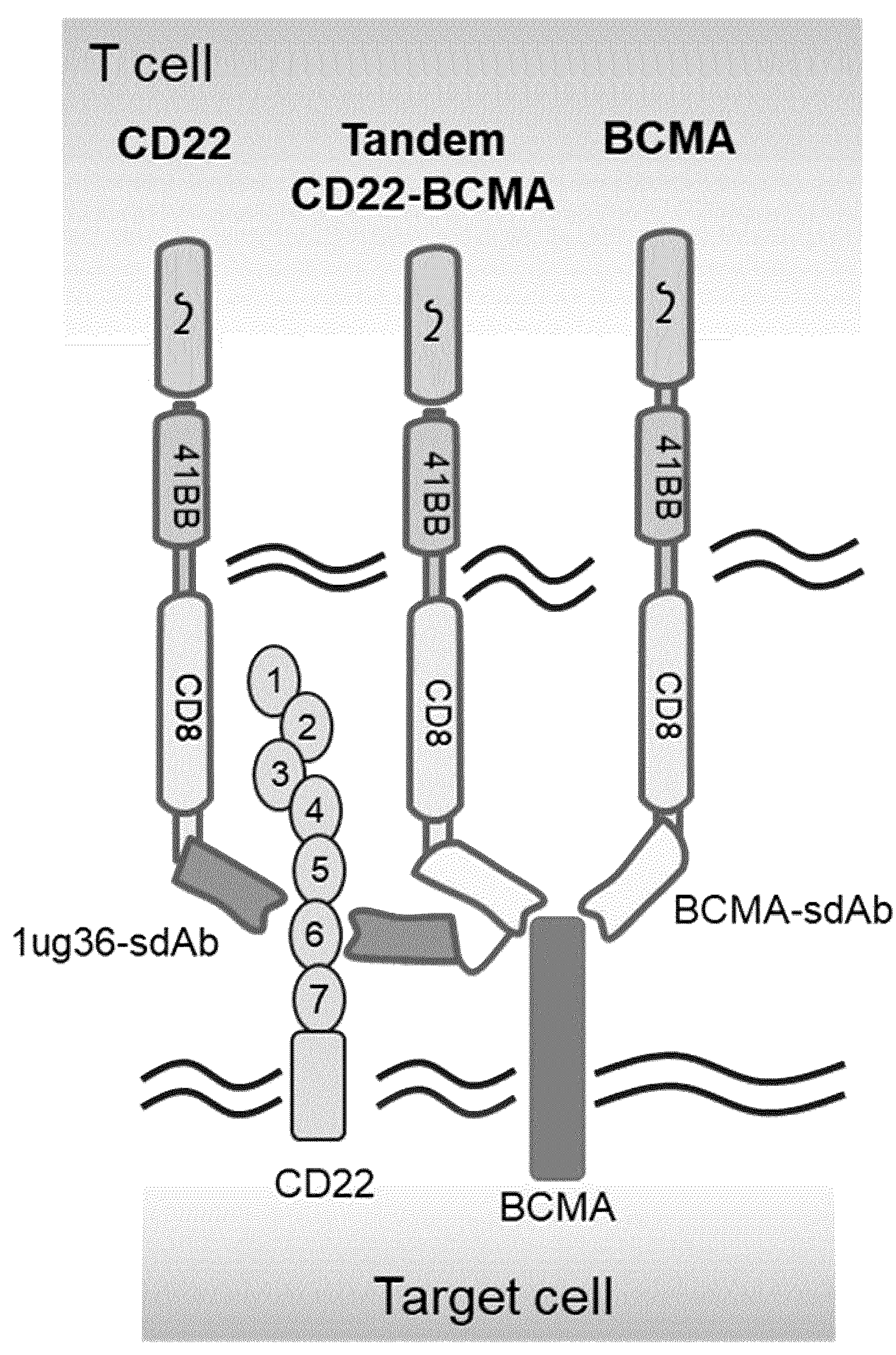
FIG. 33 depicts the molecular structure of CD22-specific CAR (left), BCMA-specific CAR (right), or Tandem-CD22-BCMA-CAR molecule (centre).

FIG. 33 depicts the molecular structure of CD22-specific CAR (left), BCMA-specific CAR (right), or Tandem-CD22-BCMA-CAR molecule (centre). Tandem constructs would contain an N-terminal CD22-sdAb sequence, followed by a linker sequence which can by another antigen specific sdAb, such as one targeting BCMA as shown here.

Figure 34:
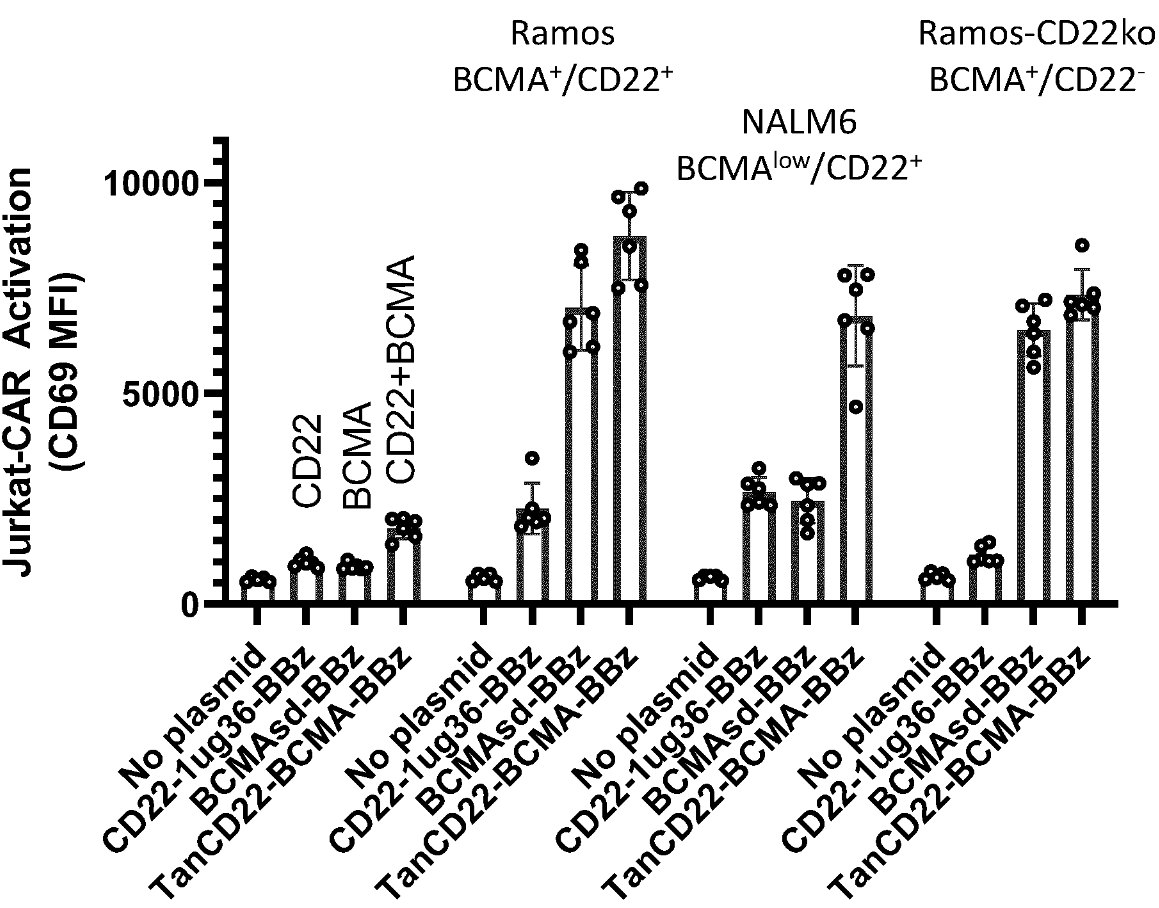
FIG. 34 depicts the results of CAR-Jurkat assay wherein Jurkat cells were transiently electroporated with varying CD22, BCMA, or CD22/BCMA-specific CAR plasmids and cultured alone or in co-culture with BCMA+/CD22+ (Ramos), BCMAlow/CD22+ (NALM6), or BCMA+/CD22− (Ramos-CD22ko) target cell lines and examined for activation status (CD69 expression).

FIG. 34 depicts the results of CAR-Jurkat assay wherein Jurkat cells were transiently electroporated with varying CD22, BCMA, or CD22/BCMA-specific CAR plasmids and cultured alone or in co-culture with BCMA+/CD22+ (Ramos), BCMAlow/CD22+ (NALM6), or BCMA+/CD22− (Ramos-CD22ko) target cell lines and examined for activation status (CD69 expression). These data demonstrate that multi-CD22 sdAb containing CAR molecules can maintain responsiveness to both target antigens, and enhance responsiveness to antigen-low target cells.

Discussion of Examples

This is the first demonstration of single domain antibodies for application in CD22 targeted CAR-T treatment. Single domain antibodies offer significant advantage over the single-chain variable fragment antibodies which are typically used in the antigen recognition domain of CAR constructs, including significantly smaller size, higher homology with human antibody sequences, enhanced modularity, and ability to target epitopes which may not be accessible to scFvs. This invention may later be combined with CD20, CD19 or BCMA targeted single domain antibodies to generate a single CAR construct targeted against multiple B-cell specific antigens.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

1. Fry, T. J. et al. CD22-targeted CAR T cells induce remission in B-ALL that is naive or resistant to CD19-targeted CAR immunotherapy. *Nature Medicine* 24, 20-28 (2018).
2. Pan, J. et al. CD22 CAR T-cell therapy in refractory or relapsed B acute lymphoblastic leukemia. *Leukemia* 1-13 (2019) doi: 10.1038/s41375-019-0488-7.
3. U.S. Patent Publication No. US 2015/0299317 A1.
4. Arbabi-Ghahroudi et al. Aggregation-resistant VHs selected by in vitro evolution tend to have disulfide-bonded loops and acidic isoelectric points *Protein Engineering, Design and Selection* 2009 Vol. 22, 59-66.
5. Feldhaus et al., 2003, *Nat. Biotechnol*. Vol. 21, 163-170.
6. Baral T N, Arbabi-Ghahroudi M. Expression of single-domain antibodies in bacterial systems. Methods Mol Biol. 2012; 911:257-75.
7. Bloemberg et al. A High-Throughput Method for Characterizing Novel Chimeric Antigen Receptors in Jurkat Cells. Molecular Therapy: Methods & Clinical Development. 2020; 16: P238-254.
8. Hussack G et al. Protein Engineering Design & Selection. 2014; 27(6); 191-198.
9. Vallera et al. IL-15 Trispecific Killer Engagers (TrikEs) Make Natural Killer Cells Specific to CD33+ Targets While Also Inducing In Vivo Expansion, and Enhanced Function. *Clinical Cancer Research*. 2012; 22(14):3440-50
10. Gleason et al. Bispecific and Trispecific Killer Cell Engagers Directly Activate Human NK Cells Through CD16 Signaling and Induce Cytotoxicity and Cytokine Production. *Mol Cancer Ther.* 2012; 11(12):2674-84
11. Gauthier et al. Multifunctional Natural Killer Cell Engagers Targeting NKp46 Trigger Protective Tumor Immunity: Cell. 2019; 177(7):1701-13.
12. Stoiber et al. Limitations in the Design of Chimeric Antigen Receptors for Cancer Therapy. Cells. 2012; 8(5): 472.
13. van der Stegen et al. The pharmacology of second-generation chimeric antigen receptors. Nat Rev Drug Discov. 2019; 14(7):499-509.
14. Henry K A et al. Llama Peripheral B-cell Populations Producing Conventional and Heavy Chain-Only IgG Subtypes Are Phenotypically Indistinguishable but Immunogenetically Distinct. *Immunogenetics* 2019 April; 71(4): 307-320.

All references referred to herein are expressly incorporated by reference in their entireties.

TABLE 8

| Table of Sequences | | | |
|---|---|---|---|
| Seq. # | Description | | Sequence |
| 1 | hCD221ug-6 | CDR1 | GFTLDYYV |
| 2 | hCD221ug-6 | CDR2 | ISSSDGVT |
| 3 | hCD221ug-6 | CDR3 | AVDKPFYDGGYYYTCPVDFDS |
| 4 | hCD221ug-10 | CDR1 | ESTFSIM |
| 5 | hCD221ug-10 | CDR2 | INSAGST |
| 6 | hCD221ug-10 | CDR3 | YVDGY |
| 7 | hCD221ug-13 | CDR1 | GGSFSSVT |
| 8 | hCD221ug-13 | CDR2 | ITWSSPST |
| 9 | hCD221ug-13 | CDR3 | AGGRTGRGTSADTDEYNY |
| 10 | hCD221ug-14 | CDR1 | GRIFRSYV |
| 11 | hCD221ug-14 | CDR2 | IGWSDT |
| 12 | hCD221ug-14 | CDR3 | AANSPPYGPQRDEFDY |
| 13 | hCD221ug-36 | CDR1 | GITFSRAA |
| 14 | hCD221ug-36 | CDR2 | VNSDSST |
| 15 | hCD221ug-36 | CDR3 | WSPGFGSY |
| 16 | hCD221ug-61 | CDR1 | MSSFSQYV |
| 17 | hCD221ug-61 | CDR2 | ITSYSNT |
| 18 | hCD221ug-61 | CDR3 | NAQYGSTFIRNHWDD |
| 19 | hCD221ug-74 | CDR1 | GFTFDDYA |
| 20 | hCD221ug-74 | CDR2 | MGSSDGAT |
| 21 | hCD221ug-74 | CDR3 | AVDKPFYDGGYRYTCPVDFGS |
| 22 | hCD221ug-75 | CDR1 | GSIFRIAV |
| 23 | hCD221ug-75 | CDR2 | ITSGGDT |
| 24 | hCD221ug-75 | CDR3 | NAKYGRDEY |
| 25 | hCD221ug-77 | CDR1 | GSIFRIAV |
| 26 | hCD221ug-77 | CDR2 | ITSGGET |
| 27 | hCD221ug-77 | CDR3 | NAKWGQYEY |
| 28 | hCD221ug-80 | CDR1 | GFTLDYYV |
| 29 | hCD221ug-80 | CDR2 | ITSDGVT |
| 30 | hCD221ug-80 | CDR3 | AVDKPFYDGGIQYTCPVDFDS |
| 31 | hCD221ug-87 | CDR1 | GSIFRIAV |
| 32 | hCD221ug-87 | CDR2 | ITSGGET |
| 33 | hCD221ug-87 | CDR3 | NAKWGRDEY |
| 34 | hCD221ug-93 | CDR1 | GSTFSSSV |
| 35 | hCD221ug-93 | CDR2 | ITSSGST |
| 36 | hCD221ug-93 | CDR3 | NAQYGRRSD |
| 37 | hCD22100ng-2 | CDR1 | GVTFDYYV |
| 38 | hCD22100ng-2 | CDR2 | MRNSDGVT |

TABLE 8-continued

Table of Sequences

| Seq. # | Description | | Sequence |
|---|---|---|---|
| 39 | hCD22100ng-2 | CDR3 | AVDKPFYDGGNYYTCPVDFDS |
| 40 | hCD22100ng-62 | CDR1 | GSISSINA |
| 41 | hCD22100ng-62 | CDR2 | ITTAGNT |
| 42 | hCD22100ng-62 | CDR3 | AGKLYVNKEYTY |
| 43 | hCD22100ng-66 | CDR1 | GFSLDYYV |
| 44 | hCD22100ng-66 | CDR2 | ISSSDGAT |
| 45 | hCD22100ng-66 | CDR3 | AVDKPFYDGGSYYTCPVDFGS |
| 46 | hCD22pas-10 | CDR1 | GFTSDYYA |
| 47 | hCD22pas-10 | CDR2 | ISSSDGVT |
| 48 | hCD22pas-10 | CDR3 | AVDKPFYDGGYLYTCPVDFDS |
| 49 | hCD22pas-16 | CDR1 | GSTFSLKA |
| 50 | hCD22pas-16 | CDR2 | INSDGSYT |
| 51 | hCD22pas-16 | CDR3 | NTMPPWP |
| 52 | hCD22pas-23 | CDR1 | GSIFRITAV |
| 53 | hCD22pas-23 | CDR2 | ITSAGET |
| 54 | hCD22pas-23 | CDR3 | NAKWGQYEH |
| 55 | hCD22pas-24 | CDR1 | GITSSINS |
| 56 | hCD22pas-24 | CDR2 | IGRGGSGST |
| 57 | hCD22pas-24 | CDR3 | LEVTTDLSSY |
| 58 | hCD22pas-32 | CDR1 | GRIFRSYV |
| 59 | hCD22pas-32 | CDR2 | IGWSDT |
| 60 | hCD22pas-32 | CDR3 | AANSPPYGPQRDEFGY |
| 61 | hCD22pas-33 | CDR1 | GFTLDSYV |
| 62 | hCD22pas-33 | CDR2 | ISSSDGVT |
| 63 | hCD22pas-33 | CDR3 | AVDKPFYDGGYLYTCPVDFDS |
| 64 | hCD22pas-48 | CDR1 | GSIFRIAV |
| 65 | hCD22pas-48 | CDR2 | ITIAGET |
| 66 | hCD22pas-48 | CDR3 | YANGGRDEY |
| 67 | hCD22pas-55 | CDR1 | GRISRSYV |
| 68 | hCD22pas-55 | CDR2 | IGCSDT |
| 69 | hCD22pas-55 | CDR3 | AEYSPPYGPQRDEFDY |
| 70 | hCD22pas-64 | CDR1 | GSTFSLNT |
| 71 | hCD22pas-64 | CDR2 | ASSDGYT |
| 72 | hCD22pas-64 | CDR3 | TWGTGRFADYIY |
| 73 | hCD22pas-72 | CDR1 | GGTFSVYT |
| 74 | hCD22pas-72 | CDR2 | IRGSGGT |
| 75 | hCD22pas-72 | CDR3 | AVRIRRTLVEPLTKETLYDY |
| 76 | hCD22pas-79 | CDR1 | GRTSSVYG |

TABLE 8-continued

| Table of Sequences | | | |
|---|---|---|---|
| Seq. # | Description | | Sequence |
| 77 | hCD22pas-79 | CDR2 | MSWSGGPT |
| 78 | hCD22pas-79 | CDR3 | AVRIRRTLLEPLTKETLYDY |
| 79 | hCD22pas-82 | CDR1 | GSIFRITV |
| 80 | hCD22pas-82 | CDR2 | ITSGGDS |
| 81 | hCD22pas-82 | CDR3 | NAKWGGDEY |
| 82 | hCD221ug-6 | Full length | QVQLVESGGGVVRPGDSLRLSCTVSGFTLDYYVMG WFRQAPGKEREVVSCISSSDGVTYYADSVKGRFTIS RDNAKNTVYLQMNSLKPEDTAIYYCAVDKPFYDGGY YYTCPVDFDSWGQGTQVTVSS |
| 83 | hCD221ug-10 | Full length | QVQLVESGGGLVQAGGSLSVSCTASESTFSIMMGW FRQAPGKQREMVAVINSAGSTNYADSAEGRFTISRD LAKKTVSLQMNSLKPEDTAVYYCYVDGYFGQGTQV TVSS |
| 84 | hCD221ug-13 | Full length | QVQLVESGGGLVQAGDSLRLSCAGSGGSFSSVTMA WFRQAPGKDREFVAAITWSSPSTYYADSVKGRFTIS RDNAKNTVYLQMNSLKPEDTAVYYCAGGRTGRGTS ADTDEYNYWGQGTQVTVSS |
| 85 | hCD221ug-14 | Full length | QVKLEESGGGLVQAGGSLRLSCAVSGRIFRSYVLG WFRQAPGKERELVARIGWSDTYYADSVKGRFTISRD NAKNTVDLQMNSLKPEDTAVYYCAANSPPYGPQRD EFDYWGQGTQVTVSS |
| 86 | hCD221ug-36 | Full length | EVQLVDSGGGLVQAGGSLRVSCEASGITFSRAAMG WYRQRPGKERERVAVVNSDSSTIYADSVKGRFTISR DNAKNTVYLQMNSLEPEDTAVYYCWSPGFGSYWG QGTQVTVSS |
| 87 | hCD221ug-61 | Full length | QVQLVESGGGLVQAGGSLRLSCAASMSSFSQYVMY WYRQAPGKQRELVATITSYSNTNYADSVKGRFTISR DNAKSIAYLQMDSLKPEDTAVYYCNAQYGSTFIRNH WDDWGQGTQVTVSS |
| 88 | hCD221ug-74 | Full length | QVKLEESGGGLVQAGGSLRLSCAGSGFTFDDYAMG WFRQAPGKEREVVSCMGSSDGATYYADSVKGRFTI SRDNAKNTVYLQMNSLKPEDTAIYYCAVDKPFYDGG YRYTCPVDFGSWGQGTQVTVSS |
| 89 | hCD221ug-75 | Full length | QVKLEESGGGLVQPGGSLRLSCAGSGSIFRIAVMNW YRQAPGKERELVAVITSGGDTHYAASVKGRFTISRD NAKNTMYLQINSLKPEDTAVYYCNAKYGRDEYWGQ GAQVTVSS |
| 90 | hCD221ug-77 | Full length | QVKLEESGGGLVQPGGSLRLSCADSGSIFRIAVMNW YRQAPGKERELVAVITSGGETHYAASVKGRFTISRD NAKNTMYLQMNSLKPEDTAVYYCNAKWGQYEYWG QGTQVTVSS |
| 91 | hCD221ug-80 | Full length | QVQLVESGGGLVQPGGSLRLSCTFSGFTLDYYVMV WFRQAPGKEREAVSCITSDGVTYYADSVKGRFTISR DNAKNTVYLQMNRVKPEDTAVYYCAVDKPFYDGGI QYTCPVDFDSWGQGAQVTVSS |
| 92 | hCD221ug-87 | Full length | QVQLVESGGGLVQPGGSLRLSCADSGSIFRIAVMN WYRQAPGKERELVAVITSGGETHYAASVKGRFTISR DNAKNTMYLQMNSLKPEDTAVYYCNAKWGRDEYW GQGTQVTVSS |
| 93 | hCD221ug-93 | Full length | QVKLEESGGGLVQAGGSLRLSCAASGSTFSSSVMN WYRQAPGKQRELVAVITSSGSTHYADSVKGRFTISR DNAKNTVNLQMNSLKPEDTAVYYCNAQYGRRSDW GQGTQVTVSS |
| 94 | hCD22100ng-2 | Full length | QVKLEESGGGLVQPGGSLRLSCTVSGVTFDYYVMG WFRQAPGKEREVVSCMRNSDGVTYYADSVKGRFTI SRDNAKNTVYLQMNSLKPDDTAIYYCAVDKPFYDGG NYYTCPVDFDSWGQGTQVTVSS |

TABLE 8-continued

| Table of Sequences | | |
|---|---|---|
| Seq. # | Description | Sequence |
| 95 | hCD22100ng-62 Full length | QVKLEESGGGLVQAGGSLRLSCAASGSISSINAMGW YRQVPGKQRELVALITTAGNTRYGDSVKGRFTISRDN ARKTVYLQMNSLKPEDTAVYYCAGKLYVNKEYTYW GQGTQVTVSS |
| 96 | hCD22100ng-66 Full length | QVQLVESGGGLVQPGGSLRLSCTVSGFSLDYYVMG WFRQAPGKEREVVSCISSSDGATYYPDSVKGRFTIS RDNAKKTVYLQMNALKPEDTAIYYCAVDKPFYDGGS YYTCPVDFGSWGQGTQVTVSS |
| 97 | hCD22pas-10 Full length | QVQLVESGGGLVQPGDSLRLSCTVSGFTSDYYAMG WFRQAPGKEREAVSCISSSDGVTYYADSVRGRFTIS RDNAKNTVYLEMNSLKPEDTAIYYCAVDKPFYDGGY LYTCPVDFDSWGQGTQVTVSS |
| 98 | hCD22pas-16 Full length | QVQLVESGGGLVQAGGSLRLSCAASGSTFSLKAMA WYRQAPGKQRERVGVINSDGSYTTDAASVQGRFTI SRDNAKNTVYLQMNSLKPEDTAVYYCNTMPPWPW GQGTQVTVSS |
| 99 | hCD22pas-23 Full length | QVQLVESGGGLVQPGGSLRLSCAASGSIFRITAVMN WYRQAPGKERELVAVITSAGETHYAESVKGRFTISR DNAKNTMYLQMNSLKPEDTAVYYCNAKWGQYEHW GQGTQGTVSS |
| 100 | hCD22pas-24 Full length | QVQLVESGGGLVQAGGSLRLSCSASGITSSINSMG WHRQAPGKQRELVASIGRGGSGSTKYADSGKGRFL ISRDNNKNILFLEMNSLKPEDTADYYCLEVTTDLSSY WGRGTQVTVSS |
| 101 | hCD22pas-32 Full length | QVQLVESGGGLVQAGGSLRLSCAVSGRIFRSYVLG WFRQAPGKERELVARIGWSDTYYADSVKGRFTISRD NAKNTVDLQMNSLKPEDTAVYYCAANSPPYGPQRD EFGYWGQGTQVTVSS |
| 102 | hCD22pas-33 Full length | QVKLEESGGGLVQPGGSLRLSCTVSGFTLDSYVMG WFRQAPGKEREAVSCISSSDGVTYYADSVKGRFTIS RDNAKNTYLQMNSLKPEDTAIYYCAVDKPFYDGGYL YTCPVDFDSWGQGIQVTVSS |
| 103 | hCD22pas-48 Full length | QVKLEESGGGLGQAGGAVRLSCADSGSIFRIAVMN WYRQAPGKERELVAVITIAGETHYAYSVKGQFTISRY NAKNTMYLQMNRLKPEDTAVYYCYANGGRDEYWG RGTQVTVSS |
| 104 | hCD22pas-55 Full length | QVKLEESGGGLGQAGGSLRLSCAVSGRISRSYVLG WFRQAPGKERELVARIGCSDTYYADSAKGRFTISRN NADNTVDLQMNSLKPEDTAVYYCAEYSPPYGPQRD EFDYWGQGTQVTVSS |
| 105 | hCD22pas-64 Full length | QVQLVESGGGLVQAGGSLRLSCAASGSTFSLNTMA WYRQAPGNQREYVAAASSDGYTNYADSVRGRFTIS RDNDKNTMYLQMNSLRPEDTAVYYCTWGTGRFADY IYWGQGTQVTVSS |
| 106 | hCD22pas-72 Full length | QVQLVESGGGLVQAGGSLRLSCAASGGTFSVYTMA WFRQAPGKEREFVAAIRGSGGTYYRDSVKGRFTISR DNAKNTVYLQMNSLKPEDTAVYYCAVRIRRTLVEPLT KETLYDYWGQGTQVTVSS |
| 107 | hCD22pas-79 Full length | QVKLEESGGGLVQPGGSLRLSCTVSGRTSSVYGMA WFRQTPGKEREFVAAMSWSGGPTYFADSVKGRFG SSRDNAKNTVYLQMNGLRPEDTAVYYCAVRIRRTLL EPLTKETLYDYWGQGTQVTVSS |
| 108 | hCD22pas-82 Full length | QVQLVESGGGLVQPGGSLRLSCAASGSIFRITVMNW HRQAPGKERELSGVITSGGDSHYAASVKGRFTIYRD NTKNTMYLQMNRLKPEDTDYYYCNAKWGGDEYWG QGTHDTGSS |
| 109 | CAR modular construct | ATGCTCAGGCTGCTCTTGGCTCTCAACTTATTCCC TTCAATTCAAGTAACAGGAGGGTCTTC[**anti_CD22_ sdAb**]GAAGACTTCCTTTGCGAGACGACGGTGGCG GGGGATCAGGTGGTGGAGGTAGCGGGGGAGGGG GCTCAGGCGGTACAACTACGCCTGCACCTCGCCC ACCGACCCCAGCACCAACCATCGCTTCACAGCCT |

TABLE 8-continued

| Table of Sequences | | |
|---|---|---|
| Seq. # | Description | Sequence |
| | | TTGAGCCTGCGACCAGAGGCATGTCGCCCTGCTG CGGGCGGTGCCGTTCATACTCGCGGACTTGATTT TGCGTGTGACGTCGTCTCGCCTTCTAAGCCCTTTT GGGTGCTGGTGGTGGTTGGTGGAGTCCTGGCTTG CTATAGCTTGCTAGTAACAGTGGCCTTTATTATTTT CTGGGTGAGGAAACGGGGCAGAAAGAAACTCCTG TATATATTCAAACAACCATTTATGCGACCAGTACAA ACTACTCAAGAGGAAGATGGCTGTAGCTGCCGATT TCCAGAAGAAGAAGAAGGAGGATGTGAACTGCTG AGAGTGAAGTTCAGCAGGAGCGCAGACGCCCCCG CGTACCAGCAGGGCCAGAACCAGCTCTATAACGA GCTCAATCTAGGACGAAGAGAGGAGTACGATGTTT TGGACAAGCGACGTGGCCGGGACCCTGAGATGG GGGGAAAGCCGCAGAGAAGGAAGAACCCTCAGG AAGGCCTGTACAATGAACTGCAGAAAGATAAGATG GCGGAGGCCTACAGTGAGATTGGGATGAAAGGCG AGCGCCGGAGGGGCAAGGGGCACGATGGCCTTT ACCAGGGACTCAGTACAGCCACCAAGGACACCTA CGACGCCCTTCACATGCAGGCCCTGCCCCCTCGC GCTAGCGCCACGAACTTCTCTCTGTTAAAGCAAGC AGGCGACGTGGAAGAAAACCCCGGTCCCATGGTG AGCAAGGGCGAGGAGGACAACATGGCCAGCCTG CCCGCCACCCACGAGCTGCACATCTTCGGCAGCA TCAACGGCGTGGACTTCGACATGGTGGGCCAGGG CACCGGCAACCCCAACGACGGCTACGAGGAGCTG AACCTGAAGAGCACCAAGGGCGACCTGCAGTTCA GCCCCTGGATTCTGGTGCCCCACATCGGCTACGG CTTCCACCAGTACCTGCCCTACCCCGACGGCATG AGCCCCTTCCAGGCCGCCATGGTGGACGGCAGC GGCTACCAGGTGCACAGGACCATGCAGTTCGAGG ACGGCGCCAGCCTGACCGTGAACTACAGGTACAC CTACGAGGGCAGCCACATCAAGGGCGAGGCCCA GGTGAAGGGCACCGGCTTCCCCGCCGACGGCCC CGTGATGACCAACAGCCTGACCGCCGCCGACTGG TGCAGGAGCAAAAAGACCTACCCCAACGACAAGA CCATCATCAGCACCTTCAAGTGGAGCTACACCACC GGCAACGGCAAGAGGTACAGGAGCACCGCCAGG ACCACCTACACCTTCGCCAAGCCCATGGCCGCCA ACTACCTGAAGAACCAGCCCATGTACGTGTTCAGA AAGACCGAGCTGAAGCACAGCAAGACCGAGCTGA ACTTCAAGGAGTGGCAGAAGGCCTTCACCGACGT GATGGGCATGGACGAGCTGTACAAGCCCAAGAAG AAGAGGAAGGTGGAGGACCCCCCCGCCGCCAAG AGGGTGAAGCTGGACTAA |
| 110 | Human CD28 Signal Peptide | MLRLLLALNLFPSIQVTG |
| 111 | Synthetic Flexible Linker Domain | GGGGSGGGGSGGGGSGG |
| 112 | Human CD8 Hinge Domain | TTTPAPRPPTPAPTIASQPLSLRPEACRPAAGGAVHT RGLDFACD |
| 113 | Human CD28 Transmembrane Domain | PSKPFWVLVVVGGVLACYSLLVTVAFIIFWVR |
| 114 | Human 4-1BB Co-stimulatory Domain | KRGRKKLLYIFKQPFMRPVQTTQEEDGCSCRFPEEE EGGCEL |
| 115 | Human CD3zeta Signaling Domain | LRVKFSRSADAPAYQQGQNQLYNELNLGRREEYDV LDKRRGRDPEMGGKPQRRKNPQEGLYNELQKDKM AEAYSEIGMKGERRRGKGHDGLYQGLSTATKDTYD ALHMQALPPR |
| 116 | M971 scFV | QVQLQQSGPGLVKPSQTLSLTCAISGDSVSSNSAAW NWIRQSPSRGLEWLGRTYYRSKWYNDYAVSVKSR! TINPDTSKNQFSLQLNSVTPEDTAVYYCAREVTGDLE DAFDIWGQGTMVTVSSGGGGSDIQMTQSPSSLSAS VGDRVTITCRASQTIWSYLNWYQQRPGKAPNLLIYA ASSLQSGVPSRFSGRGSGTDFTLTISSLQAEDFATY YCQQSYSIPQTFGQGTKLEIK |
| 117 | FMC63 scFV | DYKDHDGDYKDHDIDYKDDDDKDIQMTQTTSSLSAS LGDRVTISCRASQDISKYLNWYQQKPDGTVKLLIYHT SRLHSGVPSRFSGSGSGTDYSLTISNLEQEDIATYFC QQGNTLPYTFGGGTKLEITGSTSGSGKPGSGEGSTK |

TABLE 8-continued

| Table of Sequences | | |
|---|---|---|
| Seq. # | Description | Sequence |
| | | GEVKLQESGPGLVAPSQSLSVTCTVSGVSLPDYGVS WIRQPPRKGLEWLGVIWGSETTYYNSALKSRLTIIKD NSKSQVFLKMNSLQTDDTAIYYCAKHYYYGGSYAMD YWGQGTSVTVSS |
| 118 | Short flexible linker amino acid sequence | GGGGS |
| 119 | Bi-specific T cell engager modular construct DNA sequence | ATGGAGTTTGGGCTGAGCTGGGTTTTCCTCGTTGC TCTTTTTAGAGGTGTCCAGTGTACAGGAGGGTCTT CG[**anti_CD22_sdAb**]GAAGACTTCCTTGGAGGAGG CGGAAGT[**anti_CD3_scFv_heavy_chain**]GGCGGT GGTGGGTCAGGCGGCGGTGGGAGCGGAGGAGGT GGAAGC[**anti_CD3_scFv_light_chain**]CACCACCAC CACCACCACTAG |
| 120 | hCD221ug-36 Cloned Segment | QVQLVESGGGLVQAGGSLRVSCEASGITFSRAAMG WYRQRPGKERERVAVVNSDSSTIYADSVKGRFTISR DNAKNTVYLQMNSLEPEDTAVYYCWSPGFGSYWG QGTQVTVSS |
| 121 | hCD221ug-93 Cloned Segment | QVQLVESGGGLVQAGGSLRLSCAASMSSFSQYVMY WYRQAPGRQRELVATITSASSTSYADSVKGRFTISR DNAKSIVYLQMNSLKPEDTAVYYCNAQYGSTFIRKPY DTWGQGTQVTVSS |
| 122 | hCD221ug-10 Cloned Segment | QVQLVESGGGLVQAGGSLSVSCTASESTFSIMMGW FRQAPGKQREMVAVINSAGSTNYADSAEGRFTISRD LAKKTVSLQMNSLKPEDTAVYYCYVDGYFGQGTQV TVSS |
| 123 | hCD221ug-61 Cloned Segment | QVQLVESGGGLVQAGGSLRLSCAASMSSFSQYVMY WYRQAPGKQRELVATITSYSNTNYADSVKGRFTISR DNAKSIAYLQMDSLKPEDTAVYYCNAQYGSTFIRNH WDDWGQGTQVTVSS |
| 124 | hCD22pas-16 Cloned Segment | QVQLVESGGGLVQAGGSLRISCAASGSTFSLKAMA WYRQAPGKQRERVGVINSDGSYTTDAASVQGRFTI SRDNAKNTVYLQMNSLKPEDTAVYYCNTMPPWPW GQGTQVTVSS |
| 125 | hCD221ug-80 Cloned Segment | QVQLVESGGGLVQPGGSLRLSCTFSGFTLDYYVMG WFRQAPGKEREAVSCITSDGVTYYADSVKGRFTISR DNAKNTVYLQMNRVKPEDTAVYYCAVDKPFYDGGI QYTCPVDFDSWGQGTQVTVSS |
| 126 | Group 1 CDR1 Consensus | GXXXDXYX |
| 127 | Group 1 CDR2 Consensus | XXXXXGXT |
| 128 | Group 1 CDR3 Consensus | AVDKPFYDGGXXYTCPVDFXS |
| 129 | Group 2 CDR1 Consensus | GSXFXXXXV |
| 130 | Group 2 CDR2 Consensus | ITSXGXX |
| 131 | Group 2 CDR3 Consensus | NAXXGXXXX |
| 132 | Group 3 CDR1 Consensus | GRIXRSYV |
| 133 | Group 3 CDR2 Consensus | IGXSDT |
| 134 | Group 3 CDR3 Consensus | AXXSPPYGPQRDEFXY |
| 135 | Group 4 CDR1 Consensus | GXTXSVYX |
| 136 | Group 4 CDR2 Consensus | XXXSXGXT |
| 137 | Group 4 CDR3 Consensus | AVRIRRTLXEPLTKETLYDY |
| 138 | hCD221ug36 Example CAR construct (DNA) | ATGCTCAGGCTGCTCTTGGCTCTCAACTTATTCCC TTCAATTCAAGTAACAGGACAGGTACAGCTGGTGG AGTCTGGGGGAGGCTTGGTGCAGGCTGGGGGGT CTCTGAGAGTCTCCTGTGAAGCCTCTGGAATCACG TTCAGTCGCGCGGCCATGGCTGGTACCGCCAGC GTCCAGGCAAGGAGCGCGAACGAGTCGCAGTTGT |

TABLE 8-continued

Table of Sequences

| Seq. # | Description | Sequence |
|---|---|---|
| | | TAATAGTGATAGCAGTACAATATATGCAGACTCCG<br>TGAAGGGCCGGTTCACCATCTCCAGAGACAATGC<br>CAAGAACACAGTGTATCTGCAAATGAACAGCCTGG<br>AACCTGAGGACACGGCCGTCTATTACTGTTGGTCC<br>CCAGGGTTCGGGTCCTACTGGGGCCAGGGGACC<br>CAGGTCACCGTTTCCTCACCTTTGCGAGACGACG<br>GTGGCGGGGGATCAGGTGGTGGAGGTAGCGGGG<br>GAGGGGGCTCAGGCGGTACAACTACGCCTGCACC<br>TCGCCCACCGACCCCAGCACCAACCATCGCTTCA<br>CAGCCTTTGAGCCTGCGACCAGAGGCATGTCGCC<br>CTGCTGCGGGCGGTGCCGTTCATACTCGCGGACT<br>TGATTTTGCGTGTGACGTCGTCTCGCCTTCTAAGC<br>CCTTTTGGGTGCTGGTGGTGGTTGGTGGAGTCCT<br>GGCTTGCTATAGCTTGCTAGTAACAGTGGCCTTTA<br>TTATTTTCTGGGTGAGGAAACGGGGCAGAAAGAAA<br>CTCCTGTATATATTCAAACAACCATTTATGCGACCA<br>GTACAAACTACTCAAGAGGAAGATGGCTGTAGCTG<br>CCGATTTCCAGAAGAAGAAGAAGGAGGATGTGAA<br>CTGCTGAGAGTGAAGTTCAGCAGGAGCGCAGACG<br>CCCCCGCGTACCAGCAGGGCCAGAACCAGCTCTA<br>TAACGAGCTCAATCTAGGACGAAGAGAGGAGTAC<br>GATGTTTTGGACAAGCGACGTGGCCGGGACCCTG<br>AGATGGGGGGAAAGCCGCAGAGAAGGAAGAACC<br>CTCAGGAAGGCCTGTACAATGAACTGCAGAAAGAT<br>AAGATGGCGGAGGCCTACAGTGAGATTGGGATGA<br>AAGGCGAGCGCCGGAGGGGCAAGGGGCACGATG<br>GCCTTTACCAGGGACTCAGTACAGCCACCAAGGA<br>CACCTACGACGCCCTTCACATGCAGGCCCTGCCC<br>CCTCGC[**optional_P2A-GFP_marker**] |
| 139 | hCD221ug36 Example Bispecific T-cell Engager construct (DNA) | ATGGAGTTTGGGCTGAGCTGGGTTTTCCTCGTTGC<br>TCTTTTTAGAGGTGTCCAGTGTACAGGACAGGTAC<br>AGCTGGTGGAGTCTGGGGGAGGCTTGGTGCAGG<br>CTGGGGGGTCTCTGAGAGTCTCCTGTGAAGCCTC<br>TGGAATCACGTTCAGTCGCGCGGCCATGGGCTGG<br>TACCGCCAGCGTCCAGGCAAGGAGCGCGAACGA<br>GTCGCAGTTGTTAATAGTGATAGCAGTACAATATA<br>TGCAGACTCCGTGAAGGGCCGGTTCACCATCTCC<br>AGAGACAATGCCAAGAACAçAGTGTATCTGCAAAT<br>GAACAGCCTGGAACCTGAGGACACGGCCGTCTAT<br>TACTGTTGGTCCCCAGGGTTCGGGTCCTACTGGG<br>GCCAGGGGACCCAGGTCACCGTTTCCTCACCTTT<br>GCGAGACGACGGTGGCGGGGGATCAGGTGGTGG<br>AGGTAGCGGGGGAGGGGGCTCAGGCGGTACAAC<br>TACGCCTGCACCTCGCCCACCGACCCCAGCACCA<br>ACCATCGCTTCACAGCCTTTGAGCCTGCGACCAG<br>AGGCATGTCGCCCTGCTGCGGGCGGTGCCGTTCA<br>TACTCGCGGACTTGATTTTGCGTGTGACGTCGTCT<br>CGCTTGGAGGAGGCGGAAGT[**anti_CD3_scFv_<br>heavy_chain**]GGCGGTGGTGGGTCAGGCGGCGGTGG<br>GAGCGGAGGAGGTGGAAGC[**anti_CD3_scFv_light_<br>chain**]CACCACCACCACCACCACTAG |

The invention claimed is:

1. An isolated single domain antibody (sdAb), which binds specifically to human CD22, the sdAb comprising:

i) a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3, ii) a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6, iii) a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9, iv) a CDR1 amino acid sequence as set forth in SEQ ID NO: 10, a CDR2 amino acid sequence as set forth in SEQ ID NO: 11, and a CDR3 amino acid sequence as set forth in SEQ ID NO: 12, v) a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15, vi) a CDR1 amino acid sequence as set forth in SEQ ID NO: 16, a CDR2 amino acid sequence as set forth in SEQ ID NO: 17, and a CDR3 amino acid sequence as set forth in SEQ ID NO: 18, vii) a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21, viii) a CDR1 amino acid sequence as set forth in SEQ ID NO: 22, a CDR2 amino acid sequence as set forth in SEQ ID NO: 23, and a CDR3 amino acid sequence as set forth in SEQ ID NO: 24, ix) a CDR1 amino acid sequence as set forth in SEQ ID NO: 25, a CDR2 amino acid sequence as set forth in SEQ ID NO: 26, and a CDR3 amino acid sequence as set forth in SEQ ID NO: 27, x) a CDR1 amino acid sequence as set forth in SEQ ID NO: 28, a CDR2 amino acid sequence as set forth in SEQ ID NO: 29, and a CDR3 amino acid sequence as set forth in SEQ ID NO: 30, xi) a CDR1 amino acid sequence as set forth in SEQ ID NO: 31, a CDR2 amino acid sequence as set forth in SEQ ID NO: 32, and a CDR3 amino acid sequence as set forth in SEQ ID NO: 33, xii) a CDR1 amino acid sequence as set forth in SEQ ID NO: 34, a CDR2 amino acid sequence as set forth in SEQ ID NO: 35, and a CDR3 amino acid sequence as set forth in SEQ ID NO: 36, xiii) a CDR1 amino acid sequence as set forth in SEQ ID NO: 37, a CDR2 amino acid sequence as set forth in SEQ ID NO: 38, and a CDR3 amino acid sequence as set forth in SEQ ID NO: 39, xiv) a CDR1 amino acid sequence as set forth in SEQ ID NO: 40, a CDR2 amino acid sequence as set forth in SEQ ID NO: 41, and a CDR3 amino acid sequence as set forth in SEQ ID NO: 42, xv) a CDR1 amino acid sequence as set forth in SEQ ID NO: 43, a CDR2 amino acid sequence as set forth in SEQ ID NO: 44, and a CDR3 amino acid sequence as set forth in SEQ ID NO: 45, xvi) a CDR1 amino acid sequence as set forth in SEQ ID NO: 46, a CDR2 amino acid sequence as set forth in SEQ ID NO: 47, and a CDR3 amino acid sequence as set forth in SEQ ID NO: 48, xvii) a CDR1 amino acid sequence as set forth in SEQ ID NO: 49, a CDR2 amino acid sequence as set forth in SEQ ID NO: 50, and a CDR3 amino acid sequence as set forth in SEQ ID NO: 51, xviii) a CDR1 amino acid sequence as set forth in SEQ ID NO: 52, a CDR2 amino acid sequence as set forth in SEQ ID NO: 53, and a CDR3 amino acid sequence as set forth in SEQ ID NO: 54, xix) a CDR1 amino acid sequence as set forth in SEQ ID NO: 55, a CDR2 amino acid sequence as set forth in SEQ ID NO: 56, and a CDR3 amino acid sequence as set forth in SEQ ID NO: 57, xx) a CDR1 amino acid sequence as set forth in SEQ ID NO: 58, a CDR2 amino acid sequence as set forth in SEQ ID NO: 59, and a CDR3 amino acid sequence as set forth in SEQ ID NO: 60, xxi) a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63, xxii) a CDR1 amino acid sequence as set forth in SEQ ID NO: 64, a CDR2 amino acid sequence as set forth in SEQ ID NO: 65, and a CDR3 amino acid sequence as set forth in SEQ ID NO: 66, xxiii) a CDR1 amino acid sequence as set forth in SEQ ID NO: 67, a CDR2 amino acid sequence as set forth in SEQ ID NO: 68, and a CDR3 amino acid sequence as set forth in SEQ ID NO: 69, xxiv) a CDR1 amino acid sequence as set forth in SEQ ID NO: 70, a CDR2 amino acid sequence as set forth in SEQ ID NO: 71, and a CDR3 amino acid sequence as set forth in SEQ ID NO: 72, xxv) a CDR1 amino acid sequence as set forth in SEQ ID NO: 73, a CDR2 amino acid sequence as set forth in SEQ ID NO: 74, and a CDR3 amino acid sequence as set forth in SEQ ID NO: 75, xxvi) a CDR1 amino acid sequence as set forth in SEQ ID NO: 76, a CDR2 amino acid sequence as set forth in SEQ ID NO: 77, and a CDR3 amino acid sequence as set forth in SEQ ID NO: 78, or xxvii) a CDR1 amino acid sequence as set forth in SEQ ID NO: 79, a CDR2 amino acid sequence as set forth in SEQ ID NO: 80, and a CDR3 amino acid sequence as set forth in SEQ ID NO: 81.

2. The isolated sdAb of claim 1, comprising A) the amino acid sequence of any one of SEQ ID NO: 85 to 112 and 120 to 125, or B) an amino acid sequence that is at least 80% identical to any one of SEQ ID NO: 82 to 108 and 120 to 125 across the full length thereof.

3. The isolated sdAb of claim 1, comprising A) the amino acid sequence of any one of SEQ ID NO: 82 to 108 and 120 to 125.

4. The isolated sdAb of claim 1, which is a camelid sdAb.

5. The isolated sdAb of claim 4, which is a llama sdAb.

6. The isolated sdAb of claim 1, which is a humanized sbAb of llama origin.

7. A recombinant polypeptide comprising one or more than one sdAb as defined in claim 1.

8. A multivalent antibody comprising:

a first antigen-binding portion comprising the sdAb as defined in claim 1, and a second antigen-binding portion.

9. The multivalent antibody of claim 8, wherein the second antigen-binding portion binds specifically to a cell-surface marker of a natural killer (NK) cell.

10. The multivalent antibody of claim 8, wherein the sdAb comprises:

a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15; or a CDR1 amino acid sequence as set forth in SEQ ID NO: 7, a CDR2 amino acid sequence as set forth in SEQ ID NO: 8, and a CDR3 amino acid sequence as set forth in SEQ ID NO: 9.

11. The multivalent antibody of claim 8, wherein the sdAb comprises SEQ ID NO: 86 or SEQ ID NO: 84.

12. A method of treating a CD22-expressing cancer in a subject comprising administering to the subject the multivalent antibody as defined in claim 8.

13. A chimeric antibody receptor (CAR), which binds to human CD22, comprising the VHH sdAb as defined in claim 1.

14. The CAR of claim 13, wherein the sdAb comprises SEQ ID NO: 86, SEQ ID NO: 83, SEQ ID NO: 87, SEQ ID NO: 82, SEQ ID NO: 88, SEQ ID NO: 85, SEQ ID NO: 102, or SEQ ID NO: 84.

15. The CAR claim 13, where in the VHH sdAb comprises:

a CDR1 amino acid sequence as set forth in SEQ ID NO: 4, a CDR2 amino acid sequence as set forth in SEQ ID NO: 5, and a CDR3 amino acid sequence as set forth in SEQ ID NO: 6;

a CDR1 amino acid sequence as set forth in SEQ ID NO: 13, a CDR2 amino acid sequence as set forth in SEQ ID NO: 14, and a CDR3 amino acid sequence as set forth in SEQ ID NO: 15;

a CDR1 amino acid sequence as set forth in SEQ ID NO: 19, a CDR2 amino acid sequence as set forth in SEQ ID NO: 20, and a CDR3 amino acid sequence as set forth in SEQ ID NO: 21;

a CDR1 amino acid sequence as set forth in SEQ ID NO: 61, a CDR2 amino acid sequence as set forth in SEQ ID NO: 62, and a CDR3 amino acid sequence as set forth in SEQ ID NO: 63; or a CDR1 amino acid sequence as set forth in SEQ ID NO: 1, a CDR2 amino acid sequence as set forth in SEQ ID NO: 2, and a CDR3 amino acid sequence as set forth in SEQ ID NO: 3.

16. A recombinant nucleic acid molecule encoding the CAR as defined in claim 13.

17. An engineered cell expressing at the cell surface membrane the CAR as defined in claim 13.

18. A method of treating a CD22-expressing cancer in a subject, comprising administering to the subject the engineered cell as defined in claim 17.

19. The method of claim 12, wherein the cancer is a hematological malignancy.

20. The method of claim 18, wherein the cancer is a hematological malignancy.

* * * * *

SEQUENCE LISTING

<160> NUMBER OF SEQ ID NOS: 139

<210> SEQ ID NO 1
<211> LENGTH: 8
<212> TYPE: PRT
<213> ORGANISM: Artificial Sequence
<220> FEATURE:
<223> OTHER INFORMATION: hCD221ug-6 CDR1

<400> SEQUENCE: 1

Gly Phe Thr Leu Asp Tyr Tyr Val
1 5

<210> SEQ ID NO 2

<211> LENGTH: 8
<212> TYPE: PRT
<213> ORGANISM: Artificial Sequence
<220> FEATURE:
<223> OTHER INFORMATION: hCD221ug-6 CDR2

<400> SEQUENCE: 2

Ile Ser Ser Ser Asp Gly Val Thr
1 5

<210> SEQ ID NO 3
<211> LENGTH: 21
<212> TYPE: PRT
<213> ORGANISM: Artificial Sequence
<220> FEATURE:
<223> OTHER INFORMATION: hCD221ug-6 CDR3

<400> SEQUENCE: 3

Ala Val Asp Lys Pro Phe Tyr Asp Gly Gly Tyr Tyr Tyr Thr Cys Pro
1 5 10 15

Val Asp Phe Asp Ser
20

<210> SEQ ID NO 4
<211> LENGTH: 7
<212> TYPE: PRT
<213> ORGANISM: Artificial Sequence
<220> FEATURE:
<223> OTHER INFORMATION: hCD221ug-10 CDR1

<400> SEQUENCE: 4

Glu Ser Thr Phe Ser Ile Met
1 5

<210> SEQ ID NO 5
<211> LENGTH: 7
<212> TYPE: PRT
<213> ORGANISM: Artificial Sequence
<220> FEATURE:
<223> OTHER INFORMATION: hCD221ug-10 CDR2

<400> SEQUENCE: 5

Ile Asn Ser Ala Gly Ser Thr
1 5

<210> SEQ ID NO 6
<211> LENGTH: 5
<212> TYPE: PRT
<213> ORGANISM: Artificial Sequence
<220> FEATURE:
<223> OTHER INFORMATION: hCD221ug-10 CDR3

<400> SEQUENCE: 6

Tyr Val Asp Gly Tyr
1 5

<210> SEQ ID NO 7
<211> LENGTH: 8
<212> TYPE: PRT
<213> ORGANISM: Artificial Sequence
<220> FEATURE:
<223> OTHER INFORMATION: hCD221ug-13 CDR1

<400> SEQUENCE: 7

Gly Gly Ser Phe Ser Ser Val Thr
1 5

<210> SEQ ID NO 8
<211> LENGTH: 8
<212> TYPE: PRT
<213> ORGANISM: Artificial Sequence
<220> FEATURE:
<223> OTHER INFORMATION: hCD221ug-13 CDR2

<400> SEQUENCE: 8

Ile Thr Trp Ser Ser Pro Ser Thr
1               5

<210> SEQ ID NO 9
<211> LENGTH: 18
<212> TYPE: PRT
<213> ORGANISM: Artificial Sequence
<220> FEATURE:
<223> OTHER INFORMATION: hCD221ug-13 CDR3

<400> SEQUENCE: 9

Ala Gly Gly Arg Thr Gly Arg Gly Thr Ser Ala Asp Thr Asp Glu Tyr
1               5                   10                  15

Asn Tyr

<210> SEQ ID NO 10
<211> LENGTH: 8
<212> TYPE: PRT
<213> ORGANISM: Artificial Sequence
<220> FEATURE:
<223> OTHER INFORMATION: hCD221ug-14 CDR1

<400> SEQUENCE: 10

Gly Arg Ile Phe Arg Ser Tyr Val
1               5

<210> SEQ ID NO 11
<211> LENGTH: 6
<212> TYPE: PRT
<213> ORGANISM: Artificial Sequence
<220> FEATURE:
<223> OTHER INFORMATION: hCD221ug-14 CDR2

<400> SEQUENCE: 11

Ile Gly Trp Ser Asp Thr
1               5

<210> SEQ ID NO 12
<211> LENGTH: 16
<212> TYPE: PRT
<213> ORGANISM: Artificial Sequence
<220> FEATURE:
<223> OTHER INFORMATION: hCD221ug-14 CDR3

<400> SEQUENCE: 12

Ala Ala Asn Ser Pro Pro Tyr Gly Pro Gln Arg Asp Glu Phe Asp Tyr
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: hCD221ug-36 CDR1

<400> SEQUENCE: 13

Gly Ile Thr Phe Ser Arg Ala Ala
1               5

<210> SEQ ID NO 14
<211> LENGTH: 7
<212> TYPE: PRT
<213> ORGANISM: Artificial Sequence
<220> FEATURE:
<223> OTHER INFORMATION: hCD221ug-36 CDR2

<400> SEQUENCE: 14

Val Asn Ser Asp Ser Ser Thr
1               5

<210> SEQ ID NO 15
<211> LENGTH: 8
<212> TYPE: PRT
<213> ORGANISM: Artificial Sequence
<220> FEATURE:
<223> OTHER INFORMATION: hCD221ug-36 CDR3

<400> SEQUENCE: 15

Trp Ser Pro Gly Phe Gly Ser Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: hCD221ug-61 CDR1

<400> SEQUENCE: 16

Met Ser Ser Phe Ser Gln Tyr Val
1               5

<210> SEQ ID NO 17
<211> LENGTH: 7
<212> TYPE: PRT
<213> ORGANISM: Artificial Sequence
<220> FEATURE:
<223> OTHER INFORMATION: hCD221ug-61 CDR2

<400> SEQUENCE: 17

Ile Thr Ser Tyr Ser Asn Thr
1               5

<210> SEQ ID NO 18
<211> LENGTH: 15
<212> TYPE: PRT
<213> ORGANISM: Artificial Sequence
<220> FEATURE:
<223> OTHER INFORMATION: hCD221ug-61 CDR3

<400> SEQUENCE: 18

Asn Ala Gln Tyr Gly Ser Thr Phe Ile Arg Asn His Trp Asp Asp
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: hCD221ug-74 CDR1

<400> SEQUENCE: 19

Gly Phe Thr Phe Asp Asp Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: hCD221ug-74 CDR2

<400> SEQUENCE: 20

Met Gly Ser Ser Asp Gly Ala Thr
1 5

<210> SEQ ID NO 21
<211> LENGTH: 21
<212> TYPE: PRT
<213> ORGANISM: Artificial Sequence
<220> FEATURE:
<223> OTHER INFORMATION: hCD221ug-74 CDR3

<400> SEQUENCE: 21

Ala Val Asp Lys Pro Phe Tyr Asp Gly Gly Tyr Arg Tyr Thr Cys Pro
1 5 10 15

Val Asp Phe Gly Ser
20

<210> SEQ ID NO 22
<211> LENGTH: 8
<212> TYPE: PRT
<213> ORGANISM: Artificial Sequence
<220> FEATURE:
<223> OTHER INFORMATION: hCD221ug-75 CDR1

<400> SEQUENCE: 22

Gly Ser Ile Phe Arg Ile Ala Val
1 5

<210> SEQ ID NO 23
<211> LENGTH: 7
<212> TYPE: PRT
<213> ORGANISM: Artificial Sequence
<220> FEATURE:
<223> OTHER INFORMATION: hCD221ug-75 CDR2

<400> SEQUENCE: 23

Ile Thr Ser Gly Gly Asp Thr
1 5

<210> SEQ ID NO 24
<211> LENGTH: 9
<212> TYPE: PRT
<213> ORGANISM: Artificial Sequence
<220> FEATURE:
<223> OTHER INFORMATION: hCD221ug-75 CDR3

<400> SEQUENCE: 24

Asn Ala Lys Tyr Gly Arg Asp Glu Tyr
1 5

<210> SEQ ID NO 25
<211> LENGTH: 8
<212> TYPE: PRT
<213> ORGANISM: Artificial Sequence
<220> FEATURE:
<223> OTHER INFORMATION: hCD221ug-77 CDR1

<400> SEQUENCE: 25

Gly Ser Ile Phe Arg Ile Ala Val 1 5

<210> SEQ ID NO 26
<211> LENGTH: 7
<212> TYPE: PRT
<213> ORGANISM: Artificial Sequence
<220> FEATURE:
<223> OTHER INFORMATION: hCD221ug-77 CDR2

<400> SEQUENCE: 26

Ile Thr Ser Gly Gly Glu Thr
1 5

<210> SEQ ID NO 27
<211> LENGTH: 9
<212> TYPE: PRT
<213> ORGANISM: Artificial Sequence
<220> FEATURE:
<223> OTHER INFORMATION: hCD221ug-77 CDR3

<400> SEQUENCE: 27

Asn Ala Lys Trp Gly Gln Tyr Glu Tyr
1 5

<210> SEQ ID NO 28
<211> LENGTH: 8
<212> TYPE: PRT
<213> ORGANISM: Artificial Sequence
<220> FEATURE:
<223> OTHER INFORMATION: hCD221ug-80 CDR1

<400> SEQUENCE: 28

Gly Phe Thr Leu Asp Tyr Tyr Val
1 5

<210> SEQ ID NO 29
<211> LENGTH: 7
<212> TYPE: PRT
<213> ORGANISM: Artificial Sequence
<220> FEATURE:
<223> OTHER INFORMATION: hCD221ug-80 CDR2

<400> SEQUENCE: 29

Ile Thr Ser Asp Gly Val Thr
1 5

<210> SEQ ID NO 30
<211> LENGTH: 21
<212> TYPE: PRT
<213> ORGANISM: Artificial Sequence
<220> FEATURE:
<223> OTHER INFORMATION: hCD221ug-80 CDR3

<400> SEQUENCE: 30

Ala Val Asp Lys Pro Phe Tyr Asp Gly Gly Ile Gln Tyr Thr Cys Pro
1 5 10 15

Val Asp Phe Asp Ser
20

<210> SEQ ID NO 31
<211> LENGTH: 8
<212> TYPE: PRT
<213> ORGANISM: Artificial Sequence
<220> FEATURE:
<223> OTHER INFORMATION: hCD221ug-87 CDR1

<400> SEQUENCE: 31

```
Gly Ser Ile Phe Arg Ile Ala Val
1               5


<210> SEQ ID NO 32
<211> LENGTH: 7
<212> TYPE: PRT
<213> ORGANISM: Artificial Sequence
<220> FEATURE:
<223> OTHER INFORMATION: hCD221ug-87 CDR2

<400> SEQUENCE: 32

Ile Thr Ser Gly Gly Glu Thr
1               5


<210> SEQ ID NO 33
<211> LENGTH: 9
<212> TYPE: PRT
<213> ORGANISM: Artificial Sequence
<220> FEATURE:
<223> OTHER INFORMATION: hCD221ug-87 CDR3

<400> SEQUENCE: 33

Asn Ala Lys Trp Gly Arg Asp Glu Tyr
1               5


<210> SEQ ID NO 34
<211> LENGTH: 8
<212> TYPE: PRT
<213> ORGANISM: Artificial Sequence
<220> FEATURE:
<223> OTHER INFORMATION: hCD221ug-93 CDR1

<400> SEQUENCE: 34

Gly Ser Thr Phe Ser Ser Ser Val
1               5


<210> SEQ ID NO 35
<211> LENGTH: 7
<212> TYPE: PRT
<213> ORGANISM: Artificial Sequence
<220> FEATURE:
<223> OTHER INFORMATION: hCD221ug-93 CDR2

<400> SEQUENCE: 35

Ile Thr Ser Ser Gly Ser Thr
1               5


<210> SEQ ID NO 36
<211> LENGTH: 9
<212> TYPE: PRT
<213> ORGANISM: Artificial Sequence
<220> FEATURE:
<223> OTHER INFORMATION: hCD221ug-93 CDR3

<400> SEQUENCE: 36

Asn Ala Gln Tyr Gly Arg Arg Ser Asp
1               5


<210> SEQ ID NO 37
<211> LENGTH: 8
<212> TYPE: PRT
<213> ORGANISM: Artificial Sequence
<220> FEATURE:
<223> OTHER INFORMATION: hCD22100ng-2 CDR1

<400> SEQUENCE: 37
```

```
Gly Val Thr Phe Asp Tyr Tyr Val
1               5


<210> SEQ ID NO 38
<211> LENGTH: 8
<212> TYPE: PRT
<213> ORGANISM: Artificial Sequence
<220> FEATURE:
<223> OTHER INFORMATION: hCD22100ng-2 CDR2

<400> SEQUENCE: 38

Met Arg Asn Ser Asp Gly Val Thr
1               5


<210> SEQ ID NO 39
<211> LENGTH: 21
<212> TYPE: PRT
<213> ORGANISM: Artificial Sequence
<220> FEATURE:
<223> OTHER INFORMATION: hCD22100ng-2 CDR3

<400> SEQUENCE: 39

Ala Val Asp Lys Pro Phe Tyr Asp Gly Gly Asn Tyr Tyr Thr Cys Pro
1               5                   10                  15

Val Asp Phe Asp Ser
            20


<210> SEQ ID NO 40
<211> LENGTH: 8
<212> TYPE: PRT
<213> ORGANISM: Artificial Sequence
<220> FEATURE:
<223> OTHER INFORMATION: hCD22100ng-62 CDR1

<400> SEQUENCE: 40

Gly Ser Ile Ser Ser Ile Asn Ala
1               5


<210> SEQ ID NO 41
<211> LENGTH: 7
<212> TYPE: PRT
<213> ORGANISM: Artificial Sequence
<220> FEATURE:
<223> OTHER INFORMATION: hCD22100ng-62 CDR2

<400> SEQUENCE: 41

Ile Thr Thr Ala Gly Asn Thr
1               5


<210> SEQ ID NO 42
<211> LENGTH: 12
<212> TYPE: PRT
<213> ORGANISM: Artificial Sequence
<220> FEATURE:
<223> OTHER INFORMATION: hCD22100ng-62 CDR3

<400> SEQUENCE: 42

Ala Gly Lys Leu Tyr Val Asn Lys Glu Tyr Thr Tyr
1               5                   10


<210> SEQ ID NO 43
<211> LENGTH: 8
<212> TYPE: PRT
<213> ORGANISM: Artificial Sequence
<220> FEATURE:
<223> OTHER INFORMATION: hCD22100ng-66 CDR1
```

<400> SEQUENCE: 43

Gly Phe Ser Leu Asp Tyr Tyr Val
1 5

<210> SEQ ID NO 44
<211> LENGTH: 8
<212> TYPE: PRT
<213> ORGANISM: Artificial Sequence
<220> FEATURE:
<223> OTHER INFORMATION: hCD22100ng-66 CDR2

<400> SEQUENCE: 44

Ile Ser Ser Ser Asp Gly Ala Thr
1 5

<210> SEQ ID NO 45
<211> LENGTH: 21
<212> TYPE: PRT
<213> ORGANISM: Artificial Sequence
<220> FEATURE:
<223> OTHER INFORMATION: hCD22100ng-66 CDR3

<400> SEQUENCE: 45

Ala Val Asp Lys Pro Phe Tyr Asp Gly Gly Ser Tyr Tyr Thr Cys Pro
1 5 10 15

Val Asp Phe Gly Ser
20

<210> SEQ ID NO 46
<211> LENGTH: 8
<212> TYPE: PRT
<213> ORGANISM: Artificial Sequence
<220> FEATURE:
<223> OTHER INFORMATION: hCD22pas-10 CDR1

<400> SEQUENCE: 46

Gly Phe Thr Ser Asp Tyr Tyr Ala
1 5

<210> SEQ ID NO 47
<211> LENGTH: 8
<212> TYPE: PRT
<213> ORGANISM: Artificial Sequence
<220> FEATURE:
<223> OTHER INFORMATION: hCD22pas-10 CDR2

<400> SEQUENCE: 47

Ile Ser Ser Ser Asp Gly Val Thr
1 5

<210> SEQ ID NO 48
<211> LENGTH: 21
<212> TYPE: PRT
<213> ORGANISM: Artificial Sequence
<220> FEATURE:
<223> OTHER INFORMATION: hCD22pas-10 CDR3

<400> SEQUENCE: 48

Ala Val Asp Lys Pro Phe Tyr Asp Gly Gly Tyr Leu Tyr Thr Cys Pro
1 5 10 15

Val Asp Phe Asp Ser
20

<210> SEQ ID NO 49
<211> LENGTH: 8

<212> TYPE: PRT
<213> ORGANISM: Artificial Sequence
<220> FEATURE:
<223> OTHER INFORMATION: hCD22pas-16 CDR1

<400> SEQUENCE: 49

Gly Ser Thr Phe Ser Leu Lys Ala
1               5

<210> SEQ ID NO 50
<211> LENGTH: 8
<212> TYPE: PRT
<213> ORGANISM: Artificial Sequence
<220> FEATURE:
<223> OTHER INFORMATION: hCD22pas-16 CDR2

<400> SEQUENCE: 50

Ile Asn Ser Asp Gly Ser Tyr Thr
1               5

<210> SEQ ID NO 51
<211> LENGTH: 7
<212> TYPE: PRT
<213> ORGANISM: Artificial Sequence
<220> FEATURE:
<223> OTHER INFORMATION: hCD22pas-16 CDR3

<400> SEQUENCE: 51

Asn Thr Met Pro Pro Trp Pro
1               5

<210> SEQ ID NO 52
<211> LENGTH: 9
<212> TYPE: PRT
<213> ORGANISM: Artificial Sequence
<220> FEATURE:
<223> OTHER INFORMATION: hCD22pas-23 CDR1

<400> SEQUENCE: 52

Gly Ser Ile Phe Arg Ile Thr Ala Val
1               5

<210> SEQ ID NO 53
<211> LENGTH: 7
<212> TYPE: PRT
<213> ORGANISM: Artificial Sequence
<220> FEATURE:
<223> OTHER INFORMATION: hCD22pas-23 CDR2

<400> SEQUENCE: 53

Ile Thr Ser Ala Gly Glu Thr
1               5

<210> SEQ ID NO 54
<211> LENGTH: 9
<212> TYPE: PRT
<213> ORGANISM: Artificial Sequence
<220> FEATURE:
<223> OTHER INFORMATION: hCD22pas-23 CDR3

<400> SEQUENCE: 54

Asn Ala Lys Trp Gly Gln Tyr Glu His
1               5

<210> SEQ ID NO 55
<211> LENGTH: 8
<212> TYPE: PRT

```
<213> ORGANISM: Artificial Sequence
<220> FEATURE:
<223> OTHER INFORMATION: hCD22pas-24 CDR1

<400> SEQUENCE: 55

Gly Ile Thr Ser Ser Ile Asn Ser
1               5


<210> SEQ ID NO 56
<211> LENGTH: 9
<212> TYPE: PRT
<213> ORGANISM: Artificial Sequence
<220> FEATURE:
<223> OTHER INFORMATION: hCD22pas-24 CDR2

<400> SEQUENCE: 56

Ile Gly Arg Gly Gly Ser Gly Ser Thr
1               5


<210> SEQ ID NO 57
<211> LENGTH: 10
<212> TYPE: PRT
<213> ORGANISM: Artificial Sequence
<220> FEATURE:
<223> OTHER INFORMATION: hCD22pas-24 CDR3

<400> SEQUENCE: 57

Leu Glu Val Thr Thr Asp Leu Ser Ser Tyr
1               5                   10


<210> SEQ ID NO 58
<211> LENGTH: 8
<212> TYPE: PRT
<213> ORGANISM: Artificial Sequence
<220> FEATURE:
<223> OTHER INFORMATION: hCD22pas-32 CDR1

<400> SEQUENCE: 58

Gly Arg Ile Phe Arg Ser Tyr Val
1               5


<210> SEQ ID NO 59
<211> LENGTH: 6
<212> TYPE: PRT
<213> ORGANISM: Artificial Sequence
<220> FEATURE:
<223> OTHER INFORMATION: hCD22pas-32 CDR2

<400> SEQUENCE: 59

Ile Gly Trp Ser Asp Thr
1               5


<210> SEQ ID NO 60
<211> LENGTH: 16
<212> TYPE: PRT
<213> ORGANISM: Artificial Sequence
<220> FEATURE:
<223> OTHER INFORMATION: hCD22pas-32 CDR3

<400> SEQUENCE: 60

Ala Ala Asn Ser Pro Pro Tyr Gly Pro Gln Arg Asp Glu Phe Gly Tyr
1               5                   10                  15


<210> SEQ ID NO 61
<211> LENGTH: 8
<212> TYPE: PRT
<213> ORGANISM: Artificial Sequence
```

<220> FEATURE:
<223> OTHER INFORMATION: hCD22pas-33 CDR1

<400> SEQUENCE: 61

Gly Phe Thr Leu Asp Ser Tyr Val
1               5

<210> SEQ ID NO 62
<211> LENGTH: 8
<212> TYPE: PRT
<213> ORGANISM: Artificial Sequence
<220> FEATURE:
<223> OTHER INFORMATION: hCD22pas-33 CDR2

<400> SEQUENCE: 62

Ile Ser Ser Ser Asp Gly Val Thr
1               5

<210> SEQ ID NO 63
<211> LENGTH: 21
<212> TYPE: PRT
<213> ORGANISM: Artificial Sequence
<220> FEATURE:
<223> OTHER INFORMATION: hCD22pas-33 CDR3

<400> SEQUENCE: 63

Ala Val Asp Lys Pro Phe Tyr Asp Gly Gly Tyr Leu Tyr Thr Cys Pro
1               5                   10                  15

Val Asp Phe Asp Ser
            20

<210> SEQ ID NO 64
<211> LENGTH: 8
<212> TYPE: PRT
<213> ORGANISM: Artificial Sequence
<220> FEATURE:
<223> OTHER INFORMATION: hCD22pas-48 CDR1

<400> SEQUENCE: 64

Gly Ser Ile Phe Arg Ile Ala Val
1               5

<210> SEQ ID NO 65
<211> LENGTH: 7
<212> TYPE: PRT
<213> ORGANISM: Artificial Sequence
<220> FEATURE:
<223> OTHER INFORMATION: hCD22pas-48 CDR2

<400> SEQUENCE: 65

Ile Thr Ile Ala Gly Glu Thr
1               5

<210> SEQ ID NO 66
<211> LENGTH: 9
<212> TYPE: PRT
<213> ORGANISM: Artificial Sequence
<220> FEATURE:
<223> OTHER INFORMATION: hCD22pas-48 CDR3

<400> SEQUENCE: 66

Tyr Ala Asn Gly Gly Arg Asp Glu Tyr
1               5

<210> SEQ ID NO 67
<211> LENGTH: 8

```
<212> TYPE: PRT
<213> ORGANISM: Artificial Sequence
<220> FEATURE:
<223> OTHER INFORMATION: hCD22pas-55 CDR1

<400> SEQUENCE: 67

Gly Arg Ile Ser Arg Ser Tyr Val
1               5


<210> SEQ ID NO 68
<211> LENGTH: 6
<212> TYPE: PRT
<213> ORGANISM: Artificial Sequence
<220> FEATURE:
<223> OTHER INFORMATION: hCD22pas-55 CDR2

<400> SEQUENCE: 68

Ile Gly Cys Ser Asp Thr
1               5


<210> SEQ ID NO 69
<211> LENGTH: 16
<212> TYPE: PRT
<213> ORGANISM: Artificial Sequence
<220> FEATURE:
<223> OTHER INFORMATION: hCD22pas-55 CDR3

<400> SEQUENCE: 69

Ala Glu Tyr Ser Pro Pro Tyr Gly Pro Gln Arg Asp Glu Phe Asp Tyr
1               5                   10                  15


<210> SEQ ID NO 70
<211> LENGTH: 8
<212> TYPE: PRT
<213> ORGANISM: Artificial Sequence
<220> FEATURE:
<223> OTHER INFORMATION: hCD22pas-64 CDR1

<400> SEQUENCE: 70

Gly Ser Thr Phe Ser Leu Asn Thr
1               5


<210> SEQ ID NO 71
<211> LENGTH: 7
<212> TYPE: PRT
<213> ORGANISM: Artificial Sequence
<220> FEATURE:
<223> OTHER INFORMATION: hCD22pas-64 CDR2

<400> SEQUENCE: 71

Ala Ser Ser Asp Gly Tyr Thr
1               5


<210> SEQ ID NO 72
<211> LENGTH: 12
<212> TYPE: PRT
<213> ORGANISM: Artificial Sequence
<220> FEATURE:
<223> OTHER INFORMATION: hCD22pas-64 CDR3

<400> SEQUENCE: 72

Thr Trp Gly Thr Gly Arg Phe Ala Asp Tyr Ile Tyr
1               5                   10


<210> SEQ ID NO 73
<211> LENGTH: 8
<212> TYPE: PRT
```

```
<213> ORGANISM: Artificial Sequence
<220> FEATURE:
<223> OTHER INFORMATION: hCD22pas-72 CDR1

<400> SEQUENCE: 73

Gly Gly Thr Phe Ser Val Tyr Thr
1               5


<210> SEQ ID NO 74
<211> LENGTH: 7
<212> TYPE: PRT
<213> ORGANISM: Artificial Sequence
<220> FEATURE:
<223> OTHER INFORMATION: hCD22pas-72 CDR2

<400> SEQUENCE: 74

Ile Arg Gly Ser Gly Gly Thr
1               5


<210> SEQ ID NO 75
<211> LENGTH: 20
<212> TYPE: PRT
<213> ORGANISM: Artificial Sequence
<220> FEATURE:
<223> OTHER INFORMATION: hCD22pas-72 CDR3

<400> SEQUENCE: 75

Ala Val Arg Ile Arg Arg Thr Leu Val Glu Pro Leu Thr Lys Glu Thr
1               5                   10                  15

Leu Tyr Asp Tyr
            20


<210> SEQ ID NO 76
<211> LENGTH: 8
<212> TYPE: PRT
<213> ORGANISM: Artificial Sequence
<220> FEATURE:
<223> OTHER INFORMATION: hCD22pas-79 CDR1

<400> SEQUENCE: 76

Gly Arg Thr Ser Ser Val Tyr Gly
1               5


<210> SEQ ID NO 77
<211> LENGTH: 8
<212> TYPE: PRT
<213> ORGANISM: Artificial Sequence
<220> FEATURE:
<223> OTHER INFORMATION: hCD22pas-79 CDR2

<400> SEQUENCE: 77

Met Ser Trp Ser Gly Gly Pro Thr
1               5


<210> SEQ ID NO 78
<211> LENGTH: 20
<212> TYPE: PRT
<213> ORGANISM: Artificial Sequence
<220> FEATURE:
<223> OTHER INFORMATION: hCD22pas-79 CDR3

<400> SEQUENCE: 78

Ala Val Arg Ile Arg Arg Thr Leu Leu Glu Pro Leu Thr Lys Glu Thr
1               5                   10                  15

Leu Tyr Asp Tyr
            20
```

```
<210> SEQ ID NO 79
<211> LENGTH: 8
<212> TYPE: PRT
<213> ORGANISM: Artificial Sequence
<220> FEATURE:
<223> OTHER INFORMATION: hCD22pas-82 CDR1

<400> SEQUENCE: 79

Gly Ser Ile Phe Arg Ile Thr Val
1               5


<210> SEQ ID NO 80
<211> LENGTH: 7
<212> TYPE: PRT
<213> ORGANISM: Artificial Sequence
<220> FEATURE:
<223> OTHER INFORMATION: hCD22pas-82 CDR2

<400> SEQUENCE: 80

Ile Thr Ser Gly Gly Asp Ser
1               5


<210> SEQ ID NO 81
<211> LENGTH: 9
<212> TYPE: PRT
<213> ORGANISM: Artificial Sequence
<220> FEATURE:
<223> OTHER INFORMATION: hCD22pas-82 CDR3

<400> SEQUENCE: 81

Asn Ala Lys Trp Gly Gly Asp Glu Tyr
1               5


<210> SEQ ID NO 82
<211> LENGTH: 128
<212> TYPE: PRT
<213> ORGANISM: Artificial Sequence
<220> FEATURE:
<223> OTHER INFORMATION: hCD221ug-6 VHH

<400> SEQUENCE: 82

Gln Val Gln Leu Val Glu Ser Gly Gly Gly Val Val Arg Pro Gly Asp
1               5                   10                  15

Ser Leu Arg Leu Ser Cys Thr Val Ser Gly Phe Thr Leu Asp Tyr Tyr
            20                  25                  30

Val Met Gly Trp Phe Arg Gln Ala Pro Gly Lys Glu Arg Glu Val Val
        35                  40                  45

Ser Cys Ile Ser Ser Ser Asp Gly Val Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Val Asp Lys Pro Phe Tyr Asp Gly Gly Tyr Tyr Tyr Thr Cys Pro
            100                 105                 110

Val Asp Phe Asp Ser Trp Gly Gln Gly Thr Gln Val Thr Val Ser Ser
        115                 120                 125


<210> SEQ ID NO 83
<211> LENGTH: 110
<212> TYPE: PRT
<213> ORGANISM: Artificial Sequence
```

```
<220> FEATURE:
<223> OTHER INFORMATION: hCD221ug-10 VHH

<400> SEQUENCE: 83

Gln Val Gln Leu Val Glu Ser Gly Gly Gly Leu Val Gln Ala Gly Gly
1               5                   10                  15

Ser Leu Ser Val Ser Cys Thr Ala Ser Glu Ser Thr Phe Ser Ile Met
            20                  25                  30

Met Gly Trp Phe Arg Gln Ala Pro Gly Lys Gln Arg Glu Met Val Ala
        35                  40                  45

Val Ile Asn Ser Ala Gly Ser Thr Asn Tyr Ala Asp Ser Ala Glu Gly
    50                  55                  60

Arg Phe Thr Ile Ser Arg Asp Leu Ala Lys Lys Thr Val Ser Leu Gln
65                  70                  75                  80

Met Asn Ser Leu Lys Pro Glu Asp Thr Ala Val Tyr Tyr Cys Tyr Val
                85                  90                  95

Asp Gly Tyr Phe Gly Gln Gly Thr Gln Val Thr Val Ser Ser
            100                 105                 110


<210> SEQ ID NO 84
<211> LENGTH: 125
<212> TYPE: PRT
<213> ORGANISM: Artificial Sequence
<220> FEATURE:
<223> OTHER INFORMATION: hCD221ug-13 VHH

<400> SEQUENCE: 84

Gln Val Gln Leu Val Glu Ser Gly Gly Gly Leu Val Gln Ala Gly Asp
1               5                   10                  15

Ser Leu Arg Leu Ser Cys Ala Gly Ser Gly Gly Ser Phe Ser Ser Val
            20                  25                  30

Thr Met Ala Trp Phe Arg Gln Ala Pro Gly Lys Asp Arg Glu Phe Val
        35                  40                  45

Ala Ala Ile Thr Trp Ser Ser Pro Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Gly Arg Thr Gly Arg Gly Thr Ser Ala Asp Thr Asp Glu Tyr
            100                 105                 110

Asn Tyr Trp Gly Gln Gly Thr Gln Val Thr Val Ser Ser
        115                 120                 125


<210> SEQ ID NO 85
<211> LENGTH: 121
<212> TYPE: PRT
<213> ORGANISM: Artificial Sequence
<220> FEATURE:
<223> OTHER INFORMATION: hCD221ug-14 VHH

<400> SEQUENCE: 85

Gln Val Lys Leu Glu Glu Ser Gly Gly Gly Leu Val Gln Ala Gly Gly
1               5                   10                  15

Ser Leu Arg Leu Ser Cys Ala Val Ser Gly Arg Ile Phe Arg Ser Tyr
            20                  25                  30

Val Leu Gly Trp Phe Arg Gln Ala Pro Gly Lys Glu Arg Glu Leu Val
        35                  40                  45
```

```
Ala Arg Ile Gly Trp Ser Asp Thr Tyr Tyr Ala Asp Ser Val Lys Gly
    50                  55                  60

Arg Phe Thr Ile Ser Arg Asp Asn Ala Lys Asn Thr Val Asp Leu Gln
65                  70                  75                  80

Met Asn Ser Leu Lys Pro Glu Asp Thr Ala Val Tyr Tyr Cys Ala Ala
                85                  90                  95

Asn Ser Pro Pro Tyr Gly Pro Gln Arg Asp Glu Phe Asp Tyr Trp Gly
            100                 105                 110

Gln Gly Thr Gln Val Thr Val Ser Ser
        115                 120


<210> SEQ ID NO 86
<211> LENGTH: 114
<212> TYPE: PRT
<213> ORGANISM: Artificial Sequence
<220> FEATURE:
<223> OTHER INFORMATION: hCD221ug-36 VHH

<400> SEQUENCE: 86

Glu Val Gln Leu Val Asp Ser Gly Gly Gly Leu Val Gln Ala Gly Gly
1               5                   10                  15

Ser Leu Arg Val Ser Cys Glu Ala Ser Gly Ile Thr Phe Ser Arg Ala
            20                  25                  30

Ala Met Gly Trp Tyr Arg Gln Arg Pro Gly Lys Glu Arg Glu Arg Val
        35                  40                  45

Ala Val Val Asn Ser Asp Ser Ser Thr Ile Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Trp
                85                  90                  95

Ser Pro Gly Phe Gly Ser Tyr Trp Gly Gln Gly Thr Gln Val Thr Val
            100                 105                 110

Ser Ser


<210> SEQ ID NO 87
<211> LENGTH: 121
<212> TYPE: PRT
<213> ORGANISM: Artificial Sequence
<220> FEATURE:
<223> OTHER INFORMATION: hCD221ug-61 VHH

<400> SEQUENCE: 87

Gln Val Gln Leu Val Glu Ser Gly Gly Gly Leu Val Gln Ala Gly Gly
1               5                   10                  15

Ser Leu Arg Leu Ser Cys Ala Ala Ser Met Ser Ser Phe Ser Gln Tyr
            20                  25                  30

Val Met Tyr Trp Tyr Arg Gln Ala Pro Gly Lys Gln Arg Glu Leu Val
        35                  40                  45

Ala Thr Ile Thr Ser Tyr Ser Asn Thr Asn Tyr Ala Asp Ser Val Lys
    50                  55                  60

Gly Arg Phe Thr Ile Ser Arg Asp Asn Ala Lys Ser Ile Ala Tyr Leu
65                  70                  75                  80

Gln Met Asp Ser Leu Lys Pro Glu Asp Thr Ala Val Tyr Tyr Cys Asn
                85                  90                  95

Ala Gln Tyr Gly Ser Thr Phe Ile Arg Asn His Trp Asp Asp Trp Gly
            100                 105                 110
```

```
Gln Gly Thr Gln Val Thr Val Ser Ser
        115                 120


<210> SEQ ID NO 88
<211> LENGTH: 128
<212> TYPE: PRT
<213> ORGANISM: Artificial Sequence
<220> FEATURE:
<223> OTHER INFORMATION: hCD221ug-74 VHH

<400> SEQUENCE: 88

Gln Val Lys Leu Glu Glu Ser Gly Gly Gly Leu Val Gln Ala Gly Gly
1               5                   10                  15

Ser Leu Arg Leu Ser Cys Ala Gly Ser Gly Phe Thr Phe Asp Asp Tyr
            20                  25                  30

Ala Met Gly Trp Phe Arg Gln Ala Pro Gly Lys Glu Arg Glu Val Val
        35                  40                  45

Ser Cys Met Gly Ser Ser Asp Gly Ala Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Val Asp Lys Pro Phe Tyr Asp Gly Gly Tyr Arg Tyr Thr Cys Pro
            100                 105                 110

Val Asp Phe Gly Ser Trp Gly Gln Gly Thr Gln Val Thr Val Ser Ser
        115                 120                 125


<210> SEQ ID NO 89
<211> LENGTH: 115
<212> TYPE: PRT
<213> ORGANISM: Artificial Sequence
<220> FEATURE:
<223> OTHER INFORMATION: hCD221ug-75 VHH

<400> SEQUENCE: 89

Gln Val Lys Leu Glu Glu Ser Gly Gly Gly Leu Val Gln Pro Gly Gly
1               5                   10                  15

Ser Leu Arg Leu Ser Cys Ala Gly Ser Gly Ser Ile Phe Arg Ile Ala
            20                  25                  30

Val Met Asn Trp Tyr Arg Gln Ala Pro Gly Lys Glu Arg Glu Leu Val
        35                  40                  45

Ala Val Ile Thr Ser Gly Gly Asp Thr His Tyr Ala Ala Ser Val Lys
    50                  55                  60

Gly Arg Phe Thr Ile Ser Arg Asp Asn Ala Lys Asn Thr Met Tyr Leu
65                  70                  75                  80

Gln Ile Asn Ser Leu Lys Pro Glu Asp Thr Ala Val Tyr Tyr Cys Asn
                85                  90                  95

Ala Lys Tyr Gly Arg Asp Glu Tyr Trp Gly Gln Gly Ala Gln Val Thr
            100                 105                 110

Val Ser Ser
        115


<210> SEQ ID NO 90
<211> LENGTH: 115
<212> TYPE: PRT
<213> ORGANISM: Artificial Sequence
<220> FEATURE:
<223> OTHER INFORMATION: hCD221ug-77 VHH
```

<400> SEQUENCE: 90

```
Gln Val Lys Leu Glu Glu Ser Gly Gly Gly Leu Val Gln Pro Gly Gly
1               5                   10                  15

Ser Leu Arg Leu Ser Cys Ala Asp Ser Gly Ser Ile Phe Arg Ile Ala
            20                  25                  30

Val Met Asn Trp Tyr Arg Gln Ala Pro Gly Lys Glu Arg Glu Leu Val
        35                  40                  45

Ala Val Ile Thr Ser Gly Gly Glu Thr His Tyr Ala Ala Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Lys Trp Gly Gln Tyr Glu Tyr Trp Gly Gln Gly Thr Gln Val Thr
            100                 105                 110

Val Ser Ser
        115
```

<210> SEQ ID NO 91
<211> LENGTH: 127
<212> TYPE: PRT
<213> ORGANISM: Artificial Sequence
<220> FEATURE:
<223> OTHER INFORMATION: hCD221ug-80 VHH

<400> SEQUENCE: 91

```
Gln Val Gln Leu Val Glu Ser Gly Gly Gly Leu Val Gln Pro Gly Gly
1               5                   10                  15

Ser Leu Arg Leu Ser Cys Thr Phe Ser Gly Phe Thr Leu Asp Tyr Tyr
            20                  25                  30

Val Met Val Trp Phe Arg Gln Ala Pro Gly Lys Glu Arg Glu Ala Val
        35                  40                  45

Ser Cys Ile Thr Ser Asp Gly Val Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Arg Val Lys Pro Glu Asp Thr Ala Val Tyr Tyr Cys Ala
                85                  90                  95

Val Asp Lys Pro Phe Tyr Asp Gly Gly Ile Gln Tyr Thr Cys Pro Val
            100                 105                 110

Asp Phe Asp Ser Trp Gly Gln Gly Ala Gln Val Thr Val Ser Ser
        115                 120                 125
```

<210> SEQ ID NO 92
<211> LENGTH: 115
<212> TYPE: PRT
<213> ORGANISM: Artificial Sequence
<220> FEATURE:
<223> OTHER INFORMATION: hCD221ug-87 VHH

<400> SEQUENCE: 92

```
Gln Val Gln Leu Val Glu Ser Gly Gly Gly Leu Val Gln Pro Gly Gly
1               5                   10                  15

Ser Leu Arg Leu Ser Cys Ala Asp Ser Gly Ser Ile Phe Arg Ile Ala
            20                  25                  30

Val Met Asn Trp Tyr Arg Gln Ala Pro Gly Lys Glu Arg Glu Leu Val
        35                  40                  45
```

```
Ala Val Ile Thr Ser Gly Gly Glu Thr His Tyr Ala Ala Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Lys Trp Gly Arg Asp Glu Tyr Trp Gly Gln Gly Thr Gln Val Thr
            100                 105                 110

Val Ser Ser
        115


<210> SEQ ID NO 93
<211> LENGTH: 115
<212> TYPE: PRT
<213> ORGANISM: Artificial Sequence
<220> FEATURE:
<223> OTHER INFORMATION: hCD221ug-93 VHH

<400> SEQUENCE: 93

Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Thr Phe Ser Ser Ser
            20                  25                  30

Val Met Asn Trp Tyr Arg Gln Ala Pro Gly Lys Gln Arg Glu Leu Val
        35                  40                  45

Ala Val Ile Thr Ser Ser Gly Ser Thr His Tyr Ala Asp Ser Val Lys
    50                  55                  60

Gly Arg Phe Thr Ile Ser Arg Asp Asn Ala Lys Asn Thr Val Asn Leu
65                  70                  75                  80

Gln Met Asn Ser Leu Lys Pro Glu Asp Thr Ala Val Tyr Tyr Cys Asn
                85                  90                  95

Ala Gln Tyr Gly Arg Arg Ser Asp Trp Gly Gln Gly Thr Gln Val Thr
            100                 105                 110

Val Ser Ser
        115


<210> SEQ ID NO 94
<211> LENGTH: 128
<212> TYPE: PRT
<213> ORGANISM: Artificial Sequence
<220> FEATURE:
<223> OTHER INFORMATION: hCD22100ng-2 VHH

<400> SEQUENCE: 94

Gln Val Lys Leu Glu Glu Ser Gly Gly Gly Leu Val Gln Pro Gly Gly
1               5                   10                  15

Ser Leu Arg Leu Ser Cys Thr Val Ser Gly Val Thr Phe Asp Tyr Tyr
            20                  25                  30

Val Met Gly Trp Phe Arg Gln Ala Pro Gly Lys Glu Arg Glu Val Val
        35                  40                  45

Ser Cys Met Arg Asn Ser Asp Gly Val Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Asp Asp Thr Ala Ile Tyr Tyr Cys
                85                  90                  95

Ala Val Asp Lys Pro Phe Tyr Asp Gly Gly Asn Tyr Tyr Thr Cys Pro
            100                 105                 110
```

```
Val Asp Phe Asp Ser Trp Gly Gln Gly Thr Gln Val Thr Val Ser Ser
        115                 120                 125


<210> SEQ ID NO 95
<211> LENGTH: 118
<212> TYPE: PRT
<213> ORGANISM: Artificial Sequence
<220> FEATURE:
<223> OTHER INFORMATION: hCD22100ng-62 VHH

<400> SEQUENCE: 95

Gln Val Lys Leu Glu Glu Ser Gly Gly Gly Leu Val Gln Ala Gly Gly
1               5                   10                  15

Ser Leu Arg Leu Ser Cys Ala Ala Ser Gly Ser Ile Ser Ser Ile Asn
            20                  25                  30

Ala Met Gly Trp Tyr Arg Gln Val Pro Gly Lys Gln Arg Glu Leu Val
        35                  40                  45

Ala Ile Ile Thr Thr Ala Gly Asn Thr Arg Tyr Gly Asp Ser Val Lys
    50                  55                  60

Gly Arg Phe Thr Ile Ser Arg Asp Asn Ala Arg Lys Thr Val Tyr Leu
65                  70                  75                  80

Gln Met Asn Ser Leu Lys Pro Glu Asp Thr Ala Val Tyr Tyr Cys Ala
                85                  90                  95

Gly Lys Leu Tyr Val Asn Lys Glu Tyr Thr Tyr Trp Gly Gln Gly Thr
            100                 105                 110

Gln Val Thr Val Ser Ser
        115


<210> SEQ ID NO 96
<211> LENGTH: 128
<212> TYPE: PRT
<213> ORGANISM: Artificial Sequence
<220> FEATURE:
<223> OTHER INFORMATION: hCD22100ng-66 VHH

<400> SEQUENCE: 96

Gln Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Asp Tyr Tyr
            20                  25                  30

Val Met Gly Trp Phe Arg Gln Ala Pro Gly Lys Glu Arg Glu Val Val
        35                  40                  45

Ser Cys Ile Ser Ser Ser Asp Gly Ala Thr Tyr Tyr Pro Asp Ser Val
    50                  55                  60

Lys Gly Arg Phe Thr Ile Ser Arg Asp Asn Ala Lys Lys Thr Val Tyr
65                  70                  75                  80

Leu Gln Met Asn Ala Leu Lys Pro Glu Asp Thr Ala Ile Tyr Tyr Cys
                85                  90                  95

Ala Val Asp Lys Pro Phe Tyr Asp Gly Gly Ser Tyr Tyr Thr Cys Pro
            100                 105                 110

Val Asp Phe Gly Ser Trp Gly Gln Gly Thr Gln Val Thr Val Ser Ser
        115                 120                 125


<210> SEQ ID NO 97
<211> LENGTH: 128
<212> TYPE: PRT
<213> ORGANISM: Artificial Sequence
<220> FEATURE:
<223> OTHER INFORMATION: hCD22pas-10 VHH
```

<400> SEQUENCE: 97

```
Gln Val Gln Leu Val Glu Ser Gly Gly Gly Leu Val Gln Pro Gly Asp
1               5                   10                  15

Ser Leu Arg Leu Ser Cys Thr Val Ser Gly Phe Thr Ser Asp Tyr Tyr
            20                  25                  30

Ala Met Gly Trp Phe Arg Gln Ala Pro Gly Lys Glu Arg Glu Ala Val
        35                  40                  45

Ser Cys Ile Ser Ser Ser Asp Gly Val Thr Tyr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Glu Met Asn Ser Leu Lys Pro Glu Asp Thr Ala Ile Tyr Tyr Cys
                85                  90                  95

Ala Val Asp Lys Pro Phe Tyr Asp Gly Gly Tyr Leu Tyr Thr Cys Pro
            100                 105                 110

Val Asp Phe Asp Ser Trp Gly Gln Gly Thr Gln Val Thr Val Ser Ser
        115                 120                 125
```

<210> SEQ ID NO 98
<211> LENGTH: 114
<212> TYPE: PRT
<213> ORGANISM: Artificial Sequence
<220> FEATURE:
<223> OTHER INFORMATION: hCD22pas-16 VHH

<400> SEQUENCE: 98

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Leu Lys
            20                  25                  30

Ala Met Ala Trp Tyr Arg Gln Ala Pro Gly Lys Gln Arg Glu Arg Val
        35                  40                  45

Gly Val Ile Asn Ser Asp Gly Ser Tyr Thr Thr Asp Ala Ala Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Thr Met Pro Pro Trp Pro Trp Gly Gln Gly Thr Gln Val Thr Val
            100                 105                 110

Ser Ser
```

<210> SEQ ID NO 99
<211> LENGTH: 116
<212> TYPE: PRT
<213> ORGANISM: Artificial Sequence
<220> FEATURE:
<223> OTHER INFORMATION: hCD22pas-23 VHH

<400> SEQUENCE: 99

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Thr
            20                  25                  30

Ala Val Met Asn Trp Tyr Arg Gln Ala Pro Gly Lys Glu Arg Glu Leu
        35                  40                  45
```

```
Val Ala Val Ile Thr Ser Ala Gly Glu Thr His Tyr Ala Glu Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Asn Ala Lys Trp Gly Gln Tyr Glu His Trp Gly Gln Gly Thr Gln Gly
            100                 105                 110

Thr Val Ser Ser
        115


<210> SEQ ID NO 100
<211> LENGTH: 118
<212> TYPE: PRT
<213> ORGANISM: Artificial Sequence
<220> FEATURE:
<223> OTHER INFORMATION: hCD22pas-24 VHH

<400> SEQUENCE: 100

Gln Val Gln Leu Val Glu Ser Gly Gly Gly Leu Val Gln Ala Gly Gly
1               5                   10                  15

Ser Leu Arg Leu Ser Cys Ser Ala Ser Gly Ile Thr Ser Ser Ile Asn
            20                  25                  30

Ser Met Gly Trp His Arg Gln Ala Pro Gly Lys Gln Arg Glu Leu Val
        35                  40                  45

Ala Ser Ile Gly Arg Gly Gly Ser Gly Ser Thr Lys Tyr Ala Asp Ser
    50                  55                  60

Gly Lys Gly Arg Phe Leu Ile Ser Arg Asp Asn Asn Lys Asn Ile Leu
65                  70                  75                  80

Phe Leu Glu Met Asn Ser Leu Lys Pro Glu Asp Thr Ala Asp Tyr Tyr
                85                  90                  95

Cys Leu Glu Val Thr Thr Asp Leu Ser Ser Tyr Trp Gly Arg Gly Thr
            100                 105                 110

Gln Val Thr Val Ser Ser
        115


<210> SEQ ID NO 101
<211> LENGTH: 121
<212> TYPE: PRT
<213> ORGANISM: Artificial Sequence
<220> FEATURE:
<223> OTHER INFORMATION: hCD22pas-32 VHH

<400> SEQUENCE: 101

Gln Val Gln Leu Val Glu Ser Gly Gly Gly Leu Val Gln Ala Gly Gly
1               5                   10                  15

Ser Leu Arg Leu Ser Cys Ala Val Ser Gly Arg Ile Phe Arg Ser Tyr
            20                  25                  30

Val Leu Gly Trp Phe Arg Gln Ala Pro Gly Lys Glu Arg Glu Leu Val
        35                  40                  45

Ala Arg Ile Gly Trp Ser Asp Thr Tyr Tyr Ala Asp Ser Val Lys Gly
    50                  55                  60

Arg Phe Thr Ile Ser Arg Asp Asn Ala Lys Asn Thr Val Asp Leu Gln
65                  70                  75                  80

Met Asn Ser Leu Lys Pro Glu Asp Thr Ala Val Tyr Tyr Cys Ala Ala
                85                  90                  95

Asn Ser Pro Pro Tyr Gly Pro Gln Arg Asp Glu Phe Gly Tyr Trp Gly
            100                 105                 110
```

```
Gln Gly Thr Gln Val Thr Val Ser Ser
        115                 120


<210> SEQ ID NO 102
<211> LENGTH: 127
<212> TYPE: PRT
<213> ORGANISM: Artificial Sequence
<220> FEATURE:
<223> OTHER INFORMATION: hCD22pas-33 VHH

<400> SEQUENCE: 102

Gln Val Lys Leu Glu Glu Ser Gly Gly Gly Leu Val Gln Pro Gly Gly
1               5                   10                  15

Ser Leu Arg Leu Ser Cys Thr Val Ser Gly Phe Thr Leu Asp Ser Tyr
            20                  25                  30

Val Met Gly Trp Phe Arg Gln Ala Pro Gly Lys Glu Arg Glu Ala Val
        35                  40                  45

Ser Cys Ile Ser Ser Ser Asp Gly Val Thr Tyr Tyr Ala Asp Ser Val
    50                  55                  60

Lys Gly Arg Phe Thr Ile Ser Arg Asp Asn Ala Lys Asn Thr Tyr Leu
65                  70                  75                  80

Gln Met Asn Ser Leu Lys Pro Glu Asp Thr Ala Ile Tyr Tyr Cys Ala
                85                  90                  95

Val Asp Lys Pro Phe Tyr Asp Gly Gly Tyr Leu Tyr Thr Cys Pro Val
            100                 105                 110

Asp Phe Asp Ser Trp Gly Gln Gly Ile Gln Val Thr Val Ser Ser
        115                 120                 125


<210> SEQ ID NO 103
<211> LENGTH: 115
<212> TYPE: PRT
<213> ORGANISM: Artificial Sequence
<220> FEATURE:
<223> OTHER INFORMATION: hCD22pas-48 VHH

<400> SEQUENCE: 103

Gln Val Lys Leu Glu Glu Ser Gly Gly Gly Leu Gly Gln Ala Gly Gly
1               5                   10                  15

Ala Val Arg Leu Ser Cys Ala Asp Ser Gly Ser Ile Phe Arg Ile Ala
            20                  25                  30

Val Met Asn Trp Tyr Arg Gln Ala Pro Gly Lys Glu Arg Glu Leu Val
        35                  40                  45

Ala Val Ile Thr Ile Ala Gly Glu Thr His Tyr Ala Tyr Ser Val Lys
    50                  55                  60

Gly Gln Phe Thr Ile Ser Arg Tyr Asn Ala Lys Asn Thr Met Tyr Leu
65                  70                  75                  80

Gln Met Asn Arg Leu Lys Pro Glu Asp Thr Ala Val Tyr Tyr Cys Tyr
                85                  90                  95

Ala Asn Gly Gly Arg Asp Glu Tyr Trp Gly Arg Gly Thr Gln Val Thr
            100                 105                 110

Val Ser Ser
        115


<210> SEQ ID NO 104
<211> LENGTH: 121
<212> TYPE: PRT
<213> ORGANISM: Artificial Sequence
<220> FEATURE:
<223> OTHER INFORMATION: hCD22pas-55 VHH
```

<400> SEQUENCE: 104

```
Gln Val Lys Leu Glu Glu Ser Gly Gly Gly Leu Gly Gln Ala Gly Gly
1               5                   10                  15

Ser Leu Arg Leu Ser Cys Ala Val Ser Gly Arg Ile Ser Arg Ser Tyr
            20                  25                  30

Val Leu Gly Trp Phe Arg Gln Ala Pro Gly Lys Glu Arg Glu Leu Val
        35                  40                  45

Ala Arg Ile Gly Cys Ser Asp Thr Tyr Tyr Ala Asp Ser Ala Lys Gly
    50                  55                  60

Arg Phe Thr Ile Ser Arg Asn Asn Ala Asp Asn Thr Val Asp Leu Gln
65                  70                  75                  80

Met Asn Ser Leu Lys Pro Glu Asp Thr Ala Val Tyr Tyr Cys Ala Glu
                85                  90                  95

Tyr Ser Pro Pro Tyr Gly Pro Gln Arg Asp Glu Phe Asp Tyr Trp Gly
            100                 105                 110

Gln Gly Thr Gln Val Thr Val Ser Ser
        115                 120
```

<210> SEQ ID NO 105
<211> LENGTH: 118
<212> TYPE: PRT
<213> ORGANISM: Artificial Sequence
<220> FEATURE:
<223> OTHER INFORMATION: hCD22pas-64 VHH

<400> SEQUENCE: 105

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Leu Asn
            20                  25                  30

Thr Met Ala Trp Tyr Arg Gln Ala Pro Gly Asn Gln Arg Glu Tyr Val
        35                  40                  45

Ala Ala Ala Ser Ser Asp Gly Tyr Thr Asn Tyr Ala Asp Ser Val Arg
    50                  55                  60

Gly Arg Phe Thr Ile Ser Arg Asp Asn Asp Lys Asn Thr Met Tyr Leu
65                  70                  75                  80

Gln Met Asn Ser Leu Arg Pro Glu Asp Thr Ala Val Tyr Tyr Cys Thr
                85                  90                  95

Trp Gly Thr Gly Arg Phe Ala Asp Tyr Ile Tyr Trp Gly Gln Gly Thr
            100                 105                 110

Gln Val Thr Val Ser Ser
        115
```

<210> SEQ ID NO 106
<211> LENGTH: 126
<212> TYPE: PRT
<213> ORGANISM: Artificial Sequence
<220> FEATURE:
<223> OTHER INFORMATION: hCD22pas-72 VHH

<400> SEQUENCE: 106

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Val Tyr
            20                  25                  30

Thr Met Ala Trp Phe Arg Gln Ala Pro Gly Lys Glu Arg Glu Phe Val
        35                  40                  45
```

```
Ala Ala Ile Arg Gly Ser Gly Gly Thr Tyr Tyr Arg Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Arg Ile Arg Arg Thr Leu Val Glu Pro Leu Thr Lys Glu Thr Leu
            100                 105                 110

Tyr Asp Tyr Trp Gly Gln Gly Thr Gln Val Thr Val Ser Ser
        115                 120                 125


<210> SEQ ID NO 107
<211> LENGTH: 127
<212> TYPE: PRT
<213> ORGANISM: Artificial Sequence
<220> FEATURE:
<223> OTHER INFORMATION: hCD22pas-79 VHH

<400> SEQUENCE: 107

Gln Val Lys Leu Glu Glu Ser Gly Gly Gly Leu Val Gln Pro Gly Gly
1               5                   10                  15

Ser Leu Arg Leu Ser Cys Thr Val Ser Gly Arg Thr Ser Ser Val Tyr
            20                  25                  30

Gly Met Ala Trp Phe Arg Gln Thr Pro Gly Lys Glu Arg Glu Phe Val
        35                  40                  45

Ala Ala Met Ser Trp Ser Gly Gly Pro Thr Tyr Phe Ala Asp Ser Val
    50                  55                  60

Lys Gly Arg Phe Gly Ser Ser Arg Asp Asn Ala Lys Asn Thr Val Tyr
65                  70                  75                  80

Leu Gln Met Asn Gly Leu Arg Pro Glu Asp Thr Ala Val Tyr Tyr Cys
                85                  90                  95

Ala Val Arg Ile Arg Arg Thr Leu Leu Glu Pro Leu Thr Lys Glu Thr
            100                 105                 110

Leu Tyr Asp Tyr Trp Gly Gln Gly Thr Gln Val Thr Val Ser Ser
        115                 120                 125


<210> SEQ ID NO 108
<211> LENGTH: 115
<212> TYPE: PRT
<213> ORGANISM: Artificial Sequence
<220> FEATURE:
<223> OTHER INFORMATION: hCD22pas-82 VHH

<400> SEQUENCE: 108

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Thr
            20                  25                  30

Val Met Asn Trp His Arg Gln Ala Pro Gly Lys Glu Arg Glu Leu Ser
        35                  40                  45

Gly Val Ile Thr Ser Gly Gly Asp Ser His Tyr Ala Ala Ser Val Lys
    50                  55                  60

Gly Arg Phe Thr Ile Tyr Arg Asp Asn Thr Lys Asn Thr Met Tyr Leu
65                  70                  75                  80

Gln Met Asn Arg Leu Lys Pro Glu Asp Thr Asp Tyr Tyr Tyr Cys Asn
                85                  90                  95

Ala Lys Trp Gly Gly Asp Glu Tyr Trp Gly Gln Gly Thr His Asp Thr
```

```
        100                 105                 110

Gly Ser Ser
        115


<210> SEQ ID NO 109
<211> LENGTH: 1675
<212> TYPE: DNA
<213> ORGANISM: Artificial Sequence
<220> FEATURE:
<223> OTHER INFORMATION: CAR Construct
<220> FEATURE:
<221> NAME/KEY: misc_feature
<222> LOCATION: (62)..(63)
<223> OTHER INFORMATION: VHH sdAb inserted between these positions

<400> SEQUENCE: 109

atgctcaggc tgctcttggc tctcaactta ttcccttcaa ttcaagtaac aggagggtct      60

tcgaagactt cctttgcgag acgacggtgg cgggggatca ggtggtggag gtagcggggg     120

agggggctca ggcggtacaa ctacgcctgc acctcgccca ccgaccccag caccaaccat     180

cgcttcacag cctttgagcc tgcgaccaga ggcatgtcgc cctgctgcgg gcggtgccgt     240

tcatactcgc ggacttgatt ttgcgtgtga cgtcgtctcg ccttctaagc ccttttgggt     300

gctggtggtg gttggtggag tcctggcttg ctatagcttg ctagtaacag tggcctttat     360

tattttctgg gtgaggaaac ggggcagaaa gaaactcctg tatatattca aacaaccatt     420

tatgcgacca gtacaaacta ctcaagagga agatggctgt agctgccgat ttccagaaga     480

agaagaagga ggatgtgaac tgctgagagt gaagttcagc aggagcgcag acgcccccgc     540

gtaccagcag ggccagaacc agctctataa cgagctcaat ctaggacgaa gagaggagta     600

cgatgttttg gacaagcgac gtggccggga ccctgagatg gggggaaagc cgcagagaag     660

gaagaaccct caggaaggcc tgtacaatga actgcagaaa gataagatgg cggaggccta     720

cagtgagatt gggatgaaag gcgagcgccg gaggggcaag gggcacgatg gcctttacca     780

gggactcagt acagccacca aggacaccta cgacgccctt cacatgcagg ccctgccccc     840

tcgcgctagc gccacgaact tctctctgtt aaagcaagca ggcgacgtgg aagaaaaccc     900

cggtcccatg gtgagcaagg gcgaggagga caacatggcc agcctgcccg ccacccacga     960

gctgcacatc ttcggcagca tcaacggcgt ggacttcgac atggtgggcc agggcaccgg    1020

caaccccaac gacggctacg aggagctgaa cctgaagagc accaagggcg acctgcagtt    1080

cagcccctgg attctggtgc cccacatcgg ctacggcttc caccagtacc tgccctaccc    1140

cgacggcatg agccccttcc aggccgccat ggtggacggc agcggctacc aggtgcacag    1200

gaccatgcag ttcgaggacg gcgccagcct gaccgtgaac tacaggtaca cctacgaggg    1260

cagccacatc aagggcgagg cccaggtgaa gggcaccggc ttccccgccg acggccccgt    1320

gatgaccaac agcctgaccg ccgccgactg gtgcaggagc aaaaagacct accccaacga    1380

caagaccatc atcagcacct tcaagtggag ctacaccacc ggcaacggca agaggtacag    1440

gagcaccgcc aggaccacct acaccttcgc caagcccatg gccgccaact acctgaagaa    1500

ccagcccatg tacgtgttca gaaagaccga gctgaagcac agcaagaccg agctgaactt    1560

caaggagtgg cagaaggcct tcaccgacgt gatgggcatg gacgagctgt acaagcccaa    1620

gaagaagagg aaggtggagg acccccccgc cgccaagagg gtgaagctgg actaa         1675


<210> SEQ ID NO 110
<211> LENGTH: 18
<212> TYPE: PRT
```

```
<213> ORGANISM: Artificial Sequence
<220> FEATURE:
<223> OTHER INFORMATION: Human CD28 Signal Peptide

<400> SEQUENCE: 110

Met Leu Arg Leu Leu Leu Ala Leu Asn Leu Phe Pro Ser Ile Gln Val
1               5                   10                  15

Thr Gly


<210> SEQ ID NO 111
<211> LENGTH: 17
<212> TYPE: PRT
<213> ORGANISM: Artificial Sequence
<220> FEATURE:
<223> OTHER INFORMATION: Synthetic Flexible Linker

<400> SEQUENCE: 111

Gly Gly Gly Gly Ser Gly Gly Gly Gly Ser Gly Gly Gly Gly Ser Gly
1               5                   10                  15

Gly


<210> SEQ ID NO 112
<211> LENGTH: 45
<212> TYPE: PRT
<213> ORGANISM: Artificial Sequence
<220> FEATURE:
<223> OTHER INFORMATION: Human CD8 Hinge Domain

<400> SEQUENCE: 112

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 113
<211> LENGTH: 32
<212> TYPE: PRT
<213> ORGANISM: Artificial Sequence
<220> FEATURE:
<223> OTHER INFORMATION: Human CD28 Transmembrane Domain

<400> SEQUENCE: 113

Pro Ser Lys Pro Phe Trp Val Leu Val Val Val Gly Gly Val Leu Ala
1               5                   10                  15

Cys Tyr Ser Leu Leu Val Thr Val Ala Phe Ile Ile Phe Trp Val Arg
            20                  25                  30


<210> SEQ ID NO 114
<211> LENGTH: 42
<212> TYPE: PRT
<213> ORGANISM: Artificial Sequence
<220> FEATURE:
<223> OTHER INFORMATION: Human 4-1BB Co-stimulatory Domain

<400> SEQUENCE: 114

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

```
<210> SEQ ID NO 115
<211> LENGTH: 114
<212> TYPE: PRT
<213> ORGANISM: Artificial Sequence
<220> FEATURE:
<223> OTHER INFORMATION: Human CD3zeta Signaling Domain

<400> SEQUENCE: 115

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Gln Arg Arg Lys Asn Pro Gln Glu Gly Leu Tyr Asn Glu Leu
    50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg


<210> SEQ ID NO 116
<211> LENGTH: 236
<212> TYPE: PRT
<213> ORGANISM: Artificial Sequence
<220> FEATURE:
<223> OTHER INFORMATION: M971 scFV

<400> SEQUENCE: 116

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
        115                 120                 125

Ser Asp Ile Gln Met Thr Gln Ser Pro Ser Ser Leu Ser Ala Ser Val
    130                 135                 140

Gly Asp Arg Val Thr Ile Thr Cys Arg Ala Ser Gln Thr Ile Trp Ser
145                 150                 155                 160

Tyr Leu Asn Trp Tyr Gln Gln Arg Pro Gly Lys Ala Pro Asn Leu Leu
                165                 170                 175

Ile Tyr Ala Ala Ser Ser Leu Gln Ser Gly Val Pro Ser Arg Phe Ser
            180                 185                 190
```

```
Gly Arg Gly Ser Gly Thr Asp Phe Thr Leu Thr Ile Ser Ser Leu Gln
        195                 200                 205

Ala Glu Asp Phe Ala Thr Tyr Tyr Cys Gln Gln Ser Tyr Ser Ile Pro
    210                 215                 220

Gln Thr Phe Gly Gln Gly Thr Lys Leu Glu Ile Lys
225                 230                 235


<210> SEQ ID NO 117
<211> LENGTH: 267
<212> TYPE: PRT
<213> ORGANISM: Artificial Sequence
<220> FEATURE:
<223> OTHER INFORMATION: FMC63 scFV

<400> SEQUENCE: 117

Asp Tyr Lys Asp His Asp Gly Asp Tyr Lys Asp His Asp Ile Asp Tyr
1               5                   10                  15

Lys Asp Asp Asp Asp Lys Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
            260                 265


<210> SEQ ID NO 118
<211> LENGTH: 5
<212> TYPE: PRT
<213> ORGANISM: Artificial Sequence
<220> FEATURE:
<223> OTHER INFORMATION: Short Flexible Linker
```

<400> SEQUENCE: 118

```
Gly Gly Gly Gly Ser
1               5
```

<210> SEQ ID NO 119
<211> LENGTH: 858
<212> TYPE: DNA
<213> ORGANISM: Artificial Sequence
<220> FEATURE:
<223> OTHER INFORMATION: BiTE Construct
<220> FEATURE:
<221> NAME/KEY: misc_feature
<222> LOCATION: (72)..(73)
<223> OTHER INFORMATION: VHH sdAb inserted between these positions

<400> SEQUENCE: 119

```
atggagtttg ggctgagctg ggttttcctc gttgctcttt ttagaggtgt ccagtgtaca      60
ggagggtctt cggaagactt ccttggagga ggcggaagtc aagtgcagtt gcaacaacca     120
ggtgccgagc ttgggaaacc gggtaccagc gttaaactct cttgcaaagc atccggttat     180
acctttactt cttactggat ccattgggtc aaacaacgcc caggccaggg tctcgaatgg     240
gtgggcaaca tcaacccaaa cagcggctct atcaattata acgaaaagtt taagaataaa     300
gcaactctca cggtggataa gagcagctca accgcttata tgcaattgag tactttgacc     360
agtgaagatt tcgctgtgta ttattgcacg cgcgatacat ccggacagta ttatttcgat     420
tattggggcc aggggacaac cctgacagtg tctagcggcg gtggtgggtc aggcggcggt     480
gggagcggag gaggtggaag cgatatcgta atgagtcaat cccctagcag cttggcggta     540
agtgctgggg aacgcgttac aatgtcctgt aagagctctc aatctttgct gaattccagg     600
actaggaaga attatctggc ctggtatcaa caaaagcccg gacaaagtcc aaagctcctg     660
atttattggg ctagcaccag agagtcagga gtaccagacc ggtttactgg aagcgggtca     720
ggaaccgact ttaccctgac aatatccagc gtccaagcag aagatcttgc cgtgtactat     780
tgtattcagt cctaccactt gcgcactttt ggggggggaa caaaactcga gataaagcac     840
caccaccacc accactag                                                   858
```

<210> SEQ ID NO 120
<211> LENGTH: 114
<212> TYPE: PRT
<213> ORGANISM: Artificial Sequence
<220> FEATURE:
<223> OTHER INFORMATION: hCD221ug-36 Cloned Segment

<400> SEQUENCE: 120

```
Gln Val Gln Leu Val Glu Ser Gly Gly Gly Leu Val Gln Ala Gly Gly
1               5                   10                  15

Ser Leu Arg Val Ser Cys Glu Ala Ser Gly Ile Thr Phe Ser Arg Ala
            20                  25                  30

Ala Met Gly Trp Tyr Arg Gln Arg Pro Gly Lys Glu Arg Glu Arg Val
        35                  40                  45

Ala Val Val Asn Ser Asp Ser Ser Thr Ile Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Glu Pro Glu Asp Thr Ala Val Tyr Tyr Cys Trp
                85                  90                  95

Ser Pro Gly Phe Gly Ser Tyr Trp Gly Gln Gly Thr Gln Val Thr Val
            100                 105                 110
```

Ser Ser

<210> SEQ ID NO 121
<211> LENGTH: 121
<212> TYPE: PRT
<213> ORGANISM: Artificial Sequence
<220> FEATURE:
<223> OTHER INFORMATION: hCD221ug-93 Cloned Segment

<400> SEQUENCE: 121

```
Gln Val Gln Leu Val Glu Ser Gly Gly Gly Leu Val Gln Ala Gly Gly
1               5                   10                  15

Ser Leu Arg Leu Ser Cys Ala Ala Ser Met Ser Ser Phe Ser Gln Tyr
            20                  25                  30

Val Met Tyr Trp Tyr Arg Gln Ala Pro Gly Arg Gln Arg Glu Leu Val
        35                  40                  45

Ala Thr Ile Thr Ser Ala Ser Ser Thr Ser Tyr Ala Asp Ser Val Lys
    50                  55                  60

Gly Arg Phe Thr Ile Ser Arg Asp Asn Ala Lys Ser Ile Val Tyr Leu
65                  70                  75                  80

Gln Met Asn Ser Leu Lys Pro Glu Asp Thr Ala Val Tyr Tyr Cys Asn
                85                  90                  95

Ala Gln Tyr Gly Ser Thr Phe Ile Arg Lys Pro Tyr Asp Thr Trp Gly
            100                 105                 110

Gln Gly Thr Gln Val Thr Val Ser Ser
        115                 120
```

<210> SEQ ID NO 122
<211> LENGTH: 110
<212> TYPE: PRT
<213> ORGANISM: Artificial Sequence
<220> FEATURE:
<223> OTHER INFORMATION: hCD221ug-10 Cloned Segment

<400> SEQUENCE: 122

```
Gln Val Gln Leu Val Glu Ser Gly Gly Gly Leu Val Gln Ala Gly Gly
1               5                   10                  15

Ser Leu Ser Val Ser Cys Thr Ala Ser Glu Ser Thr Phe Ser Ile Met
            20                  25                  30

Met Gly Trp Phe Arg Gln Ala Pro Gly Lys Gln Arg Glu Met Val Ala
        35                  40                  45

Val Ile Asn Ser Ala Gly Ser Thr Asn Tyr Ala Asp Ser Ala Glu Gly
    50                  55                  60

Arg Phe Thr Ile Ser Arg Asp Leu Ala Lys Lys Thr Val Ser Leu Gln
65                  70                  75                  80

Met Asn Ser Leu Lys Pro Glu Asp Thr Ala Val Tyr Tyr Cys Tyr Val
                85                  90                  95

Asp Gly Tyr Phe Gly Gln Gly Thr Gln Val Thr Val Ser Ser
            100                 105                 110
```

<210> SEQ ID NO 123
<211> LENGTH: 121
<212> TYPE: PRT
<213> ORGANISM: Artificial Sequence
<220> FEATURE:
<223> OTHER INFORMATION: hCD221ug-61 Cloned Segment

<400> SEQUENCE: 123

```
Gln Val Gln Leu Val Glu Ser Gly Gly Gly Leu Val Gln Ala Gly Gly
```

-continued

```
1               5                   10                  15

Ser Leu Arg Leu Ser Cys Ala Ala Ser Met Ser Ser Phe Ser Gln Tyr
            20                  25                  30

Val Met Tyr Trp Tyr Arg Gln Ala Pro Gly Lys Gln Arg Glu Leu Val
        35                  40                  45

Ala Thr Ile Thr Ser Tyr Ser Asn Thr Asn Tyr Ala Asp Ser Val Lys
    50                  55                  60

Gly Arg Phe Thr Ile Ser Arg Asp Asn Ala Lys Ser Ile Ala Tyr Leu
65                  70                  75                  80

Gln Met Asp Ser Leu Lys Pro Glu Asp Thr Ala Val Tyr Tyr Cys Asn
                85                  90                  95

Ala Gln Tyr Gly Ser Thr Phe Ile Arg Asn His Trp Asp Asp Trp Gly
            100                 105                 110

Gln Gly Thr Gln Val Thr Val Ser Ser
        115                 120


<210> SEQ ID NO 124
<211> LENGTH: 114
<212> TYPE: PRT
<213> ORGANISM: Artificial Sequence
<220> FEATURE:
<223> OTHER INFORMATION: hCD22pas-16 Cloned Segment

<400> SEQUENCE: 124

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ser Leu Lys
            20                  25                  30

Ala Met Ala Trp Tyr Arg Gln Ala Pro Gly Lys Gln Arg Glu Arg Val
        35                  40                  45

Gly Val Ile Asn Ser Asp Gly Ser Tyr Thr Thr Asp Ala Ala Ser Val
    50                  55                  60

Gln Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Thr Met Pro Pro Trp Pro Trp Gly Gln Gly Thr Gln Val Thr Val
            100                 105                 110

Ser Ser


<210> SEQ ID NO 125
<211> LENGTH: 127
<212> TYPE: PRT
<213> ORGANISM: Artificial Sequence
<220> FEATURE:
<223> OTHER INFORMATION: hCD221ug80

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Thr Phe Ser Gly Phe Thr Leu Asp Tyr Tyr
            20                  25                  30

Val Met Gly Trp Phe Arg Gln Ala Pro Gly Lys Glu Arg Glu Ala Val
        35                  40                  45

Ser Cys Ile Thr Ser Asp Gly Val Thr Tyr Tyr Ala Asp Ser Val Lys
    50                  55                  60

Gly Arg Phe Thr Ile Ser Arg Asp Asn Ala Lys Asn Thr Val Tyr Leu
```

```
65                  70                  75                  80

Gln Met Asn Arg Val Lys Pro Glu Asp Thr Ala Val Tyr Tyr Cys Ala
                85                  90                  95

Val Asp Lys Pro Phe Tyr Asp Gly Gly Ile Gln Tyr Thr Cys Pro Val
            100                 105                 110

Asp Phe Asp Ser Trp Gly Gln Gly Thr Gln Val Thr Val Ser Ser
        115                 120                 125


<210> SEQ ID NO 126
<211> LENGTH: 8
<212> TYPE: PRT
<213> ORGANISM: Artificial Sequence
<220> FEATURE:
<223> OTHER INFORMATION: Group 1 CDR1 Consensus
<220> FEATURE:
<221> NAME/KEY: SITE
<222> LOCATION: (2)..(2)
<223> OTHER INFORMATION: Xaa is F or V
<220> FEATURE:
<221> NAME/KEY: SITE
<222> LOCATION: (3)..(3)
<223> OTHER INFORMATION: Xaa is T or S
<220> FEATURE:
<221> NAME/KEY: SITE
<222> LOCATION: (4)..(4)
<223> OTHER INFORMATION: Xaa is L, F, or S
<220> FEATURE:
<221> NAME/KEY: SITE
<222> LOCATION: (6)..(6)
<223> OTHER INFORMATION: Xaa is Y, D, or S
<220> FEATURE:
<221> NAME/KEY: SITE
<222> LOCATION: (8)..(8)
<223> OTHER INFORMATION: Xaa is V or A

<400> SEQUENCE: 126

Gly Xaa Xaa Xaa Asp Xaa Tyr Xaa
1               5


<210> SEQ ID NO 127
<211> LENGTH: 8
<212> TYPE: PRT
<213> ORGANISM: Artificial Sequence
<220> FEATURE:
<223> OTHER INFORMATION: Group 1 CDR2 Consensus
<220> FEATURE:
<221> NAME/KEY: SITE
<222> LOCATION: (1)..(1)
<223> OTHER INFORMATION: Xaa is I or M
<220> FEATURE:
<221> NAME/KEY: SITE
<222> LOCATION: (2)..(2)
<223> OTHER INFORMATION: Xaa is T, R, or G
<220> FEATURE:
<221> NAME/KEY: SITE
<222> LOCATION: (3)..(3)
<223> OTHER INFORMATION: Xaa is S or N
<220> FEATURE:
<221> NAME/KEY: SITE
<222> LOCATION: (4)..(4)
<223> OTHER INFORMATION: Xaa is D or S
<220> FEATURE:
<221> NAME/KEY: SITE
<222> LOCATION: (5)..(5)
<223> OTHER INFORMATION: Xaa is D or is absent
<220> FEATURE:
<221> NAME/KEY: SITE
<222> LOCATION: (7)..(7)
<223> OTHER INFORMATION: Xaa is V or A

<400> SEQUENCE: 127

Xaa Xaa Xaa Xaa Xaa Gly Xaa Thr
```

1 5

<210> SEQ ID NO 128
<211> LENGTH: 21
<212> TYPE: PRT
<213> ORGANISM: Artificial Sequence
<220> FEATURE:
<223> OTHER INFORMATION: Group 1 CDR3 Consensus
<220> FEATURE:
<221> NAME/KEY: SITE
<222> LOCATION: (11)..(11)
<223> OTHER INFORMATION: Xaa is I, N, Y, or S
<220> FEATURE:
<221> NAME/KEY: SITE
<222> LOCATION: (12)..(12)
<223> OTHER INFORMATION: Xaa is Q, Y, R, or L
<220> FEATURE:
<221> NAME/KEY: SITE
<222> LOCATION: (20)..(20)
<223> OTHER INFORMATION: Xaa is D or G

<400> SEQUENCE: 128

Ala Val Asp Lys Pro Phe Tyr Asp Gly Gly Xaa Xaa Tyr Thr Cys Pro
1 5 10 15

Val Asp Phe Xaa Ser
20

<210> SEQ ID NO 129
<211> LENGTH: 9
<212> TYPE: PRT
<213> ORGANISM: Artificial Sequence
<220> FEATURE:
<223> OTHER INFORMATION: Group 2 CDR1 Consensus
<220> FEATURE:
<221> NAME/KEY: SITE
<222> LOCATION: (3)..(3)
<223> OTHER INFORMATION: Xaa is I or T
<220> FEATURE:
<221> NAME/KEY: SITE
<222> LOCATION: (5)..(5)
<223> OTHER INFORMATION: Xaa is R or is absent
<220> FEATURE:
<221> NAME/KEY: SITE
<222> LOCATION: (6)..(6)
<223> OTHER INFORMATION: Xaa is R, S, or I
<220> FEATURE:
<221> NAME/KEY: SITE
<222> LOCATION: (7)..(7)
<223> OTHER INFORMATION: Xaa is I, S, or T
<220> FEATURE:
<221> NAME/KEY: SITE
<222> LOCATION: (8)..(8)
<223> OTHER INFORMATION: Xaa is A, S, or T

<400> SEQUENCE: 129

Gly Ser Xaa Phe Xaa Xaa Xaa Xaa Val
1 5

<210> SEQ ID NO 130
<211> LENGTH: 7
<212> TYPE: PRT
<213> ORGANISM: Artificial Sequence
<220> FEATURE:
<223> OTHER INFORMATION: Group 2 CDR2 Consensus
<220> FEATURE:
<221> NAME/KEY: SITE
<222> LOCATION: (4)..(4)
<223> OTHER INFORMATION: Xaa is G, S, or A
<220> FEATURE:
<221> NAME/KEY: SITE
<222> LOCATION: (6)..(6)
<223> OTHER INFORMATION: Xaa is E, D, or S
<220> FEATURE:

<221> NAME/KEY: SITE
<222> LOCATION: (7)..(7)
<223> OTHER INFORMATION: Xaa is T or S

<400> SEQUENCE: 130

Ile Thr Ser Xaa Gly Xaa Xaa
1               5

<210> SEQ ID NO 131
<211> LENGTH: 9
<212> TYPE: PRT
<213> ORGANISM: Artificial Sequence
<220> FEATURE:
<223> OTHER INFORMATION: Group 2 CDR3 Consensus
<220> FEATURE:
<221> NAME/KEY: SITE
<222> LOCATION: (3)..(3)
<223> OTHER INFORMATION: Xaa is K or Q
<220> FEATURE:
<221> NAME/KEY: SITE
<222> LOCATION: (4)..(4)
<223> OTHER INFORMATION: Xaa is W or Y
<220> FEATURE:
<221> NAME/KEY: SITE
<222> LOCATION: (6)..(6)
<223> OTHER INFORMATION: Xaa is Q, R, or G
<220> FEATURE:
<221> NAME/KEY: SITE
<222> LOCATION: (7)..(7)
<223> OTHER INFORMATION: Xaa is Y, D, or R
<220> FEATURE:
<221> NAME/KEY: SITE
<222> LOCATION: (8)..(8)
<223> OTHER INFORMATION: Xaa is E or S
<220> FEATURE:
<221> NAME/KEY: SITE
<222> LOCATION: (9)..(9)
<223> OTHER INFORMATION: Xaa is Y, D, or H

<400> SEQUENCE: 131

Asn Ala Xaa Xaa Gly Xaa Xaa Xaa Xaa
1               5

<210> SEQ ID NO 132
<211> LENGTH: 8
<212> TYPE: PRT
<213> ORGANISM: Artificial Sequence
<220> FEATURE:
<223> OTHER INFORMATION: Group 3 CDR1 Consensus
<220> FEATURE:
<221> NAME/KEY: SITE
<222> LOCATION: (4)..(4)
<223> OTHER INFORMATION: Xaa is F or S

<400> SEQUENCE: 132

Gly Arg Ile Xaa Arg Ser Tyr Val
1               5

<210> SEQ ID NO 133
<211> LENGTH: 6
<212> TYPE: PRT
<213> ORGANISM: Artificial Sequence
<220> FEATURE:
<223> OTHER INFORMATION: Group 3 CDR2 Consensus
<220> FEATURE:
<221> NAME/KEY: SITE
<222> LOCATION: (3)..(3)
<223> OTHER INFORMATION: Xaa is W or C

<400> SEQUENCE: 133

Ile Gly Xaa Ser Asp Thr
1               5

<210> SEQ ID NO 134
<211> LENGTH: 16
<212> TYPE: PRT
<213> ORGANISM: Artificial Sequence
<220> FEATURE:
<223> OTHER INFORMATION: Group 3 CDR3 Consensus
<220> FEATURE:
<221> NAME/KEY: SITE
<222> LOCATION: (2)..(2)
<223> OTHER INFORMATION: Xaa is A or E
<220> FEATURE:
<221> NAME/KEY: SITE
<222> LOCATION: (3)..(3)
<223> OTHER INFORMATION: Xaa is N or Y
<220> FEATURE:
<221> NAME/KEY: SITE
<222> LOCATION: (15)..(15)
<223> OTHER INFORMATION: Xaa is G or D

<400> SEQUENCE: 134

```
Ala Xaa Xaa Ser Pro Pro Tyr Gly Pro Gln Arg Asp Glu Phe Xaa Tyr
1               5                   10                  15
```

<210> SEQ ID NO 135
<211> LENGTH: 8
<212> TYPE: PRT
<213> ORGANISM: Artificial Sequence
<220> FEATURE:
<223> OTHER INFORMATION: Group 4 CDR1 Consensus
<220> FEATURE:
<221> NAME/KEY: SITE
<222> LOCATION: (2)..(2)
<223> OTHER INFORMATION: Xaa is R or G
<220> FEATURE:
<221> NAME/KEY: SITE
<222> LOCATION: (4)..(4)
<223> OTHER INFORMATION: Xaa is S or F
<220> FEATURE:
<221> NAME/KEY: SITE
<222> LOCATION: (8)..(8)
<223> OTHER INFORMATION: Xaa is G or T

<400> SEQUENCE: 135

```
Gly Xaa Thr Xaa Ser Val Tyr Xaa
1               5
```

<210> SEQ ID NO 136
<211> LENGTH: 8
<212> TYPE: PRT
<213> ORGANISM: Artificial Sequence
<220> FEATURE:
<223> OTHER INFORMATION: Group 4 CDR2 Consensus
<220> FEATURE:
<221> NAME/KEY: SITE
<222> LOCATION: (1)..(1)
<223> OTHER INFORMATION: Xaa is M or I
<220> FEATURE:
<221> NAME/KEY: SITE
<222> LOCATION: (2)..(2)
<223> OTHER INFORMATION: Xaa is S or R
<220> FEATURE:
<221> NAME/KEY: SITE
<222> LOCATION: (3)..(3)
<223> OTHER INFORMATION: Xaa is W or G
<220> FEATURE:
<221> NAME/KEY: SITE
<222> LOCATION: (5)..(5)
<223> OTHER INFORMATION: Xaa is G or is absent
<220> FEATURE:
<221> NAME/KEY: SITE
<222> LOCATION: (7)..(7)
<223> OTHER INFORMATION: Xaa is P or G

<400> SEQUENCE: 136

Xaa Xaa Xaa Ser Xaa Gly Xaa Thr
1 5

<210> SEQ ID NO 137
<211> LENGTH: 20
<212> TYPE: PRT
<213> ORGANISM: Artificial Sequence
<220> FEATURE:
<223> OTHER INFORMATION: Group 4 CDR3 Consensus
<220> FEATURE:
<221> NAME/KEY: SITE
<222> LOCATION: (9)..(9)
<223> OTHER INFORMATION: Xaa is L or V

<400> SEQUENCE: 137

Ala Val Arg Ile Arg Arg Thr Leu Xaa Glu Pro Leu Thr Lys Glu Thr
1 5 10 15

Leu Tyr Asp Tyr
20

<210> SEQ ID NO 138
<211> LENGTH: 1170
<212> TYPE: DNA
<213> ORGANISM: Artificial Sequence
<220> FEATURE:
<223> OTHER INFORMATION: hCD221ug36 Example CAR

<400> SEQUENCE: 138
atgctcaggc tgctcttggc tctcaactta ttcccttcaa ttcaagtaac aggacaggta 60
cagctggtgg agtctggggg aggcttggtg caggctgggg ggtctctgag agtctcctgt 120
gaagcctctg gaatcacgtt cagtcgcgcg gccatgggct ggtaccgcca gcgtccaggc 180
aaggagcgcg aacgagtcgc agttgttaat agtgatagca gtacaatata tgcagactcc 240
gtgaagggcc ggttcaccat ctccagagac aatgccaaga acacagtgta tctgcaaatg 300
aacagcctgg aacctgagga cacggccgtc tattactgtt ggtccccagg gttcgggtcc 360
tactggggcc aggggaccca ggtcaccgtt tcctcacctt tgcgagacga cggtggcggg 420
ggatcaggtg gtggaggtag cgggggaggg ggctcaggcg gtacaactac gcctgcacct 480
cgcccaccga ccccagcacc aaccatcgct tcacagcctt tgagcctgcg accagaggca 540
tgtcgccctg ctgcgggcgg tgccgttcat actcgcggac ttgattttgc gtgtgacgtc 600
gtctcgcctt ctaagccctt ttgggtgctg gtggtggttg gtggagtcct ggcttgctat 660
agcttgctag taacagtggc ctttattatt ttctgggtga ggaaacgggg cagaaagaaa 720
ctcctgtata tattcaaaca accatttatg cgaccagtac aaactactca agaggaagat 780
ggctgtagct gccgatttcc agaagaagaa gaaggaggat gtgaactgct gagagtgaag 840
ttcagcagga gcgcagacgc ccccgcgtac cagcagggcc agaaccagct ctataacgag 900
ctcaatctag gacgaagaga ggagtacgat gttttggaca agcgacgtgg ccgggaccct 960
gagatggggg gaaagccgca gagaaggaag aaccctcagg aaggcctgta caatgaactg 1020
cagaaagata agatggcgga ggcctacagt gagattggga tgaaaggcga gcgccggagg 1080
ggcaaggggc acgatggcct ttaccaggga ctcagtacag ccaccaagga cacctacgac 1140
gcccttcaca tgcaggccct gccccctcgc 1170

<210> SEQ ID NO 139
<211> LENGTH: 699
<212> TYPE: DNA

```
<213> ORGANISM: Artificial Sequence
<220> FEATURE:
<223> OTHER INFORMATION: hCD221ug36 Example BiTE

<400> SEQUENCE: 139

atggagtttg ggctgagctg ggttttcctc gttgctcttt ttagaggtgt ccagtgtaca     60

ggacaggtac agctggtgga gtctggggga ggcttggtgc aggctggggg gtctctgaga    120

gtctcctgtg aagcctctgg aatcacgttc agtcgcgcgg ccatgggctg gtaccgccag    180

cgtccaggca aggagcgcga acgagtcgca gttgttaata gtgatagcag tacaatatat    240

gcagactccg tgaagggccg gttcaccatc tccagagaca atgccaagaa cacagtgtat    300

ctgcaaatga acagcctgga acctgaggac acggccgtct attactgttg gtccccaggg    360

ttcgggtcct actggggcca ggggacccag gtcaccgttt cctcaccttt gcgagacgac    420

ggtggcgggg gatcaggtgg tggaggtagc gggggagggg gctcaggcgg tacaactacg    480

cctgcacctc gcccaccgac cccagcacca accatcgctt cacagccttt gagcctgcga    540

ccagaggcat gtcgccctgc tgcgggcggt gccgttcata ctcgcggact tgattttgcg    600

tgtgacgtcg tctcgcttgg aggaggcgga agtggcggtg gtgggtcagg cggcggtggg    660

agcggaggag gtggaagcca ccaccaccac caccactag                            699
```